United States Patent
Si et al.

(10) Patent No.: US 10,342,796 B2
(45) Date of Patent: Jul. 9, 2019

(54) ACRYLANILIDE DERIVATIVE, PREPARATION METHOD, AND APPLICATIONS THEREOF IN PHARMACY

(71) Applicant: Ancureall Pharmaceutical (Shanghai) Co., Ltd., Shanghai (CN)

(72) Inventors: Jutong Si, Shanghai (CN); Guan Wang, Pudong (CN); Zhihe Yang, Pudong (CN); Meifeng Jiang, Shanghai (CN); Benpo Xu, Pudong (CN); Chentao Zhou, Pudong (CN)

(73) Assignee: Ancureall Pharmaceutical (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 16/067,444

(22) PCT Filed: Dec. 30, 2016

(86) PCT No.: PCT/CN2016/113696
§ 371 (c)(1),
(2) Date: Jun. 29, 2018

(87) PCT Pub. No.: WO2017/114500
PCT Pub. Date: Jul. 6, 2017

(65) Prior Publication Data
US 2019/0015413 A1  Jan. 17, 2019

(30) Foreign Application Priority Data
Dec. 31, 2015 (CN) .......................... 2015 1 1027848

(51) Int. Cl.
| | | |
|---|---|---|
| *A61K 31/506* | (2006.01) |
| *C07D 403/12* | (2006.01) |
| *C07D 401/14* | (2006.01) |
| *C07D 405/14* | (2006.01) |
| *A61K 31/505* | (2006.01) |
| *A61K 31/551* | (2006.01) |
| *C07D 401/12* | (2006.01) |
| *C07D 403/04* | (2006.01) |
| *C07D 239/47* | (2006.01) |
| *C07D 239/48* | (2006.01) |
| *C07D 251/18* | (2006.01) |
| *A61P 35/00* | (2006.01) |
| *A61K 31/53* | (2006.01) |

(52) U.S. Cl.
CPC .......... *A61K 31/506* (2013.01); *A61K 31/505* (2013.01); *A61K 31/53* (2013.01); *A61K 31/551* (2013.01); *A61P 35/00* (2018.01); *C07D 239/47* (2013.01); *C07D 239/48* (2013.01); *C07D 251/18* (2013.01); *C07D 401/12* (2013.01); *C07D 401/14* (2013.01); *C07D 403/04* (2013.01); *C07D 403/12* (2013.01); *C07D 405/14* (2013.01)

(58) Field of Classification Search
CPC ..................................................... A61K 31/506
USPC ......................................................... 544/326
See application file for complete search history.

(56) References Cited

FOREIGN PATENT DOCUMENTS

| | | |
|---|---|---|
| CN | 105085489 | 11/2015 |
| CN | 105585565 | 5/2016 |
| CN | 106132957 | 11/2016 |
| WO | WO-2013014448 | 1/2013 |
| WO | WO-2015158310 | 10/2015 |
| WO | WO-2017114500 | 7/2017 |

OTHER PUBLICATIONS

"International Application No. PCT/CN2016/113696, International Search Report and Written Opinion dated Apr. 6, 2017", (Apr. 6, 2017), 11 pgs.

Jampilek, Josef, "Prodrugs: Pharmaceutical Design and Current Perspectives", Current Pharmaceutical Design, 2011, vol. 17, No. 32, (2011), 3480-3481.

Karaman, Rafik, "Prodrugs Design Based on Inter- and Intramolecular Chemical Processes", Chem Biol Drug Des 2013; 82: 643-668, (Aug. 16, 2013), 643-668.

Rautio, Jarkko, et al., "Prodrugs: design and clinical applications", Nature Reviews 7, (Mar. 2008), 255-270.

*Primary Examiner* — Taofiq A Solola
(74) *Attorney, Agent, or Firm* — Schwegman Lundberg & Woessner, P.A.

(57) ABSTRACT

Disclosed in the present invention are an acrylanilide compound represented by general formula (I) and a pharmaceutically acceptable salt thereof. The acrylanilide compound and the pharmaceutically acceptable salt thereof are used for treating clinical diseases by mainly acting on EGFR family casein kinases.

7 Claims, No Drawings

ACRYLANILIDE DERIVATIVE, PREPARATION METHOD, AND APPLICATIONS THEREOF IN PHARMACY

PRIORITY CLAIM TO RELATED APPLICATIONS

This application is a U.S. national stage filing under 35 U.S.C. § 371 from International Application No. PCT/CN2016/113696, filed on 30 Dec. 2016, and published as WO2017/114500 on 6 Jul. 2017, which claims the benefit under 35 U.S.C. 119 to Chinese Application No. 201511027848.4, filed on 31 Dec. 2015, the benefit of priority of each of which is claimed herein, and which applications and publication are hereby incorporated herein by reference in their entirety.

FIELD OF THE INVENTION

The present invention relates to epidermal growth factor receptor (EGFR) protein tyrosine kinase (PTK) family inhibitors and the pharmaceutical applications thereof.

BACKGROUND OF THE INVENTION

Tumor, including leukemia, is one of the major diseases causing human clinical death. The mortality rate of malignant tumors is extremely high in lung cancer, gastric cancer, breast cancer, pancreatic cancer, liver cancer, intestinal cancer and esophagus cancer. So far, there are still no effective therapeutic drugs or methods that can completely eradicate or cure cancer. There is an urgent need for high-quality anticancer drugs with good specificity, high activity, low toxicity and none drug resistance in clinical applications. The incidence, development, metastasis and deterioration of cancer are related to many factors. The abnormality of signal transduction cascades in normal cells, especially that of the multi-functional signal transduction pathways mediated by transmembrane receptor, is one of the major factors leading to cell transformation and cancerization. Protein tyrosine kinases (PTKs) are enzymes that catalyze the phosphorylation of tyrosine residues of proteins and are necessary for multi-physiological functions of cells such as growth, development, differentiation, metabolism, aging and apoptosis. In general, PTKs can be classified into two categories: membrane receptor and cytoplasmic PTKs. PTK abnormalities can directly lead to different clinical diseases, for examples, cancers, inflammations, autoimmune diseases, neurological or cardiovascular diseases. After decades of continuous efforts, people have identified many PTKs, such as EGFR, HER2/3/4, VEGFR, PDGFR, Met, IGF-1R, FGFR, CSF-1R, Trk receptor, Ephrin receptor, TAM receptor, Tie-2, FLT-3, RET, ALK, BCR-ABL, JAKs, SRC, FAK, BTK, SYK and BLK, that can be as drugable molecules for different diseases clinically. Some of such PTK inhibitors have been successfully applied in clinical practice and have demonstrated good therapeutic effects.

EGFR is a member of the EGFR family that includes four transmembrane receptor protein tyrosine kinases: EGFR (HER1/ErbB1), HER2/ErbB2, HER3/ErbB3 and HER4/ErbB4. EGFR family kinases mediate important multiple signaling pathways in cells. They can control and regulate many physiological functions of cells. Basic science researches, big genomic and clinical data indicate that genetic abnormalities of EGFR, HER2, HER3 and HER4, such as point mutation, deletion, amplification and overexpression may not only directly lead to cell malignant transformation and tumorigenesis, but also they are closely related to the proliferation, invasion, survival, metastasis, infiltration, angiogenesis and drug resistance of tumor cells.

In clinical practice, EGFR abnormal genetic variations (overexpression, point mutation, deletion, insertion, etc.) often present in patients with different cancers, especially lung cancer. Lung cancer is a kind of malignant solid tumor with extremely high death rate.

Non-small-cell lung carcinoma (NSCLC), mainly including adenocarcinoma, squamous-cell carcinoma and large cell carcinoma, accounts for about 80% of the entire lung cancer family, and high-frequency variation of EGFR often occurs in NSCLC, leading to the constitutive activation of the signaling pathways mediated by it and cell cancerization. Similarly, the genetic abnormalities of HER2/ErbB2 (such as mutation, amplification and overexpression) occur in patients with NSCLC, especially the patients showing amplification and/or overexpression of HER2/ErbB2. Besides NSCLC, the aberrations of HER2/ErbB2 frequently occur in many other cancers, some of which are even up to over 30%, such as breast cancer (20%), gastric cancer (22~25%), esophagus cancer (10~25%), pancreatic cancer (2~30%), bladder carcinoma (5~15%), salivary duct carcinoma (15~37%), cervical cancer (1~21%), malignant glioma (7~15%), followed by NSCLC (5%), colorectal cancer (2~3%), ovarian cancer (6 7%), head and neck cancer (3%), hepatocellular carcinoma (2.4%) and melanoma (0-5%). In addition, HER2 amplification and/or overexpression degree is not only positively correlated with the malignancy grade of the tumor, but also associated with acquired drug resistance of many chemotherapeutics, such as Paclitaxel/Oxaliplatin.

EGFR and HER2 have been used as drugable targets for the development of anti-cancer drugs. Up to now, a variety of new anti-cancer drugs have been successfully developed or developing, such as macromolecular monoclonal antibodies, including Cetuximab, Panitumumab and Herceptin, which target on the extracellular domain of EGFR/HER2 protein molecules, and small molecule inhibitors, such as Gefitinib, Erlotinib and Lapatinib, which work on the intracellular kinase domain of EGFR/HER2 protein molecules. They have been applied clinically for years, and have achieved good therapeutic effects. Like many other anti-cancer drugs, however, EGFR drugs also have the issue of acquired drug resistance. For example, the clinical acquired drug resistance of Gefitinib and Erlotinib or Lapatinib is up to 50%. A variety of factors can cause acquired drug resistance. Among them, the structureal change of the targeted protein molecule is a significant cause. The core structure of the first-generation EGFR inhibitor compounds applied in clinical practice is 4-anilinoquinazoline, which can combine with the active part of EGFR protein kinase, and inhibit the activity of protein kinase by competing with ATP. Genomic DNA mutation often leads to changes of protein amino acid sequence and protein structure conformation. For example, EGFR protein kinase may become constitutively active due to the protein structural changes caused by EGFR exon 19 delation, L858R point mutation of exon 21 or other mutations such as G719S, G719A, G719C, L858R, L861Q and S768I, which are PTKi-sensitive mutants and have comparatively enhanced the inhibiting effects of Gefitinib and Erlotinib on EGFR. Some variations of exon20, however, often lead to drug resistance. For example, when threonine 790, a gate-keeper in EGFR protein kinase domain, is mutated into methionine, it will significantly increase the affinity between the mutated protein kinase and ATP. The first-generation EGFR inhibitors have lost the competitive capacity with ATP which has led to drug failure and drug resistance. Due to such acquired resistance, the first-generation EGFR inhibitors show no therapeutic effect on 40-55% of NSCLC patients in clinical practice. Studies have also shown that different amino acid insertions in EGFR exon 20 can also confer drug resistance. Although the second-generation irreversible inhibitors, such as Afatinib and Neratinib, covalently binding with the cysteine 797 (Cys-797) in EGFR protein have been developed based on the structure of the first-generation EGFR inhibitors and they present certain inhibitory activity for EGFR T790M in vitro, they still show strong inhibition effects on wild type EGFR and present high adverse events and toxicity clinically. In addition, since they showed no obvious advantage on treatment of NSCLC patients with EGFR T790M expression when solely used, their clinical applications have been greatly limited. Moreover the second-generation EGFR inhibitors have also generated different degrees of acquired resistance which are related to new EGFR mutants and partially other oncogene abnormalities (such as Met/HER3 amplification, PIK3CA/BRAF mutation, NF1 loss and FGFR signaling activation).

Recent researches have shown that small molecule compound WZ4002 with 2,4-pyrimidine as the new core skeleton can work on EGFR T790M mutant with high activity while the effects on wild type EGFR are relatively weak. The early clinical trail data of the compounds CO-1686 and AZD9291 with 2,4-pyrimidine core skeleton successively developed by two pharmaceutical companies show that they have better response to patients with EGFR T790M mutation and relative low side effects. They are a new generation of effective EGFR T790M mutant inhibitors.

Inhibition of EGFR activity can effectively inhibit the growth of NSCLC, however, abnormal expressions of other genes, such as amplification and overexpression of HER2/ErbB2, amplification of HGFR (MET), as well as the amplification and rearrangement of anaplastic lymphoma kinase (ALK) are also closely related to the malignant growth and drug resistance of NSCLC. And in many other malignant tumors, such as gastric cancer, breast cancer, esophagus cancer and salivary duct carcinoma, HER2/ErbB2 is another important cancer target as well. Although anti-HER2 monoclonal antibody drug Herceptin and small molecule compound Lapatinib in the market have clinically presented favorable therapeutic effects, their problems such as acquired drug resistance and blood brain barrier, however, have limited their clinical wildly applications.

SUMMARY OF THE INVENTION

The object of the present invention is to provide an EGFR PTK family small molecule compound inhibitor with high specificity, activity and low toxicity. The inventor found that the new type of EGFR/HER2 inhibitors of the present invention have unexpected technological effects, which can effectively inhibit the growth of tumor cells with the overexpression of EGFR or HER2/ErBB2, and the different clinical common mutations, especially acquired durg resistant mutation such as EGFR T790M, with minimal side effect, thereby completed the present invention.

The present invention relates to new acrylanilide derivatives and their pharmaceutically acceptable salts, which can highly selectively act on the in vitro and in vivo growth of a variety of human tumor cell lines that express EGFR mutant genes (such as EGFR active mutant delE746-A750, acquired durg resistant mutants L858R/T790M and delE746-A750/T790M) and HER2/ERBB2 amplification in a covalently irreversible binding manner. They have value for a variety of clinical disease treatments.

EGFR PTK family is an ideal target for targeting anticancer therapy which has been successfully applied in clinic. Although the anti-EGFR/HER2 protein kinase inhibitors launched to the market can effectively improve the clinical therapeutic effects of cancer patients, the acquired resistance or severe side effects caused by drugs can significantly affect the clinical therapeutic effects of such drugs, which cannot satisfy clinical demands. The present compounds show strong antitumor activity both in vitro assays or in vivo experiments in animals. 50% growth inhibition (GI50) can effectively inhibit the growth of the cancer cell expressing different EGFR mutants, especially T790M drug-resistant mutant at nmol concentration. Moreover, the inhibition activity is relatively low, and/or little activity on cancer cell lines expressing EGFR WT normally or negatively. This will significantly reduce the risks arising from skin and gastrointestinal side effects caused by the inhibition of wild type EGFR, such as rash and diarrhea.

HER2/ErbB2 is another member of EGFR PTK family. Its abnormal expression is frequently occurring in and related to many malignant tumors. The present inventor unexpectedly found that the present compounds can strongly inhibit the growth of different tumor cell lines with high expression of HER2/ErbB2 gene (such as NCI-N87, Calu-3, AU-565, SK-BR-30, NCI-H2170 and ZR-75-30). The concentration of GI50 is in nanomole. Additionally, the present compounds also show certain growth inhibition effects on Lapatinib resistant cell line HCC1954 (Lapatinib is the only FDA-approved HER2/ERB2 selective reversible inhibitor applied in clinic to date). It can be clinically used for NSCLC and a variety of cancers such as gastric cancer, breast cancer, esophagus cancer, salivary duct carcinoma with high expression of HER2/ErbB2.

The present invention includes the following contents.

[1] A compound of formula (I), or the pharmaceutically acceptable salts, solvates or prodrugs thereof:

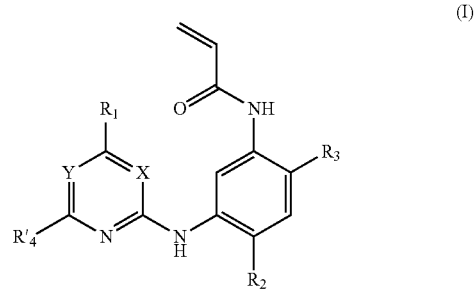

wherein:

X, Y and $R_1$ are selected from any one of a), b) and c) below:

a) When $R_1$ is —$NR_5R_6$, X and Y are identical or different from each other, and each independently selected from N and $CR_4$;

b) When $R_1$ is selected from —$OR_5$ and —$SR_5$, X and Y are identical or different from each other, and each independently selected from N and $CR_4$;

c) When $R_1$ is —$CR_5R_6$, and when $R_5$ and $R_6$ form cycle together with the carbon atoms attached to them, X is $CR_4$ and Y is N;

$R_2$ is selected from the group consisting of alkoxy, alkyl sulphanyl and $NR_6R_6$;

$R_3$ is selected from the group consisting of hydrogen, $N(R^y)(R^z)$, —$N(R^v)R^uN(R^y)(R^z)$, —$OR^uOR_6$, —$OR^uN(R^y)(R^z)$, —$SR_6$ and —$SR^uN(R^y)(R^z)$;

$R_4$ and $R'_4$ are each selected from the group consisting of hydrogen, halogen, alkyl, alkoxy, haloalkyl and cyano;

$R_5$ and $R_6$ are selected from any one of a), b) and c) below:

a) $R_5$ is optionally substituted aryl, optionally substituted heteroaryl or optionally substituted heterocyclyl; when substituted, the substituent is selected from 1~5 $R_7$ groups; wherein each $R_7$ group is independently selected from the group consisting of hydrogen, halogen, alkyl, alkenyl, alkynyl, alkoxy, hydroxyl, amino, haloalkoxy, cycloalkyl, cycloalkyl alkyl, hydroxyl alkyl, haloalkyl, aryl, aryl alkyl, heterocyclyl, heterocyclyl-alkyl, heteroaryl or heteroaryl-alkyl; the alkyl, alkenyl, alkynyl, alkoxy, amino, haloalkoxy, cycloalkyl, cycloalkyl-alkyl, hydroxyl alkyl, haloalkyl, aryl, aryl alkyl, heterocyclyl, heteroaryl or heteroaryl-alkyl is optionally substituted with 1-5 groups selected from the group consisting of halogen, alkyl, alkenyl, alkynyl, aryl, hydroxyl, alkoxy, haloalkoxy, cycloalkyl, ester group and cyano;

$R_6$ is selected from hydrogen and alkyl;

b) $R_5$ and $R_6$ form heterocyclyl, heteroaryl or fused aromatic ring together with the nitrogen atoms attached to them, and the ring contains 0-4 heteroatoms independently selected from O, S and N; when substituted, the substituent is optionally 1 to 5 groups selected from the group consisting of halogen, haloalkyl, alkyl, alkenyl and cyano;

c) $R_5$ and $R_6$ form a fused aromatic ring together with the carbon atoms attached to them, and the ring contains 0-4 heteroatoms independently selected from O, S and N; when substituted, the substituent is optionally 1 to 4 groups selected from the group consisting of halogen, haloalkyl, alkyl, alkenyl and cyano;

Each $R^u$ is independently selected from alkylenealkylene, alkenylene or alkynylene;

$R^v$ is selected from hydrogen and alkyl;

$R^y$ and $R^z$ are each independently selected from the a) and b) below:

a) $R^y$ and $R^z$ are each independently selected from the group consisting of hydrogen, alkyl, cycloalkyl, alkoxy alkyl, hydroxyl alkyl, pyrrolidyl, alkylamino or haloalkyl;

b) $R^y$ and $R^z$ form heterocyclyl or heteroaryl together with the nitrogen atoms attached to them, and the ring contains 0-4 heteroatoms independently selected from O, S and N; the ring is optionally substituted with 1-4 groups selected from the group consisting of $R_5$ and $R_7$.

[2] The compound or the pharmaceutically acceptable salts, solvates or prodrugs thereof described in [1] above, which is characterized in that the compound of formula (I) comprises the compound of formula (IIa), (IIb) or (IIc),

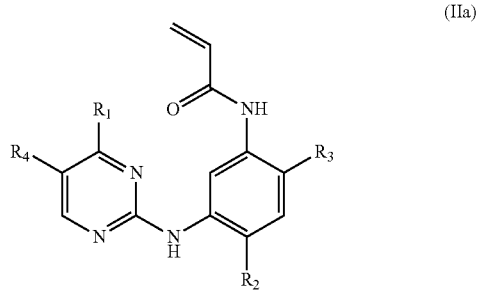
(IIa)

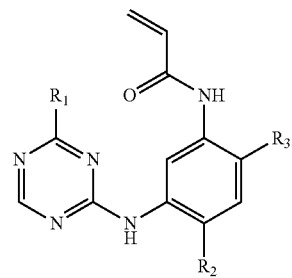
(IIb)

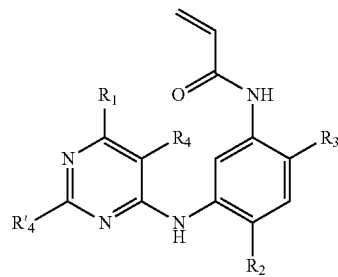
(IIc)

wherein, $R_1$ is selected from a) or b) below:

a) When the compound of formula (I) is the compound of formula IIa or IIb, $R_1$ is —$NR_5R_6$, —$OR_5$ or —$SR^5$;

b) When the compound of formula (I) is the compound of formula IIc, $R_1$ is —$NR_5R_6$; $R_5$ and $R_6$ form cycle together with the carbon atoms attached to them;

$R_2$ is alkoxy;

$R_3$ is selected from the group consisting of hydrogen, $N(R^y)(R^z)$, —$N(R^v)R^UN(R^y)(R^z)$, —$OR^uOR_6$, or —$OR^uN(R^y)(R^z)$;

$R_4$ and $R'_4$ are each independently selected from the group consisting of hydrogen, halogen, alkyl and haloalkyl;

$R_5$ and $R_6$ are selected from any one of a), b) and c) below:

a) $R_5$ is optionally substituted aryl; when substituted, the substituent is selected from 1~5 $R_7$ groups; each $R_7$ group is independently selected from the group consisting of hydrogen, halogen, alkyl, alkenyl, alkynyl, alkoxy, hydroxyl, amino, haloalkoxy, cycloalkyl, cycloalkyl alkyl, hydroxyl alkyl, haloalkyl, aryl, aryl alkyl, heterocyclyl, heterocyclyl alkyl, heteroaryl or heteroaryl alkyl; wherein the alkyl, alkenyl, alkynyl, alkoxy, amino, haloalkoxy, cycloalkyl, cycloalkyl-alkyl, hydroxyl alkyl, haloalkyl, aryl, aryl alkyl, heterocyclyl, heteroaryl or heteroaryl alkyl is optionally substituted with 1-5 groups selected from the group consisting of halogen, alkyl, alkenyl, alkynyl, aryl, hydroxyl, alkoxy, haloalkoxy, cycloalkyl, ester group and cyano;

$R_6$ is selected from hydrogen and alkyl;

b) $R_5$ and $R_6$ form fused aromatic ring together with the nitrogen atoms attached to them, and the ring contains 0-4 heteroatoms independently selected from O, S and N; when substituted, the substituent is optionally 1-4 groups selected from the group consisting of halogen, haloalkyl, alkyl, alkenyl and cyano;

c) $R_5$ and $R_6$ form fused aromatic ring together with the carbon atoms attached to them, and the ring contains 0-4 heteroatoms independently selected from O, S and N; when substituted, the substituent is optionally 1-4 groups selected from the group consisting of halogen, haloalkyl, alkyl, alkenyl and cyano;

Each $R_u$ is independently selected from alkylene;

$R^v$ is selected from hydrogen and alkyl;

Ry and Rz are each independently selected from a) or b) below:

a) $R^y$ and $R^z$ are each independently selected from the group consisting of hydrogen, alkyl and haloalkyl;

b) $R^y$ and $R^z$ form heterocyclyl together with the nitrogen atoms attached to them, and the ring contains 0-4 heteroatoms independently selected from O, S and N; the ring is optionally substituted with 1-4 groups selected from the group consisting of halogen, haloalkyl, alkyl, alkoxy alkyl, alkyl hydroxyl, $NR_6R_6$ or heterocyclyl.

[3] The compound or the pharmaceutically acceptable salts, solvates or prodrugs thereof described in [2] above, which is characterized in that the compound of formula (IIa) is the compound of formula (III):

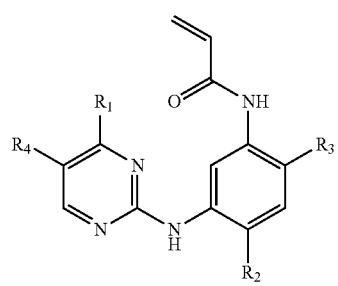

(III)

wherein, $R_1$ is selected from the group consisting of

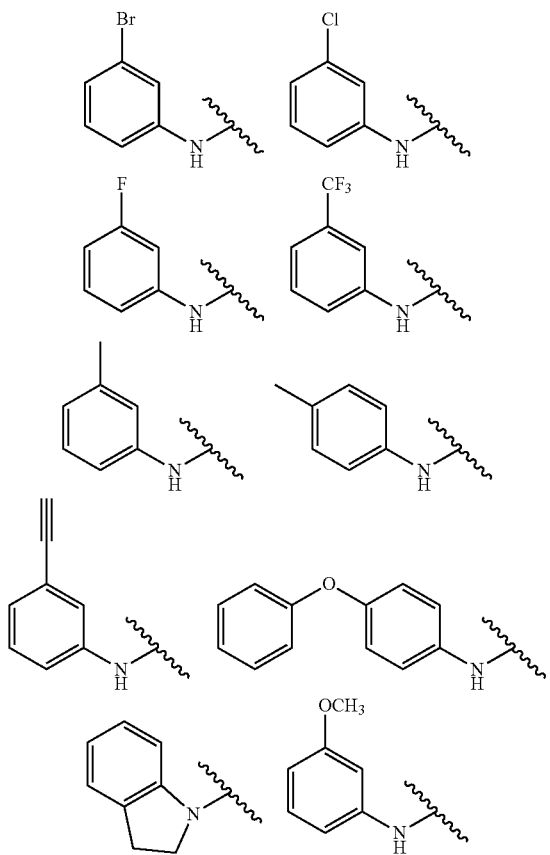

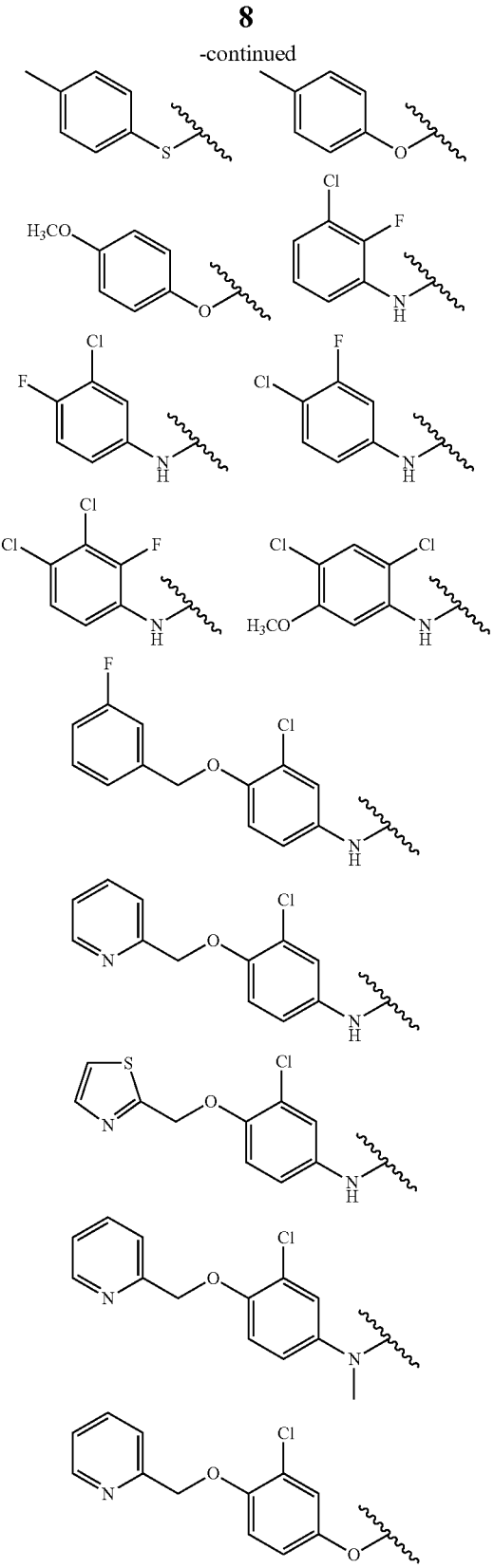

$R_2$ is selected from the group consisting of C1-C6 alkoxy and C3-C6 cycloalkyloxy;

R₃ is selected from the group consisting of

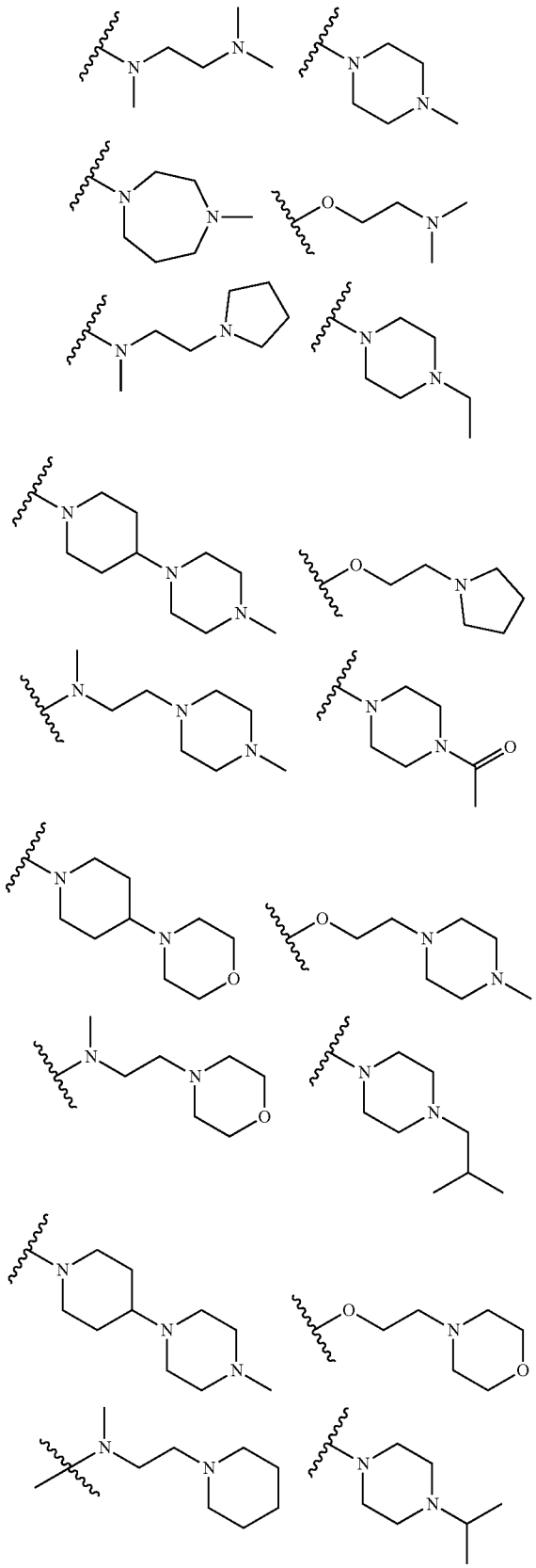

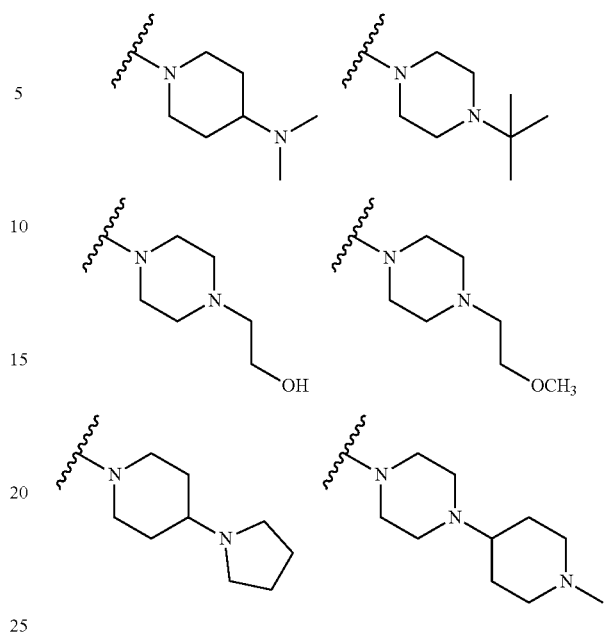

R₄ is selected from the group consisting of hydrogen, methyl, trifluoromethyl and halogen.

[4] The compound or the pharmaceutically acceptable salts, solvates or prodrugs thereof described in [2] above, which is characterized in that the compound of formula (IIa) is the compound of formula (IV):

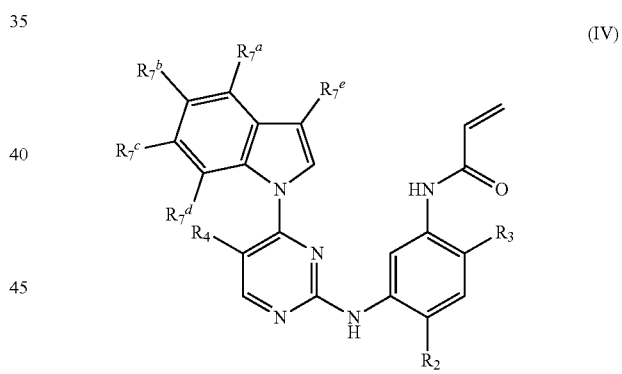

(IV)

wherein:

$R_7^a$, $R_7^b$, $R_7^c$, $R_7^d$ and $R_7^e$ are identical or different from each other, and each independently selected from the group consisting of hydrogen, halogen, alkyl, alkenyl, alkynyl, alkoxy, hydroxyl, amino, haloalkoxy, cycloalkyl, cycloalkyl alkyl, hydroxyl alkyl, haloalkyl, aryl, aryl alkyl, heterocyclyl, heterocyclyl alkyl, heteroaryl or heteroaryl alkyl; wherein the alkyl, alkenyl, alkynyl, alkoxy, amino, haloalkoxy, cycloalkyl, cycloalkyl alkyl, hydroxyl alkyl, haloalkyl, aryl, aryl alkyl, heterocyclyl, heteroaryl or heteroaryl alkyl is optionally substituted with 1-5 groups selected from the group consisting of halogen, alkyl, alkenyl, alkynyl, aryl, hydroxyl, alkoxy, haloalkoxy, cycloalkyl, ester group and cyano;

R₂ is selected from the group consisting of C1-C6 alkoxy and C3-C6 cycloalkyloxy;

$R_3$ is selected from the group consisting of
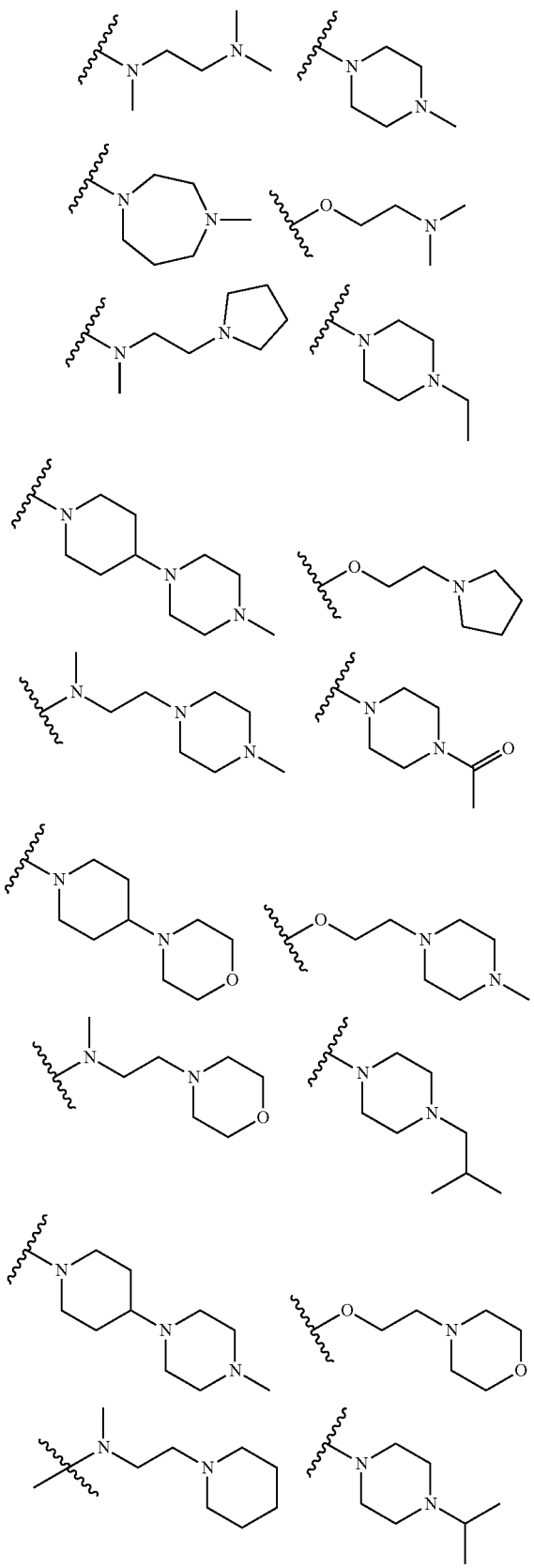
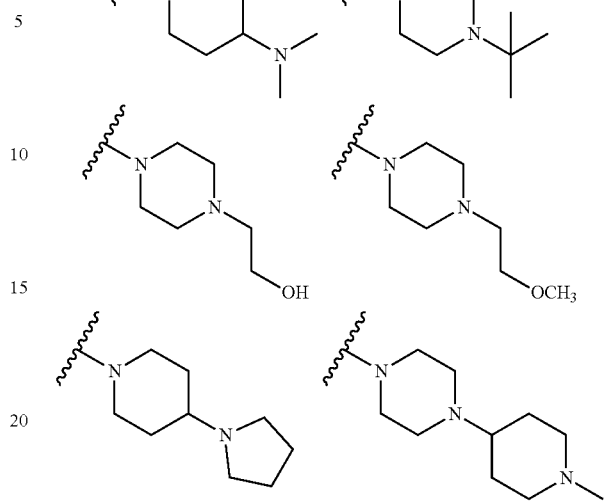
$R_4$ is selected from the group consisting of hydrogen, methyl, trifluoromethyl and halogen.
[5] The compound or the pharmaceutically acceptable salts, solvates or prodrugs thereof described in [4] above, in the compound of formula (IV):
$R_1$ is selected from the group consisting of
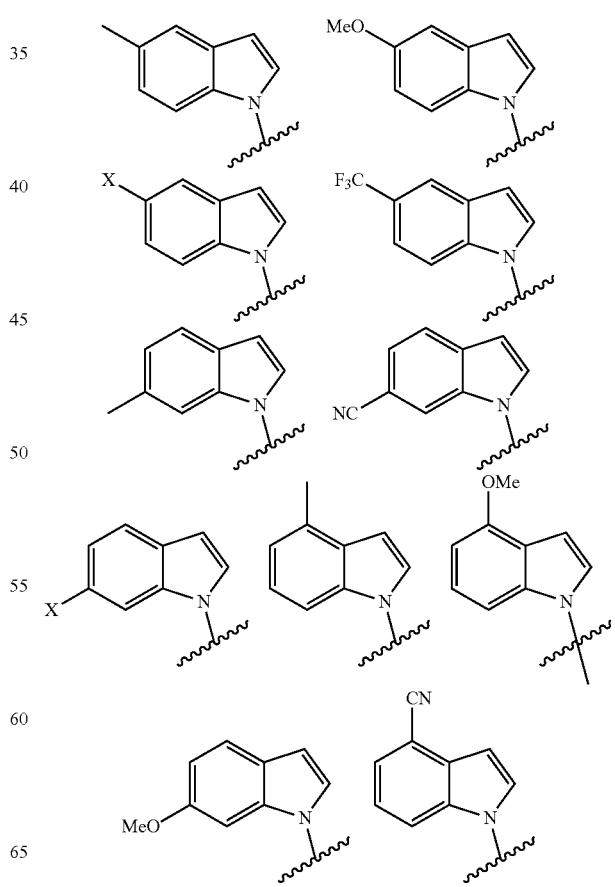

-continued

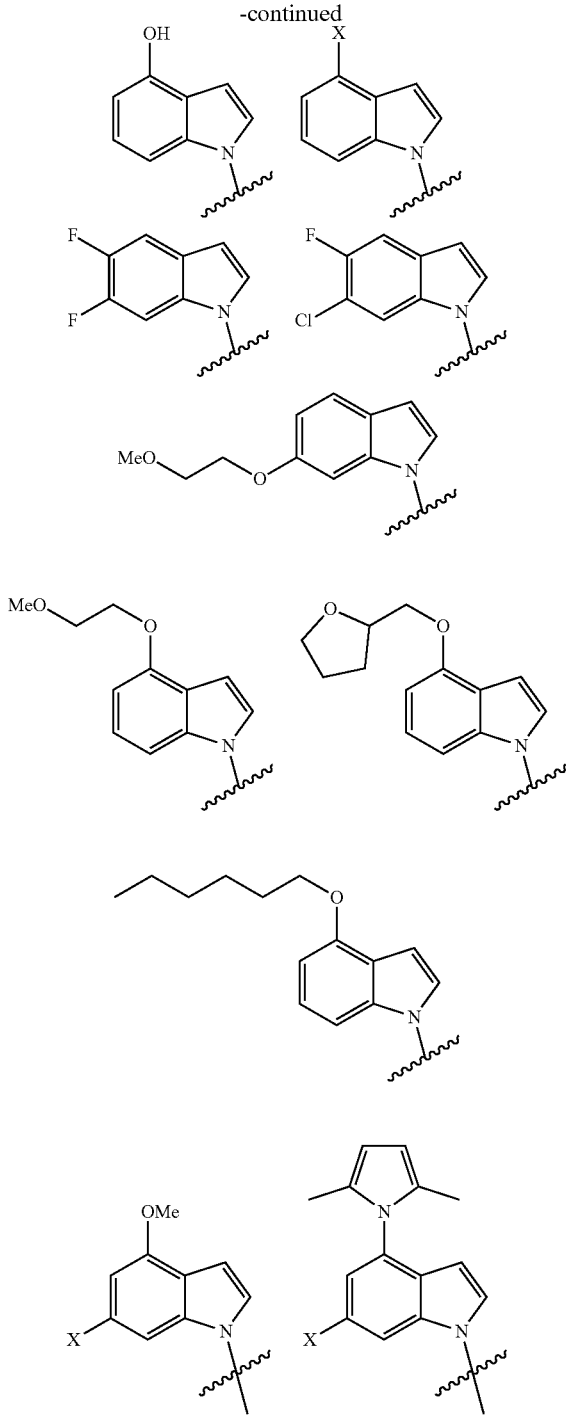

wherein, X is selected from the group consisting of fluorine, chlorine and bromine;

$R_2$ is C1-C6 alkoxy;

$R_3$ is defined as that in [4];

$R_4$ is selected from hydrogen, trifluoromethyl and chlorine.

[6] The compound or the pharmaceutically acceptable salts, solvates or prodrugs thereof described in [2] above, which is characterized in that the compound of formula (IIb) is the compound of formula (V):

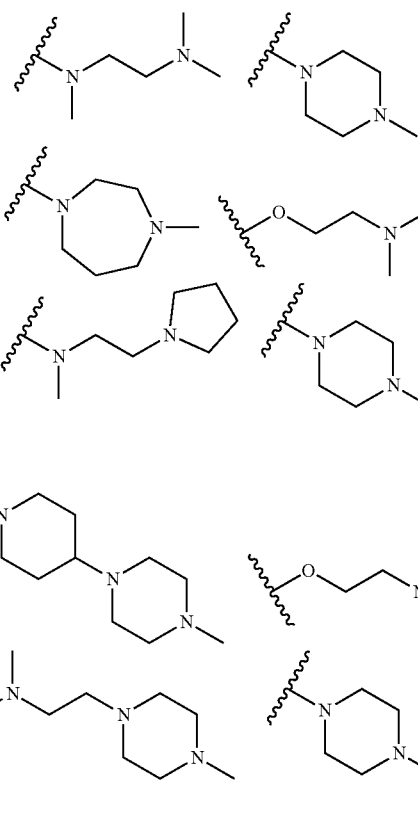

wherein, $R_7^a$, $R_7^b$, $R_7^c$, $R_7^d$ and $R_7^e$ are identical or different from each other, and each independently selected from the group consisting of hydrogen, halogen, alkyl, alkenyl, alkynyl, alkoxy, hydroxyl, amino, haloalkoxy, cycloalkyl, cycloalkyl alkyl, hydroxyl alkyl, haloalkyl, aryl, aryl alkyl, heterocyclyl, heterocyclyl alkyl, heteroaryl or heteroaryl alkyl; wherein, the alkyl, alkenyl, alkynyl, alkoxy, amino, haloalkoxy, cycloalkyl, cycloalkyl alkyl, hydroxyl alkyl, haloalkyl, aryl, aryl alkyl, heterocyclyl, heteroaryl or heteroaryl alkyl is optionally substituted with 1-5 groups selected from the group consisting of halogen, alkyl, alkenyl, alkynyl, aryl, hydroxyl, alkoxy, haloalkoxy, cycloalkyl, ester group and cyano; $R_2$ is selected from the group consisting of C1-C6 alkoxy and C3-C6 cycloalkyloxy;

$R_3$ is selected from the group consisting of

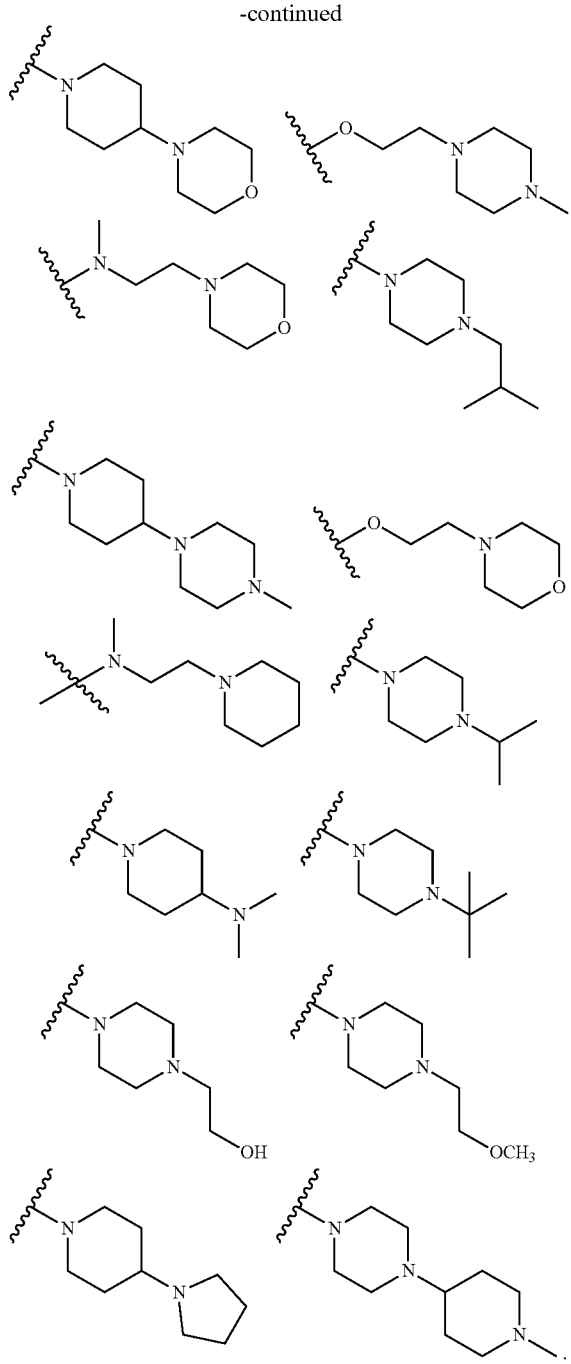
[7] The compound or the pharmaceutically acceptable salts, solvates or prodrugs thereof described in [6] above, in the compound of formula (V):
$R_1$ is selected from the group consisting of
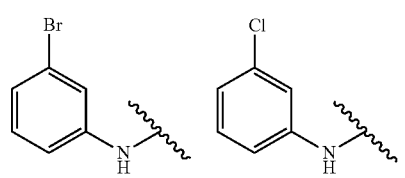
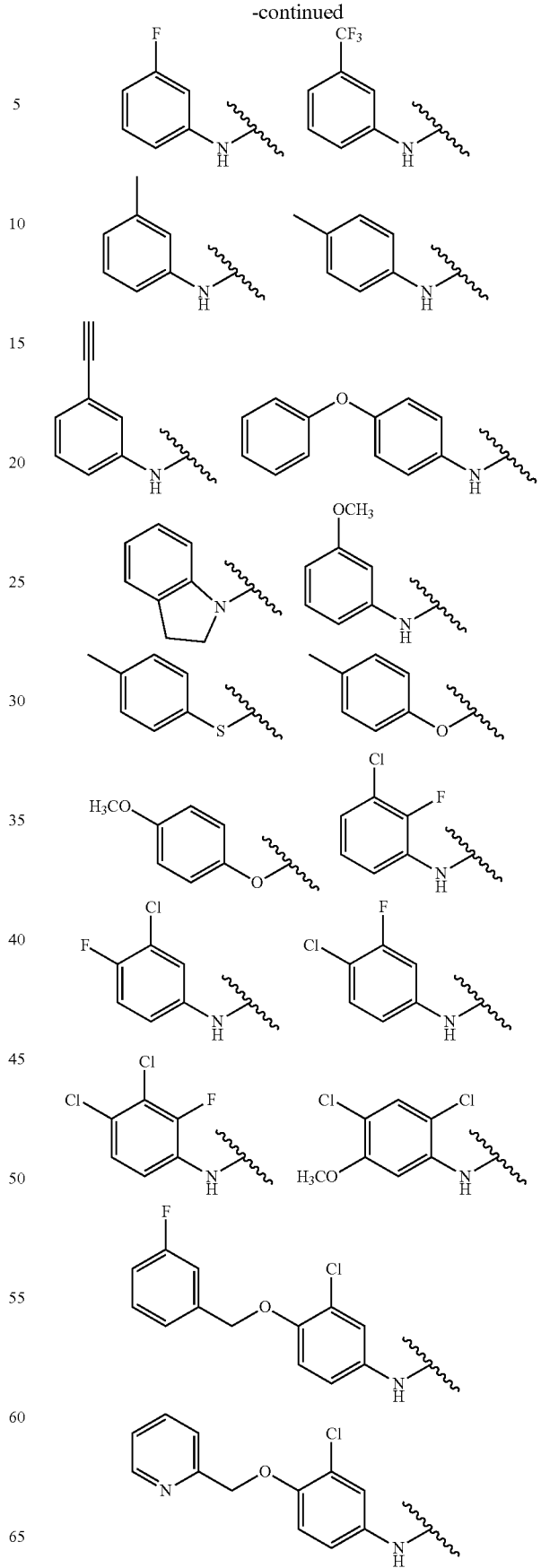

-continued

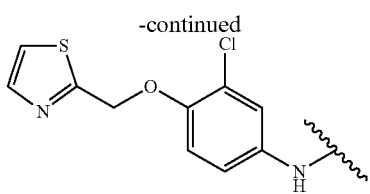

R₂ is C1-C6 alkoxy;

R₃ is defined as that in [6].

[8] The compound or the pharmaceutically acceptable salts, solvates or prodrugs thereof described in [2] above, wherein the compound of formula (IIc) is the compound of formula (VI):

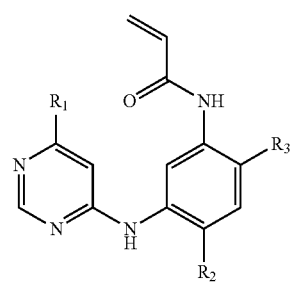

(VI)

wherein:

R₁ is selected from the group consisting of

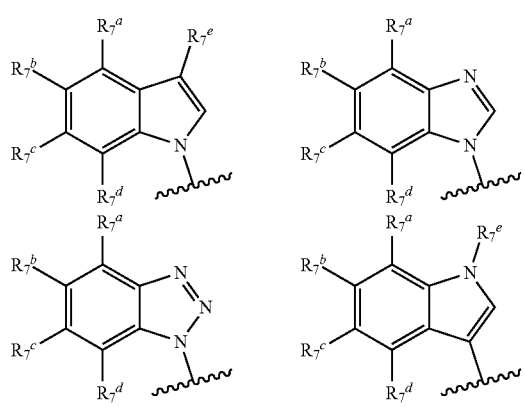

$R_7{}^a$, $R_7{}^b$, $R_7{}^c$, $R_7{}^d$ and $R_7{}^e$ are identical or different from each other, and are each independently selected from the group consisting of hydrogen, halogen, alkyl, alkenyl, alkynyl, alkoxy, hydroxyl, amino, haloalkoxy, cycloalkyl, cycloalkyl alkyl, hydroxyl alkyl, haloalkyl, aryl, aryl alkyl, heterocyclyl, heterocyclyl alkyl, heteroaryl and heteroaryl alkyl; wherein, the alkyl, alkenyl, alkynyl, alkoxy, amino, haloalkoxy, cycloalkyl, cycloalkyl alkyl, hydroxyl alkyl, haloalkyl, aryl, aryl alkyl, heterocyclyl, heteroaryl or heteroaryl alkyl is optionally substituted with 1-5 groups selected from the group consisting of halogen, alkyl, alkenyl, alkynyl, aryl, hydroxyl, alkoxy, haloalkoxy, cycloalkyl, ester group and cyano; R₂ is selected from the group consisting of C1-C6 alkoxy and C3-C6 cycloalkyloxy;

R₃ is selected from the group consisting of

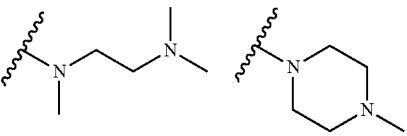

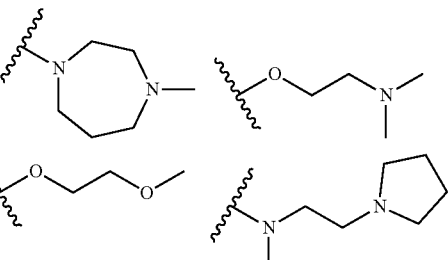

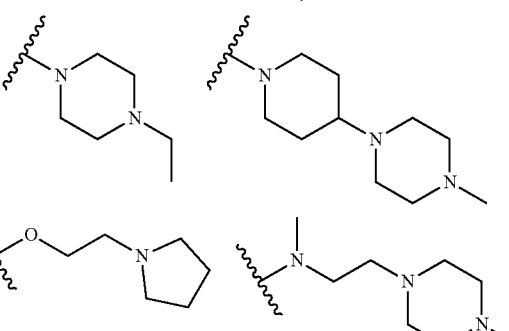

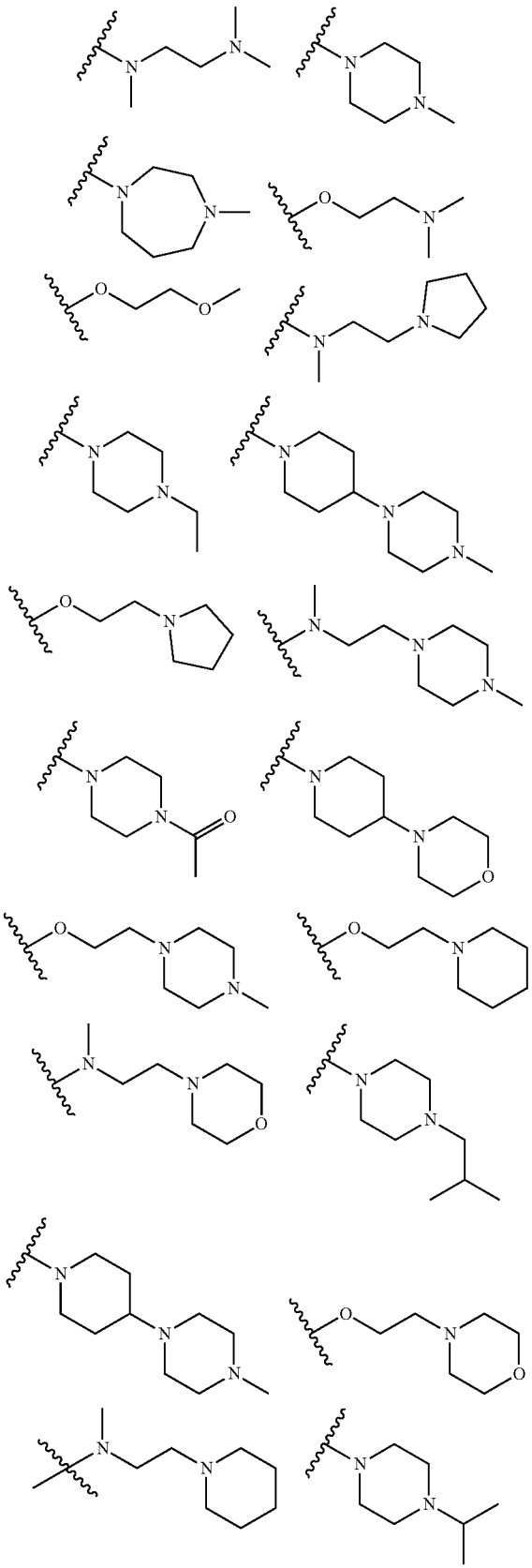

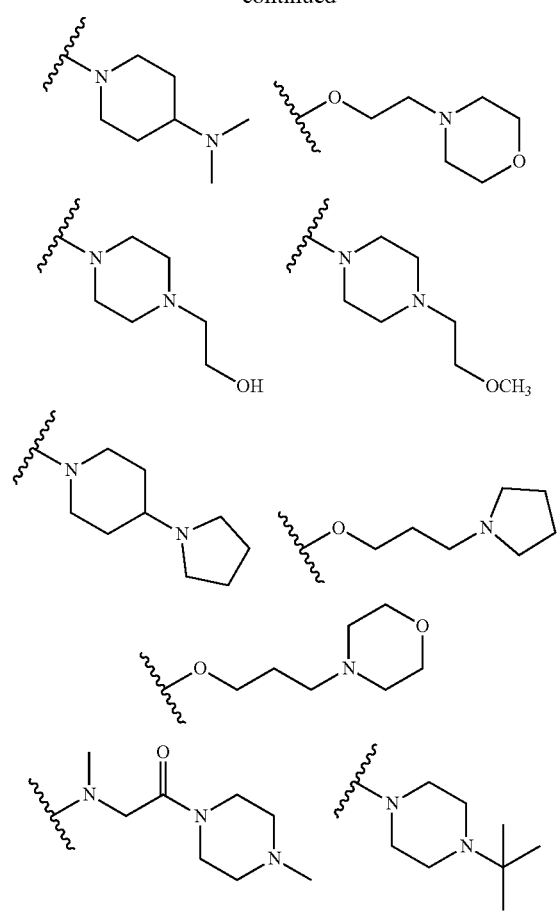
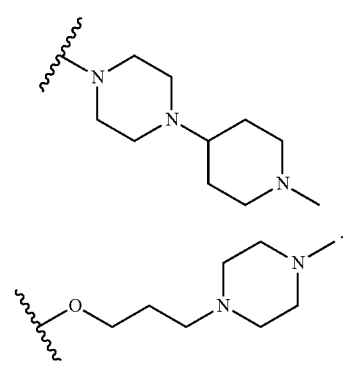
[9] The compound or the pharmaceutically acceptable salts, solvates or prodrugs thereof described in [8] above, in the compound of formula (VI):
$R_1$ is selected from the group consisting of
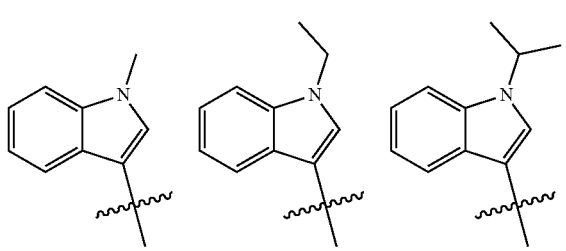
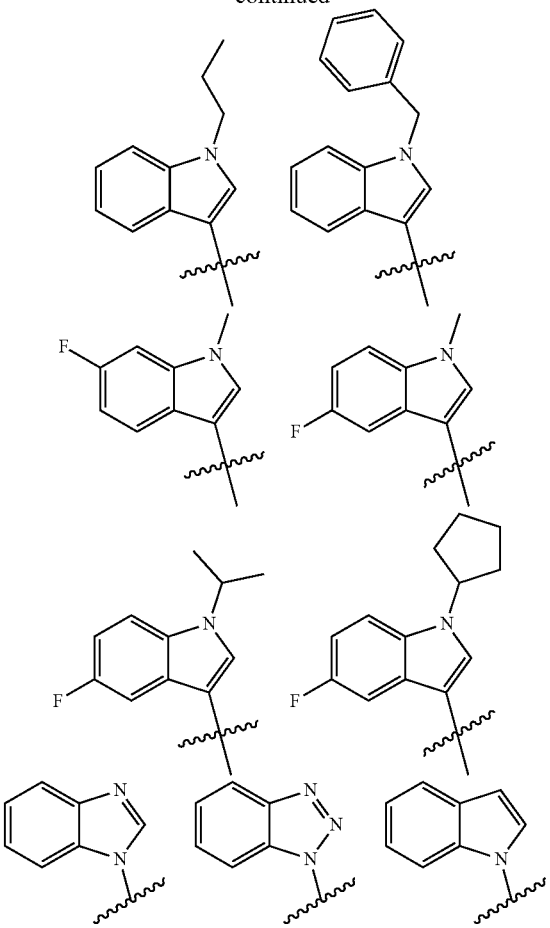
$R_2$ is C1-C6 alkoxy;
$R_3$ is selected from the group consisting of
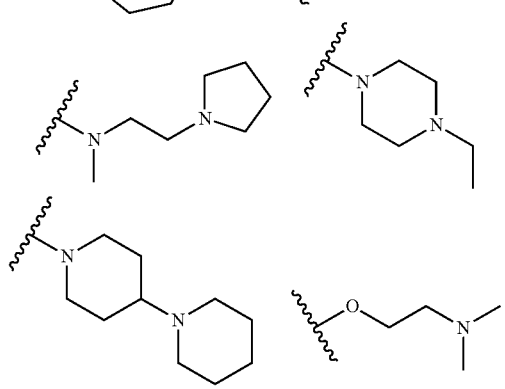

-continued
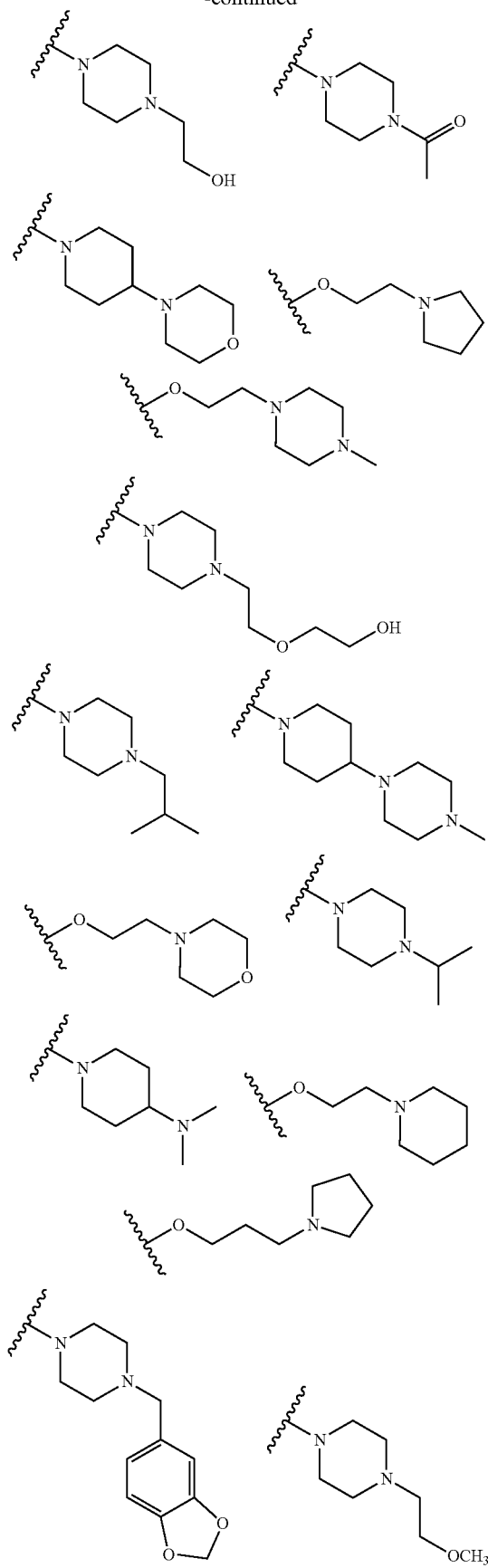
-continued
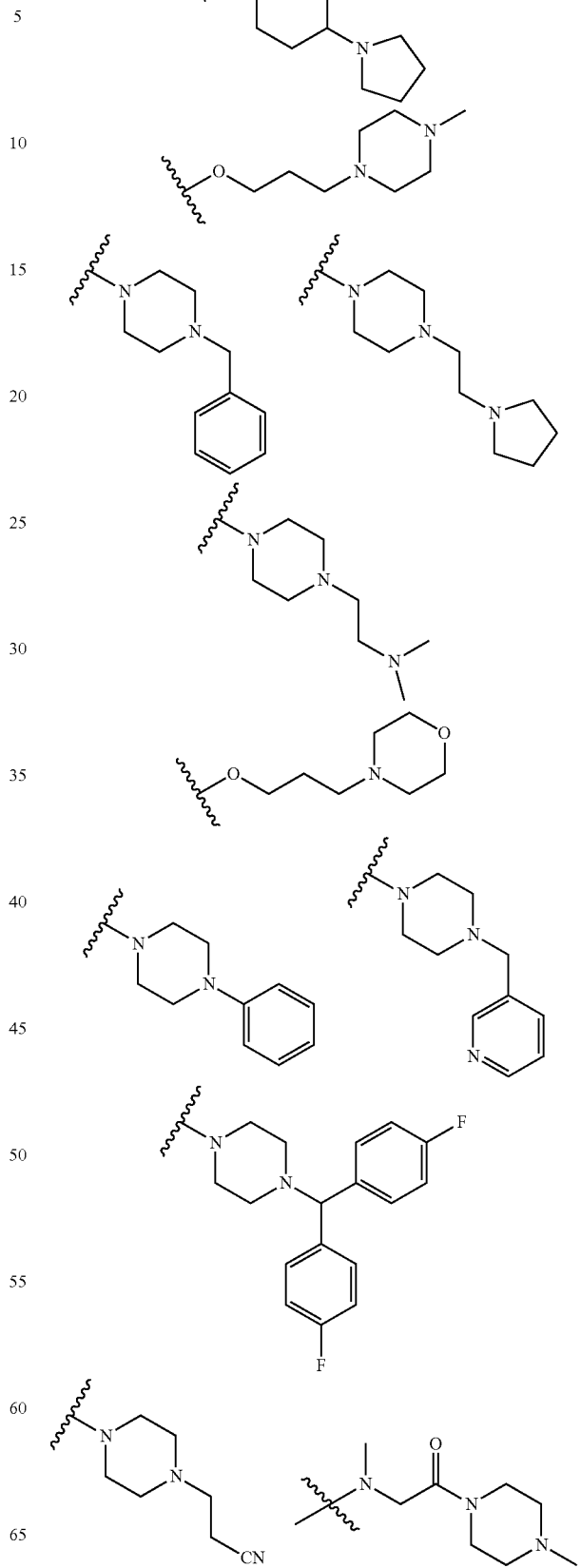

23

-continued

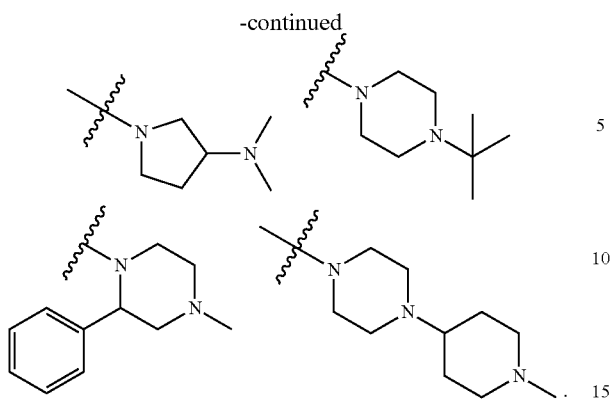

[10] The compound or the pharmaceutically acceptable salts, solvates or prodrugs thereof described in [2] above, wherein the compound of formula (IIc) is the compound of formula (VII):

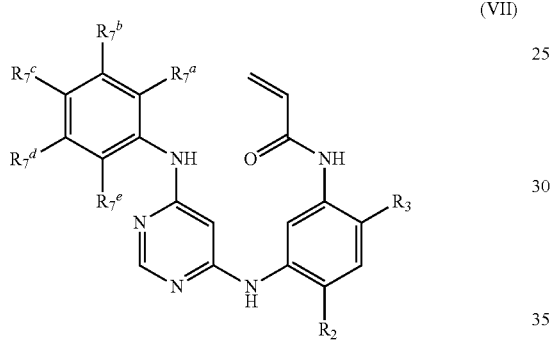

(VII)

wherein, $R_7^a$, $R_7^b$, $R_7^c$, $R_7^d$ and $R_7^e$ are identical or different from each other, and are each independently selected from the group consisting of hydrogen, halogen, alkyl, alkenyl, alkynyl, alkoxy, hydroxyl, amino, haloalkoxy, cycloalkyl, cycloalkyl alkyl, hydroxyl alkyl, haloalkyl, aryl, aryl alkyl, heterocyclyl, heterocyclyl alkyl, heteroaryl or heteroaryl-alkyl; wherein, the alkyl, alkenyl, alkynyl, alkoxy, amino, haloalkoxy, cycloalkyl, cycloalkyl alkyl, hydroxyl alkyl, haloalkyl, aryl, aryl alkyl, heterocyclyl, heteroaryl or heteroaryl-alkyl is optionally substituted with 1-5 groups selected from the group consisting of halogen, alkyl, alkenyl, alkynyl, aryl, hydroxyl, alkoxy, haloalkoxy, cycloalkyl, ester group and cyano;

$R_2$ is selected from the group consisting of C1-C6 alkoxy and C3-C6 cycloalkyloxy;

$R_3$ is defined as that in [2] above.

[11] The compound or the pharmaceutically acceptable salts, solvates or prodrugs thereof described in [10] above, in the compound of formula (VII):

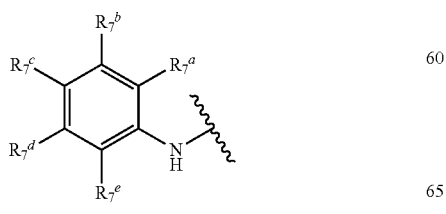

24 is selected from the group consisting of

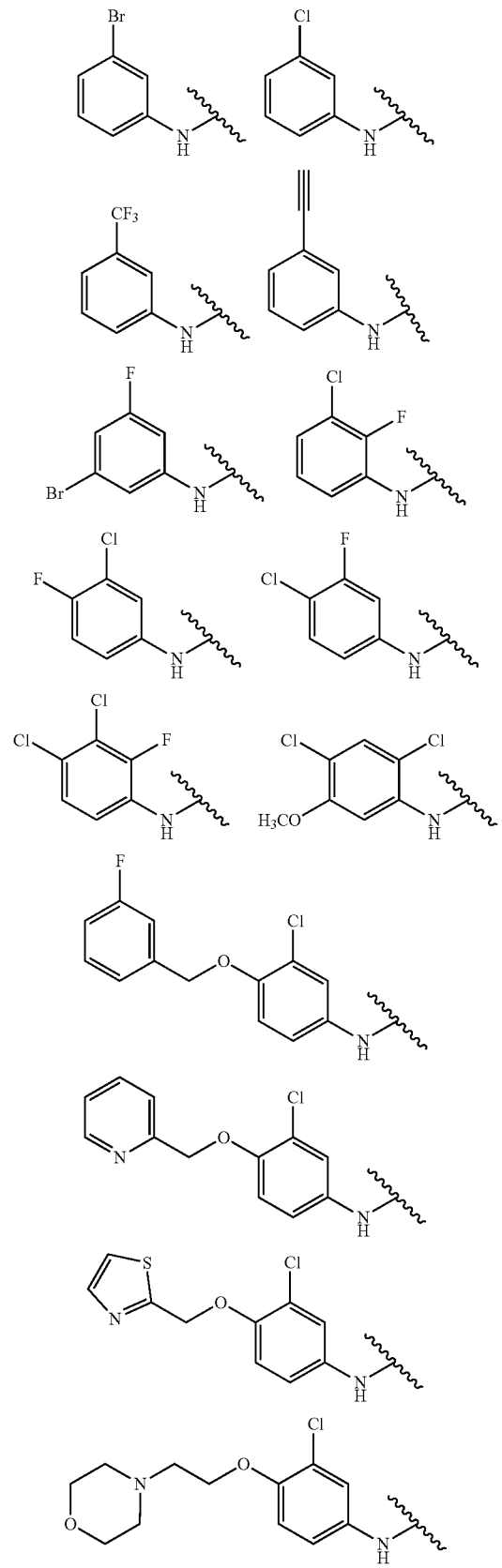

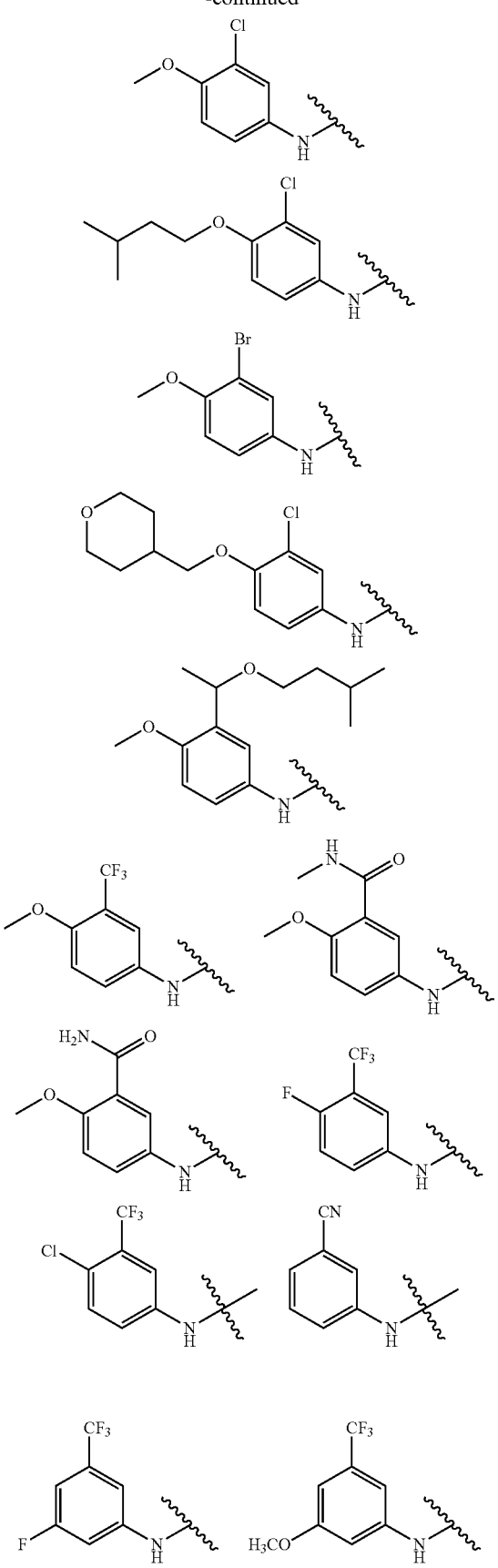
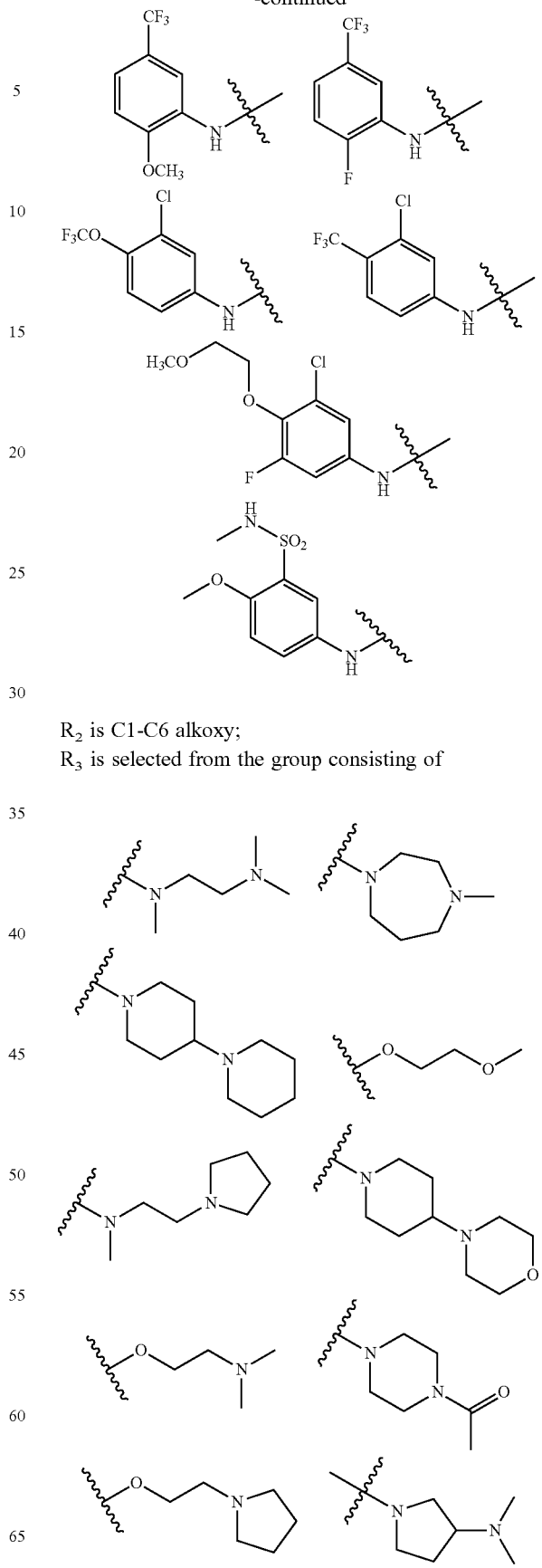
R₂ is C1-C6 alkoxy;
R₃ is selected from the group consisting of

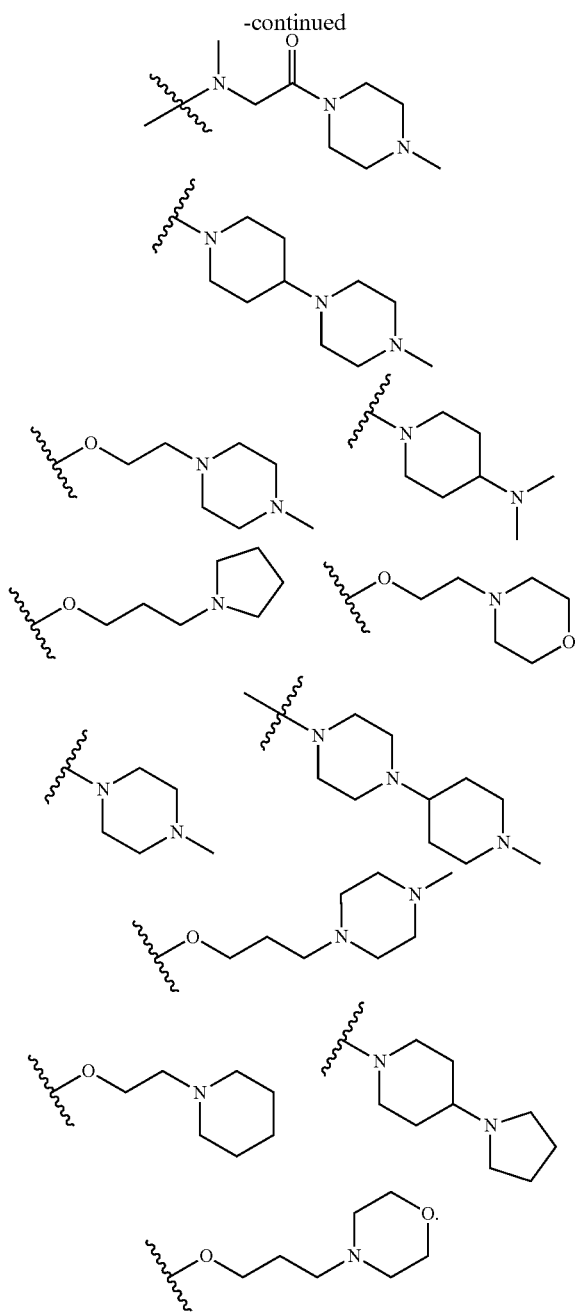

[12] The compounds or the pharmaceutically acceptable salts, solvates or prodrugs thereof described in any one of [1]~[11] above, wherein the compound is selected from the group consisting of N-(5-(4-(3-bromophenyl amino)-pyrimidin-2-ylamino)-2-(2-(dimethylamino-ethyl)-methyl-amino)-4-methoxyl-phenyl)-acrylamide;

N-(5-(4-(3-chlorophenyl amino)-pyrimidin-2-ylamino)-2-(2-(dimethylamino-ethyl)-methyl-amino)-4-methoxyl-phenyl)-acrylamide;

N-(5-(4-(3-fluorophenylamino)-pyrimidin-2-ylamino)-2-(2-(dimethyl amino-ethyl)-methyl-amino)-4-methoxyl-phenyl)-acrylamide;

N-(5-(4-(3-trifluoromethylphenylamino)-pyrimidin-2-ylamino)-2-(2-(dimethylamino-ethyl)-methyl-amino)-4-methoxyl-phenyl)-acrylamide;

N-(5-(4-(3-methylphenyl amino)-pyrimidin-2-ylamino)-2-(2-(dimethylamino-ethyl)-methyl-amino)-4-methoxyl-phenyl)-acrylamide;

N-(5-(4-(4-methylphenyl amino)-pyrimidin-2-ylamino)-2-(2-(dimethylamino-ethyl)-methyl-amino)-4-methoxyl-phenyl)-acrylamide;

N-(5-(4-(4-methylphenylthio)-pyrimidin-2-ylamino)-2-((2-dimethylamino-ethyl)-methyl-amino)-4-methoxyl-phenyl)-acrylamide;

N-(5-(4-(3-acetenylphenylamino)-pyrimidin-2-ylamino)-2-(2-(dimethylamino-ethyl)-methyl-amino)-4-methoxyl-phenyl)-acrylamide;

N-(5-(4-(4-phenoxylphenylamino)-pyrimidin-2-ylamino)-2-(2-(dimethyl amino-ethyl)-methyl-amino)-4-methoxyl-phenyl)-acrylamide;

N-(5-(4-(phenyl amino)-pyrimidin-2-ylamino)-2-(2-(dimethyl amino-ethyl)-methyl-amino)-4-methoxyl-phenyl)-acrylamide;

N-(5-(4-(3-methoxyphenoxy)-pyrimidin-2-ylamino)-2-((2-dimethylamino-ethyl)-methyl-amino)-4-methoxyl-phenyl)-acrylamide;

N-(3-(4-(3-chloro-4-fluoro-phenylamino)-pyrimidin-2-ylamino)-4-methoxyl-phenyl)-acrylamide;

N-(5-(4-(3-chlorine-4-fluorophenylamino)-pyrimidin-2-ylamino)-2-(2-(dimethylamino-ethyl)-methyl-amino)-4-methoxyl-phenyl)-acrylamide;

N-(5-(4-(3-chlorine-2-fluorophenylamino)-pyrimidin-2-ylamino)-2-(2-(dimethylamino-ethyl)-methyl-amino)-4-methoxyl-phenyl)-acrylamide;

N-(5-(4-(3,4-dichloro-2-fluorophenylamino)-pyrimidin-2-ylamino)-2-(2-(dimethylamino-ethyl)-methyl-amino)-4-methoxyl-phenyl)-acrylamide;

N-(5-(4-(2,4-dichloro-5-methoxyphenylamino)-pyrimidin-2-ylamino)-2-(2-(dimethylamino-ethyl)-methyl-amino)-4-methoxyl-phenyl)-acrylamide;

N-(5-(4-(3-chloro-4-(pyridin-2-ylmethoxy)-phenylamino)-pyrimidin-2-ylamino)-2-dimethylamino-4-methoxyl-phenyl)-acrylamide;

N-(5-(4-(3-chloro-4-(pyridin-2-ylmethoxyl)-phenylamino)-pyrimidin-2-ylamino)-2-((2-(dimethylamino)ethyl)(methyl)amino)-4-methoxyl-phenyl)-acrylamide;

N-(5-(5-chloro-4-(3-chloro-4-(pyridin-2-ylmethoxyl)-phenylamino)-pyrimidin-2-ylamino)-2-((2-(dimethylamino)ethyl)(methyl)amino)-4-methoxyl-phenyl)-acrylamide;

N-(5-(4-(3-chloro-4-(pyridin-2-ylmethoxy)-phenylamino)-pyrimidin-2-ylamino)-2-(4-morpholine-4-yl)-piperidine-1-yl)-4-methoxyl-phenyl)-acrylamide;

N-(5-(4-(3-chloro-4-(pyridin-2-ylmethoxy)-phenylamino)-pyrimidin-2-ylamino)-2-(4-(4-methylpiperazin-1-yl)-piperidin-1-yl)-4-methoxyl-phenyl)-acrylamide;

N-(5-(4-(3-chloro-4-(pyridin-2-ylmethoxy)-phenylamino)-pyrimidin-2-ylamino)-2-(4-(1-methylpiperidin-4-yl)-piperazin-1-yl)-4-methoxyl-phenyl)-acrylamide;

N-(5-(4-(3-chloro-4-(pyridin-2-ylmethoxy)-phenylamino)-pyrimidin-2-ylamino)-2-(4-methyl piperazin-1-yl)-4-methoxyl-phenyl)-acrylamide;

N-(5-(4-(3-chloro-4-(pyridin-2-ylmethoxy)-phenylamino)-pyrimidin-2-ylamino)-2-(4-(2-hydroxyethyl)piperazin-1-yl)-4-methoxyl-phenyl)-acrylamide;

N-(5-(4-(3-chloro-4-(pyridin-2-ylmethoxy)-phenylamino)-pyrimidin-2-ylamino)-2-(4-methyl-[1,4]diazepin-1-yl)-4-methoxyl-phenyl)-acrylamide;

N-(5-(4-(3-chloro-4-(pyridin-2-ylmethoxy)-phenylamino)-pyrimidin-2-ylamino)-2-(4-(piperidin-1-yl)-piperidin-1-yl)-4-methoxyl-phenyl)-acrylamide;

N-(5-(4-(3-chloro-4-(pyridin-2-ylmethoxy)-phenylamino)-pyrimidin-2-ylamino)-2-(4-acetylpiperazin-1-yl)-4-methoxyl-phenyl)-acrylamide;

N-(5-(4-(3-chloro-4-(pyridin-2-ylmethoxy)-phenyl amino)-pyrimidin-2-yl amino)-2-(4-(dimethylamino)piperazin-1-yl)-4-methoxyl-phenyl)-acrylamide;

N-(5-(-4-(3-chloro-4-(benzene-2-methoxyl)-phenylamino)-pyrimidin-2-ylamino)-2-(2-(morpholin-4-yl)-ethoxyl)-4-methoxyl-phenyl)-acryl amide;

N-(5-(4-(3-chloro-4-(3-fluorobenzyloxy)phenylamino)pyrimidin-2-ylamino)-2-((2-(dimethylamino)ethyl)(methyl)amino)-4-methoxyl-phenyl)-acrylamide;

N-(2-((2-(dimethylamino-ethyl)-methyl-amino)-5-(4-(indolin-1-yl)-pyrimidin-2-ylamino)-4-methoxyl-phenyl)-acryl amide;

N-(5-(4-(1H-indol-1-yl)-pyrimidin-2-ylamino)-4-methoxyl-2-(4-acetyl-piperazin-1-yl)-phenyl)-acrylamide;

N-(5-(4-(1H-indol-1-yl)-pyrimidin-2-ylamino)-4-methoxyl-2-(4-(4-methyl-piperazin-1-yl)-piperidin-1-yl)-phenyl)-acrylamide;

N-(5-(4-(1H-indol-1-yl)-pyrimidin-2-ylamino)-4-methoxyl-2-(4-(morpholin-4-yl)-piperidin-1-yl)-phenyl)-acrylamide;

N-(5-(4-(1H-indol-1-yl)-pyrimidin-2-ylamino)-2-(4-(cyclohexylmethyl)-piperazin-1-yl)-4-methoxylphenyl)-acrylamide;

N-(5-(4-(1H-indol-1-yl)-pyrimidin-2-amino)-4-methoxyl-2-(4-methyl-1,4-diazepin-1-yl)-phenyl)-acrylamide;

N-(2-(1,4'-bipiperidin-1'-yl-)-5-(4-(1H-indol-1-yl)-pyrimidin-2-ylamino)-4-methoxyl-phenyl)-acrylamide;

N-(5-(4-(1H-indol-1-yl)-pyrimidin-2-ylamino)-2-(4-dimethylamino-piperidin-1l-yl)-4-methoxyl-phenyl)-acrylamide;

N-(5-(4-(1H-indol-1-yl)-pyrimidin-2-ylamino)-2-(4-(2-methoxylethyl)-piperazin-1-yl)-4-methoxyl-phenyl)-acrylamide;

N-(5-(4-(1H-indol-1-yl)-pyrimidin-2-ylamino)-2-(4-pyrrolidyl-piperazin-1-yl)-4-methoxyl-phenyl)-acrylamide;

N-(5-(4-(1H-indol-1-yl)-pyrimidin-2-ylamino)-2-(4-(2-cyanoethyl)-piperazin-1-yl)-4-m ethoxyl-phenyl)-acrylamide;

N-(5-(4-(1H-indol-1-yl)-pyrimidin-2-ylamino)-2-(4-tert-butylpiperazin-1-yl)-4-methoxyl-phenyl)-acrylamide;

N-(5-(4-(1H-indol-1-yl)-pyrimidin-2-ylamino)-4-methoxyl-2-(4-(2-(pyridin-4-yl)-ethyl)-piperazin-1-yl)-phenyl)-acrylamide;

N-(5-(4-(1H-indol-1-yl)-pyrimidin-2-ylamino)-2-(4-benzylpiperazin-1-yl)-4-methoxyl-phenyl)-acrylamide;

N-(5-(4-(1H-indol-1-yl)-pyrimidin-2-ylamino)-2-(4-(benzo[d][1,3]dioxy-5-methyl)-piperazin-1-yl)-4-methoxyl-phenyl)-acrylamide;

N-(5-(4-(1H-indol-1-yl)-pyrimidin-2-ylamino)-2-(4-(2-hydroxypropyl-2-yl)-piperidin-1-yl)-4-methoxyl-phenyl)-acrylamide;

N-(5-(4-(1H-indol-1-yl)-pyrimidin-2-ylamino)-2-(4-(hydroxymethyl)-piperidin-1-yl)-4-methoxyl-phenyl)-acrylamide;

N-(5-(4-(1H-indol-1-yl)-pyrimidin-2-ylamino)-2-(4-isobutylpiperazin-1-yl)-4-methoxyl-phenyl)-acrylamide;

N-(5-(4-(1H-indol-1-yl)-pyrimidin-2-ylamino)-2-(2-(morpholin-yl)-ethoxyl)-4-methoxyl-phenyl)-acrylamide;

N-(5-(4-(1H-indol-1-yl)-pyrimidin-2-ylamino)-2-(2-dimethylamino)-ethoxyl)-4-methoxyl-phenyl)-acrylamide;

N-(5-(4-(1H-indol-1-yl)-pyrimidin-2-ylamino)-2-(2-pyrrolidin-1-yl)-ethoxyl)-4-methoxyl-phenyl)-acrylamide;

N-(5-(4-(1H-indol-1-yl)-pyrimidin-2-ylamino)-2-(2-4-methyl-piperazin-1-yl)-ethoxyl)-4-methoxyl-phenyl)-acrylamide;

N-{2-[(2-(dimethylamino)-ethyl)-methyl-amino]-4-methoxyl-5-[4-(6-methoxyl-indol-1-yl)-pyrimidin-2-ylamino]-phenyl}-acrylamide;

N-{2-[(2-(dimethylamino)-ethyl)-methyl-amino]-4-methoxyl-5-[4-(6-methyl-indol-1-yl)-pyrimidin-2-ylamino]-phenyl}-acrylamide;

N-{5-[4-(6-cyano-indol-1-yl)-pyrimidin-2-ylamino]-2-[(2-dimethylamino-ethyl)-methyl-amino]-4-methoxyl-phenyl}-acrylamide;

N-(5-(4-(6-chloro-H-indol-1-yl)-pyrimidin-2-ylamino)-2-((2-(dimethylamino-ethyl)-methyl-amino)-4-methoxyl-phenyl)-acrylamide;

N-(5-(4-(6-bromo-1H-indol-1-yl)-pyrimidin-2-ylamino)-2-((2-(dimethylamino)ethyl)-methyl-amino)-4-methoxyl-phenyl)-acrylamide;

N-(5-(4-(6-fluoro-1H-indol-1-yl)-pyrimidin-2-ylamino)-2-((2-(dimethylamino)ethyl)-methyl-amino)-4-methoxyl-phenyl)-acrylamide;

N-(5-(4-(6-fluoro-1H-indol-1-yl)-pyrimidin-2-ylamino)-2-(4-(dimethylamino)-piperidinyl)-4-methoxyl-phenyl)-acrylamide;

N-(5-(4-(6-fluoro-1H-indol-1-yl)-pyrimidin-2-ylamino)-2-(dimethylamino)-4-methoxyl-phenyl)-acrylamide;

N-(5-(4-(6-fluoro-1H-indol-1-yl)-pyrimidin-2-ylamino)-2-(4-(4-methylpiperazin-1-yl)-piperidin-1-yl)-4-methoxyl-phenyl)-acrylamide;

N-(5-(4-(6-fluoro-1H-indol-1-yl)-pyrimidin-2-ylamino)-2-(4-(1-methylpiperidin-4-yl)-piperazin-1-yl)-4-methoxyl-phenyl)-acrylamide;

N-(5-(4-(6-fluoro-1H-indol-1-yl)-pyrimidin-2-ylamino)-2-(4-(morpholin-4-yl)-piperidin-1-yl)-4-methoxyl-phenyl)-acrylamide;

N-(5-(4-(6-fluoro-1H-indol-1-yl)-pyrimidin-2-ylamino)-2-(4-(2-hydroxyl-ethyl)-piperazin-1-yl)-4-methoxyl-phenyl)-acrylamide;

N-(5-(4-(6-fluoro-1H-indol-1-yl)-pyrimidin-2-ylamino)-2-(4-methyl-piperazin-1-yl)-4-methoxyl-phenyl)-acrylamide;

N-(5-(4-(6-fluoro-1H-indol-1-yl)-pyrimidin-2-ylamino)-2-(4-acetyl-piperazin-1-yl)-4-m ethoxyl-phenyl)-acrylamide;

N-(5-(4-(6-fluoro-1H-indol-1-yl)-pyrimidin-2-ylamino)-2-(4-methyl-[1,4]diazepin-1-yl)-4-methoxyl-phenyl)-acrylamide;

N-(5-(4-(6-fluoro-1H-indol-1-yl)-pyrimidin-2-ylamino)-2-(4-(piperidin-1-yl)-piperidin-1-yl)-4-methoxyl-phenyl)-acrylamide;

N-(5-(4-(6-fluoro-1H-indol-1-yl)-pyrimidin-2-ylamino)-2-(2-4-acryloyl-piperazin-1-yl)-ethoxyl)-4-methoxyl-phenyl)-acrylamide;

N-(5-(4-(6-fluoro-1H-indol-1-yl)-pyrimidin-2-ylamino)-2-(2-(morpholin-4-yl)-ethoxyl)-4-methoxyl-phenyl)-acrylamide;

N-(5-(4-(6-fluoro-1H-indol-1-yl)-pyrimidin-2-ylamino)-2-(2-pyrrolidin-1-yl)-ethoxyl)-4-methoxyl-phenyl)-acrylamide;

N-(5-(4-(5-methyl-1H-indol-1-yl)-pyrimidin-2-ylamino)-2-((2-dimethylamino-ethyl)-methyl-amino)-4-methoxyl-phenyl)-acrylamide;

N-(5-(4-(5-methoxyl-1H-indol-1-yl)-pyrimidin-2-ylamino)-2-((2-dimethylamino-ethyl)-methyl-amino)-4-methoxyl-phenyl)-acrylamide;

2-((2-acrylamido-5-methoxyl-4-(4-(5-methoxyl-1H-indol-1-yl)-pyrimidin-2-yl)-amino)-phenyl)-methyl-N,N-dimethyl-N-ethylamine oxide;

N-(5-(4-(5-chloro-H-indol-1-yl)-pyrimidin-2-ylamino)-2-((2-dimethylamino-ethyl)-methyl-amino)-4-methoxyl-phenyl)-acrylamide;

N-(5-(4-(5-bromo-H-indol-1-yl)-pyrimidin-2-ylamino)-2-((2-dimethylamino-ethyl)-methyl-amino)-4-methoxyl-phenyl)-acrylamide;

N-(5-(4-(5-trifluoromethyl-1H-indol-1-yl)-pyrimidin-2-ylamino)-2-((2-dimethylamino-ethyl)-methyl-amino)-4-methoxyl-phenyl)-acrylamide;

N-(5-(4-(5-fluoro-1H-indol-1-yl)-pyrimidin-2-ylamino)-2-((2-(dimethylamino-ethyl-methyl-amino)-4-methoxyl-phenyl)-acrylamide;

N-(5-(4-(5-fluoro-1H-indol-1-yl)-pyrimidin-2-ylamino)-2-(4-acetyl-piperazin-1-yl)-4-m ethoxyl-phenyl)-acrylamide;

N-(5-(4-(5-fluoro-1H-indol-1-yl-)-pyrimidin-2-ylamino)-2-(4-(piperidin-4-yl)-piperidin-1-yl)-4-methoxyl-phenyl)-acrylamide;

N-(5-(4-(5-fluoro-1H-indol-1-yl)-pyrimidin-2-ylamino)-2-(4-(cyclohexylmethyl)-piperidin-1-yl)-4-methoxyl-phenyl)-acrylamide;

N-(5-(4-(5-fluoro-1H-indol-1-yl)-pyrimidin-2-ylamino)-2-(4-methyl-[1,4]diazepin-1-yl)-4-methoxyl-phenyl)-acrylamide;

N-(5-(4-(5-fluoro-1H-indol-1-yl)-pyrimidin-2-ylamino)-2-(4-(dimethylaminomethyl)-piperidin-1-yl)-4-methoxyl-phenyl)-acrylamide;

N-(5-(4-(5-fluoro-1H-indol-1-yl)-pyrimidin-2-ylamino)-2-(4-(morpholin-4-yl)-piperidin-1-yl)-4-methoxyl-phenyl)-acrylamide;

N-(5-(4-(5-fluoro-1H-indol-1-yl)-pyrimidin-2-ylamino)-2-(4-(4-methylpiperazin-1-yl)-piperidin-1-yl)-4-methoxyl-phenyl)-acrylamide;

N-(5-(4-(5-fluoro-1H-indol-1-yl)-pyrimidin-2-ylamino)-2-(4-methyl-piperazin-1-yl)-4-methoxyl-phenyl)-acrylamide;

N-(5-(4-(5-fluoro-1H-indol-1-yl)-pyrimidin-2-ylamino)-2-(4-(1-methylpiperidin-4-yl)-piperazin-1-yl)-4-methoxyl-phenyl)-acrylamide;

N-(5-(4-(5-fluoro-1H-indol-1-yl)-pyrimidin-2-ylamino)-2-(4-(2-hydroxyl-ethyl)-piperazin-1-yl)-4-methoxyl-phenyl)-acrylamide;

N-(5-(4-(5-fluoro-1H-indol-1-yl)-pyrimidin-2-ylamino)-2-(4-(2-(2-hydroxyethoxyl)-ethyl)-piperazin-1-yl)-4-methoxyl-phenyl)-acrylamide;

N-(5-(4-(5-fluoro-1H-indol-1-yl)-pyrimidin-2-ylamino)-2-(dimethylamino)-4-methoxyl-phenyl)-acrylamide;

N-(5-(4-(5-fluoro-1H-indol-1-yl)-pyrimidin-2-ylamino)-2-(2-(morpholin-4-yl)-ethoxyl)-4-methoxyl-phenyl)-acrylamide;

N-(5-(4-(5-fluoro-1H-indol-1-yl)-pyrimidin-2-ylamino)-2-(2-pyrrolidin-1-yl)-ethoxyl)-4-methoxyl-phenyl)-acrylamide;

N-(5-(4-(4-methyl-1H-indol-1-yl)-pyrimidin-2-ylamino)-2-(2-(dimethylamino-ethyl)-methyl-amino)-4-methoxyl-phenyl)-acrylamide;

N-(5-(4-(4-methoxyl-1H-indol-1-yl)-pyrimidin-2-ylamino)-2-(2-(dimethylamino-ethyl)-methyl-amino)-4-methoxyl-phenyl)-acrylamide;

N-(5-(4-(4-cyano-1H-indol-1-yl)-pyrimidin-2-ylamino)-2-(2-(dimethylamino-ethyl)-methyl-amino)-4-methoxyl-phenyl)-acrylamide;

N-(5-(4-(4-chloro-1H-indol-1-yl)-pyrimidin-2-ylamino)-2-(2-(dimethylamino-ethyl)-methyl-amino)-4-methoxyl-phenyl)-acrylamide;

N-(5-(4-(4-fluoro-1H-indol-1-yl)-pyrimidin-2-ylamino)-2-(2-(dimethylamino-ethyl)-methyl-amino)-4-methoxyl-phenyl)-acrylamide;

N-(5-(4-(5,6-difluoro-1H-indol-1-yl)-pyrimidin-2-ylamino)-2-(2-(dimethylamino-ethyl)-methyl-amino)-4-methoxyl-phenyl)-acrylamide;

N-(5-(4-(5-fluoro-6-chloro-1H-indol-1-yl)-pyrimidin-2-ylamino)-2-(2-(dimethylamino-ethyl)-methyl-amino)-4-methoxyl-phenyl)-acrylamide;

N-{5-[4-(6-chloro-5-fluoro-indol-1-yl)-pyrimidin-2-ylamino]-2-[(2-(dimethylamino-ethyl)-methyl-amino]-4-propoxyl-phenyl}-acrylamide;

N-(5-(4-benzotriazol-1-yl-pyrimidin-2-ylamino)-2-((2-dimethylamino-ethyl)-methyl-amino)-4-methoxyl-phenyl)-acrylamide;

N-(5-(4-(3-chloro-phenylamino)-[1,3,5]triazin-2-ylamino)-2-((2-dimethylamino-ethyl)-methyl-amino)-4-methoxyl-phenyl)-acrylamide;

N-(5-(4-(3-chloro-4-fluoro-phenylamino)-[1,3,5]triazin-2-ylamino)-2-((2-dimethylamino-ethyl)-methyl-amino)-4-methoxyl-phenyl)-acrylamide;

N-(5-(4-(3-chloro-2-fluoro-phenylamino)-[1,3,5]triazin-2-ylamino)-2-((2-dimethylamino-ethyl)-methyl-amino)-4-methoxyl-phenyl)-acrylamide;

N-(5-(4-(3-chloro-4-(pyridin-2-ylmethoxy)-phenylamino)-[1,3,5]triazin-2-ylamino)-2-((2-dimethylamino-ethyl)-methyl-amino)-4-methoxyl-phenyl)-acrylamide;

N-(5-(4-(3-chloro-4-(3-fluorophenylmethoxy)-phenylamino)-[1,3,5]triazin-2-ylamino)-2-((2-dimethylamino-ethyl)-methyl-amino)-4-methoxyl-phenyl)-acrylamide;

N-(5-(4-(3-trifluoromethyl-phenylamino)-[1,3,5]triazin-2-ylamino)-2-((2-dimethylamino-ethyl)-methyl-amino)-4-methoxyl-phenyl)-acrylamide;

N-(5-(4-(3-fluoro-phenylamino)-[1,3,5]triazin-2-ylamino)-2-((2-dimethylamino-ethyl)-methyl-amino)-4-methoxyl-phenyl)-acrylamide;

N-(5-(4-(3-bromo-phenylamino)-[1,3,5]triazin-2-ylamino)-2-((2-dimethylamino-ethyl)-methyl-amino)-4-methoxyl-phenyl)-acrylamide;

N-[5-[4-(3-bromo-phenylamino)-[1,3,5]triazin-2-yl amino]-2-(3-dimethylamino-pyrrolidin-1-yl)-4-methoxyl-phenyl]-acrylamide;

N-[5-[4-(3-bromo-phenylamino)-[1,3,5]triazin-2-amino]-2-(4-dimethylamino-piperidin-1-yl)-4-methoxyl-phenyl]-acrylamide;

N-[5-[4-(3-bromo-phenylamino)-[1,3,5]triazin-2-amino]-4-methoxyl-2-(4-(pyrrolidin-1-yl-piperidin-1-yl)-phenyl]-acrylamide;

N-{2-[1,4']-piperidinylpiperidin-1'-yl-5-[4-(3-bromo-phenylamino)-[1,3,5]triazin-2-amino]-4-methoxyl-phenyl}-acrylamide;

N-(5-(4-(3-bromo-phenylamino)-[1,3,5]triazin-2-ylamino)-4-methoxyl-2-(4-(4-methyl-piperazin-1-yl)-piperidin-1-yl)-phenyl)-acrylamide;

N-(5-(4-(3-bromo-phenylamino)-[1,3,5]triazin-2-ylamino)-2-(4-ethyl-piperazin-1-yl)-4-methoxyl-phenyl)-acrylamide;

N-(5-(4-(3-bromo-phenylamino)-[1,3,5]triazin-2-ylamino)-2-(4-tert-butyl-piperazin-1-yl)-4-methoxyl-phenylamino)-acrylamide;

N-(5-(4-(3-bromo-phenylamino)-[1,3,5]triazin-2-yl amino)-2-(4-(3-dimethylamino-prop yl)-piperazin-1-yl)-4-methoxyl-phenyl)-acrylamide;

N-(5-(4-(3-bromo-phenylamino)-[1,3,5]triazin-2-ylamino)-4-methoxyl-2-(4-(1-methylpiperidin-4-yl)-piperazin-1-yl)-phenyl)-acrylamide;

N-{5-[4-(3-bromo-phenyl amino)-[1,3,5]triazin-2-yl amino]-2-[4-(2-cyano-ethyl)-piperazin-1-yl]-4-methoxyl-phenyl}-acrylamide;

N-{5-[4-(3-bromo-phenylamino)-[1,3,5]triazin-2-yl amino]-2-[4-(2-hydroxyl-ethyl)-piperazin-1-yl]-4-methoxyl-phenyl}-acrylamide;

N-{5-[4-(3-bromo-phenylamino)-[1,3,5]triazin-2-ylamino)-4-methoxyl-2-(4-(2-methoxyl-ethyl)-piperazin-1-yl)-phenyl]-acrylamide;

N-(5-(4-(3-bromo-phenylamino)-[1,3,5]triazin-2-ylamino)-2-(4-cyclohexyl-methyl-piperazin-1-yl)-4-methoxyl-phenyl)-acrylamide;

N-(2-(4-acetyl-piperazin-1-yl)-5-(4-(3-bromo-phenylamino)-[1,3,5]triazin-2-ylamino)-4-methoxyl-phenyl)-acrylamide;

N-(5-(4-(3-bromo-phenylamino)-[1,3,5]triazin-2-ylamino)-4-methoxyl-2-(4-methyl-[1,4]diazepan-1-yl)-phenyl)-acrylamide;

N-[5-[4-(3-bromo-phenylamino)-[1,3,5]triazin-2-ylamino]-4-methoxyl-2-(2-morpholin-4-yl-ethoxyl)-phenyl]-acrylamide;

N-[5-[4-(3-bromo-phenylamino)-[1,3,5]triazin-2-ylamino]-4-methoxyl-2-(2-methoxyl-ethoxyl)-phenyl]-acrylamide;

N-(5-(6-(3-bromo-phenylamino)-pyrimidin-4-ylamino)-2-((2-dimethylamino-ethyl)-methyl-amino)-4-methoxyl-phenyl)-acrylamide;

N-(2-((2-dimethylamino)-ethyl)-methyl-amino)-4-methoxyl-5-(6-(3-trifluoromethyl-phenylamino)-pyrimidin-4-ylamino)-phenyl)-acrylamide;

N-(5-(6-(3-alkynyl-phenylamino)-pyrimidin-4-ylamino)-2-((2-dimethylamino-ethyl)-methyl-amino)-4-methoxyl-phenyl)-acrylamide;

N-(5-(6-(2,4-dichloro-5-methoxyl-phenylamino)-pyrimidin-4-ylamino)-2-((2-dimethylamino-ethyl)-methyl-amino)-4-methoxyl-phenyl)-acrylamide;

N-(5-(6-(2-fluoro-3,4-dichloro-phenylamino)-pyrimidin-4-ylamino)-2-((2-dimethylamino-ethyl)-methyl-amino)-4-methoxyl-phenyl)-acrylamide;

N-(5-(6-(2-fluoro-3-chloro-phenylamino)-pyrimidin-4-ylamino)-2-((2-dimethylamino-ethyl)-methyl-amino)-4-methoxyl-phenyl)-acrylamide;

N-(5-(6-(3-bromo-5-fluoro-phenylamino)-pyrimidin-4-ylamino)-2-((2-dimethylamino-ethyl)-methyl-amino)-4-methoxyl-phenyl)-acrylamide;

N-(5-(6-(3-chloro-4-fluoro-phenylamino)-pyrimidin-4-ylamino)-2-((2-dimethylamino-ethyl)-methyl-amino)-4-methoxyl-phenyl)-acrylamide;

N-(5-(6-(3-chloro-4-fluoro-phenyl amino)-2-methyl-pyrimidin-4-ylamino)-2-((2-dimethylamino-ethyl)-methyl-amino)-4-methoxyl-phenyl)-acrylamide;

N-(5-(6-(3-chloro-4-fluoro-phenylamino)-pyrimidin-4-ylamino)-2-[piperidin-1-yl]-4-methoxyl-phenyl)-acrylamide;

N-(5-(6-(3-chloro-4-fluoro-phenylamino)-pyrimidin-4-ylamino)-4-methoxyl-2-(4-morpholin-4-yl-piperidin-1-yl)-phenyl)-acrylamide;

N-(5-(6-(3-chloro-4-fluoro-phenylamino)-pyrimidin-4-ylamino)-2-(4-methyl-[1,4]diazepin-1-yl)-4-methoxyl-phenyl)-acrylamide;

N-(5-(6-(3-chloro-4-fluoro-phenylamino)-pyrimidin-4-ylamino)-4-methoxyl-2-(4-meth yl-piperazin-1-yl)-phenyl)-acrylamide;

N-(2-(4-acetyl-piperazin-1-yl)-5-(6-(3-chloro-4-fluoro-phenylamino)-pyrimidin-4-ylamino)-4-methoxyl-phenyl)-acrylamide;

N-(5-(6-(3-chloro-4-fluoro-phenylamino)-pyrimidin-4-ylamino)-4-methoxyl-2-(4-(-methylpiperidin-4-yl)-piperazin-1-yl)-phenyl)-acrylamide;

N-(5-(6-(3-chloro-4-fluoro-phenylamino)-pyrimidin-4-ylamino)-2-(2-dimethylamino-ethoxyl)-4-methoxyl-phenyl)-acrylamide;

N-(5-(6-(3-chloro-4-fluoro-phenylamino)-pyrimidin-4-ylamino)-4-methoxyl-2-(2-pyrrolidin-1-yl-ethoxyl)-phenyl)-acrylamide;

N-(5-(6-(3-chloro-4-fluoro-phenylamino)-pyrimidin-4-ylamino)-2-(2-(4-methyl-piperazin-1yl)-ethoxyl)-4-methoxyl-phenyl)-acrylamide;

N-(5-(6-(3-chloro-4-fluoro-phenylamino)-pyrimidin-4-ylamino)-4-methoxyl-2-(2-morpholin-4-yl-ethoxyl)-phenyl)-acrylamide;

N-(5-(6-(3-chloro-4-fluoro-phenylamino)-pyrimidin-4-ylamino)-2-(2-methoxylethoxyl)-4-methoxyl-phenyl)-acrylamide;

N-(5-(6-(3-chloro-4-(3-fluoro-benzyloxy)-phenylamino)-pyrimidin-4-ylamino)-2-((2-dimethylamino-ethyl)-methyl-amino)-4-methoxyl-phenyl)-acrylamide;

N-(5-(6-(3-chloro-4-(pyridin-2-ylmethoxy)-phenylamino)-pyrimidin-4-ylamino)-2-((2-dimethylamino-ethyl)-methyl-amino)-4-methoxyl-phenyl)-acrylamide;

N-(5-(6-benzimidazol-1-yl-pyrimidin-4-ylamino)-2-((2-dimethylamino-ethyl)-methyl-amino)-4-methoxyl-phenyl)-acrylamide;

N-(5-(6-benzotriazol-1-yl-pyrimidin-4-ylamino)-2-((2-dimethylamino-ethyl-methyl-amino)-4-methoxyl-phenyl)-acrylamide;

N-(4-methoxyl-5-(6-(1-methyl-1H-indol-3-yl)-pyrimidin-4-ylamino)-2-(4-methylpiperazin-1-yl)-phenyl)-acrylamide;

N-(2-(4-ethyl-piperazin-1-yl)-4-methoxyl-5-(6-(1-methyl-1H-indol-3-yl)-pyrimidin-4-ylamino)-phenyl)-acrylamide;

N-(2-(4-tert-butyl-piperazin-1-yl)-4-methoxyl-5-(6-(1-methyl-1H-indol-3-yl)-pyrimidin-4-ylamino)-phenyl)-acrylamide;

N-(4-methoxyl-5-(6-(1-methyl-1H-indol-3-yl)-pyrimidin-4-ylamino)-2-(4-(1-methylpiperidin-4-yl)-piperazin-1-yl)-phenyl)-acrylamide;

N-(2-(4-(2-hydroxyl-ethyl)-piperazin-1-yl)-4-methoxyl-5-(6-(1-methyl-1H-indol-3-yl)-pyrimidin-4-ylamino)-phenyl)-acrylamide;

N-(4-methoxyl-2-(4-(2-methoxyl-ethyl)-piperazin-1-yl)-5-(6-(1-methyl-1H-indol-3-yl)-pyrimidin-4-ylamino)-phenyl)-acrylamide;

N-(2-(4-(2-(2-hydroxyl-ethoxyl)-ethyl)-piperazin-1-yl)-4-methoxyl-5-(6-(1-methyl-1H-indol-3-yl)-pyrimidin-4-ylamino)-phenyl)-acrylamide;

N-(4-methoxyl-5-(6-(1-methyl-1H-indol-3-yl)-pyrimidin-4-ylamino)-2-(4-(2-(pyrrolidin-1-yl)-ethyl)-piperazin-1-yl)-phenyl)-acrylamide;

N-(2-(4-(2-(dimethylamino)-ethyl)-piperazin-1-yl)-4-methoxyl-5-(6-(1-methyl-1H-indol-3-yl)-pyrimidin-4-ylamino)-phenyl)-acrylamide;

N-(2-(4-acetylpiperazin-1-yl)-4-methoxyl-5-(6-(1-methyl-1H-indol-3-yl)-pyrimidin-4-yl amino)-phenyl)-acrylamide;

N-(4-methoxyl-5-(6-(1-methyl-1H-indol-3-yl)-pyrimidin-4-ylamino)-2-(4-phenylpiperazin-1-yl)-phenyl)-acrylamide;

N-(2-(4-benzylpiperazin-1-yl)-4-methoxyl-5-(6-(1-methyl-1H-indol-3-yl)-pyrimidin-4-ylamino)-phenyl)-acrylamide;

N-(4-methoxyl-5-(6-(1-methyl-1H-indol-3-yl)-pyrimidin-4-ylamino)-2-(4-(-(pyrimidin-3-ylmethyl)-piperazin-1-yl)-phenyl)-acrylamide;

N-(4-methoxyl-5-(6-(1-methyl-1H-indol-3-yl)-pyrimidin-4-ylamino)-2-(4-methyl-2-phenylpiperazin-1-yl)-phenyl)-acrylamide;

N-(2-(4-(bis-(4fluoro-phenyl)-methyl)-piperazin-1-yl)-4-methoxyl-5-(6-(1-methyl-1H-indol-3-yl)-pyrimidin-4-ylamino)-phenyl)-acrylamide;

N-(4-methoxyl-2-(4-methyl-[1,4]diazepin-1-yl)-5-(6-(1-methyl-1H-indol-3-yl)-pyrimidin-4-ylamino)-phenyl)-acrylamide;

(S)—N-(2-(3-dimethylamino-pyrrolidin-1-yl)-4-methoxyl-5-(6-(1-methyl-1H-indol-3-yl)-pyrimidin-4-ylamino)-phenyl)-acrylamide;

N-(2-(4-dimethyl amino-piperidin-1-yl)-4-methoxyl-5-(6-(1-methyl-1H-indol-3-yl)-pyrimidin-4-ylamino)-phenyl)-acrylamide;

N-(4-methoxyl-5-(6-(1-methyl-1H-indol-3-yl)-pyrimidin-4-ylamino)-2-(4-(4-methylpiperazin-1-yl)-piperidin-1-yl)-phenyl)-acrylamide;

N-(2-(4-(morpholin-4-yl)piperidin-1-yl)-4-methoxyl-5-(6-(1-methyl-1H-indol-3-yl)-pyrimidin-4-ylamino)-phenyl)-acrylamide;

N-(4-methoxyl-5-(6-(1-methyl-1H-indol-3-yl)-pyrimidin-4-ylamino)-2-(methyl-(2-pyrrolidin-1-yl-ethyl)-amino)-phenyl)-acrylamide;

N-(5-(6-(1-methyl-1H-indol-3-yl)-pyrimidin-2-ylamino)-2-((2-(dimethylamino)-ethyl-methyl-amino)-4-methoxyl-phenyl)-acrylamide;

N-{2-[(2-dimethylamino-ethyl)-methyl-amino]-5-[6-(1-methyl-1H-indol-3-yl)-pyrimidin-4-yl amino]-4-propyl-phenyl}-acrylamide;

N-{2-((2-dimethylamino-ethyl)-methylamino)-5-[6-(1-ethyl-1H-indol-3-yl)-pyrimidin-4-ylamino]-4-methoxyl-phenyl}-acryl amide;

N-{2-[(2-dimethylamino-ethyl)-methylamino]-5-[6-(1-propyl-1H-indol-3-yl)-pyrimidin-4-yl amino]-4-methoxyl-phenyl}-acrylamide;

N-{2-[(2-dimethylamino-ethyl)-methylamino]-5-[6-(1-isopropyl-1H-indol-3-yl)-pyrimidin-4-yl amino]-4-methoxyl-phenyl}-acrylamide;

N-{2-[(2-dimethylamino-ethyl)-methylamino]-5-[6-(1-isopropyl-1H-indol-3-yl)-pyrimidin-4-yl amino]-4-propoxyl-phenyl}-acrylamide;

N-(5-(6-(1-benzyl-1H-indol-3-yl)-pyrimidin-4-ylamino)-2-((2-dimethylamino-ethyl)-methyl-amino)-4-methoxyl-phenyl)-acrylamide;

N-(4-methoxyl-5-(6-(6-fluoro-1-methyl-1H-indol-3-yl)-pyrimidin-4-ylamino)-2-(2-(dimethylamino-ethyl)-methyl-amino)-phenyl)-acrylamide;

N-(2-((2-dimethylamino-ethyl)-methyl-amino)-5-(4-(5-fluoro-indol-1-yl)-pyrimidin-2-ylamino)-4-propyl-phenyl)-acrylamide;

N-(2-((2-dimethylamino-ethyl)-methylamino)-5-(6-(5-fluoro-1-methyl-1H-indol-3-yl)-pyrimidin-4-ylamino)-4-methoxyl-phenyl)-acrylamide;

N-(5-[6-(5-fluoro-1-isopropyl-1H-indol-3-yl)-pyrimidin-4-ylamino)-2-{[2-(1-oxy-pyrrolidin-1-yl)-ethyl]-methyl-amino}-4-methoxyl-phenyl)- acrylamide;

N-(5-(6-(5-fluoro-1-isopropyl-1H-indol-3-yl)-pyrimidin-4-ylamino)-4-methoxy-2-(4-(4-methyl-piperazin-1-yl)-piperidin-1-yl)-phenyl)-acrylamide;

N-(5-(6-(5-fluoro-1-isopropyl-1H-indol-3-yl)-pyrimidin-4-ylamino)-4-methoxyl-2-((2-dimethylamino-ethyl)-methyl-amino)-phenyl)-acrylamide;

2-((2-acrylamido-5-methoxyl-4-((6-(1-isopropyl-5-fluoro-1H-indol-3-yl)-pyrimidin-4-yl)-amino)-phenyl)-methyl)-N,N-dimethyl-N-ethylamine oxide;

N-(5-(6-(5-fluoro-1-cyclopentyl-1H-indol-3-yl)-pyrimidin-4-ylamino)-4-methoxyl-2-((2-dimethylamino-ethyl)-methylamino)-phenyl)-acrylamide;

N-(2-((2-(dimethylamino)-ethyl)-methylamino)-4-methoxyl-5-(2-methyl-6-(1-methyl-1H-indol-3-yl)-pyrimidin-4-yl-amino)-phenyl)-acrylamide;

N-(5-(5-methyl-6-(1-methyl-1H-indol-3-yl)-pyrimidin-4-ylamino)-4-methoxyl-2-((2-dimethylamino-ethyl)-methyl-amino)-phenyl)-acrylamide;

N-(4-methoxyl-2-(2-methoxyl-ethoxyl)-5-(6-(1-methyl-1H-indol-3-yl)-pyrimidin-4-ylamino)-phenyl)-acrylamide;

N-(5-(6-(1-methyl-H-indol-3-yl)-pyrimidin-4-ylamino)-4-methoxy-2-(2-(4-methylpiperazin-1-yl)-ethoxyl)-phenyl)-acrylamide;

N-(5-(6-(1-methyl-1H-indol-3-yl)-pyrimidin-4-ylamino)-4-methoxy-2-(2-(morpholin-4-yl)-ethoxyl)-phenyl)-acrylamide;

N-(5-(6-(1-methyl-1H-indol-3-yl)-pyrimidin-4-ylamino)-4-methoxy-2-(2-(pyrrolidin-1-yl)-ethoxyl)-phenyl)-acrylamide;

N-(5-(4-((3-chloro-4-(pyridin-2-methoxyl)phenyl)-methyl-amino)-pyrimidin-2-ylamino)-2-((2-(dimethylamino) ethyl)(methyl)amino)-4-methoxyl-phenyl)-acrylamide;

N-(5-(5-chloro-4-(3-chloro-4-(pyridin-2-methoxyl)phenoxyl)pyrimidin-2-ylamino)-2-((2-(dimethylamino) ethyl)(methyl)amino)-4-methoxyl-phenyl)-acrylamide;

N-(5-(4-(4-methoxyl-1H-indol-1-yl)-5-trifluoromethyl-pyrimidin-2-ylamino)-2-(2-(dimethylamino-ethyl)-methyl-amino)-4-methoxyl-phenyl)-acrylamide;

N-(5-(4-(4-methoxyl-1H-indol-1-yl)-5-chloro-pyrimidin-2-ylamino)-2-(2-(dimethylamino-ethyl)-methyl-amino)-4-methoxyl-phenyl)-acrylamide;

N-(5-(4-(4-hydroxyl-1H-indol-1-yl)-5-chloro-pyrimidin-2-ylamino)-2-(2-(dimethylamino-ethyl)-methyl-amino)-4-methoxyl-phenyl)-acrylamide;

N-(5-(4-(4-(2-methoxyl-ethoxyl)-1H-indol-1-yl)-pyrimidin-2-ylamino)-2-(2-(dimethylamino-ethyl)-methyl-amino)-4-methoxyl-phenyl)-acrylamide;

N-(5-(4-(4-n-hexyloxy-1H-indol-1-yl)-pyrimidin-2-ylamino)-2-(2-(dimethylamino-ethyl)-methyl-amino)-4-methoxyl-phenyl)-acrylamide;

N-(5-(4-(5-(2-methoxyl-ethoxyl)-1H-indol-1-yl)-pyrimidin-2-ylamino)-2-(2-(dimethylamino-ethyl)-methyl-amino)-4-methoxyl-phenyl)-acrylamide;

N-(5-(4-(4-methoxyl-1H-indol-1-yl)-pyrimidin-2-ylamino)-2-(4-(4-methyl-piperazin-1-yl)-piperidin-1-yl)-4-methoxyl-phenyl)-acrylamide;

N-(5-(4-(6-(2-methoxyl-ethoxyl)-1H-indol-1-yl)-pyrimidin-2-ylamino)-2-(2-(dimethylamino-ethyl)-methyl-amino)-4-methoxyl-phenyl)-acrylamide;

N-(5-(4-(4-((tetrahydrofuran-2-yl)-methoxyl)-1H-indol-1-yl)-pyrimidin-2-ylamino)-2-(2-(dimethylamino-ethyl)-methyl-amino)-4-methoxyl-phenyl)-acrylamide;

N-(5-(4-(4-methoxyl-6-bromo-H-indol-1-yl)-pyrimidin-2-ylamino)-2-(2-(dimethylamino-ethyl)-methyl-amino)-4-methoxyl-phenyl)-acrylamide;

N-(5-(4-(4-methoxyl-6-fluoro-1H-indol-1-yl)-pyrimidin-2-ylamino)-2-(2-(dimethylamino-ethyl)-methyl-amino)-4-methoxyl-phenyl)-acrylamide;

N-(5-(4-(4-methoxyl-6-chloro-H-indol-1-yl)-pyrimidin-2-ylamino)-2-(2-(dimethylamino-ethyl)-methyl-amino)-4-methoxyl-phenyl)-acrylamide;
N-(5-(4-(4-(2,5-dimethylpyrrol-1-yl)-6-bromo-1H-indol-1-yl)-pyrimidin-2-ylamino)-2-(2-(dimethylamino-ethyl)-methyl-amino)-4-methoxyl-phenyl)-acrylamide;
N-(5-(6-(3-chloro-4-(2-morpholin-4-yl-ethoxy)-phenylamino)-pyrimidin-4-ylamino)-2-((2-dimethylamino-ethyl)-methyl-amino)-4-methoxyphenyl)-acrylamide;
N-(5-(6-(3-chloro-4-(tetrahydropyran-4-yl-methoxyl)-phenylamino)-pyrimidin-4-ylamino)-2-((2-dimethylamino-ethyl)-methyl-amino)-4-methoxyphenyl)-acrylamide;
N-(5-(6-(3-(1-(3-methylbutoxy)ethyl)-4-methoxylphenylamino)-pyrimidin-4-ylamino)-2-((2-dimethylamino-ethyl)-methyl-amino)-4-methoxylphenylamino)-acrylamide;
N-(5-(6-(3-chloro-4-methoxyl-phenylamino)-pyrimidin-4-ylamino)-2-(2-dimethylamino-ethoxyl)-4-methoxyl-phenyl)-acrylamide;
N-(5-(6-(3-chloro-4-(3-methylbutoxy)-phenylamino)-pyrimidin-4-ylamino)-2-((2-dimethylaminoethyl)-methyl-amino)-4-methoxyphenyl)-acrylamide;
5-(6-(5-acrylamido-4-((2-methoxyphenyl)-methyl-amino)-2-methoxylphenylamino)-pyrimidin-4-yl)-2-methoxy-benzamide;
5-(6-(5-acrylamido-4-((2-methoxyphenyl)-methyl-amino)-2-methoxylphenylamino)-pyrimidin-4-yl)-2-methoxyl-N-methylbenzamide;
N-(5-(6-(4-methoxyl-3-trifluoromethyl-phenylamino)-pyrimidin-4-yl-amino)-2-((2-dimethylamino-ethyl)-methyl-amino)-4-methoxyl-phenyl)-acrylamide;
N-(5-(6-(3-chloro-4-(thiazol-2-ylmethoxy)-phenylamino)-pyrimidin-4-ylamino)-2-((2-dimethylamino-ethyl)-methyl-amino)-4-methoxyl-phenyl)-acrylamide;
N-(5-(6-(4-methoxyl-3-bromo-phenylamino)-pyrimidin-4-yl-amino)-2-((2-dimethylamino-ethyl)-methyl-amino)-4-methoxyl-phenyl)-acrylamide;
N-(5-(6-(4-methoxyl-3-chloro-phenylamino)-pyrimidin-4-yl-amino)-2-(2-(pyrrolidin-1-yl)-ethoxyl)-4-methoxyl-phenyl)-acrylamide;
N-(5-(6-(4-fluoro-3-trifluoromethyl-phenylamino)-pyrimidin-4-yl-amino)-2-((2-dimethylamino-ethyl)-methyl-amino)-4-methoxyl-phenyl)-acrylamide;
N-(5-(6-(3-chloro-4-methoxyl-phenylamino)-pyrimidin-4-ylamino)-2-(4-(1-methylpiperidin-4-yl)-piperazin-1-yl)-4-methoxyl-phenyl)-acrylamide;
N-(5-(6-(4-chloro-3-trifluoromethyl-phenylamino)-pyrimidin-4-yl-amino)-2-((2-dimeth ylamino-ethyl)-methyl-amino)-4-methoxyl-phenyl)-acrylamide;
N-(5-(6-(3-cyano-phenylamino)-pyrimidin-4-yl-amino)-2-((2-dimethylamino-ethyl)-methyl-amino)-4-methoxyl-phenyl)-acrylamide;
N-(5-(6-(5-fluoro-3-trifluoromethyl-phenylamino)-pyrimidin-4-yl-amino)-2-((2-dimeth ylamino-ethyl)-methyl-amino)-4-methoxyl-phenyl)-acrylamide;
N-(5-(6-(2-fluoro-5-trifluoromethyl-phenylamino)-pyrimidin-4-yl-amino)-2-((2-dimethylamino-ethyl)-methyl-amino)-4-methoxyl-phenyl)-acrylamide;
N-(5-(6-(3-methoxyl-5-trifluoromethyl-phenylamino)-pyrimidin-4-yl-amino)-2-((2-dimethylamino-ethyl)-methyl-amino)-4-methoxyl-phenyl)-acrylamide;
N-(5-(6-(2-methoxyl-5-trifluoromethyl-phenylamino)-pyrimidin-4-yl-amino)-2-((2-dimethylamino-ethyl)-methyl-amino)-4-methoxyl-phenyl)-acrylamide;
N-(5-(6-(3-chloro-4-trifluoromethyl-phenylamino)-pyrimidin-4-yl-amino)-2-((2-dimethylamino-ethyl)-methyl-amino)-4-methoxyl-phenyl)-acrylamide;
N-(5-(6-(3-chloro-4-trifluoromethoxy-phenylamino)-pyrimidin-4-yl-amino)-2-((2-dimethylamino-ethyl)-methyl-amino)-4-methoxyl-phenyl)-acrylamide;
N-(5-(6-(3-chloro-5-fluoro-4-(2-methoxyl-ethoxyl)-phenylamino)-pyrimidin-4-yl-amino)-2-((2-dimethylamino-ethyl)-methyl-amino)-4-methoxyl-phenyl)-acrylamide;
N-(5-(6-(3-methanesulfonamido-4-methoxyl-phenyl amino)-pyrimidin-4-yl-amino)-2-((2-dimethylamino-ethyl)-methyl-amino)-4-methoxyl-phenyl)-acrylamide;
N-(5-(6-(2,4-di chloro-5-methoxyl-phenyl amino)-pyrimidin-4-yl-amino)-2-(4-methyl-piperazin-1-yl)-4-methoxyl-phenyl)-acrylamide;
N-(5-(6-(2,4-dichloro-5-methoxyl-phenylamino)-pyrimidin-4-yl-amino)-2-(4-(morpholin-1-yl)-piperidin-1-yl)-4-methoxyl-phenyl)-acrylamide;
N-(5-(6-(2,4-dichloro-5-methoxyl-phenylamino)-pyrimidin-4-yl-amino)-2-(methyl-(2-(4-methyl-piperazin-1-yl)-2-oxoethyl)-amino)-4-methoxyl-phenyl)-acrylamide;
N-(5-(6-(2,4-dichloro-5-methoxyl-phenylamino)-pyrimidin-4-ylamino)-2-(2-dimethylamino-ethoxyl)-4-methoxyl-phenyl)-acrylamide;
N-(5-(6-(2,4-dichloro-5-methoxyl-phenylamino)-pyrimidin-4-yl-amino)-2-(2-(morpholin-4-yl)-ethoxyl-4-methoxyl-phenyl)-acrylamide;
N-(5-(6-(2,4-dichloro-5-methoxyl-phenylamino)-pyrimidin-4-yl-amino)-2-(2-(pyrrolidin-1-yl)-ethoxyl)-4-methoxyl-phenyl)-acrylamide;
N-(5-(6-(2,4-dichloro-5-methoxyl-phenylamino)-pyrimidin-4-yl-amino)-2-(2-(4-methyl-piperazin-1-yl)-ethoxyl)-4-methoxyl-phenyl)-acrylamide;
N-(5-(6-(2,4-dichloro-5-methoxyl-phenylamino)-pyrimidin-4-yl-amino)-2-(3-(pyrrolidin-1-yl)-propyl)-4-methoxyl-phenyl)-acrylamide;
N-(5-(6-(2,4-di chloro-5-methoxyl-phenyl amino)-pyrimidin-4-yl-amino)-2-(2-(piperidin-1-yl)-ethoxyl-4-methoxyl-phenyl)-acrylamide;
N-(5-(6-(2,4-dichloro-5-methoxyl-phenylamino)-pyrimidin-4-yl-amino)-2-(3-(4-methyl-piperazin-1-yl)-propyl)-4-methoxyl-phenyl)-acrylamide;
N-(5-(6-((2,4-dichloro-5-methoxyl-phenyl)-methyl-amino)-pyrimidin-4-ylamino)-2-((2-dimethylamino-ethyl)-methyl-amino)-4-methoxyl-phenyl)-acrylamide;
N-(5-(6-(2,4-dichloro-5-methoxyl-phenylamino)-pyrimidin-4-yl-amino)-2-(3-(morpholin-4-yl)-propoxyl-4-methoxyl-phenyl)-acrylamide;
N-(5-(6-(3-chloro-4-tert-butoxy-phenylamino)-pyrimidin-4-yl-amino)-2-((2-dimethylamino-ethyl)-methyl-amino)-4-methoxyl-phenyl)-acrylamide;
N-(5-(6-(3-acetenyl-4-methoxyl-phenylamino)-pyrimidin-4-yl-amino)-2-((2-dimethylamino-ethyl)-methyl-amino)-4-methoxyl-phenyl)-acrylamide;
N-(5-(6-(3-chloro-4-(3-methyl-oxetan-3-yl-methoxyl)-phenylamino)-pyrimidin-4-yl-amino)-2-((2-dimethylamino-ethyl)-methyl-amino)-4-methoxyl-phenyl)-acrylamide.

[13] An EGFR PTK inhibitor comprising the compound or the pharmaceutically acceptable salts thereof described in any one of [1]~[12] as effective ingredient.

[14] A HER2/ErbB2 PTK inhibitor comprising the compound or the pharmaceutically acceptable salts thereof described in any one of [1]~[12] as effective ingredient.

[15] Use of the compound or the pharmaceutically acceptable salts thereof described in any one of [1]~[12] in preparation of EGFR and/or HER2/ErbB2 PTK inhibitors.

[16] Use of the compound or the pharmaceutically acceptable salts thereof described in any one of [1]~[12] in the preparation of medicaments for the prevention or treatment of cancers.

The EGFR PTK inhibitors according to the present invention can effectively and selectively act on EGFR mutants, including acquired resistance and sensitivity types (active type). Acquired resistance EGFR mutation is arising from EGFR T790 mutation (such as T790M), and activating mutant strain is arising from mutation of EGFR exon 19, exon 18 and exon 21 (such as exon 19 deletion, G719S mutation and L858R mutation) and other mutations (such as S761I mutation).

The HER2/ErbB2 PTK inhibitors according to the present invention can effectively and selectively act on tumor cells with HER2/ErbB2 gene amplification or high expression or activating mutations (such as G776VC or V777M mutations).

DETAILED DESCRIPTION OF THE INVENTION

Unless otherwise specified, all technical and scientific terms used herein should have the same meaning generally understood by the person skilled in the field. All patents, applications, public applications and other publications are incorporated herein by reference. If there are multiple definitions for the terms used herein, unless otherwise stated, the terms in this specification shall prevail.

"Halogen" refers to fluorine, chlorine, bromine and iodine.

"Alkyl" refers to straight-chain or branched-chain alkyls including 1 to 18 carbon atoms, preferably 1 to 10 carbon atoms, more preferably 1 to 6 carbon atoms, even more preferably 1 to 4 carbon atoms, for example, methyl, ethyl, n-propyl, isopropyl, n-butyl, isobutyl, sec-butyl, tert-butyl, n-amyl, isoamyl, neo-pentyl, hexyl, isohesyl, n-heptyl, isoheptyl, n-octyl, isooctyl, n-nonyl, n-decyl and the like. In context of the present invention, "alkyl" also refers to cycloalkyl including 3 to 10 carbon atoms, preferably 3 to 8 carbon atoms and more preferably 4 to 6 carbon atoms, for example, cyclopropyl, cyclobutyl, cyclopentyl, cyclohexyl, cycloheptyl, cyclooctyl, cyclononyl, cyclodecyl, decahydronaphthaleneyl, norbornane, adamantyl and the like.

"Alkenyl" refers to straight or branched hydrocarbon chain group composed of carbon and hydrogen atoms which contains at least one double bond. It has 2-10 carbon atoms, preferably 2-6 carbon atoms, and connects to other parts of the molecule via single bond or double bond, such as ethylene, propenyl, butenyl, pentenyl, pentadienyl and hexenyl.

"Alkoxy" refers to —OR groups, wherein R refers to alkyl as defined above. Representative examples include, but are not limited to, methoxyl, ethoxyl, propoxyl, isopropoxyl, butoxyl, isobutoxy, sec-butoxy, tert-butoxy, cyclopropoxyl, cyclobutoxyl and the like.

"Alkynyl" refers to straight or branched hydrocarbon chain groups composed of carbon atoms and hydrogen atoms which contains at least one triple bond. It has 2-10 carbon atoms, preferably 2-6 carbon atoms, and connects to other parts of the molecule via single bond or triple bond, such as acetenyl, propinyl, butynyl, pentynyl and hexynyl.

"Alkylacyl" refers to R(C=O) groups, wherein R refers to alkyl as defined above. Representative examples include, but are not limited to, acetyl, propionyl, butyryl, valeryl, hexanoyl and the like.

"Aryl" refers to carbon ring system, including monocyclic, bicyclo, tricyclic and tetracyclic C6-C18 ring system, wherein at least one ring is aromatic. Aryl may be a complete aromatic group, such as phenyl, naphthyl, anthracyl and phenanthryl. Aryl may also be the combination of aromatic ring and non-aromatic ring, such as indene, fluorene and acenaphthene. Preferred aryl includes phenyl, naphthyl and the like.

"Haloalkyl" refers to alkyl as defined above with one or more hydrogen atoms replaced by halogen. Representative examples include, but not limited to, chloromethyl, trifluoromethyl, 1-chloro-2-fluoroethyl, 2,2-difluoroethyl, 2-fluoro propyl, 2-fluoro propan-2-yl, 2,2,2-trifluoroethyl, 1,1-difluoroethyl, 1,3-difluoro-2-methyl propyl, 2,2-difluorocyclopropyl, (trifluoromethyl) cyclopropyl, 4,4-difluoro cyclohexyl and 2,2,2-trifluoro-1,1-dimethyl-ethyl.

"Heterocyclyl" refers to 3-15 membered (such as 3-12 membered or 3-9 membered) heterocyclyl heterocyclyl with more than one, preferably 1 to 5 ring atoms optionally selected from O, S and N heteroatoms. Heterocyclyl may be monocyclic, bicyclo, tricyclic and tetracyclic systems. It may be fused ring or bridge ring. The N or S atoms in heterocyclyl may be optionally oxidized. The N atoms may be optionally quaternized. The heterocyclyl may be partially or fully saturated. Heterocyclic system can be connected to the main structure at any heteroatom or carbon atom to generate stable compounds. Specifically heterocyclyl includes 5-6 membered heteroaryl, such as pyrrolyl, imidazolyl, pyrazolyl, pyridinyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl; non-aromatic heterocyclic groups such as pyranyl, thiazolidinyl, pyrrolidyl, pyrrolinyl, imidazolidinyl, imidazolinyl, pyrazolidinyl, pyrazolinyl, piperidinyl, piperazinyl, morpholinyl, morpholino, thiomorpholinyl, thiomorpholino, dihydropyridinyl, tetrahydrodihydropyridinyl, tetrahydrofuranyl, tetrahydropyranyl, diazepinyl and tetrahydrodiazepinyl; bicyclo or tricyclic fused heterocyclyl such as indolyl, isoindolyl, indazolyl, dihydroindolyl, isodihydroindolyl, quinolyl, isoquinolyl, cinnolinyl, phthalazinyl, quinazolinyl, naphthyridinyl, quinoxalinyl, purinyl, pteridyl, benzopyranyl, benzimidazolyl, benzotriazolyl, benzoisoxazolyl, benzoxazolyl, benzoxadiazolyl, benzoisothiazolyl, benzothiazolyl, benzofuranyl, isobenzofuranyl, benzothienyl, benzotriazolyl, thienopyridinyl, imidazothiazolyl, benzimidazothiazolyl, pyridinopyridazinyl, quinazolinyl, quinolyl, isoquinolyl and the like; preferably pyrrolyl, furyl, imidazolyl, isoxazolyl, oxazolyl, pyrimidyl, pyridyl, thiazolyl, thienyl, morpholinyl, piperidinyl, piperazinyl, pyranyl, pyrolidinyl, indolyl, diazepinyll, benzothienyl, benzotriazolyl, benzimidazolyl and the like.

The alkyl fraction in "arylalkyl", "arylalkyloxyl", "haloarylalkyloxyl", "alkylamino", "alkylacyl" and "haloalkyl" is the same as defined above.

The aryl fraction in "aryloxy", "arylamino", "arylthio", "aryloxyl", "arylalkyl", "arylalkyloxyl", "haloarylalkyloxyl" and "haloaryl" is the same as defined above.

The heterocyclyl fraction in "heterocyclyl alkoxy" is the same as defined above, and the alkoxy fraction in it is also the same as defined above.

The "optionally substituted" in the present invention refers to not being substituted or being substituted by one or more (for example 2, 3 and 4) substituents. The substituents are selected from the group consisting of halogen, alkyl, alkenyl, alkynyl, haloalkyl, alkoxy, aryl, haloaryl, aryloxy, arylalkyl, arylalkyloxyl, heterocyclyl alkoxy, haloarylalkyloxyl, alkylamino, alkylacyl, cyano and heterocyclyl and the like. These substituents may be further substituted. For example, the alkyl selected as substituent can be optionally substituted with one or more groups selected from halogen, hydroxyl, alkoxy, alkylamino, pyrrolidinyl, phenyl, pyridinyl and halophenyl. The heterocyclyl selected as substituent can be optionally substituted with one or more groups selected from halogen, alkyl and alkoxy.

$R_1$ may be optionally substituted heterocyclyl, optionally substituted arylamino, optionally substituted arylthio or aryloxyl and the like.

$R_1$ is preferably optionally substituted indolyl, indolinyl, thienyl, indazolyl, pyrro pyridinyl, benzothienyl, benzimidazolyl or benzotriazolyl and the like, wherein the substituent is preferably halogen, alkyl, cycloalkyl, arylalkyl and cyano. $R_1$ may be, for example, indol-1-yl, indol-3-yl, 1-methyl-1H-indol-3-yl, 1-ethyl-1H-indol-3-yl, 1-propyl-1H-indol-3-yl, 1-isopropyl-1H-indol-3-yl, 1-benzyl-1H-indol-3-yl, 6-fluoro-1-methyl-1H-indol-3-yl, 5-fluoro-1-methyl-1H-indol-3-yl, 5-fluoro-1-cyclopentyl-1H-indol-3-yl, benzimidazol-1-yl or benzotriazol-1-yl and the like.

$R_1$ is preferably optionally substituted phenylamino or naphthylamino and the like, wherein the substituent is preferably halogen, alkyl, haloalkyl, alkoxy, alkynyl, aryloxy, heterocyclylalkoxy, arylalkyloxyl and haloarylalkyloxyl. $R_1$ may be, for example, phenoxylphenyl amino, methylphenylamino, halo phenylamino, methoxyphenylamino, acetenylphenylamino, trifluoromethylphenyl amino, fluorobenzyloxy phenylamino or pyridinyl methoxyphenylamino and the like, preferably halophenylamino.

$R_1$ is preferably optionally substituted phenylthio or naphthylthio and the like, wherein the substituent is preferably halogen, alkyl or alkoxy. $R_1$ may be, for example, naphthylthio, methyl phenylthio or methoxyl phenylthio and the like.

$R_1$ is preferably optionally substituted phenyloxyl or naphthyloxyl and the like, wherein the substituent is preferably halogen, alkyl or alkoxy. $R_1$ may be, for example, naphthyloxyl, methyl phenyloxyl or methoxyl phenyloxyl and the like.

$R_3$ may be optionally substituted heterocyclyl, optionally substituted alkoxy, or optionally substituted amino and the like.

$R_3$ is preferably optionally substituted piperazinyl, piperidinyl, pyrrolidinyl, diazepinyl or pyridinyl, wherein the substituent is preferably halogen, alkyl, cyano, morpholinyl, piperidinyl, alkyl piperazinyl, alkylamino, alkyl piperidinyl, hydroxyalkyl, alkoxy alkyl, hydroxyl alkoxy alkyl, pyrrolidinyl alkyl, alkylamino alkyl, alkylacyl, arylalkyl, aryl, pyridinyl alkyl or haloarylalkyl and the like. $R_3$ may be, for example, methyl piperazinyl, morpholinyl piperidinyl, methyl piperazinyl piperidinyl, dimethylamino piperidinyl, tert-butyl piperazinyl, dimethylamino pyrrolidinyl, ethyl piperazinyl, cyclohexyl methyl piperazinyl, di-piperidinyl, methyl diazepinyl, methyl piperidinyl piperazinyl, hydroxyethyl piperazineyl, methoxyl ethyl piperazinyl, hydroxyethoxyl ethyl piperazinyl, difluoro pyrrolidinyl, pyrrolidinyl piperazinyl, hydroxypropyl piperidinyl, pyridyl ethyl piperazinyl, benzodiazepine piperazinyl, pyrrolidinyl ethyl piperazinyl, cyano ethyl piperazinyl, dimethylamino ethyl piperazinyl, acetyl piperazinyl, benzyl piperazinyl, phenyl piperazinyl, pyridinyl methyl piperazinyl, 4-methyl 2-phenyl piperazinyl, bis (fluorophenyl) methyl piperazinyl and the like.

$R_3$ is preferably optionally substituted ethoxyl, propoxyl or butoxyl and the like, wherein the substituent is preferably alkyl, alkoxy, alkylamino, morpholinyl, pyrrolidinyl, alkenyl acyl or piperazinyl and the like. $R_3$ may be, for example, methoxyl ethoxyl, methyl piperazinyl ethoxyl, morpholinyl ethoxyl, pyrrolidinyl ethoxyl, acryloyl piperazinyl ethoxyl or dimethylamino ethoxyl and the like.

Preferably $R^y$ and $R^z$ in $R_3$ are each independently alkyl, haloalkyl, hydroxylalkyl, pyrrolidinyl or alkylamino and the like, wherein the N atom can be oxidized. $R_3$ may be, for example, dimethylamino, methyl(2-pyrrolidinylethyl) amino, (2-methoxyphenyl)methylamino, [2-(1-oxy-pyrrolidin-1-yl)ethyl]methylamino or methyl-N, N-dimethyl-N-oxidized ethylamino and the like.

The pharmaceutically acceptable salts of the compound of formula (I) according to the present invention may be acid addition salts or base addition salts, wherein the acid may be inorganic acid, including but not limited to hydrochloric acid, sulfuric acid, phosphoric acid and hydrobromic acid; or organic acid, including but not limited to citric acid, maleic acid, oxalic acid, formic acid, acetic acid, propionic acid, glycollic acid, benzoic acid, fumaric acid, trifluoroacetic acid, succinic acid, tartaric acid, lactic acid, glutamic acid, aspartic acid, salicylic acid, pyruvic acid, methanesulfonic acid, benzenesulfonic acid and p-benzenesulfonic acid; the base may be inorganic base, including but not limited to sodium hydroxide, potassium hydroxide, magnesium hydroxide and calcium hydroxide; or organic base, including but not limited to ammonium hydroxide, triethylamine, arginine or lysine.

The compound of formula (I) or the pharmaceutically acceptable salts thereof according to the present invention can be present in the form of solvate or non-solvate, such as hydrate form.

The prodrug of the compound of formula (I) according to the present invention should follow the prodrug design principle. The compound of formula (I) can be released by enzymolysis, hydrolyzation, acidolysis or metabolic degradation under normal physiological conditions. Prodrug includes, but not limited to esterification of the hydroxyl groups of the compounds (such as formation of phosphate and carbonate), as well as the protection of amino groups and carboxyl groups. Prodrug design shall reference to (1) Karaman R, Prodrugs design based on inter- and intramolecular chemical processes. Chem Biol Drug Des. 82(6): 643-68, 2013; (2) Rautio J et al. Prodrugs: design and clinical applications. Nat Rev Drug Discov. 7(3):255-70, 2008; (3) Jampilek J. Prodrugs: pharmaceutical design and current perspectives. Curr Pharm Des. 17(32):3480-1, 2011; (4) Bundgaard H. Design of Progrugs. Elservier, 1985.

On the other hand, the compound of formula (I) or the pharmaceutically acceptable salts or predrugs thereof according to the present invention can be formulated into clinically applicable pharmaceutical compositions. According to the clinical indications, drug administration approaches and ways, the pharmaceutical preparations include, but not limited to, oral preparations such as tablets, gels, soft/hard capsules, emulsions, dispersive powder, granules, water/oil suspensions; injections such as intravenous injection, muscle injection, intraperitoneal injection, rectal suppositories and intracranial injection, which may be aqueous solution and oil solution; local preparations such as creams, ointments, gels, water/oil solution and clathrate compound preparations; inhalant preparations such as fine powder, liquid aerosols and various dosage forms suitable for in vivo implantation.

The present pharmaceutical composition can be added with conventional pharmaceutical adjuvants as required. Such pharmaceutical adjuvants should comply with preparation process rules for pharmaceutical preparations, and should be compatible with the active ingredients. The adjuvants for solid oral preparation include, but not limited to, mannitol, lactose, starch, magnesium stearate, cellulose, glucose, saccharose, cyclodextrin and molecular carrier vitamin E-PEG1000 which can promote intestinal absorption.

Appropriate amount of colorant, sweetening agent, flavoring agent and preservative can be added to oral preparation.

The compound of formula (I) according to the present invention can be administrated to warm-blooded animals at a dosage of 0.1-100 mg/kg.

The pharmaceutical compositions comprising the compound of formula (I) or the pharmaceutically acceptable salts thereof are mainly applied for the treatment of clinical diseases related to EGFR and/or HER2, including but not limited to cancers, diabetes inflammation, immune system diseases, cardiovascular diseases, neurological diseases and respiratory diseases.

Among the above clinical diseases, cancers include, but not limited to lung cancer, gastric cancer, liver cancer, breast cancer, nasopharynx cancer, pancreatic cancer, ovarian cancer, cervical cancer, colorectal cancer, glioma, melanoma, prostatic cancer, renal carcinoma, esophagus cancer, mesothelioma, head and neck cancer, bladder carcinoma, salivary gland cancer, anaplastic large cell lymphoma (ALCL), leukemia, lymphoma including non-Hodgkin's lymphoma (NHL) and multiple myeloma.

The pharmaceutical compositions of the present invention can be used separately or combined with one or more routine clinical therapies such as surgery, radiation therapy, chemotherapy, immunotherapy, oncolytic virus, RNAi, cancer adjuvant therapy, which includes, but not limited to the following antitumor drugs and therapeutic methods:

1) Alkylating agents, e.g. Cisplatin, Carboplatin, Oxaliplatin, Chlorambucil, Cyclophosphamide, Mechlorethamine Hydrochloride, Melphalan, Temozolomide, Busulfan and Nitrosoureas.

2) Antitumor antibiotics, e.g. Adriamycin, Bleomycin, Doxorubicin, Daunorubicin, Pharmorubicin, Idarubicin, Mitomycin C, Actinomycin and Mithramycin; antimitotic drugs such as Vincristine, Vincaleukoblastinum, Vindesine, Vinorelbine, Taxol, Docetaxel and Polo kinase inhibitor.

3) Anti-metabolism and antifolic agents, e.g. Fluoropyrimidine, Methotrexate, Cytarabine, Raltitrexed and Hydroxyurea.

4) Topoisomerase inhibitors, e.g. Epipodophyllotoxin and Camptothecin.

5) Growth hormone inhibitors, including but not limited to anti-estrogen and anti-androgen drugs, such as Tamoxifen, Fulvestrant, Toremifene, Raloxifene, Droloxifene, Idoxifene, and Bicalutamide, Flutamide, Nilutamide and Cyproterone Acetate.

LHRH antagonists or LHRH agonists, e.g. Goserelin, Leuprorelin and Buserelin; progestogens e.g. Megestrol Acetate.

Aromatase inhibitors, e.g. Anastrozole, Letrozole, Vorozole, Exemestane, and 5a-reductase inhibitors, e.g. Finasteride.

6) Anti-tumor invasion agents, including but not limited to c-Src kinase family inhibitors, metalloproteinase inhibitors, urokinase plasminogen activator inhibitors or anti-heparanase monoclonal antibodies.

7) Cell growth inhibitors, including but not limited to monoclonal antibodies against growth factors or growth factor receptors such as anti-HER2 antibody Trastuzumab, anti-EGFR antibodies Panitumumab and Cetuximab etc, and small molecular inhibitors of protein tyrosine or serine/threonine kinases such as FLT3, c-Kit, Abl, FGFR, PDGFR, CSF-1R, IGFR, Aurora, Ras, Raf, MEK, AKT, PI3K, cyclin-dependent kinases include CDK2, CDK4 and CDK6 inhibitors.

8) Anti-angiogenic agents, including but not limited to Bevacizumab, a monoclonal antibody against vascular endothelial growth factor (VEGF), and small molecular inhibitors of VEGF receptor tyrosine kinases.

9) Cancer immunotherapy, e.g. immunotherapeutic drugs and methods. Including but not limited to which improve the immunogenicity of the tumor cells of patients, such as cytokines IL-2, IL-4 or GM-CSF; methods to reduce the anergy of T cells such as against immune checkpoint inhibitors PD-1/PD-L1 monoclonal antibodies; methods of using transducted immune cells such as cytokine transducted dendritic cells; methods to reduce the functions of immunosuppressive cells including regulatory T cells, myeloid-derived suppressor cells, and dendritic cells expressing indoleamine 2,3-deoxygenase; and cancer vaccine therapy using antigenic proteins or peptides associated with tumor.

10) Chimeric antigen receptor T cell therapy (CAR-T).

11) Tumor-targeted gene therapy, such as CRISPR-Cas 9, RNAi and gene transduction.

It should be noted that if the number of the substituents is not specified (such as haloalkyl), one or more substituents are allowable. For example, "haloalkyl" may contain one or more the same or different halogens.

In the present invention, if the chemical structure and chemical name are contradictory to each other, the chemical structure shall prevail.

Unless otherwise specified, the abbreviations of any protection groups and other compounds used herein are expressed in the conventional recognized form, or according to IUPAC-IUB Commission on Biochemical Nomenclature (Reference to Biochem. 1972, 77:942-944).

EXAMPLES

The present invention will be illustrated in detail with reference to the following examples. However, it should not be understood that the present invention is limited to these examples.

Example 1

Preparation of N-(5-(4-(3-bromophenylamino)-pyrimidin-2-ylamino)-2-(2-(dimethylamino-ethyl)-methyl-amino)-4-methoxyl-phenyl)-acrylamide (Compound 1)

Compound 1

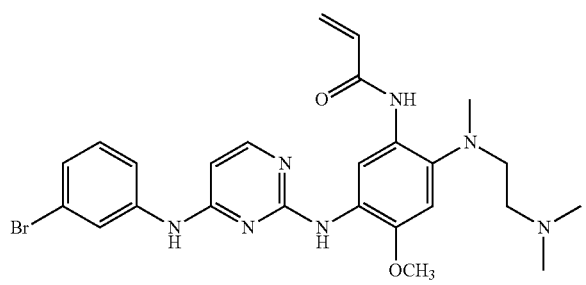 [SMILES: C=CC(=O)Nc1cc(Nc2nccc(Nc3cccc(Br)c3)n2)c(OC)cc1N(C)CCN(C)C]

Step 1: Preparation of (3-bromo-phenyl)-(2-chloro-pyrimidin-4-yl)-amine

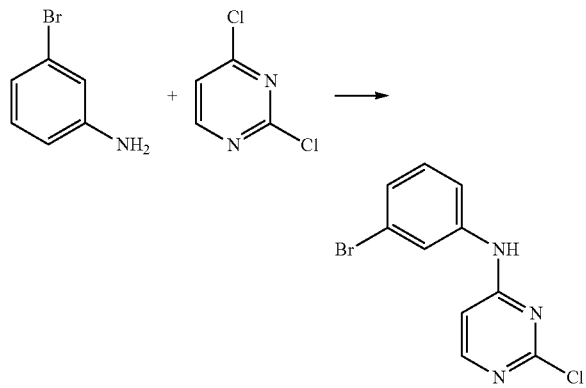

3-Bromoaniline (2.7 g, 15 mmol), 2,4-dichloro pyrimidine (2.7 g, 18 mmol) and sodium bicarbonate (2.5 g, 30 mmol) were added to 30 mL of isopropyl alcohol, and then heated to 85° C. with stirring for 10 h. The isopropyl alcohol was removed under reduced pressure, and the residues were added with water and ethyl acetate. The ethyl acetate phase was dried and concentrated. The residues were purified via flash column chromatography on silica to give (3-bromo-phenyl)-(2-chloro-pyrimidin-4-yl)-amine (2.5 g). m/z: ESI MH+285.9

Step 2: Preparation of $N^4$-(3-bromophenyl)-$N^2$-(4-((2-dimethylamino-ethyl)-methyl-amino)-2-methoxyl-5-nitro-phenyl)-pyrimidin-2,4-diamine Toluenesulfonate

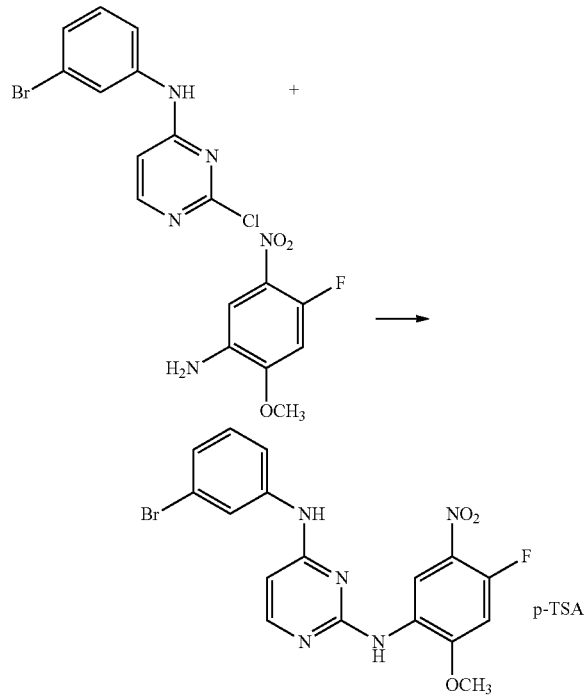

(3-Bromo-phenyl)-(2-chloro-pyrimidin-4-yl)-amine (1.4 g, 5 mmol), 2-methoxyl-4-fluoro-5-nitroaniline (0.9 g, 5 mmol) and p-toluenesulfonic acid (1.03 g, 6 mmol) were added to 15 mL of 2-amyl alcohol and then heated for 3 h at 115° C. The reaction mixture was cooled down to room temperature and filtered. The filter cake was washed with methyl tertiary butyl ether twice and then dried to give $N^4$-(3-bromophenyl)-$N^2$-(4-((2-dimethylamino-ethyl)-methyl-amino)-2-methoxyl-5-nitro-phenyl)-pyrimidin-2,4-diamine toluenesulfonate. m/z: ESI MH+ 434.0

Step 3: Preparation of $N^4$-(4-(3-bromophenyl amino)-pyrimidin-2-yl)-$N^1$-(2-dimethylamino-ethyl)-5-methoxyl-$N^1$-methyl-phenyl-1,2,4-triamine

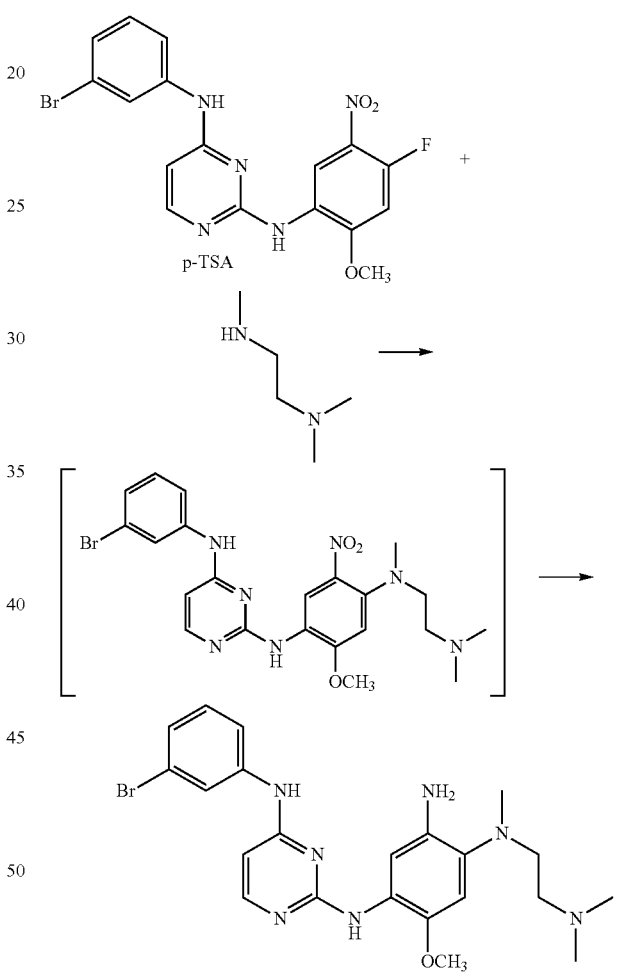

$N^4$-(3-bromophenyl)-$N^2$-(4-((2-dimethylamino-ethyl)-methyl-amino)-2-methoxyl-5-nitro-phenyl)-pyrimidin-2,4-diamine toluenesulfonate (0.6 g, 1 mmol), N,N,N'-trimethyl ethylenediamine (0.15 g, 1.5 mmol) and anhydrous potassium carbonate (0.42 g, 3 mmol) were added to 2 mL of DMF, and then heated for 3 h at 90° C. The reaction mixture was cooled down to room temperature, and then added with water and ethyl acetate. The ethyl acetate layer was concentrated, and the residues were added with iron powder (0.28 g, 5 mmol), ammonia chloride (0.27 g, 5 mmol), water (5 mL) and ethanol (15 mL). The mixture was heated for 5 h at 80° C. The iron sludge was filtered out while hot, and the filtrate was added with water and dichloromethane after concentration. The dichloromethane phase was dried and concentrated. The residues were purified via column chromatography to give N⁴-(4-(3-bromophenyl amino)-pyrimidin-2-yl)-N¹-(2-dimethylamino-ethyl)-5-methoxyl-N¹-methyl-phenyl-1,2,4-triamine (0.24 g). m/z: ESI MH+ 486.1

Step 4: Preparation of N-(5-(4-(3-bromophenyl amino)-pyrimidin-2-ylamino)-2-(2-(dimethylamino-ethyl)-methyl-amino)-4-methoxyl-phenyl)-acrylamide

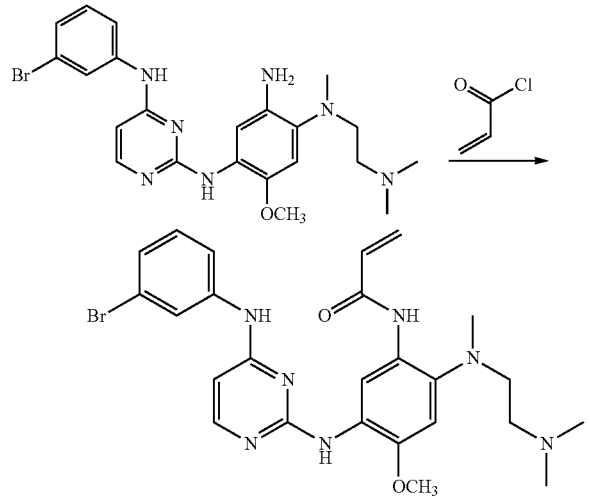

N⁴-(4-(3-bromophenyl amino)-pyrimidin-2-yl)-N¹-(2-dimethylamino-ethyl)-5-methoxyl-N¹-methyl-phenyl-1,2,4-triamine (0.24 g, 0.5 mmol) and N,N-di(isopropyl)ethylamine (0.2 g, 1.5 mmol) were added to tetrahydrofuran. The mixture was cooled down under ice-water bath and added with acryloyl chloride (0.05 g, 0.55 mmol) dropwise. The reaction mixture was stirred for 1 hour after addition and then stirred for 2 hours under room temperature. The mixture was added with water and dichloromethane. The dichloromethane phase was dried with anhydrous Na₂SO₄ and then concentrated. The residues were purified by column chromatography to provide the title compound (70 mg).

Example 2

Preparation of N-(5-(4-(3-methoxyphenoxy)-pyrimidin-2-ylamino)-2-((2-dimethylamino-ethyl)-methyl-amino)-4-methoxyl-phenyl)-acrylamide (Compound 11)

Compound 11

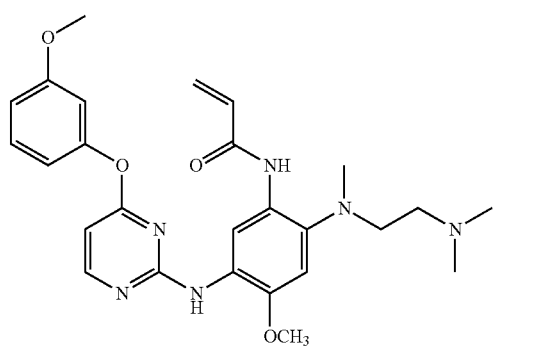

Step 1: 2-chloro-4-(3-methoxyl phenyl) pyrimidine

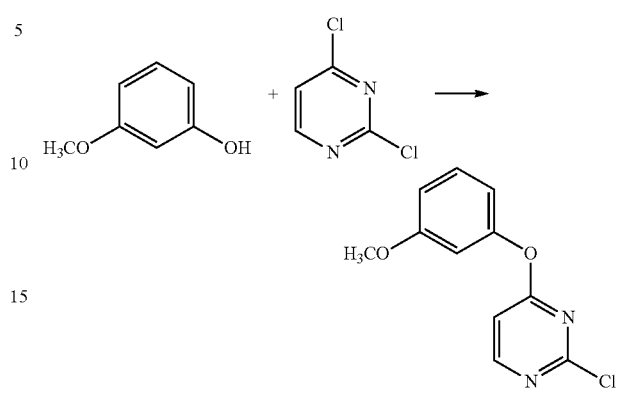

3-Methoxyl phenol (500 mg, 4 mmol), 2,4-dichloro pyrimidine (900 mg, 6 mmol) and potassium carbonate (1.1 g, 8 mmol) were added to 5 mL of DMF, and heated overnight at 60° C. The reaction mixture was poured to water, and then extracted with ethyl acetate. The ethyl acetate layer was dried and then concentrated. The residues were purified by column chromatography to give 2-chloro-4-(3-methoxylphenyl)pyrimidine (0.63 g). m/z: ESI MH+237.1.

The steps 2 to 4 of Example 1 were repeated to give the title compound.

Example 3

Preparation of N-(5-(4-(3-chloro-4-(pyridin-2-methoxyl)phenyl amino) pyrimidin-2-ylamino)-2-((2-(dimethylamino)ethyl)(methyl)amino)-4-methoxyl-phenyl)-acrylamide (Compound 18)

Compound 18

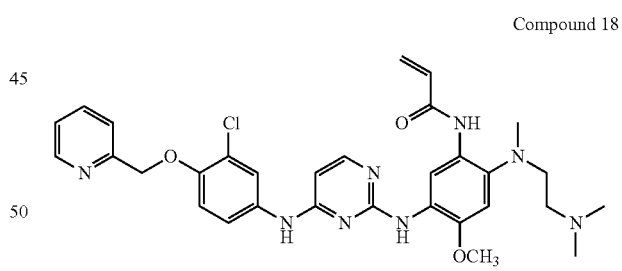

Step 1: Preparation of (3-chloro-4-(pyridin-2-yl-methoxyl)phenyl)-(2-chloro pyrimidin-4-yl)-amine

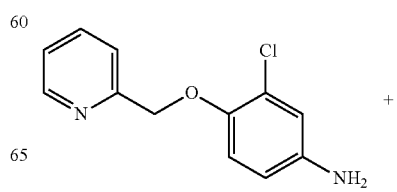

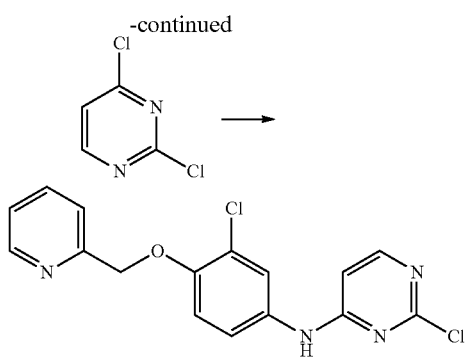

3-Chloro-4-(pyridin-2-yl-methoxyl)aniline (58.7 g, 250 mmol), 2,4-dichloro pyrimidine (44.7 g, 300 mmol) and sodium bicarbonate (31.5 g, 375 mmol) were added to 400 mL of isopropyl alcohol And then heated under oil bath at 85° C. for 24 h. The reaction mixture was cooled down to the room temperature and then added with 500 mL of water. The mixture was filtered and the solid was washed with 500 mL of water, and then dried to give the intermediate (84 g). m/z: ESI MH+ 347.0.

Step 2: Synthesis of $N^4$-(3-chloro-4-(pyridin-2-yl-methoxyl)-phenyl)-$N^2$-(4-fluoro-2-methoxyl-5-nitro-phenyl)-pyrimidin-2,4-diamine mesylate

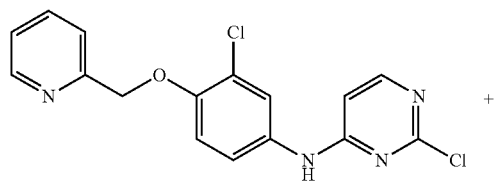

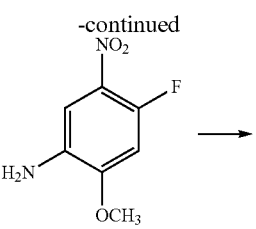

(3-Chloro-4-(pyridin-2-yl-methoxyl)phenyl)-(2-chloro pyrimidin-4-yl)-amine (1.75 g, 5 mmol), 2-methoxyl-4-fluoro-5-nitroaniline (0.98 g, 5.25 mmol) and methanesulfonic acid (0.96 g, 10 mmol) were added to 20 mL of isopropyl alcohol and then heated at 75° C. for 12 h. The reaction mixture was cooled to room temperature and dried to give $N^4$-(3-fluoro-4-(pyridin-2-yl-methoxyl)-phenyl)-$N^2$-(4-fluoro-2-methoxyl-5-nitro-phenyl)-pyrimidin-2,4-diamine mesylate (2.1 g). m/z: ESI MH+ 497.1.

Step 3: Synthesis of $N^4$-(4-(3-chloro-4-(pyridin-2-yl-methoxyl) phenylamino)-pyrimidin-2-yl)-$N^1$-(2-dimethylamino-ethyl)-5-methoxyl-$N^1$-methyl-phenyl-1,2,4-triamine

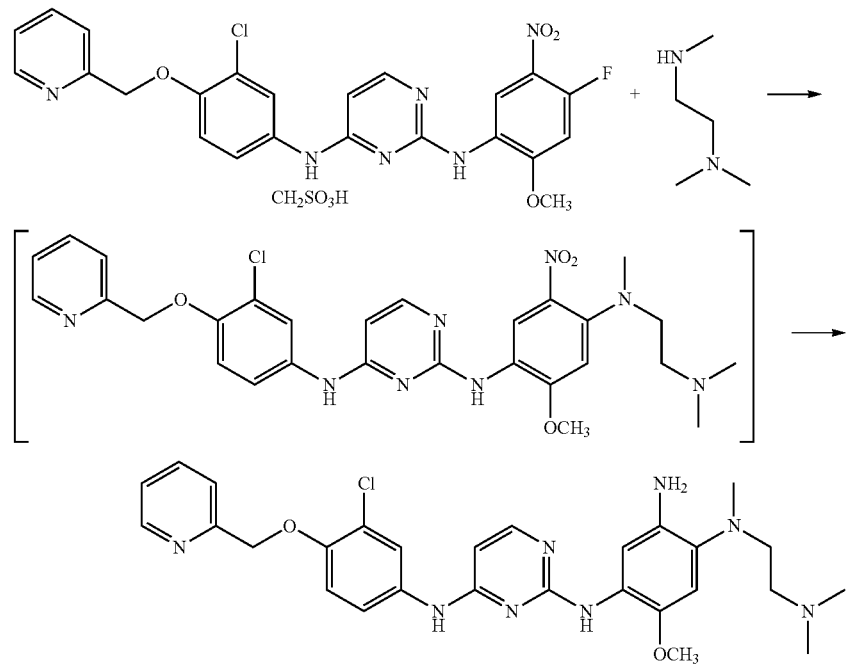

$N^4$-(3-chloro-4-(pyridin-2-yl-methoxyl)-phenyl)-$N^2$-(4-fluoro-2-methoxyl-5-nitro-phenyl)-pyrimidin-2,4-diamine mesylate (11.8 g, 20 mmol), N,N,N'-trimethyl ethylenediamine (3.06 g, 30 mmol) and anhydrous potassium carbonate (8.3 g, 60 mmol) were added to 40 mL of DMF and then heated at 90° C. for 4 h. The reaction mixture was cooled to room temperature, and then added with water and ethyl acetate. After the concentration of ethyl acetate, iron powder (5.6 g, 100 mmol), ammonia chloride (5.6 g, 105 mmol), water (80 mL) and ethanol (80 mL) were added and then heated at 80° C. for 5 h. The iron sludge was filtered out while hot. The filtrate was concentrated and then added with water and dichloromethane. The dichloromethane layer was dried and then concentrated. The residues were purified by, column chromatography to give $N^4$-(4-(3-chloro-4-(pyridin-2-yl-methoxyl)phenylamino)-pyrimidin-2-yl)-$N^1$-(2-dimethylamino-ethyl)-5-methoxyl-N-methyl-phenyl-1,2,4-triammonium (3.1 g), m/z: ESI MH+ 549.3.

Step 4: N-(5-(4-(3-chloro-4-(pyridin-2-ylmethoxy) phenylamino)-pyrimidin-2-ylamino)-2-((2-(dimethylamino)ethyl)(methyl)amino)-4-methoxyl-phenyl)-acrylamide

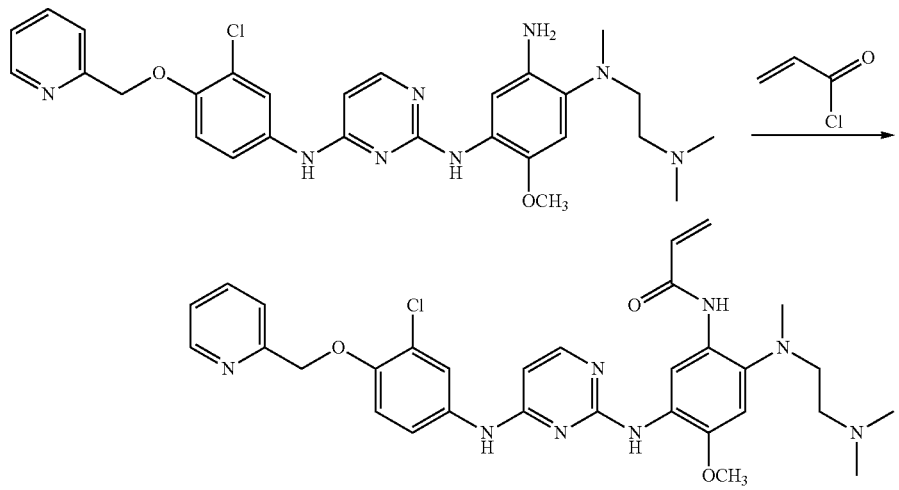

$N^4$-(4-(3-chloro-4-(pyridin-2-yl-methoxyl) phenylamino)-pyrimidin-2-yl)-$N^1$-(2-dimethylamino-ethyl)-5-methoxyl-$N^1$-methyl-phenyl-1,2,4-triamine (0.55 g, 1 mmol) and N,N-di(isopropyl)ethylamine (0.38 g, 3 mmol) were added to tetrahydrofuran. The mixture was cooled in ice-water bath and then added with acryloyl chloride (0.11 g, 1.2 mmol). After addition, the mixture was stirred for 1 hour, and then was brought to room temperature and continued stirred for 2 hours. The reaction mixture was added with water and dichloromethane. The dichloromethane layer was dried with anhydrous $Na_2SO_4$ and then concentrated. The residues were purified by column chromatography to give the title compound (110 mg).

Example 4

Preparation of N-(5-(-4-(3-chloro-4-(benzene-2-methoxyl)-phenylamino)-pyrimidin-2-ylamino)-2-(2-(morpholin-4-yl)-ethoxyl)-4-methoxyl-phenyl)-acrylamide (Compound 29)

Compound 29

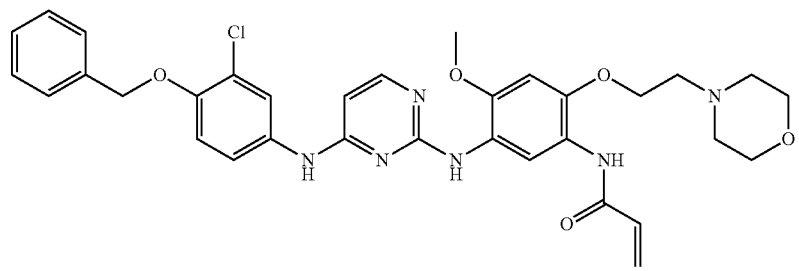

Steps 1 and 2 are the same as those in Example 3.

Step 3: Synthesis of N²-(5-amino-2-methoxyl-4-(2-morpholin-4-yl-ethoxyl)-phenyl)-N⁴-(3-chloro-4-(pyridin-2-methoxyl)-phenyl)-pyrimidyl-2,4-diamine

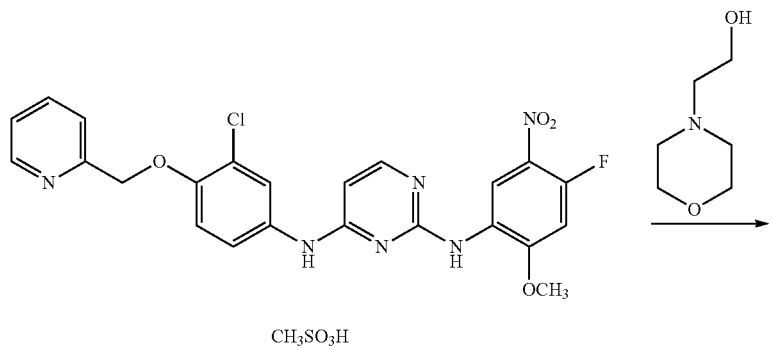

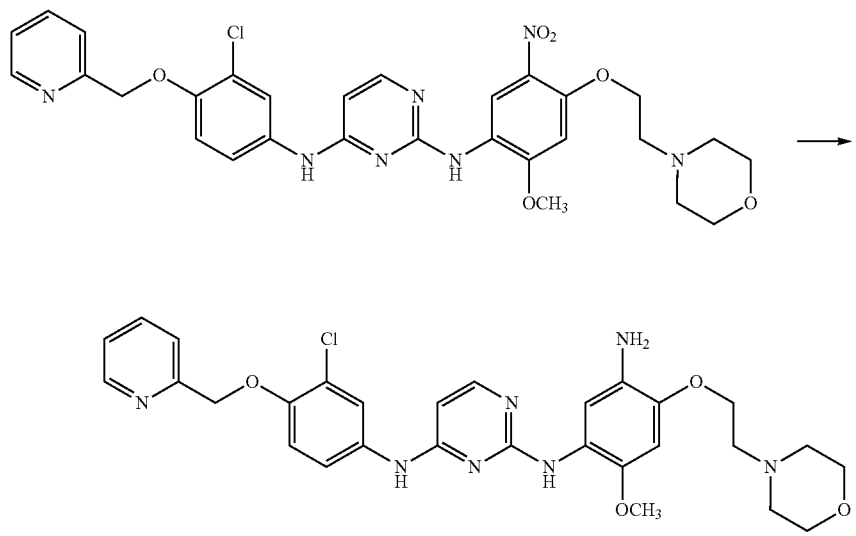

N⁴-(3-chloro-4-(pyridin-2-yl-methoxyl)-phenyl)-N²-(4-fluoro-2-methoxyl-5-nitro-phenyl)-pyrimidin-2,4-diamine mesylate (0.59 g, 1 mmol), 4-(2-hydroxyethyl morpholine) (0.2 g, 1.5 mmol) and sodium hydroxide (0.12 g, 3 mmol) were added to 3 mL of DMF and then heated at 60° C. for 3 h. The reaction mixture was cooled down to room temperature and then added with water and ethyl acetate. After the concentration of ethyl acetate layer, iron powder (0.28 g, 5 mmol), ammonia chloride (0.27 g, 5 mmol), water (5 mL) and ethanol (15 mL) were added and then heated at 80° C. for 5 h. The iron sludge was filtered out while hot. The filtrate was concentrated and then added with water and dichloromethane. The dichloromethane layer was dried, and then concentrated. The residues were purified by column chromatography to give N²-(5-amino-2-methoxyl-4-(2-morpholin-4-yl-ethoxyl)-phenyl)-N⁴-(3-chloro-4-(pyridin-2-methoxyl)-phenyl)-pyrimidyl-2,4-diamine (0.21 g), m/z: ESI MH+ 578.3.

Step 4 of Example 3 was repeated to give the title compound.

Example 5

Preparation of N-(5-(4-(3,4-dichloro-2-fluorophenylamino)-pyrimidin-2-ylamino)-2-(2-(dimethylamino-ethyl)-methyl-amino)-4-methoxyl-phenyl)-acrylamide (Compound 15)

Compound 15

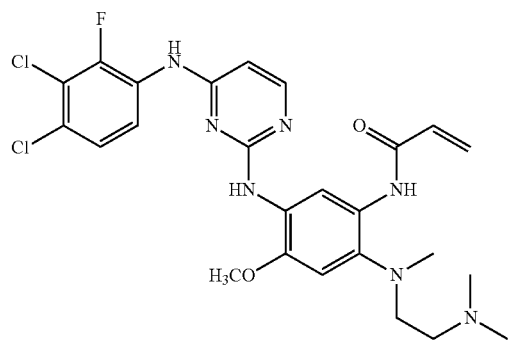

Step 1: Preparation of (3,4-dichloro-2-fluorophenyl)-(2-chloropyrimidin-4-yl)-amine

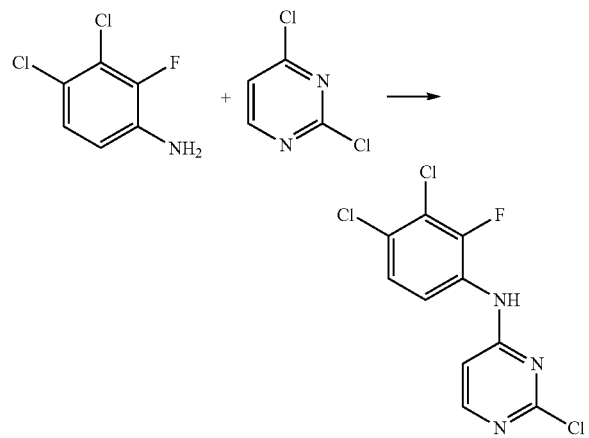

3,4-Dichloro-2-fluoroaniline (1.8 g, 10 mmol), 2,4-dichloropyrimidine (2.25 g, 15 mmol) and hydrochloric acid (0.5 mL, 12 M) were added to 5 mL of isopropyl alcohol and then put to reflux for 2 h. The reaction mixture was cooled down to room temperature and then filtered to give the title intermediate (1.2 g). m/z: ESI MH+ 292.0.

Steps 2~4 of Example 1 were repeated to give the title compound.

Compounds 1-6, 8-10, 12-14 and 30-31 in Table 1 were prepared according to the same procedures as Example 1. Compounds 7 and 11 in Table 1 were prepared according to the same procedures as Example 2. Compounds 17-28 in Table 1 were prepared according to the same procedures as Example 3. Compound 29 in Table 1 was prepared according to the same procedures as Example 4. Compounds 15-16 in Table 1 were prepared according to the same procedures as Example 5.

TABLE 1

| Comp. | Structure | Name | Data |
|---|---|---|---|
| 1 | (structure) | N-(5-(4-(3-bromophenylamino)-pyrimidin-2-ylamino)-2-(2-(dimethylamino-ethyl)-methyl-amino)-4-methoxyl-phenyl)-acrylamide | $^1$H-NMR (DMSO-$d_6$) δ: 2.20 (s, 6H), 2.31 (t, 2H), 2.70 (s, 3H), 2.86 (t, 2H), 3.80 (s, 3H), 5.72 (dd, 1H), 6.14-6.20 (m, 2H), 6.38 (dd, 1H), 6.99 (s, 1H), 7.05 (d, 1H), 7.12 (t, 1H), 7.70 (d, 1H), 7.80 (br, 1H), 7.96 (s, 1H), 7.99 (d, 1H), 8.59 (s, 1H), 9.45 (s, 1H), 10.05 (s, 1H). m/z: ESI MH$^+$ 540.0 |
| 2 | (structure) | N-(5-(4-(3-chlorophenylamino)-pyrimidin-2-ylamino)-2-(2-(dimethylamino-ethyl)-methyl-amino)-4-methoxyl-phenyl)-acrylamide | $^1$H-NMR (DMSO-$d_6$) δ: 2.22 (s, 6H), 2.32 (t, 2H), 2.71 (s, 3H), 2.87 (t, 2H), 3.79 (s, 3H), 5.72 (m, 1H), 6.15-6.20 (m, 2H), 6.38 (dd, 1H), 6.92 (dd, 1H), 7.00 (s, 1H), 7.18 (t, 1H), 7.57 (dd, 1H), 7.75 (t, 1H), 7.99 (m, 2H), 8.58 (s, 1H), 9.46 (s, 1H), 10.05 (s, 1H). m/z: ESI MH$^+$ 496.1 |
| 3 | (structure) | N-(5-(4-(3-fluorophenylamino)-pyrimidin-2-ylamino)-2-(2-(dimethylamino-ethyl)-methyl-amino)-4-methoxyl-phenyl)-acrylamide | $^1$H-NMR (DMSO-$d_6$) δ: 2.21 (s, 6H), 2.32 (t, 2H), 2.71 (s, 3H), 2.87 (t, 2H), 3.78 (s, 3H), 5.71 (m, 1H), 6.15-6.18 (m, 2H), 6.37 (dd, 1H), 6.67 (m, 1H), 6.99 (s, 1H), 7.18-7.28 (m, 2H), 7.71 (d, 1H), 7.99 (d, 1H), 8.03 (s, 1H), 8.57 (s, 1H), 9.49 (s, 1H), 10.01 (s, 1H). m/z: ESI MH$^+$ 480.1 |

TABLE 1-continued

| Comp. | Structure | Name | Data |
|---|---|---|---|
| 4 | 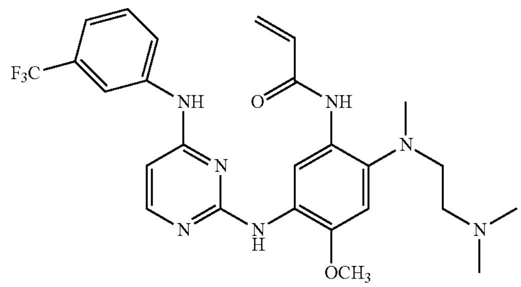 [SMILES: C=CC(=O)Nc1cc(Nc2nccc(Nc3cccc(C(F)(F)F)c3)n2)c(OC)cc1N(C)CCN(C)C] | N-(5-(4-(3-trifluoro-methylphenylamino)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.24 (s, 6H), 2.35 (t, 2H), 2.70 (s, 3H), 2.89 (t, 2H), 3.79 (s, 3H), 5.72 (dd, 1H), 6.14-6.22 (m, 2H), 6.39 (dd, 1H), 6.98 (s, 1H), 7.21 (d, 1H), 7.38 (t, 1H), 7.81 (s, 1H), 7.93 (s, 1H), 8.02 (d, 1H), 8.12 (d, 1H), 8.62 (s, 1H), 9.65 (s, 1H), 10.06 (s, 1H). m/z: ESI MH$^+$ 530.1 |
| 5 | 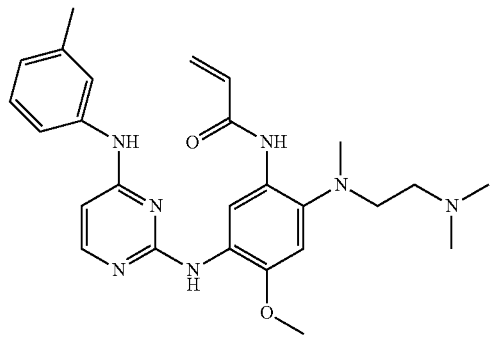 [SMILES: C=CC(=O)Nc1cc(Nc2nccc(Nc3cccc(C)c3)n2)c(OC)cc1N(C)CCN(C)C] | N-(5-(4-(3-methyl-phenylamino)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.21 (s, 9H), 2.31 (t, 2H), 2.70 (s, 3H), 2.86 (t, 2H), 3.80 (s, 3H), 5.72 (dd, 1H), 6.16-6.21 (m, 2H), 6.39 (dd, 1H), 6.72 (d, 1H), 6.98 (s, 1H), 7.07 (t, 1H), 7.36 (s, 1H), 7.50 (d, 1H), 7.78 (s, 1H), 7.95 (d, 1H), 8.66 (s, 1H), 9.21 (s, 1H), 10.08 (s, 1H). m/z: ESI MH$^+$ 476.2 |
| 6 | 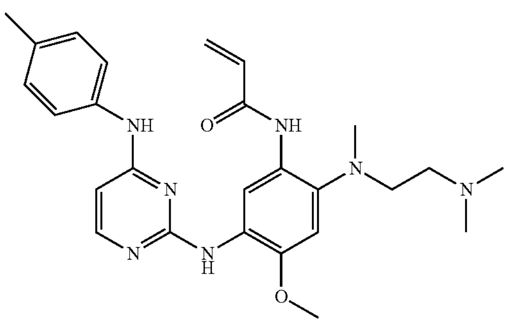 | N-(5-(4-(4-methyl-phenylamino)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.20 (s, 3H), 2.22 (s, 6H), 2.31 (t, 2H), 2.71 (s, 3H), 2.88 (t, 2H), 3.81 (s, 3H), 5.73 (dd, 1H), 6.14-6.21 (m, 2H), 6.40 (dd, 1H), 6.98-7.01 (m, 3H), 7.49 (d, 2H), 7.08 (s, 1H), 7.93 (d, 1H), 8.65 (s, 1H), 9.21 (s, 1H), 10.13 (s, 1H). m/z: ESI MH$^+$ 476.2 |
| 7 | 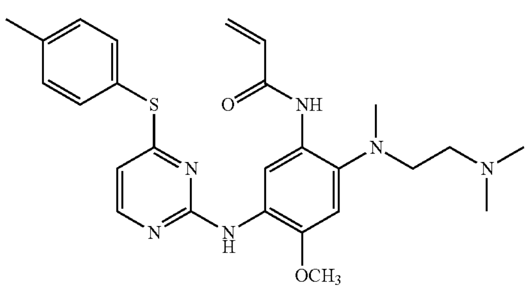 | N-(5-(4-(4-methyl-phenylthio)-pyrimidin-2-ylamino)-2-((2-dimethylamino-ethyl)-methyl-amino)-4-methoxyl-phenyl)-acrylamide | $^1$H-NMR (DMSO-d$_6$) δ: 2.20 (s, 6H), 2.31 (t, 2H), 2.37 (s, 3H), 2.69 (s, 3H), 2.86 (t, 2H), 3.79 (s, 3H), 5.74 (dd, 1H), 6.05 (d, 1H), 6.23 (dd, 1H), 6.39 (dd, 1H), 6.97 (s, 1H), 7.33 (d, 2H), 7.52 (d, 2H), 8.07 (d, 1H), 8.23 (s, 1H), 8.61 (s, 1H), 10.07 (s, 1H). m/z: ESI MH$^+$ 493.4 |
| 8 | 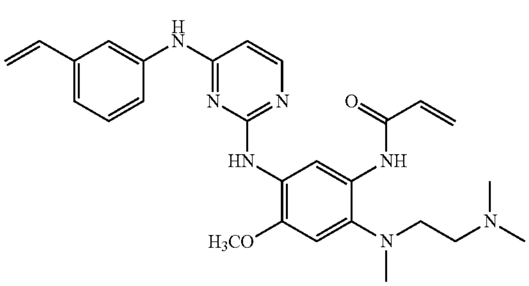 [SMILES: C=CC(=O)Nc1cc(Nc2nccc(Nc3cccc(C=C)c3)n2)c(OC)cc1N(C)CCN(C)C] | N-(5-(4-(3-acetenyl-phenylamino)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.21 (s, 6H), 2.31 (t, 2H), 2.71 (s, 3H), 2.87 (t, 2H), 3.80 (s, 3H), 4.13 (s, 1H), 5.72 (dd, 1H), 6.16-6.21 (m, 2H), 6.38 (dd, 1H), 6.99 (s, 1H), 7.01 (d, 1H), 7.17 (t, 1H), 7.52 (s, 1H), 7.88-7.90 (m, 2H), 7.98 (d, 1H), 8.62 (s, 1H), 9.38 (s, 1H), 10.06 (s, 1H). m/z: ESI MH$^+$ 486.1 |

TABLE 1-continued

| Comp. | Structure | Name | Data |
|---|---|---|---|
| 9 | 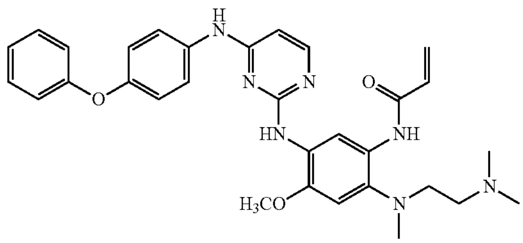 [SMILES: C=CC(=O)Nc1cc(Nc2nccc(Nc3ccc(Oc4ccccc4)cc3)n2)c(OC)cc1N(C)CCN(C)C] | N-(5-(4-(4-phenoxyl-phenylamino)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.15 (s, 6H), 2.25 (t, 2H), 2.65 (s, 3H), 2.82 (br, 2H), 3.78 (s, 3H), 5.67 (dd, 1H), 6.13-6.18 (m, 2H), 6.31 (dd, 1H), 6.85-6.96 (m, 5H), 7.09 (d, 1H), 7.35 (m, 2H), 7.64 (d, 2H), 7.81 (s, 1H), 7.95 (d, 1H), 8.62 (s, 1H), 9.33 (s, 1H), 10.10 (s, 1H). m/z: ESI MH$^+$ 554.2 |
| 10 | 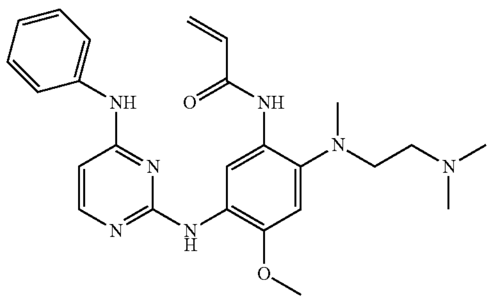 [SMILES: C=CC(=O)Nc1cc(Nc2nccc(Nc3ccccc3)n2)c(OC)cc1N(C)CCN(C)C] | N-(5-(4-(phenyl-amino)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.22 (s, 6H), 2.30 (t, 2H), 2.71 (s, 3H), 2.87 (t, 2H), 3.80 (s, 3H), 5.73 (dd, 1H), 6.17-6.21 (m, 2H), 6.40 (dd, 1H), 6.89 (t, 1H), 6.98 (s, 1H), 7.19 (t, 2H), 7.62 (d, 2H), 7.80 (s, 1H), 7.96 (d, 1H), 8.64 (s, 1H), 9.29 (s, 1H), 10.11 (s, 1H). m/z: ESI MH$^+$ 462.1 |
| 11 | 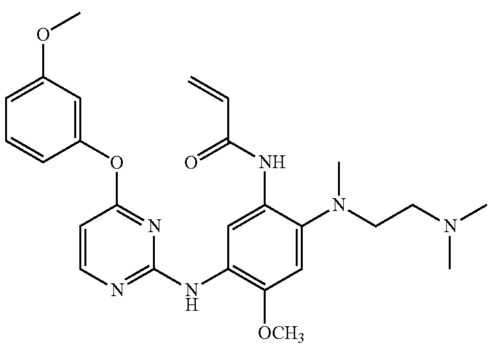 [SMILES: C=CC(=O)Nc1cc(Nc2nccc(Oc3cccc(OC)c3)n2)c(OC)cc1N(C)CCN(C)C] | N-(5-(4-(3-methoxy-phenoxy)-pyrimidin-2-ylamino)-2-((2-dimethylamino-ethyl)-methyl-amino)-4-methoxyl-phenyl)-acrylamide | $^1$H-NMR (DMSO-d$_6$) δ: 2.22 (s, 6H), 2.34 (t, 2H), 2.69 (s, 3H), 2.87 (t, 2H), 3.76 (s, 3H), 3.78 (s, 3H), 5.75 (dd, 1H), 6.02 (s, 1H), 6.22 (dd, 1H), 6.40 (dd, 1H), 6.72-6..76 (m, 2H), 6.83 (dd, 1H), 6.97 (s, 1H), 7.33 (t, 1H), 8.22 (s, 1H), 8.45 (s, 1H), 8.84 (s, 1H), 10.08 (s, 1H). m/z: ESI MH$^+$ 493.4 |
| 12 | 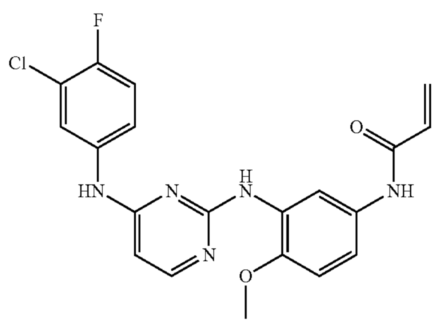 [SMILES: C=CC(=O)Nc1ccc(OC)c(Nc2nccc(Nc3ccc(F)c(Cl)c3)n2)c1] | N-(3-(4-(3-chloro-4-fluoro-phenylamino)-pyrimidin-2-ylamino)-4-methoxyl-phenyl)-acrylamide | $^1$H-NMR (CDCl$_3$) δ: 3.89 (s, 3H), 5.75-5.78 (d, 1H), 6.11-6.13 (d, 1H), 6.21-6.27 (m, 1H,), 6.39-6.44 (d, 1H), 6.83-6.85 (d, 1H), 7.11-7.15 (m, 2H), 6.25-6.27 (m, 1H), 7.37-7.40 (m, 2H), 7.51-7.54 (dd, 1H), 7.62 (s, 1H), 8.07-8.08 (d, 1H), 8.56-8.56 (d, 1H). m/z: ESI MH$^+$ 414.1. |
| 13 | 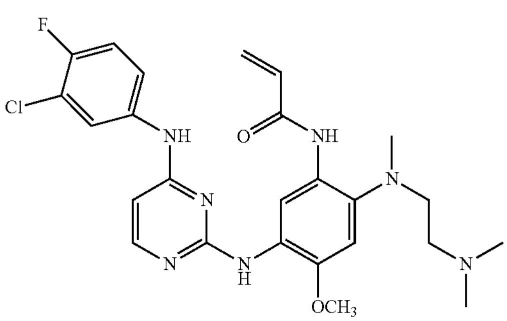 [SMILES: C=CC(=O)Nc1cc(Nc2nccc(Nc3ccc(F)c(Cl)c3)n2)c(OC)cc1N(C)CCN(C)C] | N-(5-(4-(3-chloro-4-fluorophenyl-amino)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.22 (s, 6H), 2.33 (t, 2H), 2.70 (s, 3H), 2.88 (t, 2H), 3.79 (s, 3H), 5.71 (dd, 1H), 6.13-6.18 (m, 2H), 6.38 (dd, 1H), 6.99 (s, 1H), 7.18 (t, 1H), 7.52-7.57 (m, 1H), 7.88 (dd, 1H), 7.96 (s, 1H), 7.98 (d, 1H), 8.58 (s, 1H), 9.47 (s, 1H), 10.02 (s, 1H). m/z: ESI MH$^+$ 513.1 |

TABLE 1-continued

| Comp. | Structure | Name | Data |
|---|---|---|---|
| 14 | 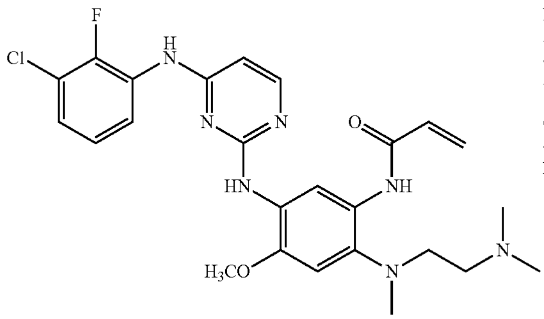 [SMILES: C=CC(=O)Nc1cc(Nc2nccc(Nc3cccc(Cl)c3F)n2)c(OC)cc1N(C)CCN(C)C] | N-(5-(4-(3-chloro-2-fluorophenyl-amino)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.21 (s, 6H), 2.29 (t, 2H), 2.70 (s, 3H), 2.86 (br, 2H), 3.78 (s, 3H), 5.73 (dd, 1H), 6.18 (dd, 1H), 6.34-6.41 (m, 2H), 6.96-7.00 (m, 2H), 7.13 (m, 1H), 7.87 (s, 1H), 8.02 (d, 1H), 8.10 (m, 1H), 8.58 (s, 1H), 9.20 (s, 1H), 10.08 (s, 1H). m/z: ESI MH$^+$ 514.1 |
| 15 | 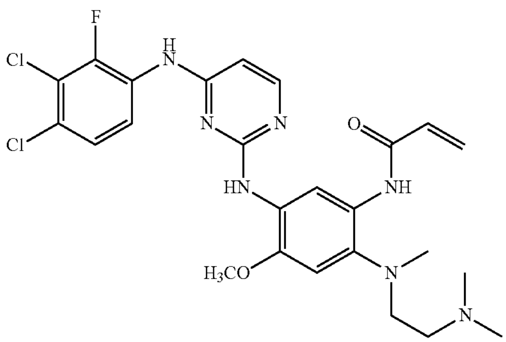 [SMILES: C=CC(=O)Nc1cc(Nc2nccc(Nc3ccc(Cl)c(Cl)c3F)n2)c(OC)cc1N(C)CCN(C)C] | N-(5-(4-(3,4-dichloro-2-fluorophenylamino)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.23 (s, 6H), 2.32 (t, 2H), 2.70 (s, 3H), 2.88 (t, 2H), 3.78 (s, 3H), 5.72 (dd, 1H), 6.17 (dd, 1H), 6.34-6.42 (m, 2H), 6.99 (s, 1H), 7.17 (d, 1H), 7.93 (s, 1H), 8.03 (d, 1H), 8.19 (t, 1H), 8.56 (s, 1H), 9.32 (s, 1H), 10.11 (s, 1H). m/z: ESI MH$^+$ 548.1 |
| 16 | 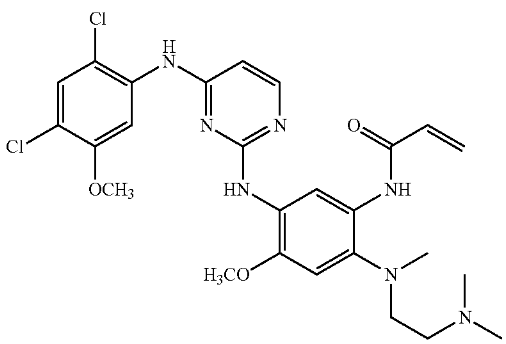 [SMILES: C=CC(=O)Nc1cc(Nc2nccc(Nc3cc(OC)c(Cl)cc3Cl)n2)c(OC)cc1N(C)CCN(C)C] | N-(5-(4-(2,4-dichloro-5-methoxyphenyl-amino)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.21 (s, 6H), 2.29 (t, 2H), 2.68 (s, 3H), 2.84 (t, 2H), 3.66 (s, 3H), 3.77 (s, 3H), 5.70 (dd, 1H), 6.15 (dd, 1H), 6.33 (dd, 1H), 6.39 (d, 1H), 6.93 (s, 1H), 7.54 (s, 1H), 7.71 (s, 1H), 7.75 (s, 1H), 8.03 (d, 1H), 8.70 (s, 1H), 8.88 (s, 1H), 10.06 (s, 1H). m/z: ESI MH$^+$ 560.1 |
| 17 | 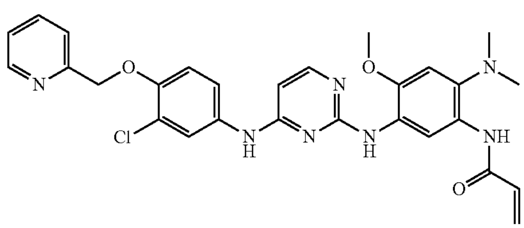 [SMILES: C=CC(=O)Nc1cc(Nc2nccc(Nc3ccc(OCc4ccccn4)c(Cl)c3)n2)c(OC)cc1N(C)C] | N-(5-(4-(3-chloro-4-(pyridin-2-ylmethoxy)-phenylamino)-pyrimidin-2-ylamino)-2-dimethylamino-4-methoxyl-phenyl)-acrylamide | $^1$H-NMR (DMSO-d$_6$): 2.64 (s, 3H), 3.81 (s, 3H), 5.20 (s, 2H), 5.63-5.66 (d, 1H), 6.09-6.10 (d, 1H), 6.13-6.17 (dd, 1H), 6.66-6.72 (m, 1H), 6.82 (s, 1H), 7.03-7.05 (d, 1H), 7.35-7.38 (t, 1H), 7.54-7.56 (d, 1H), 7.57-7.60 (dd, 1H), 7.67 (s, 1H), 7.82 (s, 1H), 7.85-7.89 (t, 1H), 7.92-7.93 (d, 1H), 8.28 (s, 1H), 8.59-8.60 (d, 1H), 9.25-9.27 (m, 2H). m/z: ESI MH$^+$ 546.2 |
| 18 | 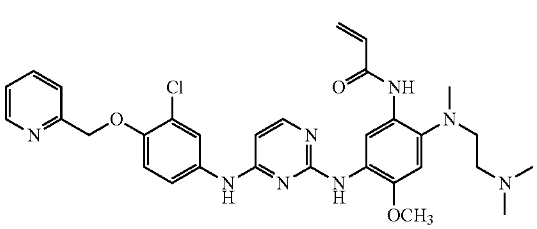 [SMILES: C=CC(=O)Nc1cc(Nc2nccc(Nc3ccc(OCc4ccccn4)c(Cl)c3)n2)c(OC)cc1N(C)CCN(C)C] | N-(5-(4-(3-chloro-4-(pyridin-2-ylmethoxyl) phenylamino)-pyrimidin-2-ylamino)-2-((2-(dimethylamino) ethyl)(methyl) amino)-4-methoxyl-phenyl)-acrylamide | 1H-NMR (DMSO-d$_6$) δ: 2.26 (s, 6H), 2.33 (t, 2H), 2.69 (s, 3H), 2.93 (t, 2H), 3.81 (s, 3H), 5.19 (s, 2H), 5.71 (dd, 1H), 6.10 (d, 1H), 6.19 (dd, 1H), 6.44 (dd, 1H), 6.98 (s, 1H), 7.04 (d, 1H), 7.36 (m, 1H), 7.53-7.57 (m, 2H), 7.73 (d, 1H), 7.85 (s, 1H), 7.87 (m, 1H), 7.95 (d, 1H), 8.60 (br, 2H), |

| Comp. | Structure | Name | Data |
|---|---|---|---|
| | | | 9.31 (s, 1H), 9.98 (s, 1H). m/z: ESI MH+ 603.1 |
| 19 | 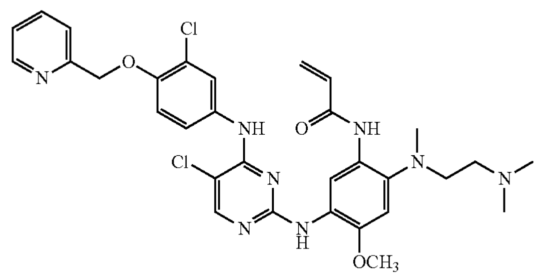 [SMILES: C=CC(=O)Nc1cc(Nc2ncc(Cl)c(Nc3ccc(OCc4ccccn4)c(Cl)c3)n2)c(OC)cc1N(C)CCN(C)C] | N-(5-(5-chloro-4-(3-chloro-4-(pyridin-2-methoxyl)phenylamino)-pyrimidin-2-ylamino)-2-((2-(dimethylamino)ethyl)(methyl)amino)-4-methoxyl-phenyl)-acrylamide | $^1$H-NMR (DMSO-d$_6$) δ: 2.17 (s, 6H), 2.30 (t, 2H), 2.69 (s, 3H), 2.86 (t, 2H), 3.76 (s, 3H), 5.19 (s, 2H), 5.68 (dd, 1H), 6.17 (d, 1H), 6.37 (dd, 1H), 6.97 (s, 1H), 7.00 (d, 1H), 7.37 (m, 1H), 7.54 (d, 1H), 7.61 (d, 1H), 7.73 (d, 1H), 7.85 (s, 1H), 8.06 (s, 1H), 8.13 (s, 1H), 8.40 (s, 1H), 8.59 (d, 1H), 8.68 (s, 1H), 10.01 (s, 1H). m/z: ESI MH+ 637.5 |
| 20 | 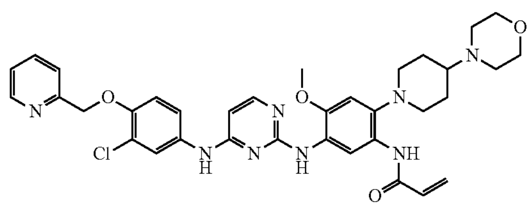 [SMILES: C=CC(=O)Nc1cc(Nc2nccc(Nc3ccc(OCc4ccccn4)c(Cl)c3)n2)c(OC)cc1N1CCC(N2CCOCC2)CC1] | N-(5-(4-(3-chloro-4-(pyridin-2-ylmethoxy)-phenylamino)-pyrimidin-2-ylamino)-2-(4-morpholin-4-yl)-piperidin-1-yl)-4-methoxyl-phenyl)-acrylamide | $^1$H-NMR (CDCl$_3$-d) δ: 1.67 (m, 2H), 2.08 (m, 2H), 2.32 (m, 1H), 2.64 (m, 4H), 2.74 (m, 2H), 3.05 (m, 2H), 3.81 (m, 4H), 3.88 (s, 3H), 5.29 (s, 2H), 5.75 (dd, 1H), 6.09 (d, 1H), 6.29 (m, 1H), 6.37 (d, 1H), 6.74 (s, 1H), 6.96 (d, 1H), 7.21 (m, 2H), 7.27 (m, 1H), 7.44 (m, 2H), 7.67 (d, 1H), 7.78 (m, 1H), 8.03 (d, 1H), 8.55 (s, 1H), 8.62 (d, 1H), 9.65 (s, 1H). m/z: ESI MH+ 671.2 |
| 21 | 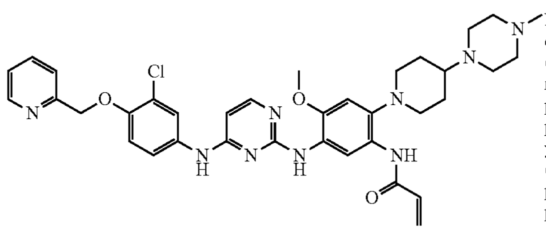 [SMILES: C=CC(=O)Nc1cc(Nc2nccc(Nc3ccc(OCc4ccccn4)c(Cl)c3)n2)c(OC)cc1N1CCC(N2CCN(C)CC2)CC1] | N-(5-(4-(3-chloro-4-(pyridin-2-yl-methoxy)-phenylamino)-pyrimidin-2-ylamino)-2-(4-(4-methyl-piperazin-1-yl)-piperidin-1-yl)-4-methoxyl-phenyl)-acrylamide | $^1$H-NMR (DMSO-d$_6$) δ: 1.68-1.77 (m, 2H), 1.87-1.89 (m, 2H), 1.98-2.03 (m, 1H), 2.45 (s, 3H), 2.50-2.53 (m, 2H), 2.65-2.73 (m, 8H), 3.04-3.06 (m, 2H), 3.79 (s, 3H), 5.20 (s, 2H), 5.68 (dd, 1H), 6.11 (d, 1H), 6.15-6.19 (dd, 1H), 6.61-6.68 (m, 1H), 6.83 (s, 1H), 7.05 (d, 1H), 7.37 (m, 1H), 7.56 (m, 2H), 7.69 (d, 1H), 7.84-7.89 (m, 2H), 7.94 (d, 1H), 8.32 (s, 1H), 8.59 (m, 1H), 8.96 (s, 1H), 9.32 (d, 1H). m/z: ESI MH+ 684.2 |
| 22 | 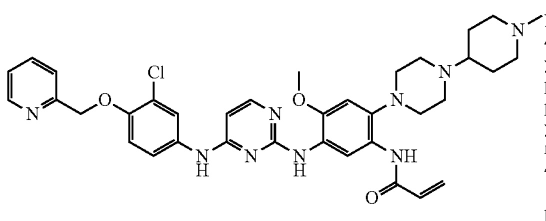 | N-(5-(4-(3-chloro-4-(pyridin-2-ylmethoxy)-phenylamino)-pyrimidin-2-ylamino)-2-(4-(1-methylpiperidin-4-yl)-piperazin-1-yl)-4-methoxyl-phenyl)-acrylamide | $^1$H-NMR (CDCl$_3$-d) δ: 9.68 (d, 1H), 8.62 (d, 1H), 8.57 (s, 1H), 8.04 (m, 1H), 7.80 (m, 1H), 7.68 (d, 1H), 7.46 (m, 2H), 7.23 (m, 2H), 7.09 (m, 1H), 6.96 (d, 1H), 6.78 (s, 1H), 6.38 (d, 1H), 6.28 (m, 1H), 6.12 (d, 1H), 5.76 (dd, 1H), 5.29 (s, 2H), 3.87 (s, 3H), 3.25 (m, 2H), 2.92 (m, 4H), 2.76 (m, 4H), 2.57 (m, 5H), 2.24 (m, 1H), 2.05 (m, 4H). m/z: ESI MH+ 684.4 |

| Comp. | Structure | Name | Data |
|---|---|---|---|
| 23 | 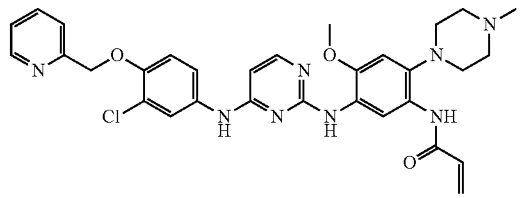 [SMILES: C=CC(=O)Nc1cc(Nc2nccc(Nc3ccc(OCc4ccccn4)c(Cl)c3)n2)c(OC)cc1N1CCN(C)CC1] | N-(5-(4-(3-chloro-4-(pyridin-2-ylmethoxy)-phenylamino)-pyrimidin-2-ylamino)-2-(4-methylpiperazin-1-yl)-4-methoxyl-phenyl)-acrylamide | 1H-NMR (DMSO-d₆) δ: 2.25 (s, 3H), 2.52 (s, 4H), 2.85 (s, 4H), 3.81 (s, 3H), 5.20 (s, 2H), 5.66-5.69 (d, 1H), 6.10-6.12 (d, 1H), 6.13-6.18 (1H, d), 6.55-6.62 (1H, m), 6.84 (s, 1H), 7.05-7.07 (1H, d), 7.35-7.38 (1H, t), 7.54-7.56 (t, 2H), 7.69 (s, 1H), 7.82 (s, 1H), 7.85-7.89 (1H, t), 7.93-7.94 (1H, d), 8.31 (s, 1H), 8.59-8.60 (1H, d), 8.97 (s, 1H), 9.29 (s, 1H); m/z: ESI MH⁺ 601.2 |
| 24 | 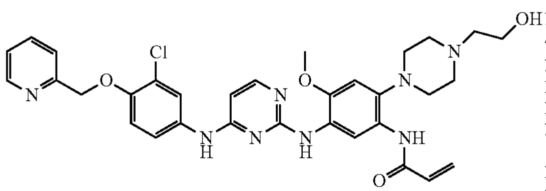 | N-(5-(4-(3-chloro-4-(pyridin-2-ylmethoxy)-phenylamino)-pyrimidin-2-ylamino)-2-(4-(2-hydroxyethyl)piperazin-1-yl)-4-methoxyl-phenyl)-acrylamide | ¹H-NMR (CDCl₃-d) δ: 9.64 (s, 1H), 8.61 (m, 2H), 8.03 (d, 1H), 7.78 (m, 1H), 7.67 (d, 1H), 7.54 (s, 1H), 7.46 (d, 1H), 7.23 (m, 2H), 6.96 (d, 1H), 6.78 (s, 1H), 6.36 (dd, 1H), 6.31 (m, 1H), 6.11 (d, 1H), 5.76 (dd, 1H), 5.29 (s, 2H), 3.89 (s, 3H), 3.12 (t, 2H), 2.96 (m, 4H), 2.77 (m, 4H), 2.70 (t, 2H). m/z: ESI MH⁺ 631.2 |
| 25 | 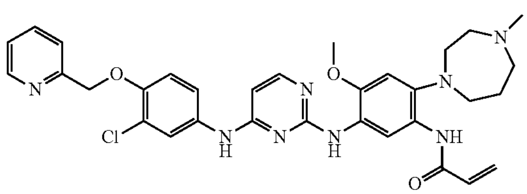 [SMILES: C=CC(=O)Nc1cc(Nc2nccc(Nc3ccc(OCc4ccccn4)c(Cl)c3)n2)c(OC)cc1N1CCCN(C)CC1] | N-(5-(4-(3-chloro-4-(pyridin-2-ylmethoxy)-phenylamino)-pyrimidin-2-ylamino)-2-(4-methyl-[1,4]diazepin-1-yl)-4-methoxyl-phenyl)-acrylamide | ¹H-NMR (CDCl₃-d) δ: 1.27 (m, 3H), 1.97 (m, 2H), 2.78 (m, 4H), 3.14 (m, 4H), 3.85 (s, 3H), 5.27 (s, 2H), 5.74 (dd, 1H), 6.09 (dd, 1H), 6.40 (dd, 1H), 6.75 (s, 1H), 6.90 (d, 1H), 7.27 (m, 2H), 7.39 (m, 1H), 7.45 (m, 1H), 7.60 (m, 1H), 7.67 (d, 1H), 7.77 (m, 1H), 7.98 (d, 1H), 8.61 (s, 1H), 9.01 (d, 1H), 9.51 (s, 1H). m/z: ESI MH⁺ 615.2 |
| 26 | 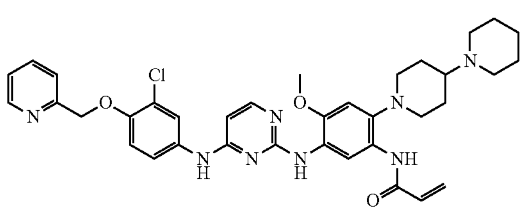 [SMILES: C=CC(=O)Nc1cc(Nc2nccc(Nc3ccc(OCc4ccccn4)c(Cl)c3)n2)c(OC)cc1N1CCC(N2CCCCC2)CC1] | N-(5-(4-(3-chloro-4-(pyridin-2-ylmethoxy)-phenylamino)-pyrimidin-2-ylamino)-2-(4-(piperidin-1-yl)-piperidin-1-yl)-4-methoxyl-phenyl)-acrylamide | ¹H-NMR (DMSO-d₆) δ: 9.70 (s, 1H), 9.34 (s, 1H), 9.00 (s, 1H), 8.61 (dd, 1H), 8.34 (s, 1H), 7.94 (d, 1H), 7.88 (d, 1H), 7.73 (d, 1H), 7.55 (d, 2H), 7.38 (m, 1H), 7.07 (d, 1H), 6.83 (s, 1H), 6.65 (m, 1H), 6.21 (d, 1H), 6.17 (d, 1H), 5.70 (d, 1H), 5.21 (s, 2H), 3.81 (s, 3H), 3.13 (m, 2H), 3.00 (m, 2H), 2.73 (m, 2H), 2.50 (m, 2H), 2.11 (m, 2H), 1.98 (m, 3H), 1.80 (m, 4H), 1.46 (m, 2H). m/z: ESI MH⁺ 669.2 |

TABLE 1-continued

| Comp. | Structure | Name | Data |
|---|---|---|---|
| 27 | 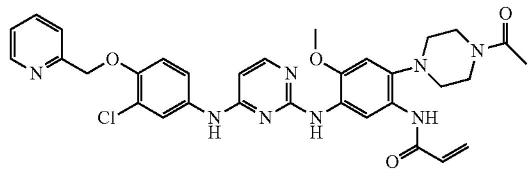 [SMILES: C=CC(=O)Nc1cc(Nc2nccc(Nc3ccc(OCc4ccccn4)c(Cl)c3)n2)c(OC)cc1N1CCN(C(C)=O)CC1] | N-(5-(4-(3-chloro-4-(pyridin-2-ylmethoxy)-phenylamino)-pyrimidin-2-ylamino)-2-(4-acetylpiperazin-1-yl)-4-methoxyl-phenyl)-acrylamide | $^1$H-NMR (CDCl$_3$-d) δ: 2.18 (s, 3H), 2.88 (m, 4H), 3.66 (br, 2H), 3.82 (br, 2H), 3.88 (s, 3H), 5.29 (s, 2H), 5.76 (dd, 1H), 6.11 (dd, 1H), 6.28 (m, 1H), 6.38 (d, 1H), 6.70 (s, 1H), 6.96 (d, 1H), 7.22 (d, 1H), 7.27 (br, 2H), 7.45 (d, 1H), 7.55 (br, 1H), 7.68 (d, 1H), 7.79 (m, 1H), 8.04 (d, 1H), 8.54 (s, 1H), 8.62 (d, 1H), 9.67 (s, 1H). m/z: ESI MH$^+$ 629.3 |
| 28 | 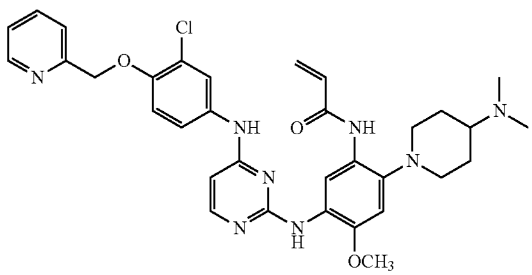 [SMILES: C=CC(=O)Nc1cc(Nc2nccc(Nc3ccc(OCc4ccccn4)c(Cl)c3)n2)c(OC)cc1N1CCC(N(C)C)CC1] | N-(5-(4-(3-chloro-4-(pyridin-2-ylmethoxy)-phenylamino)-pyrimidin-2-ylamino)-2-(4-(dimethylamino)piperazin-1-yl)-4-methoxyl-phenyl)-acrylamide | $^1$H-NMR (DMSO-d$_6$) δ: 1.64-1.72 (m, 2H), 1.84 (d, 2H), 2.16-2.23 (m, 7H), 2.66 (t, 2H), 3.03 (t, 2H), 3.79 (s, 3H), 5.19 (s, 2H), 5.68 (dd, 1H), 6.09-6.19 (m, 2H), 6.63 (dd, 1H), 6.83 (s, 1H), 7.04 (d, 1H), 7.37 (m, 1H), 7.53-7.58 (m, 2H), 7.67 (d, 1H), 7.83-7.90 (m, 2H), 7.93 (d, 1H), 8.32 (s, 1H), 8.58 (d, 1H), 8.97 (s, 1H), 9.29 (s, 1H). m/z: ESI MH$^+$ 629.2 |
| 29 | 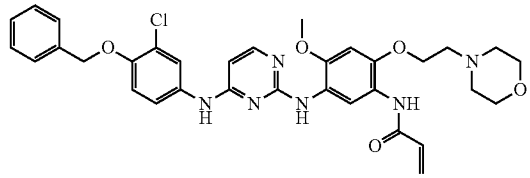 [SMILES: C=CC(=O)Nc1cc(Nc2nccc(Nc3ccc(OCc4ccccc4)c(Cl)c3)n2)c(OC)cc1OCCN1CCOCC1] | N-(5-(-4-(3-chloro-4-(benzene-2-methoxyl)-phenylamino)-pyrimidin-2-ylamino)-2-(2-(morpholin-4-yl)-ethoxyl)-4-methoxyl-phenyl)-acrylamide | $^1$H-NMR (CDCl$_3$-d) δ: 2.50 (m, 4H), 2.74 (m, 2H), 3.56-3.58 (m, 4H), 3.81 (s, 3H), 4.20 (t, 2H), 5.19 (m, 2H), 5.6 (d, 1H), 6.08 (dd, 1H), 6.15 (dd, 1H), 6.56 (dd, 1H), 6.86 (s, 1H), 7.06 (d, 1H), 7.38 (m, 1H), 7.54 (m, 2H), 7.71 (d, 1H), 7.85-7.88 (m, 2H), 7.91 (m, 1H), 8.20 (s, 1H), 8.61 (m, 1H), 9.18 (s, 1H), 9.27 (s, 1H). m/z: ESI MH$^+$ 632.2 |
| 30 | 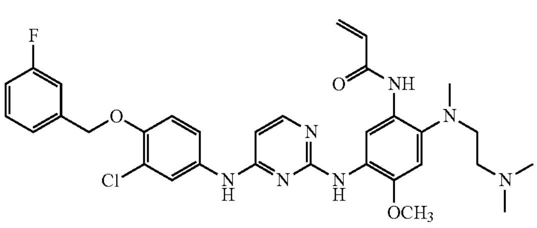 [SMILES: C=CC(=O)Nc1cc(Nc2nccc(Nc3ccc(OCc4cccc(F)c4)c(Cl)c3)n2)c(OC)cc1N(C)CCN(C)C] | N-(5-(4-(3-chloro-4-(3-fluorobenzyloxy)phenylamino)pyrimidin-2-ylamino)-2-((2-(dimethylamino)ethyl)(methyl)amino-4-methoxyl-phenyl)-acrylamide | $^1$H-NMR (DMSO-d$_6$) δ: 2.19 (s, 6H), 2.31 (t, 2H), 2.70 (s, 3H), 2.86 (t, 2H), 3.80 (s, 3H), 5.14 (s, 2H), 5.70 (dd, 1H), 6.12 (d, 1H), 6.18 (dd, 1H), 6.39 (dd, 1H), 6.98 (s, 1H), 7.04 (d, 1H), 7.18 (m, 1H), 7.25-7.30 (m, 2H), 7.43-7.54 (m, 2H), 7.76 (d, 1H), 7.85 (s, 1H), 7.94 (d, 1H), 8.63 (s, 1H), 9.29 (s, 1H), 10.04 (s, 1H). m/z: ESI MH$^+$ 620.2 |

TABLE 1-continued

| Comp. | Structure | Name | Data |
|---|---|---|---|
| 31 | 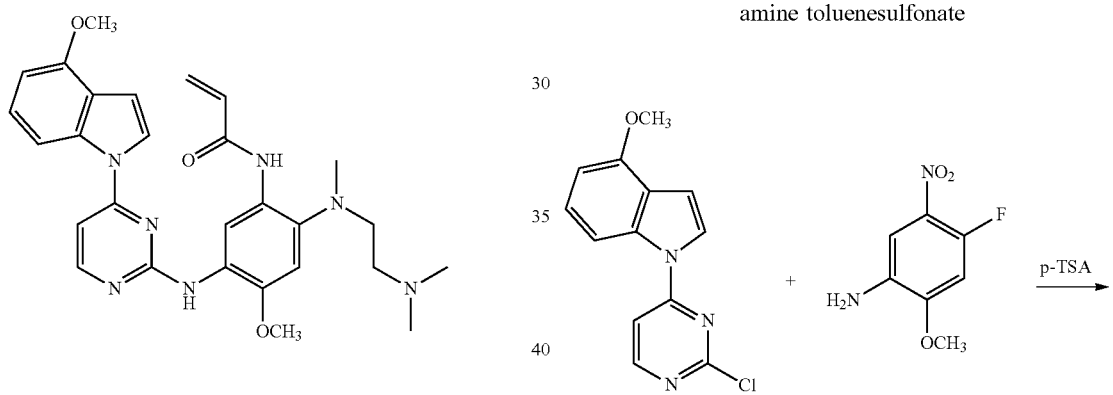 | N-(2-((2-(dimethyl-amino-ethyl)-methyl-amino)-5-(4-(indolin-1-yl)-pyrimidin-2-ylamino)-4-methoxyl-phenyl)-acrylamide | $^1$H-NMR (DMSO-d$_6$) δ: 2.21 (s, 6H), 2.33 (t, 2H), 2.73 (s, 3H), 2.90 (t, 2H), 3.16 (t, 2H), 3.78 (s, 3H), 4.00 (t, 2H), 5.71 (dd, 1H), 6.15-6.21 (m, 2H), 6.39 (dd, 1H), 6.84 (t, 1H), 6.96 (t, 1H), 7.01 (s, 1H), 7.17 (d, 1H), 8.01 (s, 1H), 8.08-8.15 (m, 2H), 8.59 (s, 1H), 10.10 (s, 1H). m/z: ESI MH$^+$ 488.2 |

Example 6

Preparation of N-(5-(4-(4-methoxyl-1H-indol-1-yl)-pyrimidin-2-ylamino)-2-(2-(dimethylamino-ethyl)-methyl-amino)-4-methoxyl-phenyl)-acrylamide (Compound 99)

Compound 99

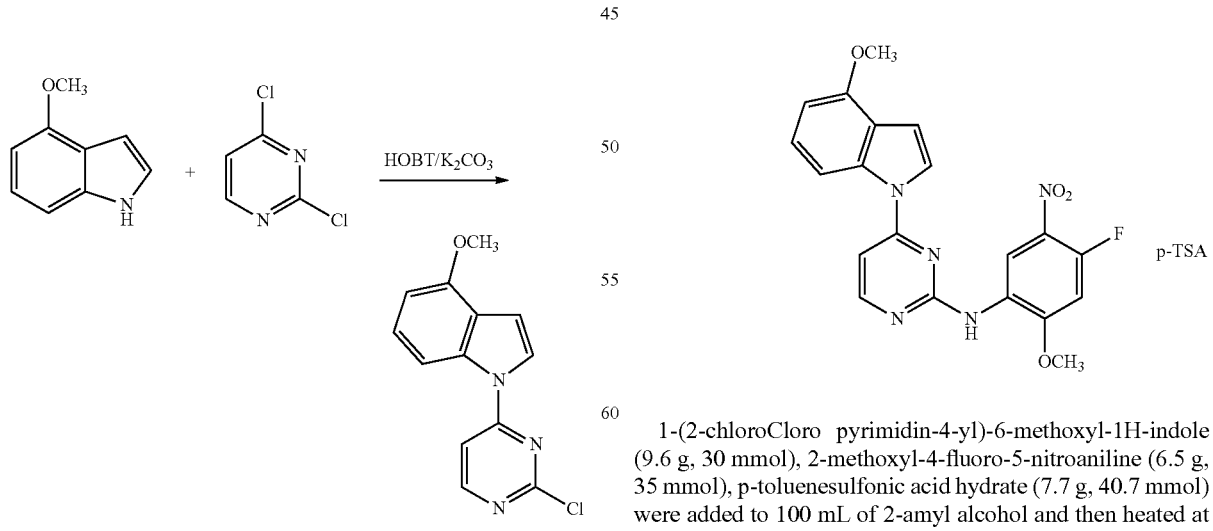

Step 1: Preparation of 1-(2-chloropyrimidin-4-yl)-6-methoxyl-1H-indole

4-Methoxyl indole (4.5 g, 30 mmol), 2,4-dichloro pyrimidine (6.8 g, 45 mmol), HOBT (0.8 g, 6 mmol), anhydrous potassium carbonate (8.4 g, 60 mmol) were added to 25 mL of DMF and then stirred at 75° C. for 15 h. The reaction mixture was added with water and then filtered. The solid was added to 50 mL of isopropyl alcohol and stirred under reflux. The reaction mixture was cooled down to the room temperature and then filtered and dried to provide the crude intermediate (9.6 g). MS m/zES+MH+ 260.1.

Step 2: Preparation of (4-fluoro-2-methoxyl-5-nitro-phenyl)-[4-(4-methoxyl-indol-1-yl)-pyrimidin-2-yl]-amine toluenesulfonate 1-(2-chloroCloro pyrimidin-4-yl)-6-methoxyl-1H-indole (9.6 g, 30 mmol), 2-methoxyl-4-fluoro-5-nitroaniline (6.5 g, 35 mmol), p-toluenesulfonic acid hydrate (7.7 g, 40.7 mmol) were added to 100 mL of 2-amyl alcohol and then heated at 100° C. for 2 h. The reaction mixture was cooled to room temperature, and then filtered and dried to give the crude title product (11 g). MS m/z: ES+MH+ 410.1.

Step 3: Preparation of N⁴-(2-dimethylaminoethyl)-2-methoxyl-N-(4-(4-methoxyl-indol-1-yl)-pyrimidin-2-yl)-N⁴-methyl-5-nitro-1,4-phenylenediamine

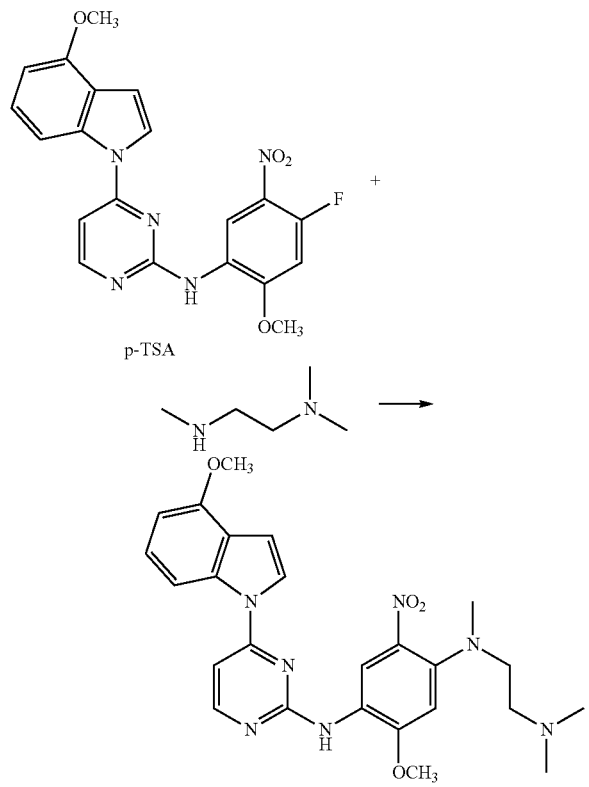

(4-Fluoro-2-methoxyl-5-nitro-phenyl)-(4-(4-methoxyl-indol-1-yl)-pyrimidin-2-yl)-amine toluenesulfonate (1.1 g, 1.89 mmol), trimethyl ethylenediamine (0.27 g, 2.64 mmol) and potassium carbonate (0.65 g, 4.7 mmol) were added to 5 mL of DMF and then heated at 70° C. for 4 h. The reaction mixture was cooled to room temperature, and then added with water and ethyl acetate. The ethyl acetate layer was dried and concentrated. The residues were purified by column chromatography to give the title intermediate (0.4 g). MS m/z: ES+MH+ 492.2.

Step 4: Preparation of N¹-(2-dimethylaminoethyl)-5-methoxyl-N⁴-(4-(4-methoxyl-indol-1-yl)-pyrimidin-2-yl)-N¹-methyl-1,2,4-benzenetriamine

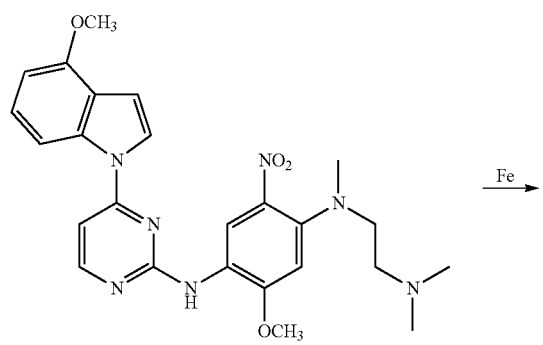

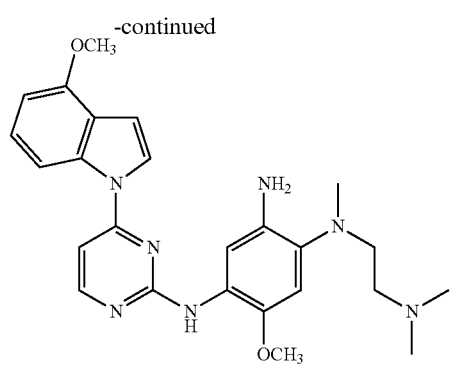

N⁴-(2-dimethylaminoethyl)-2-methoxyl-N-(4-(4-methoxyl-indol-1-yl)-pyrimidin-2-yl)-N⁴-methyl-5-nitro-1,4-phenylenediamine (0.4 g, 0.8 mmol), iron powder (0.34 g, 6 mmol) and ammonium chloride (0.33 g, 6 mmol) were added to 10 mL of ethanol and then heated at 70° C. for 2 h. The iron sludge was filtered out and the filtrate was concentrated. The residues were purified by column chromatography to give the title intermediate (0.15 g). MS m/z: ES+MH+ 462.3.

Step 5: Preparation of N-(5-(4-(4-methoxyl-1H-indol-1-yl)-pyrimidin-2-ylamino)-2-(2-(dimethyl-amino-ethyl)-methyl-amino)-4-methoxyl-phenyl)-acrylamide

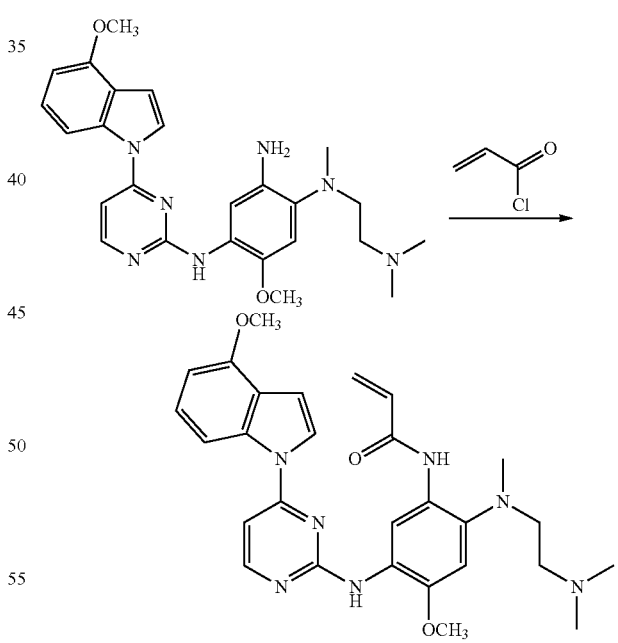

Add N¹-(2-dimethylaminoethyl)-5-methoxyl-N⁴-[4-(4-methoxyl-indol-1-yl)-pyrimidin-2-yl]-N¹-methyl-1,2,4-benzenetriamine (0.15 g, 0.32 mmol) and N,N-diisopropyl ethylamine (0.13 g, 1 mmol) were added to 3 mL of tetrahydrofuran, and then added with acryloyl chloride at 0° C. (45 mg, 0.5 mmol). The mixture was stirred for 2 h, and then added with water and ethyl acetate. A column chromatography gives the title compound (45 mg).

Example 7

Preparation of N-(5-(4-(6-fluoro-1H-indol-1-yl)-pyrimidin-2-ylamino)-2-(2-(morpholin-4-yl)-ethoxyl)-4-methoxyl-phenyl)-acrylamide (compound 75)

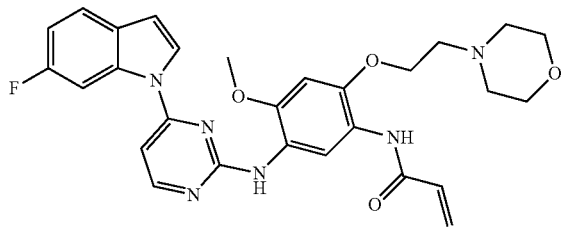

Compound 75

Step 1 and 2: Preparation of N-(4-(6-fluoro-1H-indol-1-yl) pyrimidin-2-yl)-4-fluoro-2-methoxyl-5-nitroaniline Steps 1 and 2 are the same as that in Example 6 except for replacing 4-methoxylindole with 6-fluoroindole.

Step 3: Synthesis of N-(4-(6-fluoro-1H-indol-1-yl) pyrimidin-2-yl)-4-(2-morpholin-4-yl-ethoxyl)-2-methoxyl-5-nitroaniline

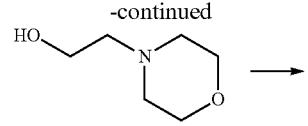

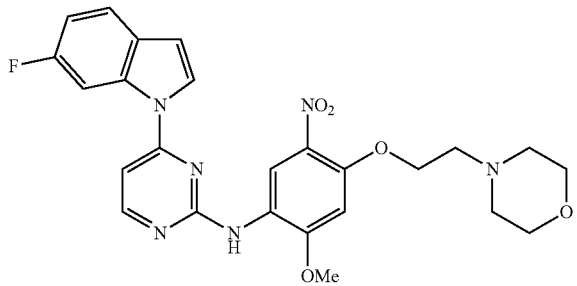

N-(4-(6-fluoro-1H-indol-1-yl)pyrimidin-2-yl)-4-fluoro-2-methoxyl-5-nitroaniline (1.1 g, 2 mmol), 2-(morpholin-4-yl) ethanol (0.39 g, 3 mmol) and sodium hydroxide (0.2 g, 5 mmol) were added to 5 mL of DMF, and then heated under oil bath at 60° C. for 3 h. The reaction mixture was added with water and ethyl acetate. The organic layer was dried and then concentrated. The residues were purified by column chromatography to give the title intermediate (0.45 g). m/z: ESI MH$^+$ 508.2, Steps 4 and 5 of Example 6 were repeated to give the title compound.

Compounds 32-52, 57-73, 77-95, 98-105 in Table 2 were prepared following the method in Example 6.

Compounds 53-56, 74-76, 96-97 in Table 2 were prepared following the method in Example 7.

TABLE 2

| Comp. | Structure | Name | Data |
|---|---|---|---|
| 32 | 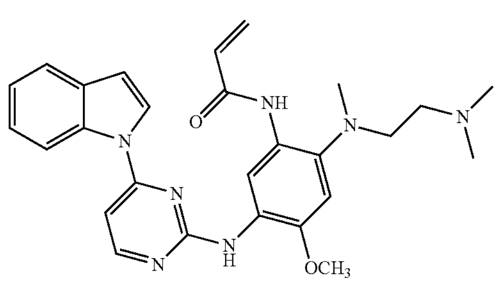 [SMILES: C=CC(=O)Nc1cc(Nc2nccc(-n3ccc4ccccc43)n2)c(OC)cc1N(C)CCN(C)C] | N-(5-(4-(-1H-indol-1-yl)-pyrimidin-2-ylamino)-2-((2-(dimethyl-amino)-ethyl-methyl-amino)-4-methoxyl-phenyl)-acrylamide | $^1$H-NMR (DMSO-d$_6$) δ: 2.22 (s, 6H), 2.31 (t, 2H), 2.75 (s, 3H), 2.91 (t, 2H), 3.77 (s, 3H), 5.74 (dd, 1H), 6.21 (dd, 1H), 6.41 (dd, 1H), 6.78 (d, 1H), 7.06-7.17 (m, 4H), 7.59 (d, 1H), 8.14 (d, 1H), 8.38-8.40 (m, 2H), 8.50 (d, 2H), 8.67 (s, 1H), 10.11 (s, 1H). m/z: ESI MH$^+$ 486.6 |

TABLE 2-continued

| Comp. | Structure | Name | Data |
|---|---|---|---|
| 33 | 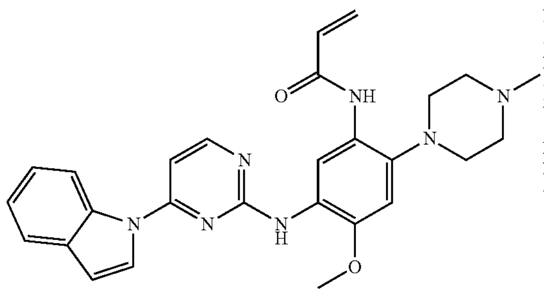 | N-(5-(4-(1H-indol-1-yl)-pyrimidin-2-ylamino)-4-methoxyl-2-(4-methyl-piperazin-1-yl)-phenyl)-acrylamide | $^1$H-NMR (DMSO-d$_6$) δ: 2.28 (s, 3H), 2.57 (s, 4H), 2.90-2.92 (t, 4H), 3.79 (s, 3H), 5.70-5.72 (dd, 1H), 6.16-6.21 (dd, 1H), 6.59-6.66 (m, 1H), 6.77-6.78 (d, 1H), 6.90 (s, 1H), 7.12-7.18 (m, 3H), 7.58-7.60 (dd, 1H), 8.12-8.13 (d, 1H), 8.21 (s, 1H), 8.38-8.39 (d, 1H), 8.41 (s, 1H), 8.63 (s, 1H), 9.03 (s, 1H). m/z: ESI MH$^+$ 484.2 |
| 34 | 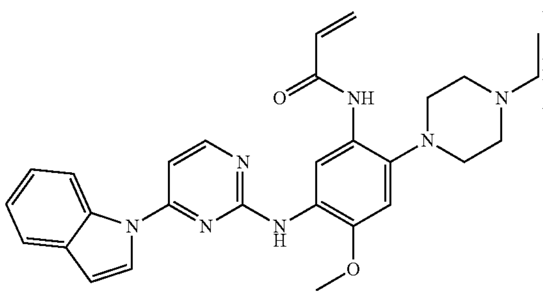 | N-(5-(4-(1H-indol-1-yl)-pyrimidin-2-ylamino)-4-methoxyl-2-(4-ethyl-piperazin-1-yl)-phenyl)-acrylamide | $^1$H-NMR (DMSO-d$_6$) δ: 1.03-1.07 (t, 3H), 2.40-2.45 (q, 2H), 2.61 (s, 4H), 2.91 (s, 4H), 3.79 (s, 3H), 5.69-5.72 (d, 1H), 6.16-6.20 (d, 1H), 6.59-6.66 (m, 1H), 6.77-6.78 (d, 1H), 6.91 (s, 1H), 7.12-7.18 (m, 3H), 7.58-7.59 (d, 1H), 8.12-8.13 (d, 1H), 8.22 (s, 1H), 8.38-8.39 (d, 1H), 8.41 (s, 1H), 8.63 (s, 1H), 9.04 (s, 1H). m/z: ESI MH$^+$ 498.2 |
| 35 | 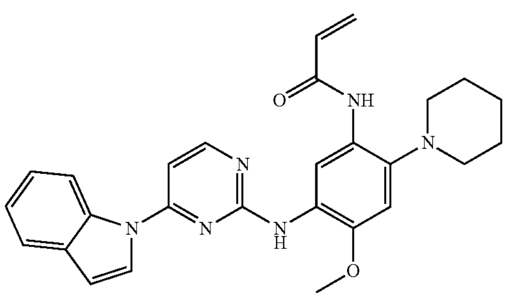 [SMILES: C=CC(=O)Nc1cc(Nc2nccc(-n3ccc4ccccc43)n2)c(OC)cc1N1CCCCC1] | N-(5-(4-(1H-indol-1-yl)-pyrimidin-2-ylamino)-4-methoxyl-2-(piperidin-1-yl)-phenyl)-acrylamide | $^1$H-NMR (DMSO-d$_6$) δ: 1.56 (s, 2H), 1.75 (t, 4H), 2.84-2.86 (t, 4H), 3.78 (s, 3H), 5.70-5.73 (d, 1H), 6.17-6.21 (d, 1H), 6.62-6.68 (m, 1H), 6.77-6.78 (d, 1H), 6.89 (s, 1H), 7.10-7.18 (m, 3H), 7.58-7.60 (d, 1H), 8.12-8.13 (d, 1H), 8.25 (s, 1H), 8.37-8.39 (d, 1H), 8.42 (s, 1H), 8.62 (s, 1H), 9.01 (s, 1H). m/z: ESI MH$^+$ 469.2 |
| 36 | 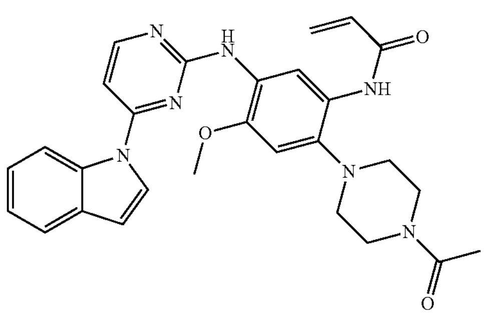 [SMILES: C=CC(=O)Nc1cc(Nc2nccc(-n3ccc4ccccc43)n2)c(OC)cc1N1CCN(C(C)=O)CC1] | N-(5-(4-(1H-indol-1-yl)-pyrimidin-2-ylamino)-4-methoxyl-2-(4-acetyl-piperazin-1-yl)-phenyl)-acrylamide | $^1$H-NMR (DMSO-d$_6$) δ: 2.07 (s, 3H), 2.85-2.89 (dt, 4H), 3.68-3.69 (q, 4H), 3.78 (s, 3H), 5.71-5.74 (d, 1H), 6.18-6.22 (dd, 1H), 6.65-6.72 (m, 1H), 6.77-6.78 (d, 1H), 6.93 (s, 1H), 7.12-7.18 (m, 3H), 7.58-7.60 (dd, 1H), 8.12-8.13 (d, 1H), 8.33 (s, 1H), 8.38-8.40 (d, 1H), 8.42 (s, 1H), 8.64 (s, 1H), 9.16 (s, 1H). m/z: ESI MH$^+$ 512.2 |

TABLE 2-continued

| Comp. | Structure | Name | Data |
|---|---|---|---|
| 37 | 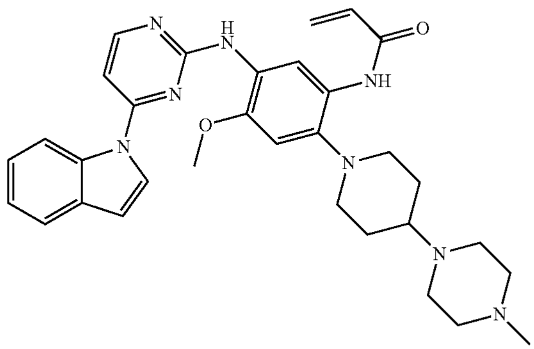 [SMILES: C=CC(=O)Nc1cc(Nc2nccc(-n3ccc4ccccc43)n2)c(OC)cc1N1CCC(N2CCN(C)CC2)CC1] | N-(5-(4-(1H-indol-1-yl)-pyrimidin-2-ylamino)-4-methoxyl-2-(4-(4-methyl-piperazin-1-yl)-piperidin-1-yl)-phenyl)-acrylamide | ¹H-NMR (DMSO-d₆) δ: 1.23 (s, 3H), 1.72-1.78 (d, 2H), 1.89-1.91 (d, 2H), 1.99 (t, 1H), 2.61 (t, 2H), 2.70-2.76 (t, 4H), 3.10-3.12 (d, 2H), 3.42 (t, 4H), 3.77 (s, 3H), 5.70-5.73 (d, 1H), 6.17-6.22 (dd, 1H), 6.64-6.71 (m, 1H), 6.76-6.77 (d, 1H), 6.88 (s, 1H), 7.09-7.17 (m, 3H), 7.58-7.60 (dd, 1H), 8.12-81.3 (d, 1H), 8.24 (s, 1H), 8.37-8.39 (d, 1H), 8.41 (s, 1H), 8.62 (s, 1H), 9.02 (s, 1H). m/z: ESI MH⁺ 567.3 |
| 38 | 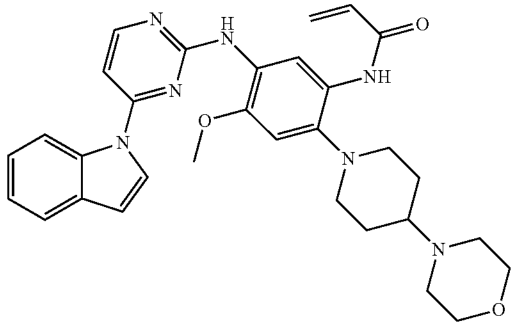 [SMILES: C=CC(=O)Nc1cc(Nc2nccc(-n3ccc4ccccc43)n2)c(OC)cc1N1CCC(N2CCOCC2)CC1] | N-(5-(4-(1H-indol-1-yl)-pyrimidin-2-ylamino)-4-methoxyl-2-(4-(morpholin-4-yl)-piperidin-1-yl)-phenyl)-acrylamide | ¹H-NMR (DMSO-d₆) δ: 1.76-1.77 (t, 2H), 1.93 (s, 2H), 2.56 (s, 4H), 2.68 (t, 1H), 2.70-2.75 (t, 2H), 3.09-3.12 (d, 2H), 3.63 (s, 4H), 3.78 (s, 3H), 5.70-5.73 (d, 1H), 6.16-6.21 (dd, 1H), 6.64-6.69 (m, 1H), 6.76-6.77 (d, 1H), 6.88 (s, 1H), 7.11-7.17 (m, 3H), 7.58-7.60 (dd, 1H), 8.11-8.12 (d, 1H), 8.24 (s, 1H), 8.37-8.39 (d, 1H), 8.40 (s, 1H), 8.62 (s, 1H), 9.03 (s, 1H). m/z: ESI MH⁺ 554.2 |
| 39 | 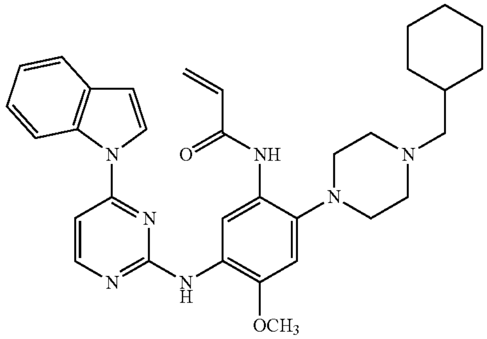 [SMILES: C=CC(=O)Nc1cc(Nc2nccc(-n3ccc4ccccc43)n2)c(OC)cc1N1CCN(CC2CCCCC2)CC1] | N-(5-(4-(1H-indol-1-yl)-pyrimidin-2-ylamino)-2-(4-(cyclohexyl methyl)-piperazin-1-yl)-4-methoxyl phenyl)-acrylamide | ¹H-NMR (DMSO-d₆) δ: 1.14-1.27 (m, 5H), 1.64-1.70 (m, 4H), 1.78 (d, 2H), 2.19 (d, 2H), 2.58 (br, 4H), 2.90 (br, 4H), 3.79 (s, 3H), 5.72 (dd, 1H), 6.18 (dd, 1H), 6.61 (dd, 1H), 6.77 (d, 1H), 6.93 (s, 1H), 7.10-7.18 (m, 3H), 7.59 (dd, 1H), 8.12 (d, 1H), 8.25 (s, 1H), 8.37-8.43 (m, 2H), 8.61 (s, 1H), 9.03 (s, 1H). m/z: ESI MH⁺ 565.2 |
| 40 | 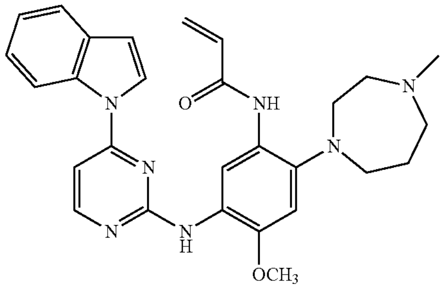 [SMILES: C=CC(=O)Nc1cc(Nc2nccc(-n3ccc4ccccc43)n2)c(OC)cc1N1CCCN(C)CC1] | N-(5-(4-(1H-indol-1-yl)-pyrimidin-2-ylamino)-4-methoxyl-2-(4-methyl-1,4-diazepin-1-yl)-phenyl)-acrylamide | ¹H-NMR (DMSO-d₆) δ: 1.90 (m, 2H), 2.36 (s, 3H), 2.72 (br, 4H), 3.19 (br, 4H), 3.78 (s, 3H), 5.73 (dd, 1H), 6.20 (dd, 1H), 6.59 (dd, 1H), 6.77 (d, 1H), 6.89 (s, 1H), 7.10-7.18 (m, 3H), 7.59 (dd, 1H), 8.09 (s, 1H), 8.12 (d, 1H), 8.37-8.42 (m, 2H), 8.57 (s, 1H), 9.19 (s, 1H). m/z: ESI MH⁺ 498.2 |

TABLE 2-continued

| Comp. | Structure | Name | Data |
|---|---|---|---|
| 41 | 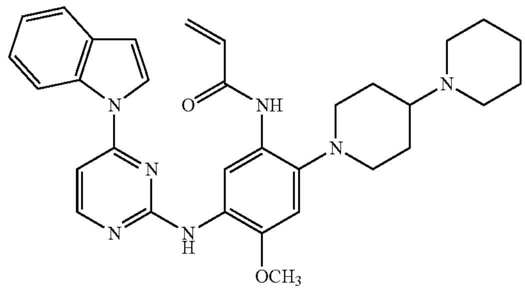 [SMILES: C=CC(=O)Nc1cc(Nc2nccc(-n3ccc4ccccc43)n2)c(OC)cc1N1CCC(N2CCCCC2)CC1] | N-(2-(1,4'-bipiperidin-1'-yl)-5-(4-(1H-indol-1-yl)-pyrimidin-2-ylamino)-4-methoxyl-phenyl)-acrylamide | $^1$H-NMR (DMSO-$d_6$) δ: 1.42 (m, 2H), 1.54 (br, 4H), 1.82 (br, 4H), 2.39 (m, 1H), 2.56 (br, 4H), 2.72 (t, 2H), 3.10 (d, 2H), 3.78 (s, 3H), 5.72 (dd, 1H), 6.19 (dd, 1H), 6.69 (dd, 1H), 6.77 (d, 1H), 6.88 (s, 1H), 7.10-7.18 (m, 3H), 7.59 (dd, 1H), 8.12 (d, 1H), 8.24 (s, 1H), 8.37-8.42 (m, 2H), 8.61 (s, 1H), 9.01 (s, 1H). m/z: ESI MH$^+$ 552.2 |
| 42 | 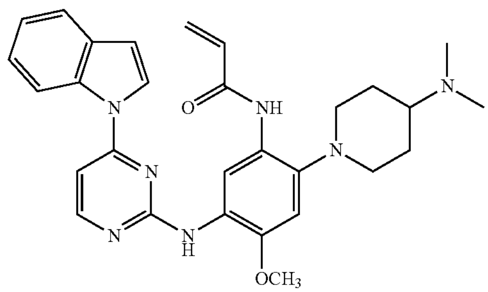 [SMILES: C=CC(=O)Nc1cc(Nc2nccc(-n3ccc4ccccc43)n2)c(OC)cc1N1CCC(N(C)C)CC1] | N-(5-(4-(1H-indol-1-yl) pyrimidin-2-ylamino)-2-(4-dimethylamine-piperidin-1-yl)-4-methoxyl-phenyl)-acrylamide | $^1$H-NMR (DMSO-$d_6$) δ: 1.75 (m, 2H), 1.88 (d, 2H), 2.79 (s, 7H), 2.72 (t, 2H), 3.10 (d, 2H), 3.78 (s, 3H), 5.72 (dd, 1H), 6.19 (dd, 1H), 6.68 (dd, 1H), 6.77 (d, 1H), 6.89 (s, 1H), 7.10-7.18 (m, 3H), 7.59 (dd, 1H), 8.12 (d, 1H), 8.24 (s, 1H), 8.37-8.42 (m, 2H), 8.62 (s, 1H), 9.04 (s, 1H). m/z: ESI MH$^+$ 512.2 |
| 43 | 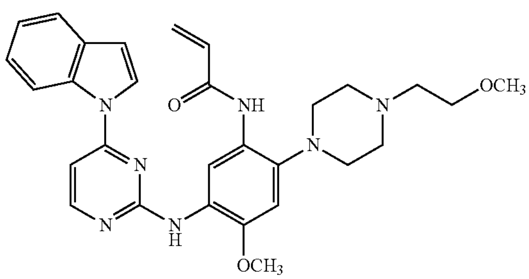 [SMILES: C=CC(=O)Nc1cc(Nc2nccc(-n3ccc4ccccc43)n2)c(OC)cc1N1CCN(CCOC)CC1] | N-(5-(4-(1H-indol-1-yl)-pyrimidin-2-ylamino)-2-(4-(2-methoxyl-ethyl)-piperazin-1-yl)-4-methoxyl-phenyl)-acrylamide | $^1$H-NMR (DMSO-$d_6$) δ: 2.57 (t, 2H), 2.67 (br, 4H), 2.90 (br, 4H), 3.26 (s, 3H), 3.49 (t, 2H), 3.79 (s, 3H), 5.71 (dd, 1H), 6.18 (dd, 1H), 6.63 (dd, 1H), 6.77 (d, 1H), 6.92 (s, 1H), 7.10-7.18 (m, 3H), 7.59 (dd, 1H), 8.11 (d, 1H), 8.23 (s, 1H), 8.37-8.42 (m, 2H), 8.62 (s, 1H), 9.04 (s, 1H). m/z: ESI MH$^+$ 528.2 |
| 44 | 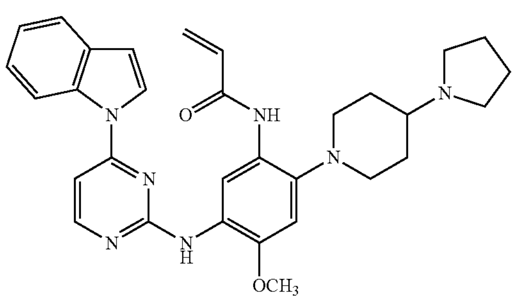 [SMILES: C=CC(=O)Nc1cc(Nc2nccc(-n3ccc4ccccc43)n2)c(OC)cc1N1CCC(N2CCCC2)CC1] | N-(5-(4-(1H-indol-1-yl) pyrimidin-2-ylamino)-2-(4-pyrrolidinyl-piperazin-1-yl)-4-methoxyl-phenyl)-acrylamide | $^1$H-NMR (DMSO-$d_6$) δ: 1.23 (s, 1H), 1.72-1.82 (m, 6H), 2.00 (d, 2H), 2.60-2.77 (m, 6H), 3.07 (d, 2H), 3.78 (s, 3H), 5.71 (dd, 1H), 6.19 (dd, 1H), 6.66 (dd, 1H), 6.77 (d, 1H), 6.90 (s, 1H), 7.10-7.18 (m, 3H), 7.59 (dd, 1H), 8.13 (d, 1H), 8.25 (s, 1H), 8.37-8.42 (m, 2H), 8.62 (s, 1H), 9.04 (s, 1H). m/z: ESI MH$^+$ 538.2 |
| 45 | 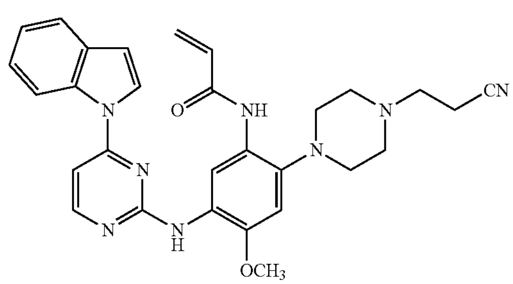 [SMILES: C=CC(=O)Nc1cc(Nc2nccc(-n3ccc4ccccc43)n2)c(OC)cc1N1CCN(CCC#N)CC1] | N-(5-(4-(1H-indol-1-yl)-pyrimidin-2-ylamino)-2-(4-(2-cyanoethyl)-piperazin-1-yl)-4-methoxyl-phenyl)-acrylamide | $^1$H-NMR (DMSO-$d_6$) δ: 2.68-3.75 (m, 8H), 2.92 (br, 4H), 3.79 (s, 3H), 5.71 (dd, 1H), 6.18 (dd, 1H), 6.62 (dd, 1H), 6.76 (d, 1H), 6.93 (s, 1H), 7.10-7.18 (m, 3H), 7.59 (dd, 1H), 8.10 (d, 1H), 8.24 (s, 1H), 8.37-8.42 (m, 2H), 8.62 (s, 1H), 9.05 (s, 1H). m/z: ESI MH$^+$ 523.1 |

TABLE 2-continued

| Comp. | Structure | Name | Data |
|---|---|---|---|
| 46 | 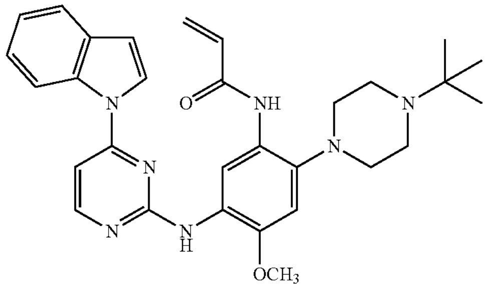 [SMILES: C=CC(=O)Nc1cc(Nc2nccc(-n3ccc4ccccc43)n2)c(OC)cc1N1CCN(C(C)(C)C)CC1] | N-(5-(4-(1H-indol-1-yl)-pyrimidin-2-ylamino)-2-(4-tert-butylpiperazin-1-yl)-4-methoxyl-phenyl)-acrylamide | $^1$H-NMR (DMSO-$d_6$) δ: 1.09 (s, 9H), 2.75 (br, 4H), 2.88 (br, 4H), 3.79 (s, 3H), 5.71 (dd, 1H), 6.18 (dd, 1H), 6.65 (dd, 1H), 6.77 (d, 1H), 6.93 (s, 1H), 7.11-7.19 (m, 3H), 7.60 (dd, 1H), 8.13 (d, 1H), 8.24 (s, 1H), 8.37-8.43 (m, 2H), 8.62 (s, 1H), 9.05 (s, 1H). m/z: ESI MH$^+$ 526.2 |
| 47 | 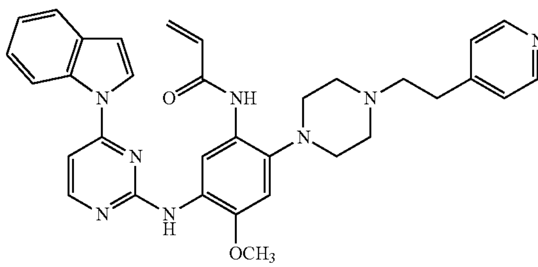 | N-(5-(4-(1H-indol-1-yl)pyrimidin-2-ylamino)-4-methoxyl-2-(4-(2-(pyridin-4-yl)-ethyl)-piperazin-1-yl)-phenyl)-acrylamide | $^1$H-NMR (DMSO-$d_6$) δ: 2.65-2.73 (br, 6H), 2.83 (t, 2H), 2.91 (br, 4H), 3.79 (s, 3H), 5.72 (dd, 1H), 6.19 (dd, 1H), 6.64 (dd, 1H), 6.77 (d, 1H), 6.91 (s, 1H), 7.11-7.19 (m, 3H), 7.32 (d, 2H), 7.59 (dd, 1H), 8.12 (d, 1H), 8.23 (s, 1H), 8.36-8.43 (m, 2H), 8.47 (d, 2H), 8.62 (s, 1H), 9.06 (s, 1H). m/z: ESI MH$^+$ 575.2 |
| 48 | 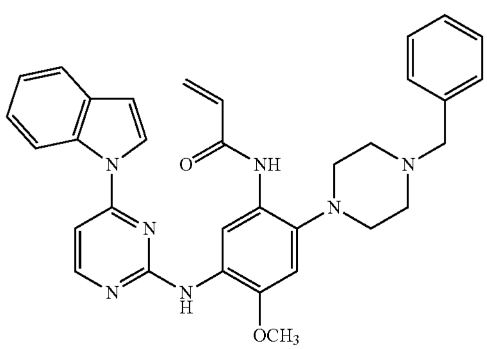 [SMILES: C=CC(=O)Nc1cc(Nc2nccc(-n3ccc4ccccc43)n2)c(OC)cc1N1CCN(Cc2ccccc2)CC1] | N-(5-(4-(1H-indol-1-yl)-pyrimidin-2-ylamino)-2-(4-benzyl-piperazin-1-yl)-4-methoxyl-phenyl)-acrylamide | $^1$H-NMR (DMSO-$d_6$) δ: 2.63 (br, 4H), 2.93 (br, 4H), 3.58 (s, 2H), 3.79 (s, 3H), 5.71 (dd, 1H), 6.18 (dd, 1H), 6.62 (dd, 1H), 6.77 (d, 1H), 6.94 (s, 1H), 7.11-7.19 (m, 3H), 7.28 (m, 1H), 7.33-7.37 (m, 4H), 7.59 (dd, 1H), 8.11 (d, 1H), 8.24 (s, 1H), 8.36-8.43 (m, 2H), 8.62 (s, 1H), 9.06 (s, 1H). m/z: ESI MH$^+$ 560.2 |
| 49 | 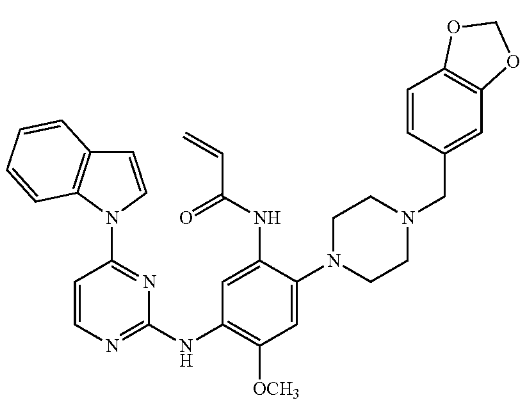 [SMILES: C=CC(=O)Nc1cc(Nc2nccc(-n3ccc4ccccc43)n2)c(OC)cc1N1CCN(Cc2ccc3c(c2)OCO3)CC1] | N-(5-(4-(1H-indol-1-yl)-pyrimidin-2-ylamino)-2-(4-(benzo[d][1,3]dioxy-5-methyl)-piperazin-1-yl)-4-methoxyl-phenyl)-acrylamide | $^1$H-NMR (DMSO-$d_6$) δ: 2.61 (br, 4H), 2.91 (br, 4H), 3.49 (s, 2H), 3.79 (s, 3H), 5.71 (dd, 1H), 6.00 (s, 2H), 6.18 (dd, 1H), 6.61 (dd, 1H), 6.77 (d, 1H), 6.81 (dd, 1H), 6.89 (d, 1H), 6.91-6.93 (m, 2H), 7.11-7.19 (m, 3H), 7.59 (dd, 1H), 8.11 (d, 1H), 8.24 (s, 1H), 8.37-8.43 (m, 2H), 8.62 (s, 1H), 9.05 (s, 1H). m/z: ESI MH$^+$ 604.2 |

TABLE 2-continued

| Comp. | Structure | Name | Data |
|---|---|---|---|
| 50 | 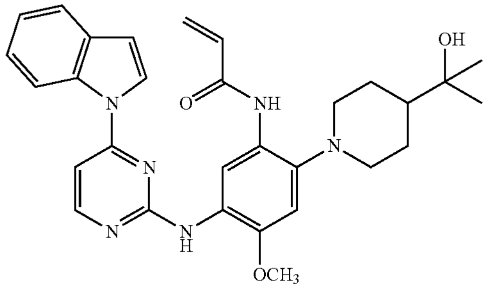 [SMILES: C=CC(=O)Nc1cc(Nc2nccc(-n3ccc4ccccc43)n2)c(OC)cc1N1CCC(C(C)(C)O)CC1] | N-(5-(4-(1H-indol-1-yl)-pyrimidin-2-ylamino)-2-(4-(2-hydroxy-propyl-2-yl)-piperidin-1-yl)-4-methoxyl-phenyl)-acrylamide | $^1$H-NMR (DMSO-d$_6$) δ: 1.12 (s, 6H), 1.34 (m, 1H), 1.56 (m, 2H), 1.80 (d, 2H), 2.65 (t, 2H), 3.12 (d, 2H), 3.78 (s, 3H), 4.20 (s, 1H), 5.72 (dd, 1H), 6.18 (dd, 1H), 6.65 (dd, 1H), 6.77 (d, 1H), 6.87 (s, 1H), 7.10-7.19 (m, 3H), 7.59 (dd, 1H), 8.12 (d, 1H), 8.22 (s, 1H), 8.36-8.42 (m, 2H), 8.61 (s, 1H), 9.03 (s, 1H). m/z: ESI MH$^+$ 527.2 |
| 51 | 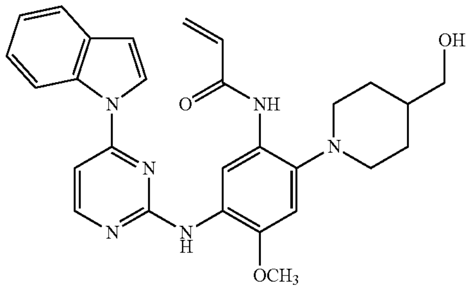 [SMILES: C=CC(=O)Nc1cc(Nc2nccc(-n3ccc4ccccc43)n2)c(OC)cc1N1CCC(CO)CC1] | N-(5-(4-(1H-indol-1-yl)-pyrimidin-2-ylamino)-2-(4-(hydroxy-methyl)-piperidin-1-yl)-4-methoxyl-phenyl)-acrylamide | $^1$H-NMR (DMSO-d$_6$) δ: 1.41-1.55 (m, 3H), 1.80 (br, 2H), 2.68 (t, 2H), 3.06 (d, 2H), 3.35 (m, 2H), 3.78 (s, 3H), 4.54 (br, 1H), 5.70 (dd, 1H), 6.18 (dd, 1H), 6.65 (dd, 1H), 6.77 (d, 1H), 6.90 (s, 1H), 7.11-7.18 (m, 3H), 7.60 (dd, 1H), 8.12 (d, 1H), 8.23 (s, 1H), 8.37-8.43 (m, 2H), 8.62 (s, 1H), 9.01 (s, 1H). m/z: ESI MH$^+$ 499.2 |
| 52 | 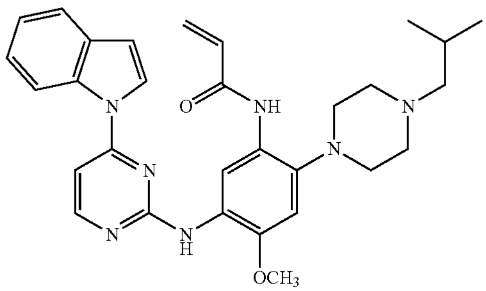 [SMILES: C=CC(=O)Nc1cc(Nc2nccc(-n3ccc4ccccc43)n2)c(OC)cc1N1CCN(CC(C)C)CC1] | N-(5-(4-(1H-indol-1-yl)-pyrimidin-2-ylamino)-2-(4-isobutyl-piperazin-1-yl)-4-methoxyl-phenyl)-acrylamide | $^1$H-NMR (DMSO-d$_6$) δ: 0.90 (d, 6H), 1.82 (m, 1H), 2.14 (d, 2H), 2.58 (br, 4H), 2.92 (br, 4H), 3.79 (s, 3H), 5.72 (dd, 1H), 6.18 (dd, 1H), 6.62 (dd, 1H), 6.77 (d, 1H), 6.93 (s, 1H), 7.11-7.19 (m, 3H), 7.59 (dd, 1H), 8.12 (d, 1H), 8.24 (s, 1H), 8.37-8.43 (m, 2H), 8.62 (s, 1H), 9.04 (s, 1H). m/z: ESI MH$^+$ 526.2 |
| 53 | 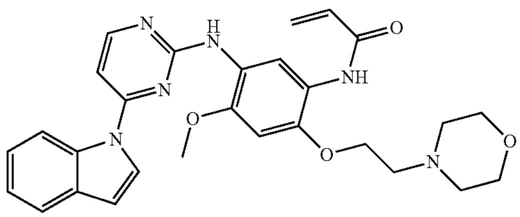 [SMILES: C=CC(=O)Nc1cc(Nc2nccc(-n3ccc4ccccc43)n2)c(OC)cc1OCCN1CCOCC1] | N-(5-(4-(1H-indol-1-yl)-pyrimidin-2-ylamino)-2-(2-(morpholinyl)ethoxyl)-4-methoxyl-phenyl)-acrylamide | $^1$H-NMR (DMSO-d$_6$) δ: 2.51 (t, 4H), 2.76 (t, 2H), 3.59 (t, 4H), 3.79 (s, 3H), 4.26 (t, 2H), 5.68-5.71 (dd, 1H), 6.15-6.19 (dd, 1H), 6.57-6.63 (m, 1H), 6.76-6.77 (d, 1H), 6.92 (s, 1H), 7.09-7.16 (m, 3H), 7.57-7.59 (d, 1H), 8.09-8.10 (d, 1H), 8.16 (s, 1H), 8.35-8.37 (s, 1H), 8.40 (s, 1H), 8.62 (s, 1H), 9.25 (s, 1H). m/z: ESI MH$^+$ 515.2 |
| 54 | 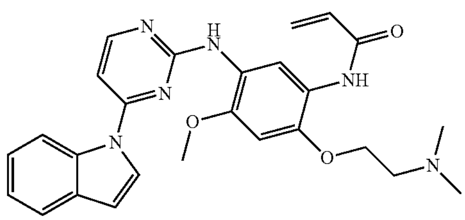 [SMILES: C=CC(=O)Nc1cc(Nc2nccc(-n3ccc4ccccc43)n2)c(OC)cc1OCCN(C)C] | N-(5-(4-(1H-indol-1-yl)-pyrimidin-2-ylamino)-2-(2-dimethyl-amino)-ethoxyl)-4-methoxyl-phenyl)-acrylamide | $^1$H-NMR (DMSO-d$_6$) δ: 2.29 (s, 6H), 2.62-2.65 (t, 2H), 3.78 (s, 3H), 4.22-4.24 (t, 2H), 5.70-5.73 (dd, 1H), 6.16-6.21 (dd, 1H), 6.45-6.52 (m, 1H), 6.76-6.77 (d, 1H), 6.96 (s, 1H), 7.09-7.16 (m, 3H), 7.57-7.59 (d, 1H), 8.10-8.11 (d, 1H), 8.28 (s, 1H), 8.36-8.38 (d, 1H), 8.42 (s, 1H), 8.63 (s, 1H), 9.72 (s, 1H). m/z: ESI MH$^+$ 473.2 |

TABLE 2-continued

| Comp. | Structure | Name | Data |
|---|---|---|---|
| 55 | 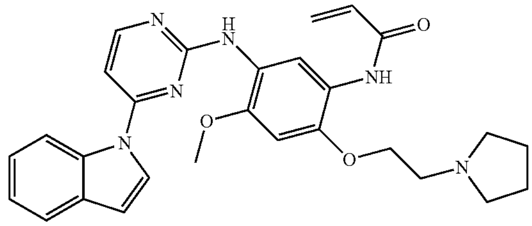 [SMILES: C=CC(=O)Nc1cc(Nc2nccc(-n3ccc4ccccc43)n2)c(OC)cc1OCCN1CCCC1] | N-(5-(4-(1H-indol-1-yl)pyrimidin-2-ylamino)-2-(2-pyrrolidin-1-yl)-ethoxyl)-4-methoxyl-phenyl)-acrylamide | $^1$H-NMR (DMSO-d$_6$) δ: 1.74 (s, 4H), 2.60 (s, 4H), 2.83 (s, 2H), 3.79 (s, 3H), 4.25-4.27 (t, 2H), 5.69-5.72 (dd, 1H), 6.15-6.20 (dd, 1H), 6.49-6.56 (m, 1H), 6.76-6.77 (d, 1H), 6.95 (s, 1H), 7.08-7.16 (m, 3H), 7.57-7.59 (dd, 1H), 8.10-8.11 (d, 1H), 8.24 (s, 1H), 8.36-8.37 (d, 1H), 8.39 (s, 1H), 8.62 (s, 1H), 9.49 (s, 1H). m/z: ESI MH$^+$ 499.2 |
| 56 | 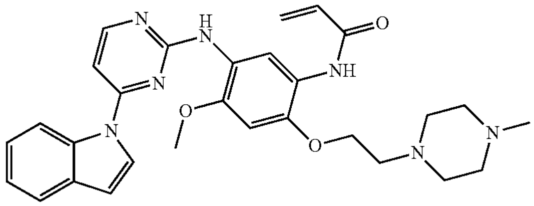 [SMILES: C=CC(=O)Nc1cc(Nc2nccc(-n3ccc4ccccc43)n2)c(OC)cc1OCCN1CCN(C)CC1] | N-(5-(4-(1H-indol-1-yl)-pyrimidin-2-ylamino)-2-(2-4-methyl-piperazin-1-yl)-ethoxyl)-4-methoxyl-phenyl)-acrylamide | $^1$H-NMR (DMSO-d$_6$) δ: 1.24 (s, 3H), 2.40 (s, 4H), 2.67 (t, 2H), 2.80 (s, 4H), 3.80 (s, 3H), 4.26 (t, 2H), 5.68-5.71 (dd, 1H), 6.16-6.20 (dd, 1H), 6.57-6.64 (m, 1H), 6.76-6.77 (d, 1H), 6.91 (s, 1H), 7.09-7.17 (m, 3H), 7.57-7.59 (d, 1H), 8.10-8.11 (d, 1H), 8.14 (s, 1H), 8.36-8.37 (d, 1H), 8.41 (s, 1H), 8.62 (s, 1H), 9.23 (s, 1H). m/z: ESI MH$^+$ 528.2 |
| 57 | 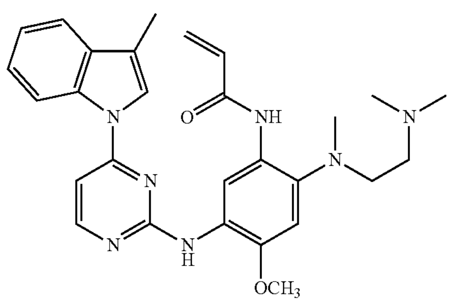 [SMILES: C=CC(=O)Nc1cc(Nc2nccc(-n3cc(C)c4ccccc43)n2)c(OC)cc1N(C)CCN(C)C] | N-(5-(4-(3-methyl-1H-indol-1-yl)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.22 (s, 6H), 2.29 (d, 3H), 2.35 (t, 2H), 2.75 (s, 3H), 2.92 (t, 2H), 3.79 (s, 3H), 5.74 (m, 1H), 6.22 (dd, 1H), 6.41 (dd, 1H), 7.05-7.19 (m, 4H), 7.53 (d, 1H), 7.99 (d, 1H), 8.34-8.39 (br, 2H), 8.54 (s, 1H), 8.62 (s, 1H), 10.14 (s, 1H). m/z: ESI MH$^+$ 500.1 |
| 58 | 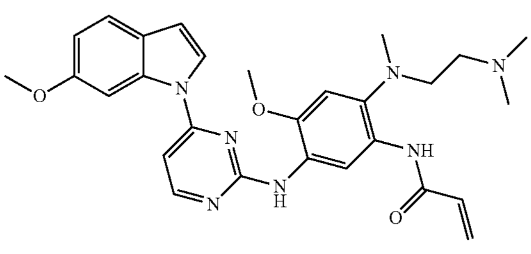 | N-{2-[(2-dimethyl-amino)-ethyl)-methyl-amino]-4-methoxyl-5-[4-(6-methoxyl-indol-1-yl)-pyrimidin-2-ylamino]-phenyl}-acrylamide | $^1$H-NMR (DMSO-d$_6$) δ: 10.33 (s, 1H), 9.89 (s, 1H), 8.60 (s, 1H) 8.45 (s, 1H), 8.39 (d, 1H), 8.07 (s, 1H), 8.00 (d, 1H), 7.49 (d, 1H), 7.12 (d, 1H), 7.00 (s, 1H), 6.85 ((d, 1H), 6.70 (d, 1H), 6.22 (d, 1H), 5.72 (d, 1H), 3.81 (s, 3H), 3.71 (s, 3H), 3.09 (t, 2H), 2.68 (s, 3H), 2.51 (m, 8H). m/z: ESI MH$^+$ 516.3 |
| 59 | 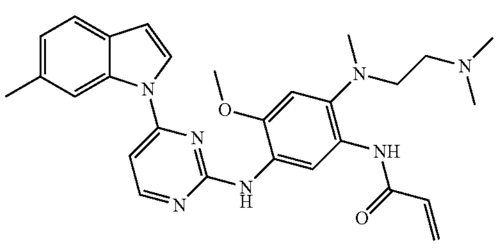 | N-{2-[(2-dimethyl-amino)-ethyl)-methyl-amino]-4-methoxyl-5-[4-(6-methyl-indol-1-yl)-pyrimidin-2-ylamino]-phenyl}-acrylamide | $^1$H-NMR (DMSO-d$_6$) δ: 10.32 (s, 1H), 9.83 (s, 1H), 8.62 (s, 1H), 8.45 (s, 1H), 8.39 (d, 1H), 8.30 (s, 1H), 8.07 (d, 1H), 7.46 (d, 1H), 7.13 (d, 1H), 7.00 (m, 2H), 6.71 ((d, 1H), 6.20 (d, 1H), 5.71 (d, 1H), 3.82 (s, 3H), 3.18 (t, 2H), 2.67 (s, 3H), 2.51 (m, 8H), 2.33 (s, 3H). m/z: ESI MH$^+$ 500.3 |

TABLE 2-continued

| Comp. | Structure | Name | Data |
|---|---|---|---|
| 60 | | N-{5-[4-(6-cyano-indol-1-yl)-pyrimidin-2-ylamino]-2-[(2-dimethylamino-ethyl)-methyl-amino]-4-methoxyl-phenyl}-acrylamide| | ¹H-NMR (DMSO-d₆) δ: 10.02 (s, 1H), 9.01 (s, 2H), 8.47 (s, 1H), 8.43 (m, 2H), 7.80 (d, 1H), 7.54 (s, 1H), 7.18 (d, 1H), 7.10 (s, 1H), 6.94 ((d, 1H), 6.38 (m, 1H), 6.18 (d, 1H), 5.72 (d, 1H), 3.85 (s, 3H), 2.91 (t, 2H), 2.76 (s, 3H), 2.36 (t, 2H), 2.21 (s, 6H). m/z: ESI MH⁺ 511.1 |
| 61 | 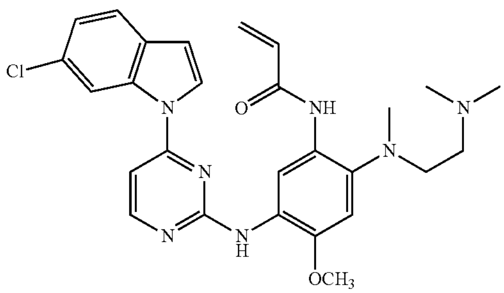 [SMILES: C=CC(=O)Nc1cc(Nc2nccc(-n3ccc4ccc(Cl)cc43)n2)c(OC)cc1N(C)CCN(C)C] | N-(5-(4-(6-chloro-1H-indol-1-yl)-pyrimidin-2-ylamino)-2-((2-(dimethylamino)ethyl)-methyl-amino)-4-methoxyl-phenyl)-acrylamide | ¹H-NMR (DMSO-d₆) δ: 2.21 (s, 6H), 2.36 (t, 2H), 2.75 (s, 3H), 2.89 (2H, t), 3.80 (s, 3H), 5.72 (dd, 1H), 6.18 (dd, 1H), 6.38 (dd, 1H), 6.80 (d, 1H), 7.07 (s, 1H), 7.11 (d, 1H), 7.17 (dd, 1H), 7.59 (d, 1H), 8.17 (d, 1H), 8.40 (d, 1H), 8.46 (s, 1H), 8.48 (br, 1H), 8.84 (s, 1H), 10.04 (s, 1H). m/z: ESI MH⁺ 520.1 |
| 62 | 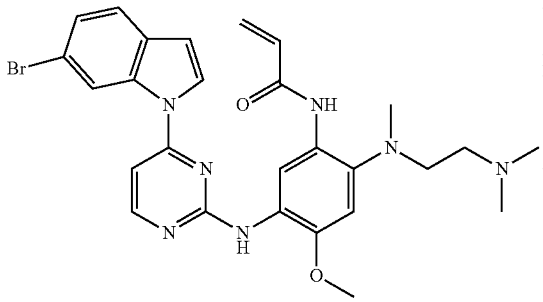 [SMILES: C=CC(=O)Nc1cc(Nc2nccc(-n3ccc4ccc(Br)cc43)n2)c(OC)cc1N(C)CCN(C)C] | N-(5-(4-(6-bromo-1H-indol-1-yl)-pyrimidin-2-ylamino)-2-((2-(dimethylamino)ethyl)-methyl-amino)-4-methoxyl-phenyl)-acrylamide | ¹H-NMR (DMSO-d₆) δ: 2.22 (s, 6H), 2.37 (t, 2H), 2.74 (s, 3H), 2.90 (t, 2H), 3.81 (s, 3H), 5.72 (m, 1H), 6.17 (dd, 1H), 6.39 (dd, 1H), 6.81 (d, 1H), 7.08 (s, 1H), 7.12 (d, 1H), 7.30 (dd, 1H), 7.55 (d, 1H), 8.16 (d, 1H), 8.40 (d, 1H), 8.48 (s, 1H), 8.63 (1H, br), 8.80 (s, 1H), 10.01 (s, 1H). m/z: ESI MH⁺ 564.1 |
| 63 | 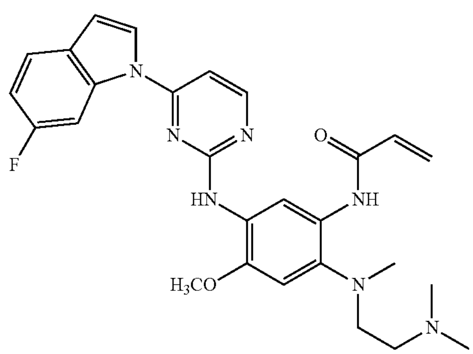 [SMILES: C=CC(=O)Nc1cc(Nc2nccc(-n3ccc4ccc(F)cc43)n2)c(OC)cc1N(C)CCN(C)C] | N-(5-(4-(6-fluoro-1H-indol-1-yl)-pyrimidin-2-ylamino)-2-((2-(dimethylamino)ethyl)-methyl-amino)-4-methoxyl-phenyl)-acrylamide | ¹H-NMR (DMSO-d₆) δ: 2.22 (s, 6H), 2.36 (t, 2H), 2.75 (s, 3H), 2.90 (t, 2H), 3.77 (s, 3H), 5.72 (dd, 1H), 6.18 (dd, 1H), 6.38 (dd, 1H), 6.79 (d, 1H), 7.01 (m, 1H), 7.06 (s, 1H), 7.12 (d, 1H), 7.58 (m, 1H), 8.14 (d, 1H), 8.23 (br, 1H), 8.39 (d, 1H), 8.47 (s, 1H), 8.86 (s, 1H), 10.10 (s, 1H). m/z: ESI MH⁺ 504.2 |
| 64 | 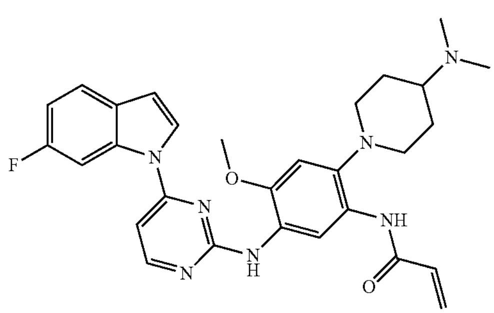 [SMILES: C=CC(=O)Nc1cc(Nc2nccc(-n3ccc4ccc(F)cc43)n2)c(OC)cc1N1CCC(N(C)C)CC1] | N-(5-(4-(6-fluoro-1H-indol-1-yl)-pyrimidin-2-ylamino)-2-(4-(dimethylamino)-piperidinyl)-4-methoxyl-phenyl)-acrylamide | ¹H-NMR (CDCl₃-d) δ: 2.01 (m, 2H), 2.26 (m, 2H), 2.72 (s, 6H), 2.80 (t, 2H), 2.90 (s, 1H), 3.20 (m, 2H), 3.91 (s, 3H), 5.76 (d, 1H), 6.36 (dd, 2H), 6.71 (dd, 1H), 6.77 (s, 1H), 6.84 (d, 1H), 6.98 (t, 1H), 7.53 (m, 2H), 7.90 (d, 1H), 8.12 (d, 1H), 8.39 (s, 1H), 8.48 (d, 1H), 9.33 (s, 1H). m/z: ESI MH⁺ 530.2 |

TABLE 2-continued

| Comp. | Structure | Name | Data |
|---|---|---|---|
| 65 | 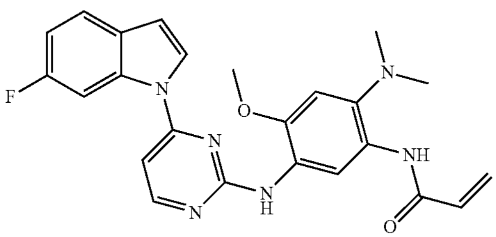 [SMILES: C=CC(=O)Nc1cc(Nc2nccc(-n3ccc4ccc(F)cc43)n2)c(OC)cc1N(C)C] | N-(5-(4-(6-fluoro-1H-indol-1-yl)-pyrimidin-2-ylamino)-2-(dimethylamino)-4-methoxyl-phenyl)-acrylamide | $^1$H-NMR (CDCl$_3$-d) δ: 2.70 (s, 6H), 3.93 (s, 3H), 5.74 (dd, 1H), 6.35 (dd, 2H), 6.71 (dd, 1H), 6.84 (dd, 2H), 6.97 (t, 1H), 7.50-7.54 (m, 2H), 7.93 (d, 1H), 8.12 (d, 1H), 8.48 (m, 2H), 9.36 (s, 1H). m/z: ESI MH$^+$ 447.1 |
| 66 | 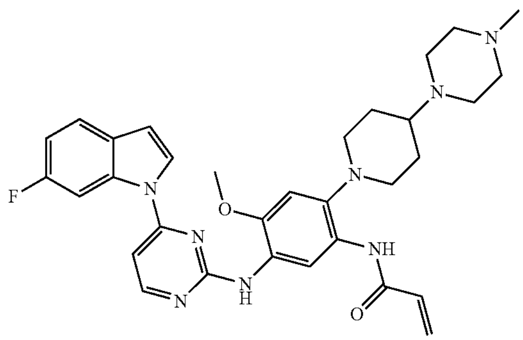 [SMILES: C=CC(=O)Nc1cc(Nc2nccc(-n3ccc4ccc(F)cc43)n2)c(OC)cc1N1CCC(N2CCN(C)CC2)CC1] | N-(5-(4-(6-fluoro-1H-indol-1-yl)-pyrimidin-2-ylamino)-2-(4-(4-methyl-piperazin-1-yl)-piperidin-1-yl)-4-methoxyl-phenyl)-acrylamide | $^1$H-NMR (CD$_3$OD-d$_4$) δ: 1.82-1.86 (m, 2H), 2.06-2.08 (m, 2H), 2.64 (s, 3H), 2.66 (m, 1H), 2.80-2.88 (m, 4H), 2.90-3.10 (m, 6H), 3.20 (m, 2H), 3.90 (s, 3H), 5.78 (d, 1H), 6.29 (m, 1H), 6.50-6.57 (m, 1H), 6.73 (d, 1H), 6.91-6.94 (m, 1H), 6.96 (m, 1H), 7.02 (d, 1H), 7.52 (m, 1H), 7.95 (d, 1H), 8.16 (m, 1H), 8.37 (d, 1H), 8.64 (s, 1H). m/z: ESI MH$^+$ 585.3 |
| 67 | 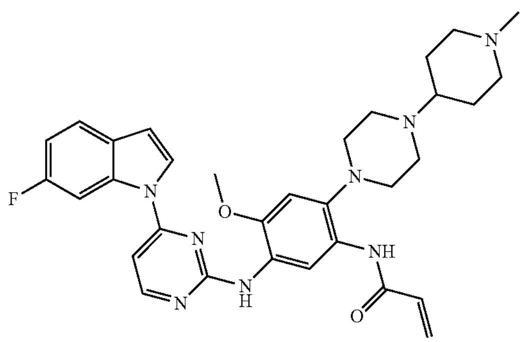 [SMILES: C=CC(=O)Nc1cc(Nc2nccc(-n3ccc4ccc(F)cc43)n2)c(OC)cc1N1CCN(C2CCN(C)CC2)CC1] | N-(5-(4-(6-fluoro-1H-indol-1-yl)-pyrimidin-2-ylamino)-2-(4-(1-methylpiperidin-4-yl)-piperazin-1-yl)-4-methoxyl-phenyl)-acrylamide | $^1$H-NMR (DMSO-d$_6$) δ: 2.06 (br, 4H), 2.52 (m, 3H), 2.57 (s, 3H), 2.79 (br, 4H), 2.97 (br, 4H), 3.27 (br, 2H), 3.90 (s, 3H), 5.76 (d, 1H), 6.29-6.39 (m, 2H), 6.71 (d, 1H), 6.84 (d, 2H), 6.97 (ms, 1H), 7.50-7.55 (m, 2H), 7.92 (d, 1H), 8.12 (d, 1H), 8.48 (d, 1H), 8.53 (s, 1H), 9.39 (s, 1H). m/z: ESI MH$^+$ 585.3 |
| 68 | 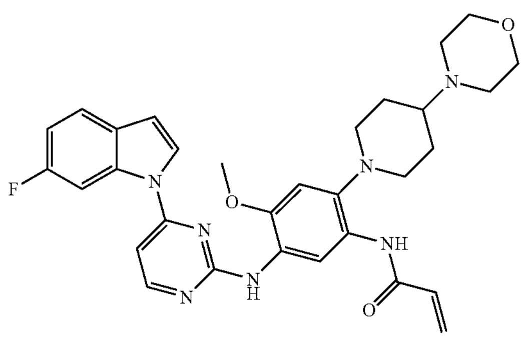 [SMILES: C=CC(=O)Nc1cc(Nc2nccc(-n3ccc4ccc(F)cc43)n2)c(OC)cc1N1CCC(N2CCOCC2)CC1] | N-(5-(4-(6-fluoro-1H-indol-1-yl)-pyrimidin-2-ylamino)-2-(4-(morpholin-4-yl)-piperidin-1-yl)-4-methoxyl-phenyl)-acrylamide | $^1$H-NMR (DMSO-d$_6$) δ: 1.73 (m, 2H), 1.90 (m, 2H), 2.28 (m, 1H), 2.53 (m, 4H), 2.71 (t, 2H), 3.11 (m, 2H), 3.61 (m, 4H), 3.76 (s, 3H), 5.70 (d, 1H), 6.15-6.20 (d, 1H), 6.63-6.70 (m, 1H), 6.78 (d, 1H), 6.90 (s, 1H), 7.02 (m, 1H), 7.10 (d, 1H), 7.56-7.60 (m, 1H), 8.12 (d, 1H), 8.15 (s, 1H), 8.22 (m, 1H), 8.37 (d, 1H), 8.84 (s, 1H), 8.94 (s, 1H). m/z: ESI MH$^+$ 572.2 |
| 69 | 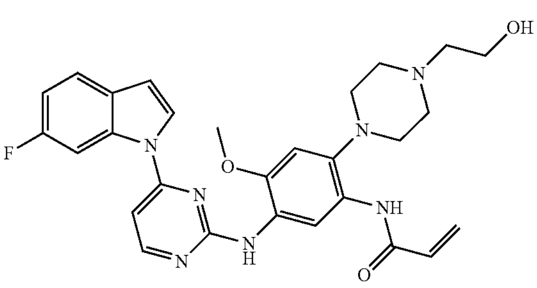 [SMILES: C=CC(=O)Nc1cc(Nc2nccc(-n3ccc4ccc(F)cc43)n2)c(OC)cc1N1CCN(CCO)CC1] | N-(5-(4-(6-fluoro-1H-indol-1-yl)-pyrimidin-2-ylamino)-2-(4-(2-hydroxyl-ethyl)-piperazin-1-yl)-4-methoxyl-phenyl)-acrylamide | $^1$H-NMR (CDCl$_3$-d) δ: 9.40 (s, 1H), 8.54 (s, 1H), 8.48 (d, 1H), 8.12 (d, 1H), 7.92 (d, 1H), 7.50-7.54 (m, 2H), 6.97 (t, 1H), 6.84 (m, 2H), 6.71 (d, 1H), 6.30-6.35 (m, 2H), 5.74 (d, 1H), 3.93 (s, 3H), 3.72 (t, 2H), 3.00 (m, 4H), 2.77 (m, 4H), 2.70 (t, 2H), 2.03 (s, 1H). m/z: ESI MH$^+$ 532.2 |

TABLE 2-continued

| Comp. | Structure | Name | Data |
|---|---|---|---|
| 70 | 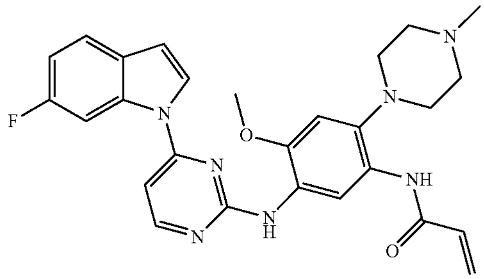 [SMILES: C=CC(=O)Nc1cc(Nc2nccc(-n3ccc4ccc(F)cc43)n2)c(OC)cc1N1CCN(C)CC1] | N-(5-(4-(6-fluoro-1H-indol-1-yl)-pyrimidin-2-ylamino)-2-(4-methyl-piperazin-1-yl)-4-methoxyl-phenyl)-acrylamide | ¹H-NMR (CDCl₃-d) δ: 9.38 (s, 1H), 8.51 (s, 1H), 8.48 (d, 1H), 8.13 (d, 1H), 7.92 (m, 1H), 7.60 (s, 1H), 7.51 (m, 1H), 6.97 (m, 1H), 6.84 (m, 2H), 6.70 (d, 1H), 6.30-6.40 (m, 2H), 5.75 (d, 1H), 3.91 (s, 3H), 3.02 (m, 4H) 2.78 (m, 4H), 2.48 (s, 3H). m/z: ESI MH⁺ 502.2 |
| 71 | 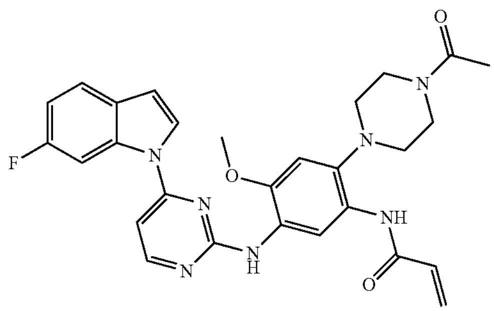 [SMILES: C=CC(=O)Nc1cc(Nc2nccc(-n3ccc4ccc(F)cc43)n2)c(OC)cc1N1CCN(C(C)=O)CC1] | N-(5-(4-(6-fluoro-1H-indol-1-yl)-pyrimidin-2-ylamino)-2-(4-acetyl-piperazin-1-yl)-4-methoxyl-phenyl)-acrylamide | ¹H-NMR (CDCl₃-d) δ: 9.39 (s, 1H), 8.48 (d, 2H), 8.12 (d, 1H), 7.90 (s, 1H), 7.56 (s, 1H), 7.52 (m, 1H), 6.97 (m, 1H), 6.84 (d, 1H), 6.76 (s, 1H), 6.71 (d, 1H), 6.30-6.35 (m, 2H), 5.75 (d, 1H), 3.91 (s, 3H), 3.83 (m, 2H), 3.67 (m, 2H), 2.91 (m, 4H), 2.18 (s, 3H). m/z: ESI MH⁺ 530.2 |
| 72 | 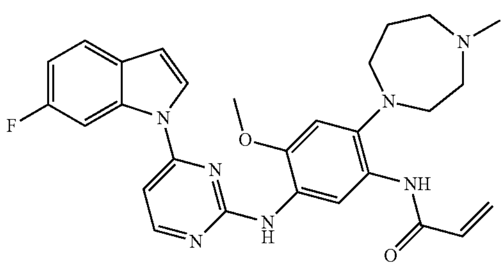 [SMILES: C=CC(=O)Nc1cc(Nc2nccc(-n3ccc4ccc(F)cc43)n2)c(OC)cc1N1CCCN(C)CC1] | N-(5-(4-(6-fluoro-1H-indol-1-yl)-pyrimidin-2-ylamino)-2-(4-methyl-[1,4]diazepin-1-yl)-4-methoxyl-phenyl)-acrylamide | ¹H-NMR (CDCl₃-d) δ: 9.09 (s, 1H), 9.05 (s, 1H), 8.46 (d, 1H), 8.10 (d, 1H), 7.90 (m, 1H), 7.54 (s, 1H), 7.52 (m, 1H), 6.98 (m, 1H), 6.83 (m, 2H), 6.70 (d, 2H), 6.40 (m, 1H), 5.73 (d, 1H), 3.90 (s, 3H), 3.20 (m, 2H), 2.98 (m, 3H) 2.80 (m, 2H), 2.33 (m, 2H), 1.96 (m, 4H). m/z: ESI MH⁺ 516.2 |
| 73 | 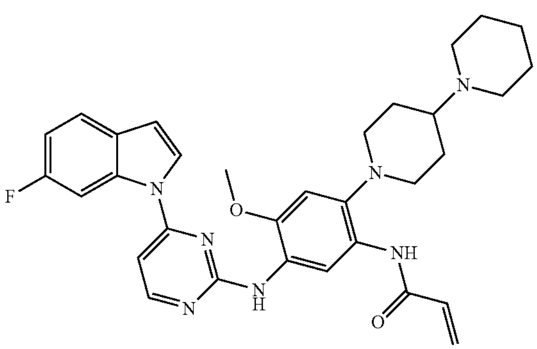 [SMILES: C=CC(=O)Nc1cc(Nc2nccc(-n3ccc4ccc(F)cc43)n2)c(OC)cc1N1CCC(N2CCCCC2)CC1] | N-(5-(4-(6-fluoro-1H-indol-1-yl)-pyrimidin-2-ylamino)-2-(4-(piperidin-1-yl)-piperidin-1-yl)-4-methoxyl-phenyl)-acrylamide | ¹H-NMR (CDCl₃-d) δ: 9.34 (s, 1H), 8.48 (d, 1H), 8.38 (s, 1H), 8.11 (d, 1H), 7.91 (m, 1H), 7.50-7.54 (m, 2H), 6.98 (m, 1H), 6.84 (d, 1H), 6.76 (s, 1H), 6.71 (d, 1H), 6.36-6.38 (m, 2H), 5.75 (d, 1H), 3.91 (s, 3H), 3.20 (m, 2H), 2.98 (m, 4H), 2.80 (m, 2H), 2.35 (m, 1H), 2.00 (m, 4H), 1.68 (m, 4H), 1.27 (m, 2H). m/z: ESI MH⁺ 570.2 |
| 74 | 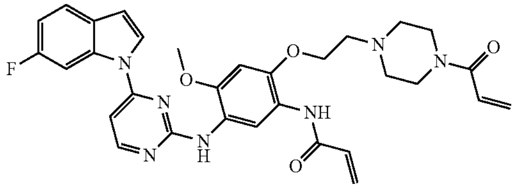 [SMILES: C=CC(=O)Nc1cc(Nc2nccc(-n3ccc4ccc(F)cc43)n2)c(OC)cc1OCCN1CCN(C(=O)C=C)CC1] | N-(5-(4-(6-fluoro-1H-indol-1-yl)-pyrimidin-2-ylamino)-2-(2-4-acryloyl-piperazin-1-yl)-ethoxyl)-4-methoxyl-phenyl)-acrylamide | ¹H-NMR (CDCl₃-d) δ: 9.40 (s, 1H), 8.57 (s, 1H), 8.48 (d, 1H), 8.12 (d, 1H), 7.93 (s, 1H), 7.58 (s, 1H), 7.52 (m, 1H), 6.97 (m, 1H), 6.85 (s, 2H), 6.72 (d, 1H), 6.47 (d, 1H), 6.33-6.40 (m, 2H), 6.22 (m, N 1H), 5.90 (d, 1H), 5.75 (d, 1H), 4.39 (m, 2H), 3.91 (s, 3H), 2.97 (s, 4H), 2.83 (m, 2H), 2.77 (s, 4H) m/z: ESI MH⁺ 586.2 |

TABLE 2-continued

| Comp. | Structure | Name | Data |
|---|---|---|---|
| 75 | 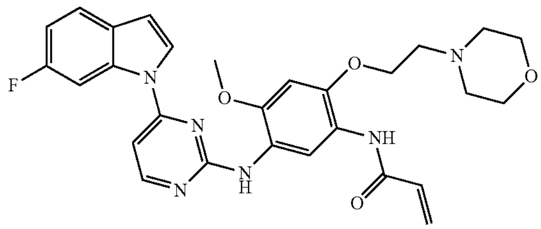 [SMILES: C=CC(=O)Nc1cc(Nc2nccc(-n3ccc4ccc(F)cc43)n2)c(OC)cc1OCCN1CCOCC1] | N-(5-(4-(6-fluoro-1H-indol-1-yl)-pyrimidin-2-ylamino)-2-(2-(morpholin-4-yl)-ethoxyl)-4-methoxyl-phenyl)-acrylamide | $^1$H-NMR (CDCl$_3$-d) δ: 9.23 (s, 1H), 8.51 (s, 1H), 8.45 (d, 1H), 8.13 (d, 1H), 7.85 (m, 1H), 7.51 (m, 1H), 7.37 (s, 1H), 6.96 (m, 1H), 6.80 (d, 1H), 6.70 (d, 1H), 6.66 (s, 1H), 6.40 (d, 2H), 5.74 (t, 1H), 4.24 (t, 2H), 3.90 (s, 3H), 3.80 (m, 4H), 2.78 (m, 2H), 2.61 (m, 4H). m/z: ESI MH$^+$ 533.2 |
| 76 | 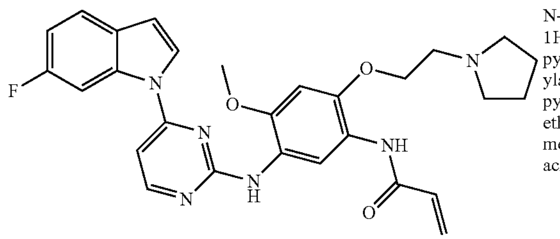 | N-(5-(4-(6-fluoro-1H-indol-1-yl)-pyrimidin-2-ylamino)-2-(2-pyrrolidin-1-yl)-ethoxyl)-4-methoxyl-phenyl)-acrylamide | $^1$H-NMR (DMSO-d$_6$) δ: 9.64 (s, 1H), 8.84 (s, 1H), 8.36 (d, 1H), 8.18 (m, 2H), 8.11 (d, 1H), 7.58 (m, 1H), 7.09 (d, 1H), 7.03 (m, 1H), 6.92 (s, 1H), 6.78 (d, 1H), 6.71 (m, 1H), 6.20 (d, 1H), 5.67 (d, 1H), 4.34 (t, 2H), 3.78 (s, 3H), 3.26 (t, 2H), 3.00 (s, 4H), 1.88 (s, 4H). m/z: ESI MH$^+$ 517.2 |
| 77 | 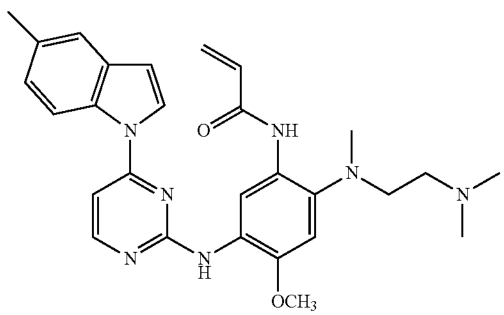 | N-(5-(4-(5-methyl-1H-indol-1-yl)-pyrimidin-2-ylamino)-2-((2-dimethylamino-ethyl)-methyl-amino)-4-methoxyl-phenyl)-acrylamide | $^1$H-NMR (DMSO-d$_6$) δ: 2.23 (s, 6H), 2.35 (s, 3H), 2.37 (br, 2H), 2.76 (s, 3H), 2.93 (br, 2H), 3.78 (s, 3H), 5.74 (m, 1H), 6.19 (dd, 1H), 6.41 (dd, 1H), 6.69 (d, 1H), 6.90 (d, 1H), 7.06 (s, 1H), 7.10 (d, 1H), 7.36 (s, 1H), 8.10 (d, 1H), 8.28 (br, 1H), 8.37 (d, 1H), 8.55 (s, 1H), 8.60 (s, 1H), 10.12 (s, 1H). m/z: ESI MH$^+$ 500.1 |
| 78 | 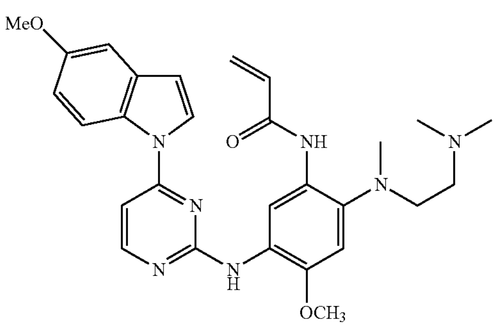 [SMILES: C=CC(=O)Nc1cc(Nc2nccc(-n3ccc4cc(OC)ccc43)n2)c(OC)cc1N(C)CCN(C)C] | N-(5-(4-(5-methoxyl-1H-indol-1-yl)-pyrimidin-2-ylamino)-2-((2-dimethylamino-ethyl)-methyl-amino)-4-methoxyl-phenyl)-acrylamide | $^1$H-NMR (DMSO-d$_6$) δ: 2.22 (s, 6H), 2.34 (t, 2H), 2.74 (s, 3H), 2.91 (t, 2H), 3.75 (s, 3H), 3.76 (s, 3H), 5.72 (m, 1H), 6.18 (dd, 1H), 6.40 (dd, 1H), 6.65 (dd, 1H), 6.69 (d, 1H), 7.05-7.09 (m, 3H), 8.08 (d, 1H), 8.28 (br, 1H), 8.34 (d, 1H), 8.50 (s, 1H), 8.62 (s, 1H), 10.14 (s, 1H). m/z: ESI MH$^+$ 516.2 |
| 79 | 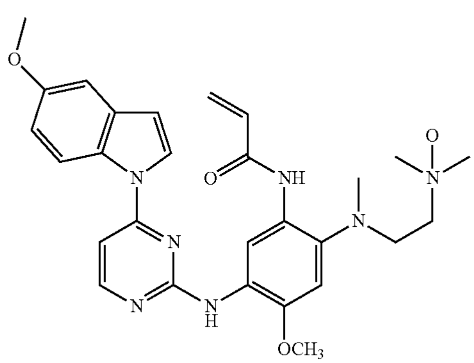 | 2-((2-acrylamido-5-methoxyl-4-(4-(5-methoxyl-1H-indol-1-yl)-pyrimidin-2-yl)-amino)-phenyl)-methyl-N,N-dimethyl-N-ethylamine oxide | $^1$H-NMR (DMSO-d$_6$) δ: 2.76 (s, 3H), 3.25-3.29 (m, 8H), 3.47 (br, 2H), 3.77 (s, 3H), 3.78 (s, 3H), 5.58 (m, 1H), 6.09 (dd, 1H) 6.69-6.72 (m, 2H), 6.98 (s, 1H), 7.06-7.16 (m, 3H), 8.08 (d, 1H), 8.28-8.35 (br, 2H), 8.49 (s, 1H), 8.62 (s, 1H), 12.23 (s, 1H). m/z: ESI MH$^+$ 532.3 |

TABLE 2-continued

| Comp. | Structure | Name | Data |
|---|---|---|---|
| 80 | 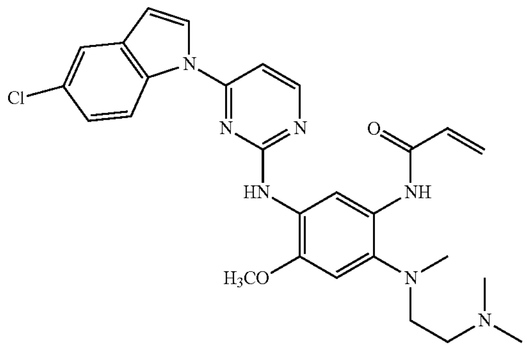 [SMILES: C=CC(=O)Nc1cc(Nc2nccc(-n3ccc4cc(Cl)ccc43)n2)c(OC)cc1N(C)CCN(C)C] | N-(5-(4-(5-chloro-1H-indol-1-yl)-pyrimidin-2-ylamino)-2-((2-dimethylamino-ethyl)-methyl-amino)-4-methoxyl-phenyl)-acrylamide | $^1$H-NMR (DMSO-$d_6$) δ: 2.21 (s, 6H), 2.36 (br, 2H), 2.77 (s, 3H), 2.93 (br, 2H), 3.78 (s, 3H), 5.74 (m, 1H), 6.19 (dd, 1H), 6.41 (dd, 1H), 6.77 (d, 1H), 7.04 (d, 1H), 7.08 (s, 1H), 7.14 (d, 1H), 7.66 (dd, 1H), 8.22 (d, 1H), 8.41 (d, 1H), 8.42 (br, 1H), 8.50 (s, 1H), 8.75 (s, 1H), 10.12 (s, 1H). m/z: ESI MH$^+$ 520.1 |
| 81 | 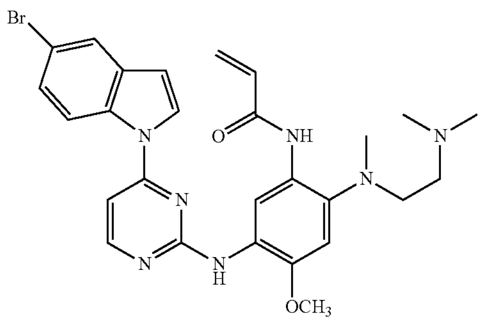 [SMILES: C=CC(=O)Nc1cc(Nc2nccc(-n3ccc4cc(Br)ccc43)n2)c(OC)cc1N(C)CCN(C)C] | N-(5-(4-(5-bromo-1H-indol-1-yl)-pyrimidin-2-ylamino)-2-((2-dimethylamino-ethyl-methyl-amino)-4-methoxyl-phenyl)-acrylamide | $^1$H-NMR (DMSO-$d_6$) δ: 2.22 (s, 6H), 2.35 (t, 2H), 2.75 (s, 3H), 2.92 (t, 2H), 3.78 (s, 3H), 5.74 (m, 1H), 6.19 (dd, 1H), 6.41 (dd, 1H), 6.76 (d, 1H), 7.07 (s, 1H), 7.12-7.16 (m, 2H), 7.79 (d, 1H), 8.19 (d, 1H), 8.37 (br, 1H), 8.41 (d, 1H), 8.51 (s, 1H), 8.73 (s, 1H), 10.14 (s, 1H). m/z: ESI MH$^+$ 564.1 |
| 82 | 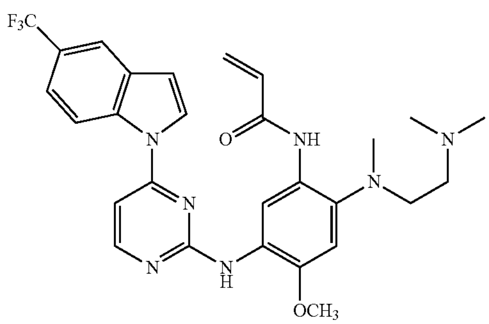 [SMILES: C=CC(=O)Nc1cc(Nc2nccc(-n3ccc4cc(C(F)(F)F)ccc43)n2)c(OC)cc1N(C)CCN(C)C] | N-(5-(4-(5-trifluoromethyl-1H-indol-1-yl)-pyrimidin-2-ylamino)-2-((2-dimethylamino-ethyl)-methyl-amino)-4-methoxyl-phenyl)-acrylamide | $^1$H-NMR (DMSO-$d_6$) δ: 2.21 (s, 6H), 2.34 (t, 2H), 2.76 (s, 3H), 2.93 (t, 2H), 3.77 (s, 3H), 5.71 (m, 1H), 6.18 (dd, 1H), 6.40 (dd, 1H), 6.93 (d, 1H), 7.09 (s, 1H), 7.18 (d, 1H), 7.31 (d, 1H), 8.00 (s, 1H), 8.30 (d, 1H), 8.46 (d, 1H), 8.55 (s, 1H), 8.57 (br, 1H), 8.78 (s, 1H), 10.17 (s, 1H). m/z: ESI MH$^+$ 554.1 |
| 83 | 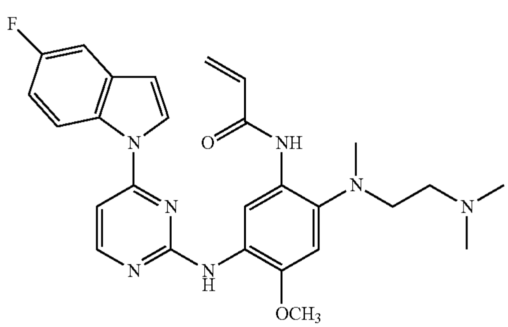 [SMILES: C=CC(=O)Nc1cc(Nc2nccc(-n3ccc4cc(F)ccc43)n2)c(OC)cc1N(C)CCN(C)C] | N-(5-(4-(5-fluoro-1H-indol-1-yl)-pyrimidin-2-ylamino)-2-((2-(dimethylamino-ethyl)-methyl-amino)-4-methoxyl-phenyl)-acrylamide | $^1$H-NMR (DMSO-$d_6$) δ: 2.22 (s, 6H), 2.35 (br, 2H), 2.76 (s, 3H), 2.92 (br, 2H), 3.78 (s, 3H), 5.73 (m, 1H), 6.20 (dd, 1H), 6.39 (dd, 1H), 6.77 (d, 1H), 6.88 (m, 1H), 7.07 (s, 1H), 7.13 (d, 1H), 7.38 (dd, 1H), 8.22 (d, 1H), 8.40 (d, 1H), 8.46 (br, 1H), 8.51 (s, 1H), 8.72 (s, 1H), 10.11 (s, 1H). m/z: ESI MH$^+$ 504.1 |

TABLE 2-continued

| Comp. | Structure | Name | Data |
|---|---|---|---|
| 84 | 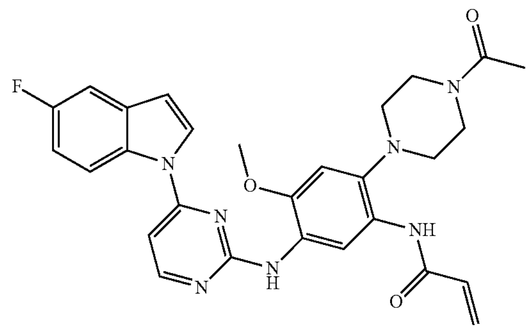 [SMILES: C=CC(=O)Nc1cc(Nc2nccc(-n3ccc4cc(F)ccc43)n2)c(OC)cc1N1CCN(C(C)=O)CC1] | N-(5-(4-(5-fluoro-1H-indol-1-yl)-pyrimidin-2-ylamino)-2-(4-acetyl-piperazin-1-yl)-4-methoxyl-phenyl)-acrylamide | $^1$H-NMR (DMSO-d$_6$) δ: 2.07 (s, 3H), 2.85-2.91 (m, 4H), 3.69 (m, 4H), 3.78 (s, 3H), 5.71-5.74 (dd, 1H), 6.17-6.22 (dd, 1H), 6.66-6.70 (m, 1H), 6.78 (d, 1H), 6.90-6.93 (m, 2H), 7.14 (d, 1H), 7.40 (dd, 1H), 8.22 (d, 1H), 8.29 (m, 1H), 8.40 (m, 1H), 8.48 (m, 1H), 8.70 (s, 1H), 9.18 (s, 1H). m/z: ESI MH$^+$ 530.2 |
| 85 | 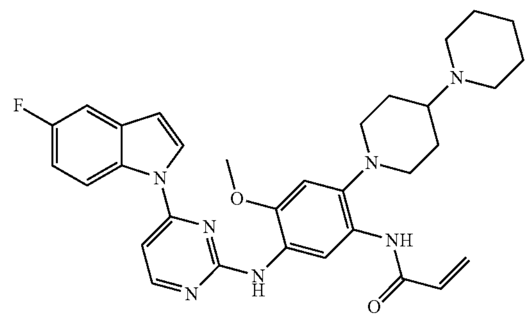 | N-(5-(4-(5-fluoro-1H-indol-1-yl-)-pyrimidin-2-ylamino)-2-(4-(piperidin-4-yl)-piperidin-1-yl)-4-methoxyl-phenyl)-acrylamide | $^1$H-NMR (DMSO-d$_6$) δ: 1.72 (m, 2H), 1.85 (br, 4H), 2.00 (m, 3H), 2.14 (m, 2H), 2.80 (t, 2H), 3.02 (br, 2H), 3.18 (t, 2H), 3.44 (t, 2H), 3.79 (s, 3H), 5.72 (d, 1H), 6.23 (d, 1H), 6.66-6.70 (m, 1H), 6.78 (d, 1H), 6.90-6.93 (m, 2H), 7.14 (d, 1H), 7.41 (m, 1H), 8.22 (m, 2H), 8.40 (br, 1H), 8.71 (s, 1H), 9.10 (s, 1H), 9.86 (s, 1H),. m/z: ESI MH$^+$ 570.3 |
| 86 | 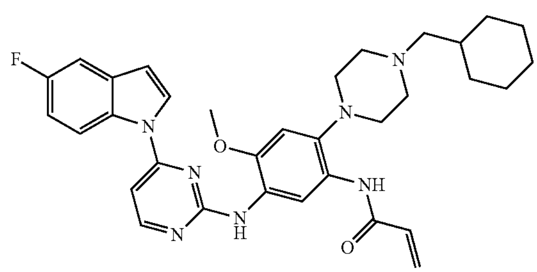 [SMILES: C=CC(=O)Nc1cc(Nc2nccc(-n3ccc4cc(F)ccc43)n2)c(OC)cc1N1CCN(CC2CCCCC2)CC1] | N-(5-(4-(5-fluoro-1H-indol-1-yl)-pyrimidin-2-ylamino)-2-(4-(cyclohexyl-methyl)-piperidin-1-yl)-4-methoxyl-phenyl)-acrylamide | $^1$H-NMR (CDCl$_3$-d) δ: 9.47 (s, 1H), 8.56 (br, 1H), 8.49 (d, 1H), 8.28 (m, 1H), 8.09 (s, 1H), 7.62 (s, 1H), 7.28 (d, 1H), 7.02 (m, 1H), 6.89 (d, 1H), 6.86 (s, 1H), 6.71 (d, 1H), 6.39 (d, 1H), 6.32 (m, 1H), 5.78 (d, 1H), 3.91 (s, 3H), 3.03 (br, 4H), 2.75 (br, 4H), 2.40 (m, 2H), 1.64-1.88 (m, 11H). m/z: ESI MH$^+$ 584.2 |
| 87 | 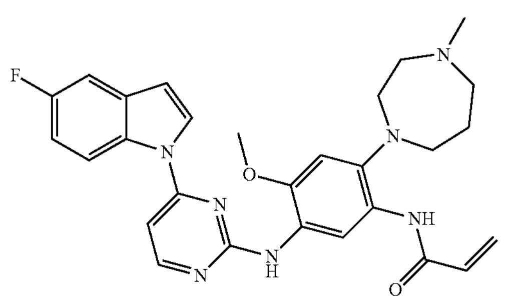 [SMILES: C=CC(=O)Nc1cc(Nc2nccc(-n3ccc4cc(F)ccc43)n2)c(OC)cc1N1CCCN(C)CC1] | N-(5-(4-(5-fluoro-1H-indol-1-yl)-pyrimidin-2-ylamino)-2-(4-methyl-[1,4] diazepin-1-yl)-4-methoxyl-phenyl)-acrylamide | $^1$H-NMR (DMSO-d$_6$) δ: 1.97 (m, 2H), 2.90 (s, 3H), 3.16 (m, 4H), 3.26 (br, 4H), 3.78 (s, 3H), 5.73 (d, 1H), 6.17-6.22 (d, 1H), 6.62-6.69 (m, 1H), 6.77 (d, 1H), 6.91-6.98 (m, 2H), 7.13 (d, 1H), 7.40 (dd, 1H), 8.05 (s, 1H), 8.21 (d, 1H), 8.38 (d, 1H), 8.40 (br, 1H), 8.66 (s, 1H), 9.24 (s, 1H). m/z: ESI MH$^+$ 516.2 |
| 88 | 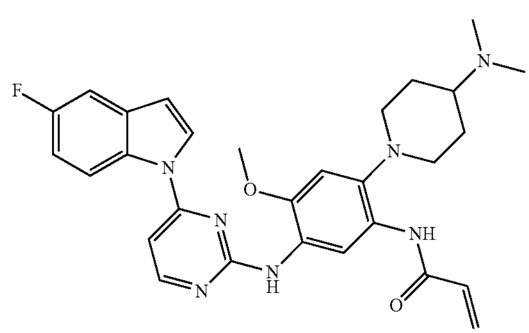 [SMILES: C=CC(=O)Nc1cc(Nc2nccc(-n3ccc4cc(F)ccc43)n2)c(OC)cc1N1CCC(N(C)C)CC1] | N-(5-(4-(5-fluoro-1H-indol-1-yl)-pyrimidin-2-ylamino)-2-(4-(dimethylamino-methyl)-piperidin-1-yl)-4-methoxyl-phenyl)-acrylamide | $^1$H-NMR (CDCl$_3$-d) δ: 2.06 (br, 2H), 2.29 (br, 2H), 2.77 (s, 6H), 2.80 (m, 2H), 3.00 (br, 1H), 3.20 (br, 2H), 3.92 (s, 3H), 5.79 (d, 1H), 6.33 (m, 1H), 6.41 (d, 1H), 6.71 (s, 1H), 6.74 (s, 1H), 6.89 (d, 1H), 7.01 (m, 1H), 7.28 (m, 1H), 7.62 (s, 1H), 8.08 (s, 1H), 8.27 (m, 1H), 8.39 (s, 1H), 8.48 (d, 1H), 9.43 (s, 1H). m/z: ESI MH$^+$ 530.2 |

| Comp. | Structure | Name | Data |
|---|---|---|---|
| 89 | 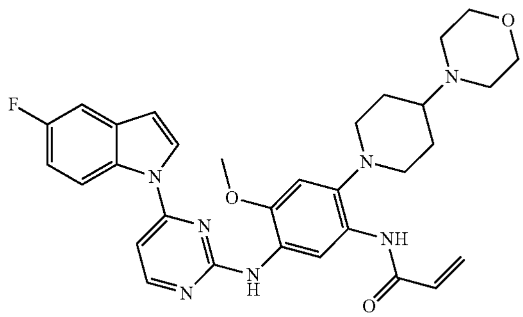 | N-(5-(4-(5-fluoro-1H-indol-1-yl)-pyrimidin-2-ylamino)-2-(4-(morpholin-4-yl)-piperidin-1-yl)-4-methoxyl-phenyl)-acrylamide | ¹H-NMR (CDCl₃-d) δ: 1.68 (m, 2H), 2.10 (br, 2H), 2.32 (m, 1H), 2.64 (br, 4H), 2.76 (t, 2H), 3.11 (br, 2H), 3.80 (m, 4H), 3.92 (s, 3H), 5.76 (d, 1H), 6.31 (m, 1H), 6.39-6.43 (d, 1H), 6.71 (d, 1H), 6.78 (s, 1H), 6.89 (d, 1H), 6.99-7.03 (m, 1H), 7.27 (m, 1H), 7.59 (s, 1H), 8.10 (s, 1H), 8.28 (m, 1H), 8.49 (d, 2H), 9.48 (s, 1H). m/z: ESI MH⁺ 572.2 |
| 90 | 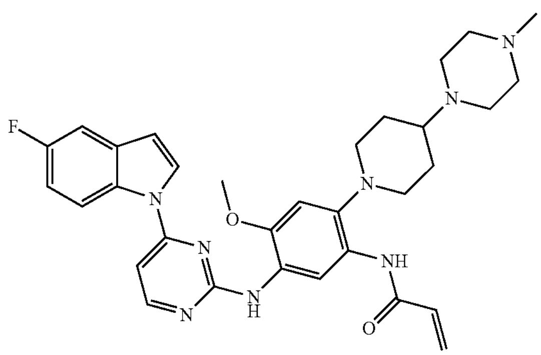 [SMILES: C=CC(=O)Nc1cc(Nc2nccc(-n3ccc4cc(F)ccc43)n2)c(OC)cc1N1CCC(N2CCN(C)CC2)CC1] | N-(5-(4-(5-fluoro-1H-indol-1-yl)-pyrimidin-2-ylamino)-2-(4-(4-methyl-piperazin-1-yl)-piperidin-1-yl)-4-methoxyl-phenyl)-acrylamide | ¹H-NMR (DMSO-d₆) δ: 1.76 (m, 2H), 1.89 (m, 2H), 2.01 (m, 1H), 2.30 (s, 3H), 2.40 (m, 2H), 2.72 (m, 6H), 3.08 (br, 4H), 3.78 (s, 3H), 5.75 (d, 1H), 6.19 (d, 1H), 6.68 (m, 1H), 6.77 (d, 1H), 6.88 (s, 1H), 6.93 (m, 1H), 7.13 (d, 1H), 7.40 (dd, 1H), 8.21 (m, 2H), 8.39 (d, 1H), 8.44 (br, 1H), 8.68 (s, 1H), 9.05 (s, 1H). m/z: ESI MH⁺ 585.2 |
| 91 | 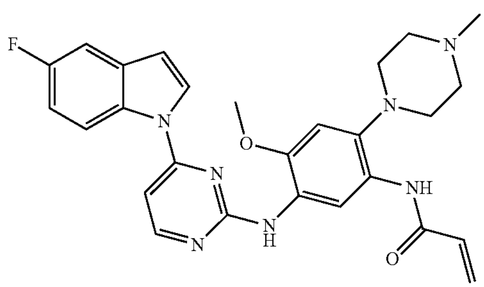 [SMILES: C=CC(=O)Nc1cc(Nc2nccc(-n3ccc4cc(F)ccc43)n2)c(OC)cc1N1CCN(C)CC1] | N-(5-(4-(5-fluoro-1H-indol-1-yl)-pyrimidin-2-ylamino)-2-(4-methylpiperazin-1-yl)-4-methoxyl-phenyl)-acrylamide | ¹H-NMR (CDCl₃-d) δ: 2.44 (s, 3H), 2.67 (m, 4H), 2.96 (m, 4H), 3.90 (s, 3H), 5.78 (d, 1H), 6.33 (m, 1H), 6.40 (d, 1H), 6.70 (d, 1H), 6.82 (s, 1H), 6.88 (d, 1H), 7.02 (m, 1H), 7.29 (s, 1H), 7.62 (s, 1H), 8.09 (s, 1H), 8.28 (m, 1H), 8.49 (d, 1H), 8.57 (s, 1H), 9.49 (s, 1H). m/z: ESI MH⁺ 502.2 |
| 92 | 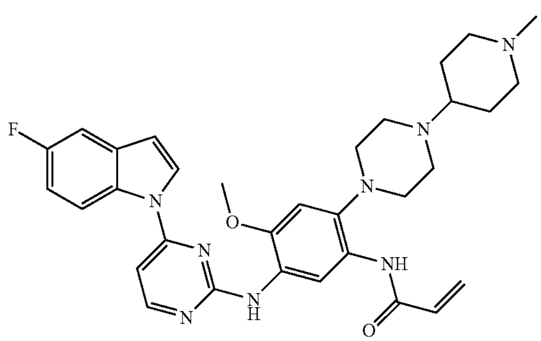 [SMILES: C=CC(=O)Nc1cc(Nc2nccc(-n3ccc4cc(F)ccc43)n2)c(OC)cc1N1CCN(C2CCN(C)CC2)CC1] | N-(5-(4-(5-fluoro-1H-indol-1-yl)-pyrimidin-2-ylamino)-2-(4-(1-methylpiperidin-4-yl)-piperazin-1-yl)-4-methoxyl-phenyl)-acrylamide | ¹H-NMR (CDCl₃-d) δ: 1.75 (m, 2H), 2.10 (m, 2H), 2.52 (m, 2H), 2.57 (s, 3H), 2.74 (m, 1H), 2.87 (m, 4H), 3.02 (m, 4H), 3.26 (br, 2H), 3.92 (s, 3H), 5.78 (d, 1H), 6.29 (d, 1H), 6.50-6.53 (m, 1H), 6.73 (d, 1H), 6.94-6.97 (m, 2H), 7.05 (d, 1H), 7.27 (d, 1H), 8.04 (d, 1H), 8.37-8.43 (m, 2H), 8.72 (s, 1H). m/z: ESI MH⁺ 585.2 |
| 93 | 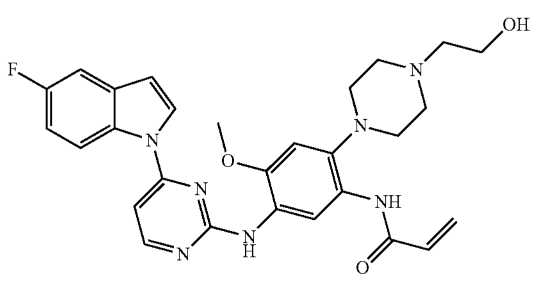 [SMILES: C=CC(=O)Nc1cc(Nc2nccc(-n3ccc4cc(F)ccc43)n2)c(OC)cc1N1CCN(CCO)CC1] | N-(5-(4-(5-fluoro-1H-indol-1-yl)-pyrimidin-2-ylamino)-2-(4-(2-hydroxylethyl)-piperazin-1-yl)-4-methoxyl-phenyl)-acrylamide | ¹H-NMR (DMSO-d₆) δ: 1.88 (s, 4H), 3.00 (s, 4H), 3.26 (t, 2H), 3.78 (s, 3H), 4.34 (t, 2H), 5.67 (d, 1H), 6.20 (d, 1H), 6.71 (d, 1H), 6.78 (d, 1H), 6.92 (s, 1H), 7.03 (m, 1H), 7.09 (d, 1H), 7.58 (m, 1H), 8.11 (d, 1H), 8.18 (m, 2H), 8.36 (d, 1H), 8.84 (s, 1H), 9.64 (s, 1H). m/z: ESI MH⁺ 532.2 |

TABLE 2-continued

| Comp. | Structure | Name | Data |
|---|---|---|---|
| 94 | 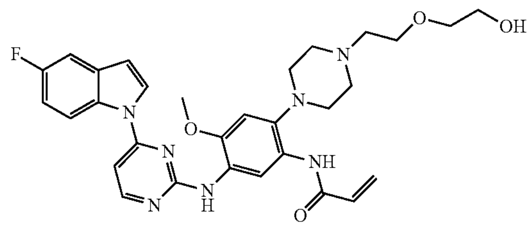 [SMILES: C=CC(=O)Nc1cc(Nc2nccc(-n3ccc4cc(F)ccc43)n2)c(OC)cc1N1CCN(CCOCCO)CC1] | N-(5-(4-(5-fluoro-1H-indol-1-yl)-pyrimidin-2-ylamino)-2-(4-(2-(2-hydroxy-ethoxyl)-ethyl)-piperazin-1-yl)-4-methoxyl-phenyl)-acrylamide | $^1$H-NMR (CDCl$_3$-d) δ: 2.75-2.81 (m, 6H), 3.00 (br, 4H), 3.68 (br, 2H), 3.77 (br, 4H), 3.92 (s, 3H), 5.78 (dd, 1H), 6.31 (m, 1H), 6.39-6.44 (dd, 1H), 6.71 (d, 1H), 6.84 (s, 1H), 6.89 (d, 1H), 7.02 (m, 1H), 7.26 (d, 1H), 7.62 (s, 1H), 8.09 (s, 1H), 8.28 (m, 1H), 8.49 (d, 1H), 8.53 (s, 1H), 9.48 (s, 1H). LC-MS: ESI MH$^+$ 576.3 |
| 95 | 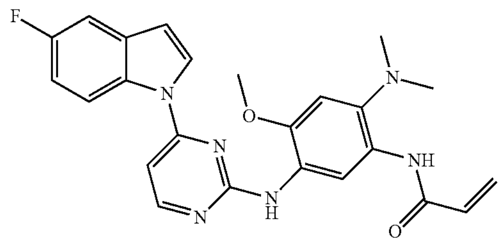 [SMILES: C=CC(=O)Nc1cc(Nc2nccc(-n3ccc4cc(F)ccc43)n2)c(OC)cc1N(C)C] | N-(5-(4-(5-fluoro-1H-indol-1-yl)-pyrimidin-2-ylamino)-2-(dimethylamino)-4-methoxyl-phenyl)-acrylamide | $^1$H-NMR (CDCl$_3$-d) δ: 2.69 (s, 6H), 3.92 (s, 3H), 5.77 (d, 1H), 6.41 (d, 2H), 6.70 (d, 1H), 6.81-6.87 (br, 2H), 6.99 (m, 1H), 7.28 (d, 1H), 7.59 (s, 1H), 8.09 (s, 1H), 8.29 (m, 1H), 8.51 (br, 2H), 9.45 (s, 1H). m/z: ESI MH$^+$ 447.1 |
| 96 | 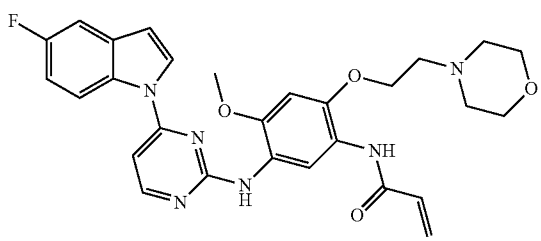 [SMILES: C=CC(=O)Nc1cc(Nc2nccc(-n3ccc4cc(F)ccc43)n2)c(OC)cc1OCCN1CCOCC1] | N-(5-(4-(5-fluoro-1H-indol-1-yl)pyrimidin-2-ylamino)-2-(2-(morpholin-4-yl)-ethoxyl)-4-methoxyl-phenyl)-acrylamide | $^1$H-NMR (CDCl$_3$-d) δ: 2.60 (t, 4H), 2.76 (t, 2H), 3.80 (t, 4H), 3.91 (s, 3H), 4.22 (t, 2H), 5.78 (d, 1H), 6.44 (m, 2H), 6.64 (s, 1H), 6.69 (d, 1H), 6.85 (d, 1H), 6.98 (m, 1H), 7.27 (m, 1H), 7.46 (s, 1H), 8.03 (s, 1H), 8.29 (m, 1H), 8.47 (m, 2H), 9.37 (s, 1H). m/z: ESI MH$^+$ 533.2 |
| 97 | 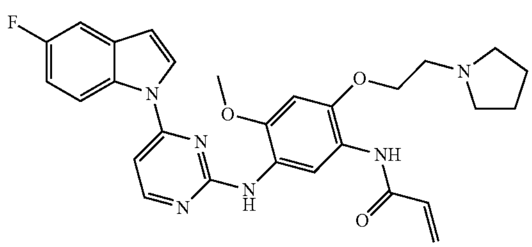 [SMILES: C=CC(=O)Nc1cc(Nc2nccc(-n3ccc4cc(F)ccc43)n2)c(OC)cc1OCCN1CCCC1] | N-(5-(4-(5-fluoro-1H-indol-1-yl)-pyrimidin-2-ylamino)-2-(2-pyrrolidin-1-yl)-ethoxyl)-4-methoxyl-phenyl)-acrylamide | $^1$H-NMR (DMSO-d$_6$) δ: 1.87 (s, 4H), 2.96 (s, 4H), 3.26 (t, 2H), 3.80 (s, 3H), 4.35 (t, 2H), 5.70 (d, 1H), 6.20 (d, 1H), 6.70 (m, 1H), 6.76 (d, 1H), 6.92 (m, 2H), 7.10 (d, 1H), 7.38 (dd, 1H), 8.18 (m, 2H), 8.38 (m, 2H), 8.69 (s, 1H), 9.70 (s, 1H). m/z: ESI MH$^+$ 517.2 |
| 98 | 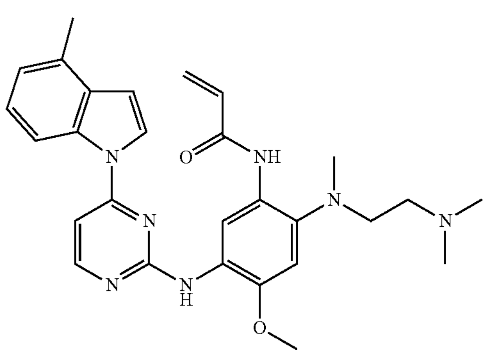 [SMILES: C=CC(=O)Nc1cc(Nc2nccc(-n3ccc4c(C)cccc43)n2)c(OC)cc1N(C)CCN(C)C] | N-(5-(4-(4-methyl-1H-indol-1-yl)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.22 (s, 6H), 2.34 (t, 2H), 2.48 (s, 3H), 2.76 (s, 3H), 2.91 (t, 2H), 3.77 (s, 3H), 5.73 (m, 1H), 6.21 (dd, 1H), 6.40 (dd, 1H), 6.82 (d, 1H), 6.95-7.01 (m, 2H), 7.06 (s, 1H), 7.13 (d, 1H), 8.13 (d, 1H), 8.23 (br, 1H), 8.39 (d, 1H), 8.55 (s, 1H), 8.64 (s, 1H), 10.13 (s, 1H). m/z: ESI MH$^+$ 500.1 |

TABLE 2-continued

| Comp. | Structure | Name | Data |
|---|---|---|---|
| 99 | 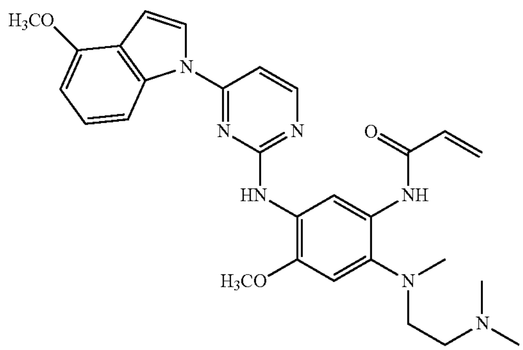 [SMILES: C=CC(=O)Nc1cc(Nc2nccc(-n3ccc4c(OC)cccc43)n2)c(OC)cc1N(C)CCN(C)C] | N-(5-(4-(4-methoxyl-1H-indol-1-yl)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.21 (s, 6H), 2.35 (t, 2H), 2.75 (s, 3H), 2.91 (br, 2H), 3.77 (s, 3H), 3.88 (s, 3H), 5.74 (dd, 1H), 6.21 (dd, 1H), 6.41 (dd, 1H), 6.70 (d, 1H), 6.75 (d, 1H), 7.00-7.05 (m, 2H), 7.11 (d, 1H), 7.98 (d, 1H), 8.02 (d, 1H), 8.39 (d, 1H), 8.54 (s, 1H), 8.64 (s, 1H), 10.14 (s, 1H). m/z: ESI MH$^+$ 516.2 |
| 100 | 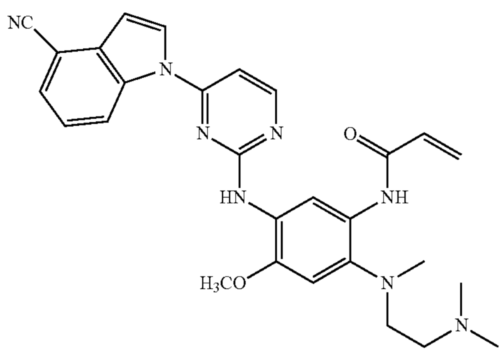 [SMILES: C=CC(=O)Nc1cc(Nc2nccc(-n3ccc4c(C#N)cccc43)n2)c(OC)cc1N(C)CCN(C)C] | N-(5-(4-(4-cyano-1H-indol-1-yl)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.23 (s, 6H), 2.37 (br, 2H), 2.76 (s, 3H), 2.93 (br, 2H), 3.77 (s, 3H), 5.74 (m, 1H), 6.20 (dd, 1H), 6.41 (dd, 1H), 6.93 (d, 1H), 7.05 (s, 1H), 7.02-7.25 (m, 2H), 7.69 (d, 1H), 8.44-8.48 (m, 3H,), 8.78 (br, 1H), 8.87 (s, 1H), 10.11 (s, 1H). m/z: ESI MH$^+$ 511.1 |
| 101 | 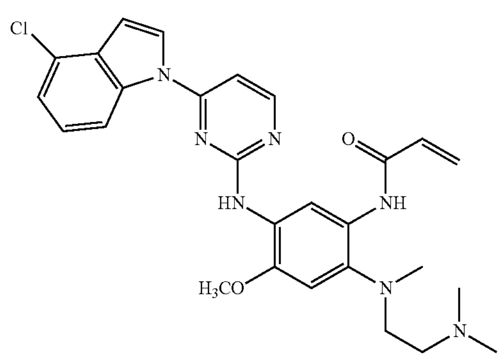 [SMILES: C=CC(=O)Nc1cc(Nc2nccc(-n3ccc4c(Cl)cccc43)n2)c(OC)cc1N(C)CCN(C)C] | N-(5-(4-(4-chloro-1H-indol-1-yl)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.22 (s, 6H), 2.35 (br, 2H), 2.76 (s, 3H), 2.92 (br, 2H), 3.78 (s, 3H), 5.73 (m, 1H), 6.20 (dd, 1H), 6.40 (dd, 1H), 6.81 (d, 1H), 7.07 (s, 1H), 7.08 (t, 1H), 7.17 (d, 1H), 7.25 (dd, 1H), 8.27 (d, 1H), 8.41 (br, 1H), 8.43 (d, 1H), 8.51 (s, 1H), 8.79 (s, 1H), 10.13 (s, 1H). m/z: ESI MH$^+$ 520.1 |
| 102 | 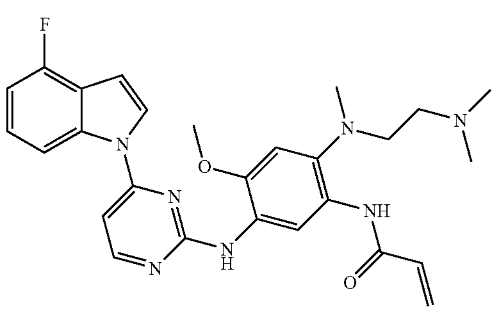 [SMILES: C=CC(=O)Nc1cc(Nc2nccc(-n3ccc4c(F)cccc43)n2)c(OC)cc1N(C)CCN(C)C] | N-(5-(4-(4-fluoro-1H-indol-1-yl)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.41 (s, 6H), 2.51 (t, 2H), 2.71 (s, 3H), 3.07 (t, 2H), 3.79 (s, 3H), 5.70 (d, 1H), 6.23 (d, 1H), 6.70 (br, 1H), 6.96 ((m, 1H), 7.03 (s, 1H), 7.11 (m, 1H), 7.17 (d, 1H), 8.20 (d, 2H), 8.28 (d, 1H), 8.44 (m, 2H), 8.76 (s, 1H), 10.03 (s, 1H). m/z: ESI MH$^+$ 504.2 |

TABLE 2-continued

| Comp. | Structure | Name | Data |
|---|---|---|---|
| 103 | 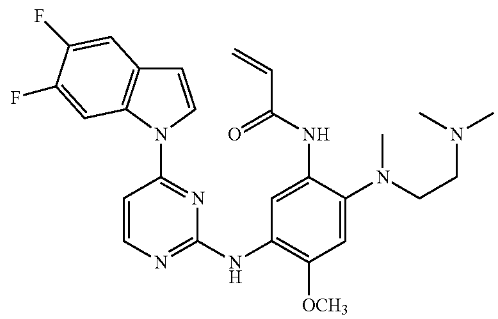 [SMILES: C=CC(=O)Nc1cc(Nc2nccc(-n3ccc4cc(F)c(F)cc43)n2)c(OC)cc1N(C)CCN(C)C] | N-(5-(4-(5,6-difluoro-1H-indol-1-yl)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.22 (s, 6H), 2.36 (t, 2H), 2.75 (s, 3H), 2.90 (t, 2H), 3.76 (s, 3H), 5.72 (m, 1H), 6.17 (dd, 1H), 6.39 (dd, 1H), 6.78 (d, 1H), 7.06 (s, 1H), 7.13 (d, 1H), 7.60 (m, 1H), 8.21 (d, 1H), 8.39 (d, 1H), 8.44 (br, 1H), 8.47 (s, 1H), 8.91 (s, 1H), 10.10 (s, 1H). m/z: ESI MH$^+$ 522.1 |
| 104 | 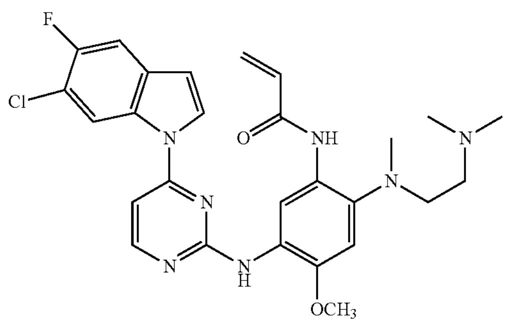 [SMILES: C=CC(=O)Nc1cc(Nc2nccc(-n3ccc4cc(F)c(Cl)cc43)n2)c(OC)cc1N(C)CCN(C)C] | N-(5-(4-(5-fluoro-6-chloro-1H-indol-1-yl)-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.22 (s, 6H), 2.36 (t, 2H), 2.75 (s, 3H), 2.89 (t, 2H), 3.79 (s, 3H), 5.71 (m, 1H), 6.16 (dd, 1H), 6.39 (dd, 1H), 6.81 (d, 1H), 7.08 (s, 1H), 7.13 (d, 1H), 7.61 (d, 1H), 8.26 (d, 1H), 8.41 (d, 1H), 8.46 (s, 1H), 8.62 (br, 1H), 8.89 (s, 1H), 10.05 (s, 1H). m/z: ESI MH$^+$ 538.1 |
| 105 | 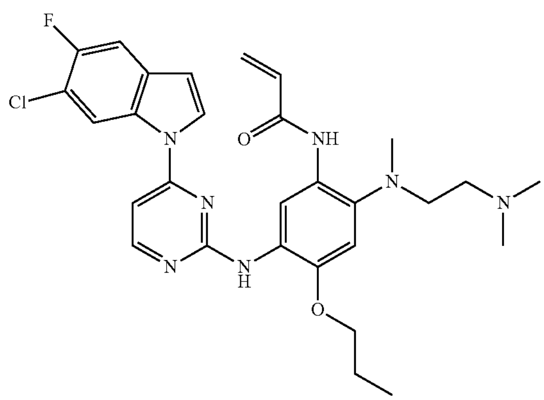 [SMILES: C=CC(=O)Nc1cc(Nc2nccc(-n3ccc4cc(F)c(Cl)cc43)n2)c(OCCC)cc1N(C)CCN(C)C] | N-{5-[4-(6-chloro-5-fluoro-indol-1-yl)-pyrimidin-2-ylamino]-2-[(2-dimethylamino-ethyl)-methyl-amino]-4-propyl-phenyl}-acrylamide | $^1$H-NMR (DMSO-d$_6$) δ: 0.75 (t, 3H), 1.59 (m, 2H), 2.33 (br, 6H), 2.48 (br, 2H), 2.70 (s, 3H), 2.91 (br, 2H), 3.96 (t, 2H), 5.72 (dd, 1H), 6.19 (dd, 1H), 6.50 (br, 1H), 6.81 (d, 1H), 7.05 (s, 1H), 7.14 (d, 1H), 7.61 (d, 1H), 8.25 (d, 1H), 8.42-8.44 (m, 2H), 8.61 (br, 1H), 8.80 (s, 1H), 9.95 (s, 1H). m/z: ESI MS$^+$ 566.2 |

Example 8

Preparation of N-(5-(4-(-1H-benzo[d]imidazol-1-yl)pyrimidin-2-ylamino)-2-((2-(dimethylamino)ethyl)(methyl)amino)-4-methoxyl)phenyl)acrylamide (Compound 106)

Compound 106

Step 1: Synthesis of 1-(2-chloropyrimidin-4-yl)-1H-benzimidazole

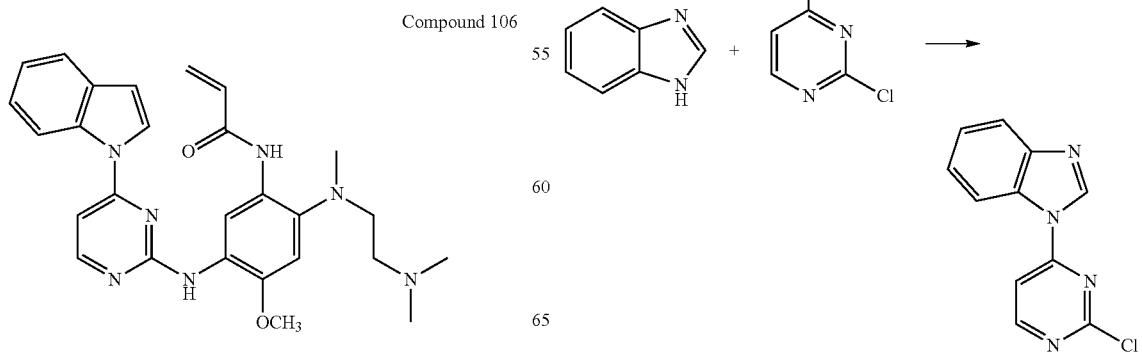

Benzimidazole (2.4 g, 20 mmol), potassium carbonate (5.6 g, 40 mmol) and 2,4-dichloropyrimidine (4.5 g, 30 mmol) were added to 5 mL of DMF, and then stirred for 1 h at room temperature. The reaction mixture was poured to water and then extracted by ethyl acetate. The ethyl acetate layer was dried and then concentrated. The residues were purified by column chromatography to give the title intermediate (2.1 g). m/z: ESI MH+ 231.0.

Steps 2~5 of Example 6 were repeated to give the target compounds.

Compounds 106-107 in Table 3 were prepared following the method in Example 1.

Step 1: Preparation of (3-chlorophenyl)-(4-chloro-[1,3,5]triazin-2-yl)-amine

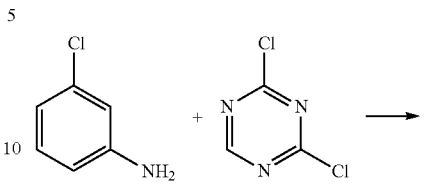

TABLE 3

| Comp. | Structure | Name | Data |
|---|---|---|---|
| 106 | 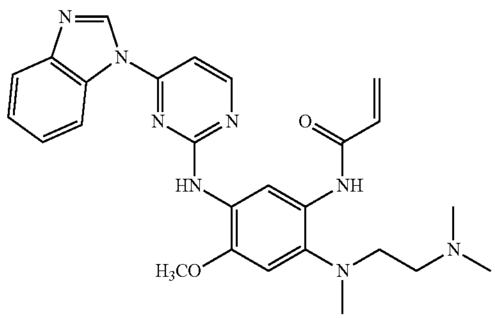 [SMILES: C=CC(=O)Nc1cc(Nc2nccc(-n3cnc4ccccc43)n2)c(OC)cc1N(C)CCN(C)C] | N-(5-(4-(-1H-benzo[d]imidazol-1-yl)-pyrimidin-2-ylamino)-2-((2-(dimethylamino)-ethyl)(methyl)amino)-4-methoxyl-phenyl)-acrylamide | $^1$H-NMR (DMSO-d$_6$) δ: 2.23 (s, 6H), 2.38 (t, 2H), 2.76 (s, 3H), 2.92 (t, 2H), 3.77 (s, 3H), 5.74 (dd, 1H), 6.21 (dd, 1H), 6.42 (dd, 1H), 7.07 (s, 1H), 7.21 (t, 1H), 7.28-7.33 (m, 2H), 7.73 (d, 1H), 8.26 (br, 1H), 8.50-8.53 (m, 2H), 8.91 (s, 1H), 9.13 (s, 1H), 10.14 (s, 1H). m/z: ESI MH$^+$ 487.2 |
| 107 | 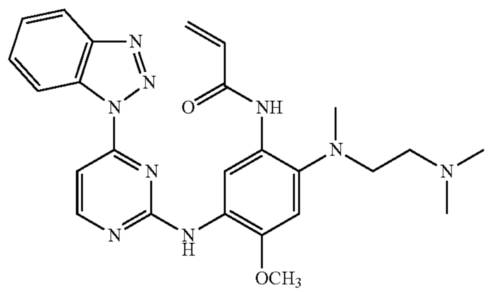 [SMILES: C=CC(=O)Nc1cc(Nc2nccc(-n3nnc4ccccc43)n2)c(OC)cc1N(C)CCN(C)C] | N-(5-(4-benzotriazol-1-yl-pyrimidin-2-ylamino)-2-((2-dimethylamino-ethyl-methyl-amino)-4-methoxyl-phenyl)-acrylamide | $^1$H-NMR (DMSO-d$_6$) δ: 2.23 (s, 6H), 2.37 (br, 2H), 2.78 (s, 3H), 2.94 (br, 2H), 3.77 (s, 3H), 5.73 (m, 1H), 6.19 (dd, 1H), 6.42 (dd, 1H), 7.09 (s, 1H), 7.51-7.55 (m, 3H), 8.19 (m, 1H), 8.35 (br, 1H), 8.45 (s, 1H), 8.60 (d, 1H), 9.17 (s, 1H), 10.14 (s, 1H). m/z: ESI MH$^+$ 488.1 |

Example 9

Preparation of N-(5-(4-(3-chloro-phenylamino)-[1,3,5]triazin-2-ylamino)-2-((2-dimethylamino-ethyl)-methyl-amino)-4-methoxyl-phenyl)-acrylamide (Compound 108)

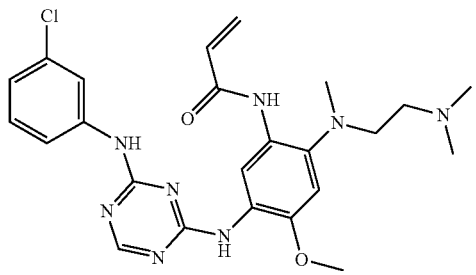

Compound 108

-continued

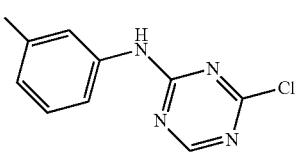

3-Chloroaniline (2.56 g, 20 mmol) and DIEA (3.08 g, 24 mmol) were added to 20 mL of DMF, and then cooled in ice-salt bath. A solution of 2,4-dichloro-1,3,5-triazine (3.29 g, 22 mmol) in DMF was added dropwise, and the mixture was stirred for 2.5 h under ice-salt bath. The reaction mixture was poured to water, and then added with ethyl acetate. The ethyl acetate layer was dried and concentrated. The residues were purified by column chromatography to give the title intermediate (3.65 g). m/z: ESI MH+ 241.0.

Steps 2~4 of Example 1 were repeated to give the target compound.

Compounds 108-130 in Table 4 were prepared following the method in Example 9.

Compounds 131-132 in Table 4 were prepared according to steps 1 and 2 of Example 9 and steps 3 and 4 of Example 4.

TABLE 4

| Comp. | Structure | Name | Data |
|---|---|---|---|
| 108 | 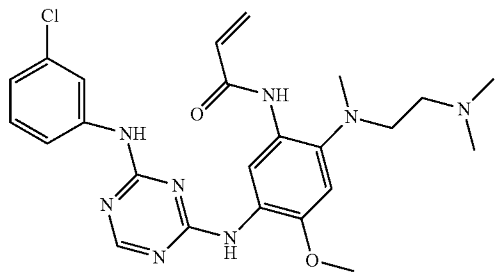 [SMILES: C=CC(=O)Nc1cc(Nc2ncnc(Nc3cccc(Cl)c3)n2)c(OC)cc1N(C)CCN(C)C] | N-(5-(4-(3-chloro-phenylamino)-[1,3,5]triazin-2-ylamino)-2-( (2-dimethylamino-ethyl)-methyl-amino)-4-methoxyl-phenyl)-acrylamide | $^1$H-NMR (DMSO-$d_6$) δ: 2.01 (s, 6H), 2.17 (t, 2H), 2.73 (s, 3H), 2.87 (t, 2H), 3.77 (s, 3H), 5.74 (dd, 1H), 6.21 (dd, 1H), 6.40 (m, 1H), 6.96 (s, 1H), 7.02 (s, 1H), 7.17 (s, 1H), 7.49 (s, 1H), 7.82 (s, 1H), 8.28 (s, 1H), 8.31 (s, 1H), 9.04 (s, 1H), 9.83 (s, 1H), 10.04 (s, 1H). m/z: ESI MH$^+$ 496.21 |
| 109 | 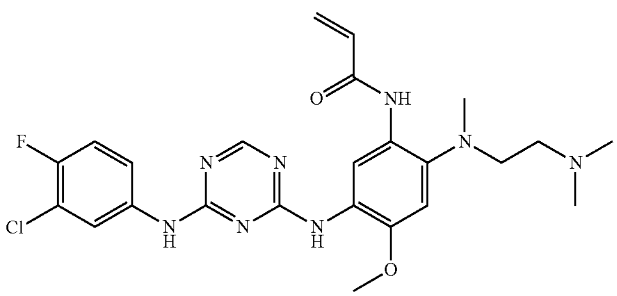 [SMILES: C=CC(=O)Nc1cc(Nc2ncnc(Nc3ccc(F)c(Cl)c3)n2)c(OC)cc1N(C)CCN(C)C] | N-(5-(4-(3-chloro-4-fluoro-phenylamino)-[1,3,5]triazin-2-ylamino)-2-((2-dimethylamino-ethyl)-methyl-amino)-4-methoxyl-phenyl)-acrylamide | $^1$H-NMR (DMSO-$d_6$) δ: 2.21 (s, 6H), 2.34-2.36 (t, 2H), 2.73 (s, 3H), 2.86-2.89 (t, 2H), 3.77 (s, 3H), 5.72-5.76 (m, 1H), 6.17-6.21 (m, 1H), 6.36-6.43 (m, 1H), 7.02 (s, 1H), 7.18 (br, 1H), 7.52 (br, 1H), 7.93 (br, 1H), 8.27 (s, 1H), 8.32 (s, 1H), 9.04 (br, 1H), 9.85 (s, 1H), 10.04 (s, 1H). m/z ESI MH$^+$ 515.2 |
| 110 | 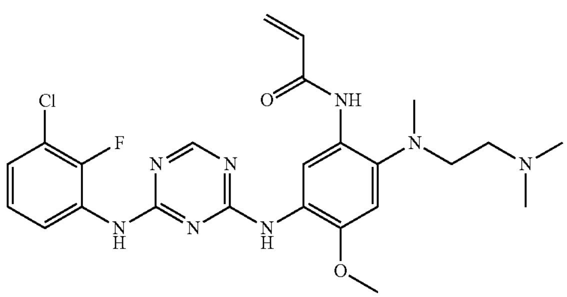 [SMILES: C=CC(=O)Nc1cc(Nc2ncnc(Nc3cccc(Cl)c3F)n2)c(OC)cc1N(C)CCN(C)C] | N-(5-(4-(3-chloro-2-fluoro-phenylamino)-[1,3,5]triazin-2-ylamino)-2-((2-dimethylamino-ethyl)-methyl-amino)-4-methoxyl-phenyl)-acrylamide | $^1$H-NMR (DMSO-$d_6$) δ: 2.20 (s, 6H), 2.32 (t, 2H), 2.70 (s, 3H), 2.84-2.87 (t, 2H), 3.76 (s, 3H), 5.73-5.76 (dd, 1H), 6.19-6.23 (dd, 1H), 6.36-6.43 (m, 1H), 6.97 (s, 1H), 7.03 (s, 1H), 7.27 (s, 1H), 7.66 (1H, t), 8.24 (s, 1H), 8.30 (s, 1H), 8.78 (s, 1H), 9.43 (s, 1H), 10.05 (s, 1H). m/z: ESI MH$^+$ 515.2 |
| 111 | 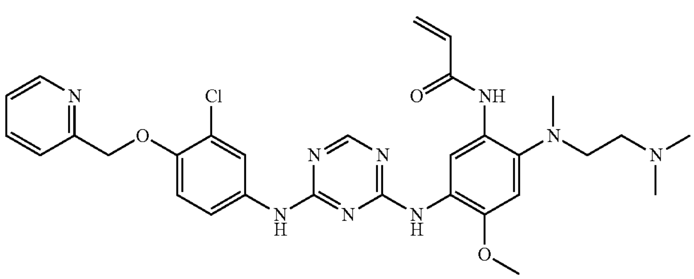 [SMILES: C=CC(=O)Nc1cc(Nc2ncnc(Nc3ccc(OCc4ccccn4)c(Cl)c3)n2)c(OC)cc1N(C)CCN(C)C] | N-(5-(4-(3-chloro-4-(pyridin-2-ylmethoxy)-phenylamino)-[1,3,5]triazin-2-ylamino)-2-((2-dimethylamino-ethyl)-methyl-amino)-4-methoxyl-phenyl)-acrylamide | $^1$H-NMR (DMSO-$d_6$) δ: 2.20 (s, 6H), 2.32-2.35 (t, 2H), 2.72 (s, 3H), 2.85-2.88 (t, 2H), 3.76 (s, 3H), 5.18 (s, 2H), 5.71-5.74 (d, 1H), 6.17-6.22 (d, 1H), 6.36-6.42 (m, 1H), 7.01 (s, 2H), 7.34-7.37 (q, 1H), 7.51-7.53 (d, 2H), 7.83-7.88 (m, 2H), 8.23 (s, 1H), 8.32 (s, 1H), 8.58-8.59 (d, 1H), 8.98 (s, 1H), 9.68 (s, 1H), 10.05 (s, 1H). m/z: ESI MH$^+$ 604.3 |
| 112 | 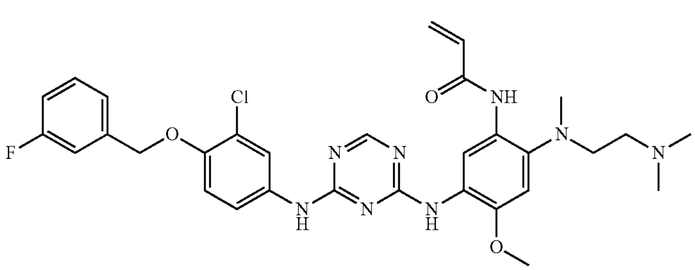 [SMILES: C=CC(=O)Nc1cc(Nc2ncnc(Nc3ccc(OCc4cccc(F)c4)c(Cl)c3)n2)c(OC)cc1N(C)CCN(C)C] | N-(5-(4-(3-chloro-4-(3-fluorophenylmethoxy)-phenylamino)-[1,3,5]triazin-2-ylamino)-2-((2-dimethylamino-ethyl)-methyl-amino)-4-methoxyl-phenyl)-acrylamide | $^1$H-NMR (DMSO-$d_6$) δ: 2.21 (s, 6H), 2.35 (t, 2H), 2.72 (s, 3H), 2.86-2.89 (t, 2H), 3.77 (s, 3H), 5.14 (s, 2H), 5.71-5.72 (d, 1H), 6.18-6.22 (d, 1H), 6.37-6.44 (m, 1H), 7.01 (s, 2H), 7.14-7.19 (t, 1H), 7.25-7.27 (m, 2H), 7.42-7.48 (m, 2H), 7.84 (s, 1H), 8.23 (s, 1H), 8.33 (s, 1H), 8.96 (s, 1H), 9.67 (s, 1H), 10.03 (s, 1H). m/z: ESI MH$^+$ 621.2 |

TABLE 4-continued

| Comp. | Structure | Name | Data |
|---|---|---|---|
| 113 | 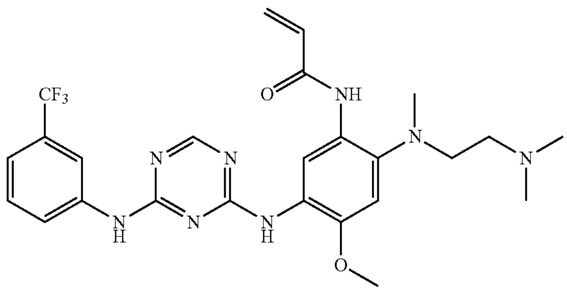 [SMILES: C=CC(=O)Nc1cc(Nc2ncnc(Nc3cccc(C(F)(F)F)c3)n2)c(OC)cc1N(C)CCN(C)C] | N-(5-(4-(3-trifluoromethyl-phenylamino)-[1,3,5]triazin-2-ylamino)-2-((2-dimethylamino-ethyl)-methyl-amino)-4-methoxyl-phenyl)-acrylamide | $^1$H-NMR (DMSO-d$_6$) δ: 2.21 (s, 6H), 2.36 (t, 2H), 2.73 (s, 3H), 2.88 (t, 2H), 3.76 (s, 3H), 5.74 (dd, 1H), 6.21 (d, 1H), 6.39 (m, 1H), 7.00 (s, 1H), 7.26 (s, 1H), 7.37 (s, 1H), 8.00 (m, 2H), 8.30 (s, 1H), 8.33 (s, 1H), 8.98 (s, 1H), 9.94 (s, 1H), 10.06 (s, 1H). m/z: ESI MH$^+$ 530.24 |
| 114 | 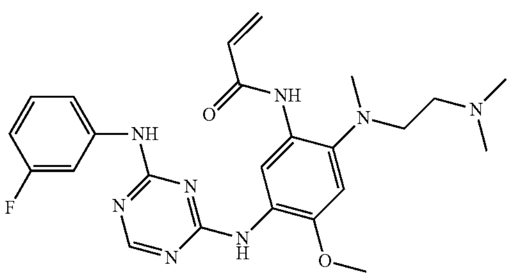 [SMILES: C=CC(=O)Nc1cc(Nc2ncnc(Nc3cccc(F)c3)n2)c(OC)cc1N(C)CCN(C)C] | N-(5-(4-(3-fluoro-phenylamino)-[1,3,5]triazin-2-ylamino)-2-((2-dimethylamino-ethyl)-methyl-amino)-4-methoxyl-phenyl)-acrylamide | $^1$H-NMR (DMSO-d$_6$) δ: 2.21 (s, 6H), 2.34 (t, 2H), 2.73 (s, 3H), 2.86 (t, 2H), 3.76 (s, 3H), 6.72 (dd, 1H), 6.17 (dd, 1H), 6.38 (m, 1H), 6.71 (s, 1H), 7.02 (m, 1H), 7.19 (s, 1H), 7.34 (m, 1H), 7.69 (s, 1H), 8.28 (s, 1H), 8.33 (s, 1H), 9.08 (s, 1H), 9.86 (s, 1H), 10.07 (s, 1H). m/z: ESI MH$^+$ 480.24 |
| 115 | 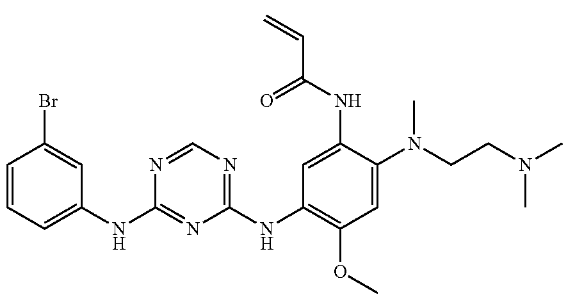 [SMILES: C=CC(=O)Nc1cc(Nc2ncnc(Nc3cccc(Br)c3)n2)c(OC)cc1N(C)CCN(C)C] | N-(5-(4-(3-bromo-phenylamino)-[1,3,5]triazin-2-ylamino)-2-((2-dimethylamino-ethyl)-methyl-amino)-4-methoxyl-phenyl)-acrylamide | $^1$H-NMR (DMSO-d$_6$) δ: 2.20 (s, 6H), 2.33-2.36 (t, 2H), 2.72 (s, 3H), 2.86-2.89 (t, 2H), 3.77 (s, 3H), 5.71-5.75 (dd, 1H), 6.17-6.22 (dd, 1H), 6.36-6.43 (m, 1H), 7.02-7.09 (m, 3H), 7.63 (s, 1H), 7.91 (s, 1H), 8.27 (s, 1H), 8.30 (s, 1H), 9.00 (s, 1H), 9.80 (s, 1H), 10.04 (s, 1H). m/z: ESI MH$^+$ 541.1 |
| 116 | 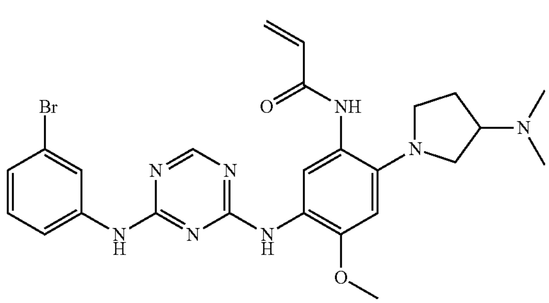 [SMILES: C=CC(=O)Nc1cc(Nc2ncnc(Nc3cccc(Br)c3)n2)c(OC)cc1N1CCC(N(C)C)C1] | N-[5-[4-(3-bromo-phenylamino)-[1,3,5]triazin-2-ylamino]-2-(3-dimethylamino-pyrrolidin-1-yl)-4-methoxyl-phenyl]-acrylamide | $^1$H-NMR (DMSO-d$_6$) δ: 2.09 (s, 2H), 2.17 (s, 6H), 2.67 (s, 2H), 3.18 (s, 1H), 3.22 (s, 2H), 3.77 (s, 3H), 5.66 (dd, 1H), 6.15 (d, 1H), 6.50 (m, 2H), 7.14 (m, 2H), 7.24 (s, 1H), 7.60 (s, 1H), 7.89 (s, 1H), 8.24 (s, 1H), 8.90 (s, 1H), 9.35 (s, 1H), 9.78 (s, 1H); m/z: ESI MH$^+$ 552.16 |

| Comp. | Structure | Name | Data |
|---|---|---|---|
| 117 | 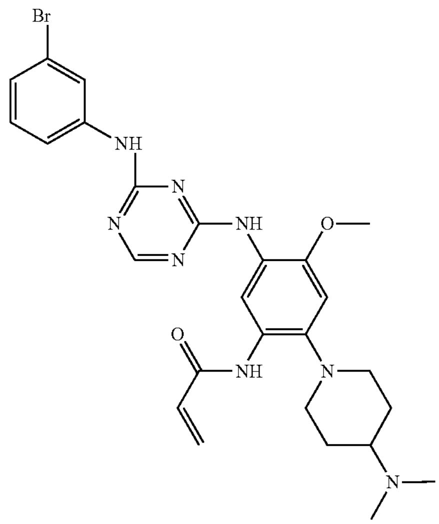 [SMILES: C=CC(=O)Nc1cc(Nc2ncnc(Nc3cccc(Br)c3)n2)c(OC)cc1N1CCC(N(C)C)CC1] | N-[5-[4-(3-bromo-phenylamino)-[1,3,5]triazin-2-amino]-2-(4-dimethylamino-piperidin-1-yl)-4-methoxyl-phenyl]-acrylamide | $^1$H-NMR (CDCl3-d) δ: 1.81 (s, 6H), 2.67-2.70 (m, 2H), 2.75 (s, 3H), 2.93-2.96 (m, 4H), 3.70-3.73 (m, 2H), 3.90 (s, 3H), 5.78-5.81 (d, 1H), 6.26-6.33 (m, 1H), 6.40-6.44 (d, 1H), 6.79 (s, 1H), 7.20 (s, 2H), 7.53-7.59 (m, 2H), 7.93 (s, 1H), 8.43 (s, 1H), 8.54 (s, 1H), 9.55 (s, 1H). m/z: ESI MH$^+$ 567.1 |
| 118 | 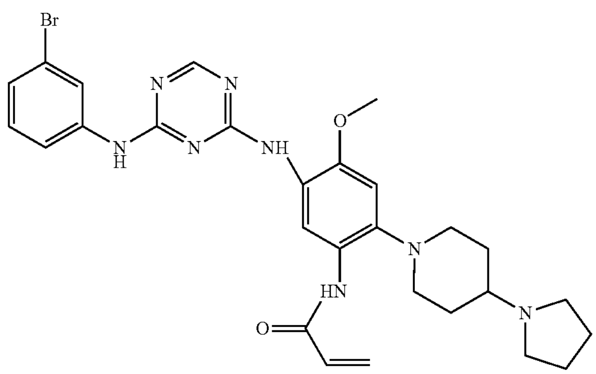 [SMILES: C=CC(=O)Nc1cc(Nc2ncnc(Nc3cccc(Br)c3)n2)c(OC)cc1N1CCC(N2CCCC2)CC1] | N-[5-[4-(3-bromo-phenylamino)-[1,3,5]triazin-2-amino]-4-methoxyl-2-(4-(pyrrolidin-1-yl-piperidin-1-yl)-phenyl-acrylamide | $^1$H-NMR (DMSO-d6) δ: 1.75 (s, 6H) 1.97-1.99 (d, 2H), 2.68-2.73 (m, 6H) 3.04-3.07 (d, 2H), 3.78 (s, 3H), 5.71-5.76 (m, 1H), 6.17-6.22 (d, 1H) 6.61-6.68 (m, 1H) 6.87 (s, 1H) 7.11 (s, 2H), 7.99 (s, 2H) 8.27 (s, 1H) 8.97 (s, 1H) 9.81 (s, 1H), m/z: ESI MH$^+$ 593.2 |
| 119 | 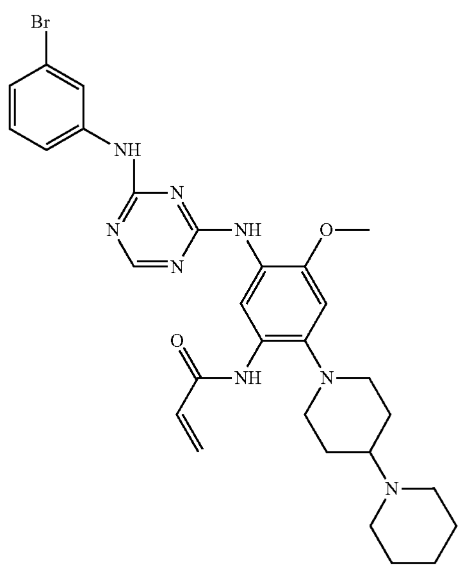 [SMILES: C=CC(=O)Nc1cc(Nc2ncnc(Nc3cccc(Br)c3)n2)c(OC)cc1N1CCC(N2CCCCC2)CC1] | N-{2-[1,4']-piperidin-1'-yl-5-[4-(3-bromo-phenylamino)-[1,3,5]triazin-2-amino]-4-methoxyl-phenyl}-acrylamide | $^1$H-NMR (DMSO-d$_6$) δ: 9.81 (s, 1H), 8.95 (s, 2H), 8.27 (s, 2H), 7.98 (s, 1H), 7.11 (s, 2H), 6.85 (s, 1H), 6.64-6.71 (m, 1H), 6.17-6.22 (d, 1H), 5.70-5.76 (m,1H), 3.77 (s, 3H), 3.07-3.09 (d, 2H), 2.66-2.68 (m, 2H), 1.81 (s, 4H), 1.40-1.53 (m, 6H), 1.24 (s, 2H), 1.04-1.08 (m, 1H), 0.82-0.87 (m, 1H) m/z: ESI MH$^+$ 607.2 |

TABLE 4-continued

| Comp. | Structure | Name | Data |
|---|---|---|---|
| 120 | 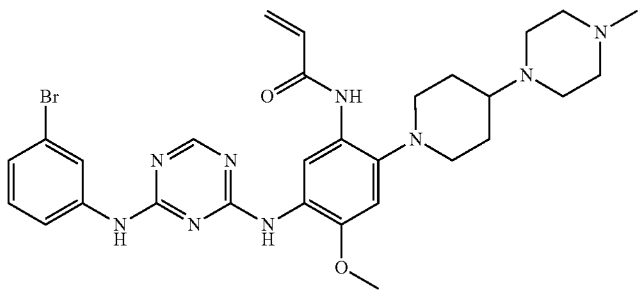 [SMILES: C=CC(=O)Nc1cc(Nc2ncnc(Nc3cccc(Br)c3)n2)c(OC)cc1N1CCC(N2CCN(C)CC2)CC1] | N-{5-[4-(3-bromo-phenylamino)-[1,3,5]triazin-2-ylamino)-4-methoxyl-2-(4-(4-methyl-piperazin-1-yl)-piperidin-1-yl)-phenyl}-acrylamide | ¹H-NMR (DMSO-d₆) δ: 1.72 (q, 2H), 1.85 (d, 2H), 2.24 (s, 3H), 2.36 (s, 1H), 2.46 (m, 4H), 2.58 (m, 4H), 2.70 (t, 2H), 3.08 (d, 2H), 3.77 (s, 3H), 5.70 (d, 1H), 6.17 (d, 1H), 6.68 (m, 1H), 6.85 (s, 1H), 7.18 (m, 2H), 7.62 (s, 1H), 7.95 (m, 2H), 8.27 (s, 1H), 8.95 (m, 2H), 9.81 (s, 1H); m/z: ESI MH⁺ 621.22 |
| 121 | 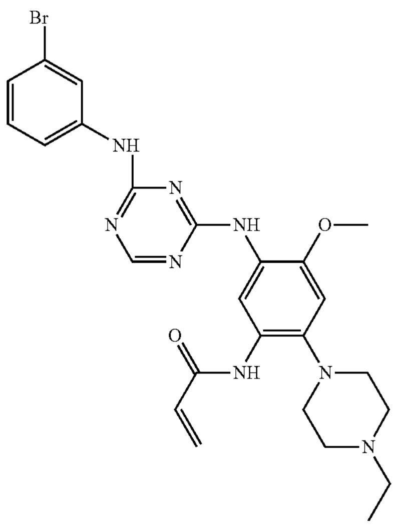 | N-[5-[4-(3-bromo-phenylamino)-[1,3,5]triazin-2-amino]-2-(4-ethyl-piperazin-1-yl)-4-methoxyl-phenyl]-acrylamide | ¹H-NMR (CDCl3-d) δ: 1.15-1.19 (m, 3H) 1.27-1.32 (m, 4H) 2.51-2.58 (m, 2H) 2.93-2.95 (m, 4H) 3.85 (s, 3H), 5.77-5.79 (d, 1H) 6.26-6.33 (m, 1H) 6.39-6.43 (d, 1H) 6.81 (s, 1H) 7.17 (s, 1H) 7.51-7.53 (d, 1H) 7.62 (s, 1H) 7.91 (s, 1H) 8.41 (s, 1H) 8.58 (s, 1H) 9.51 (s, 1H).m/z: ESI MH⁺ 567.0 |
| 122 | 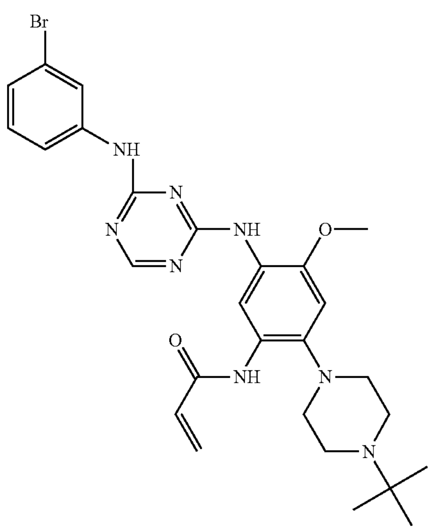 [SMILES: C=CC(=O)Nc1cc(Nc2ncnc(Nc3cccc(Br)c3)n2)c(OC)cc1N1CCN(C(C)(C)C)CC1] | N-[5-[4-(3-bromo-phenylamino)-[1,3,5]triazin-2-amino]-2-(4-tert-butyl-piperazin-1-yl)-4-methoxyl-phenylamino]-acrylamide | ¹H-NMR (CDCl3-d) δ: 1.17 (s, 9H) 2.79 (s, 4H) 2.93 (s, 4H), 3.86 (s, 3H) 5.78-5.81 (d, 1H) 6.28-6.35 (m, 1H) 6.40-6.45 (d, 1H) 6.85 (s, 1H) 7.19-7.21 (d, 2H) 7.53-7.55 (m, 2H) 7.93 (s, 1H) 8.43 (s, 1H) 8.63 (s, 1H), 9.53 (s, 1H).m/z: ESI MH⁺ 581.2 |

TABLE 4-continued

| Comp. | Structure | Name | Data |
|---|---|---|---|
| 123 | 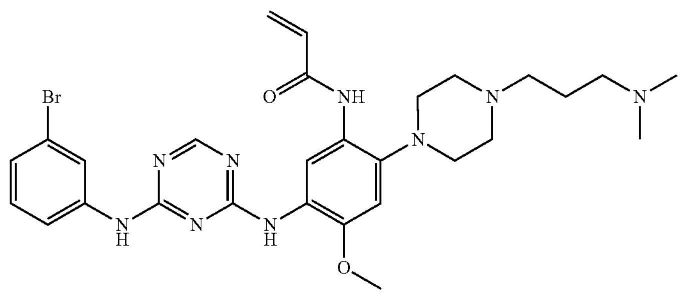 [SMILES: C=CC(=O)Nc1cc(Nc2ncnc(Nc3cccc(Br)c3)n2)c(OC)cc1N1CCN(CCCN(C)C)CC1] | N-{5-[4-(3-bromo-phenylamino)-[1,3,5]triazin-2-ylamino]-2-[4-(3-dimethylamino-propyl)-piperazin-1-yl]-4-methoxyl-phenyl}-acrylamide | $^1$H-NMR (DMSO-d$_6$) δ: 1.62 (m, 2H), 2.18 (s, 6H), 2.32 (t, 2H), 2.38 (t, 2H), 2.59 (m, 4H), 2.88 (m, 4H), 3.78 (s, 3H), 5.70 (d, 1H), 6.20 (d, 1H), 6.62 (m, 1H), 6.89 (s, 1H), 7.11 (m, 2H), 7.62 (s, 1H), 7.90 (m, 2H), 8.27 (s, 1H), 8.98 (m, 2H), 9.82 (s, 1H); m/z: ESI MH$^+$ 609.22 |
| 124 | 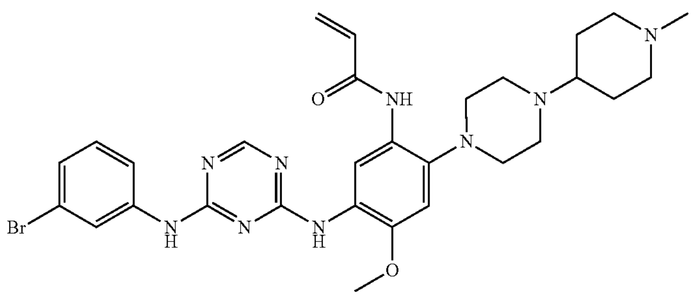 [SMILES: C=CC(=O)Nc1cc(Nc2ncnc(Nc3cccc(Br)c3)n2)c(OC)cc1N1CCN(C2CCN(C)CC2)CC1] | N-{5-[4-(3-bromo-phenylamino)-[1,3,5]triazin-2-ylamino]-4-methoxyl-2-(4-(1-piperazin-4-yl)-piperazin-1-yl)-phenyl}-acrylamide | $^1$H-NMR (DMSO-d$_6$) 1.50 (t, 2H), 1.80 (d, 2H), 2.00 (m, 2H), 2.22 (s, 3H), 2.56 (s, 1H), 2.71 (m, 4H), 2.89 (m, 6H), 3.78 (s, 3H), 5.70 (d, 1H), 6.16 (d, 1H), 6.66 (m, 1H), 6.89 (s, 1H), 7.11 (m, 2H), 7.63 (s, 1H), 7.98 (m, 2H), 8.27 (s, 1H), 8.99 (m, 2H), 9.82 (s, 1H); m/z: ESI MH$^+$ 621.22 |
| 125 | 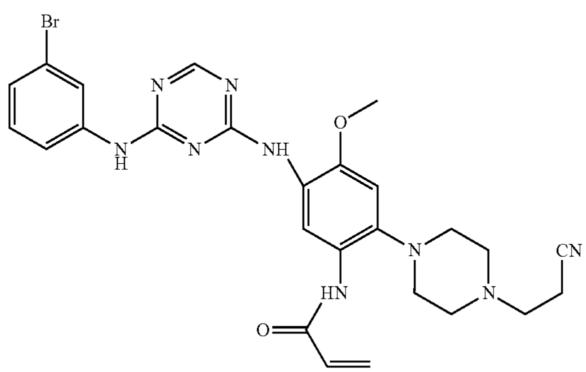 [SMILES: C=CC(=O)Nc1cc(Nc2ncnc(Nc3cccc(Br)c3)n2)c(OC)cc1N1CCN(CCC#N)CC1] | N-{5-[4-(3-bromo-phenylamino)-[1,3,5]triazin-2-amino]-2-[4-(2-cyano-ethyl)-piperazin-1-yl]-4-methoxyl-phenyl}-acrylamide | $^1$H-NMR (CDCl3-d) δ: 2.59-2.63 (m, 2H), 2.75 (s, 3H), 2.80-2.84 (m, 2H), 2.95 (m, 4H), 3.89 (s, 3H), 5.79-5.81 (d, 1H), 6.26-6.33 (m, 1H), 6.40-6.44 (d, 1H), 6.79 (s, 1H), 7.20 (s, 2H), 7.54 (s, 1H), 7.60-7.61 (d, 1H), 7.94 (s, 1H), 8.42 (s, 1H), 8.49-8.52 (d, 1H), 9.54 (s, 1H). m/z: ESI MH$^+$ 579.2 |
| 126 | 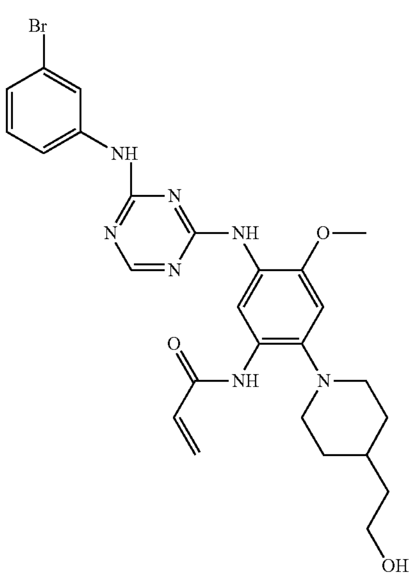 [SMILES: C=CC(=O)Nc1cc(Nc2ncnc(Nc3cccc(Br)c3)n2)c(OC)cc1N1CCC(CCO)CC1] | N-{5-[4-(3-bromo-phenylamino)-[1,3,5]triazin-2-amino]-2-[4-[2-hydroxyl-ethyl)-piperazin-1-yl]-4-methoxyl-phenyl}-acrylamide | $^1$H-NMR (CDCl3-d) δ: 2.67-2.70 (m, 2H), 2.73-2.76 (m, 4H), 2.93-2.96 (m, 4H), 3.70-3.73 (m, 2H), 3.89 (s, 3H), 5.78-5.81 (d, 1H), 6.26-6.33 (m, 1H), 6.40-6.44 (d, 1H), 6.79 (s, 1H), 7.20 (s, 2H), 7.53-7.59 (m, 2H), 7.93 (s, 1H), 8.43 (s, 1H), 8.54 (s, 1H), 9.55 (s, 1H). m/z: ESI MH$^+$ 567.0 |

TABLE 4-continued

| Comp. | Structure | Name | Data |
|---|---|---|---|
| 127 | 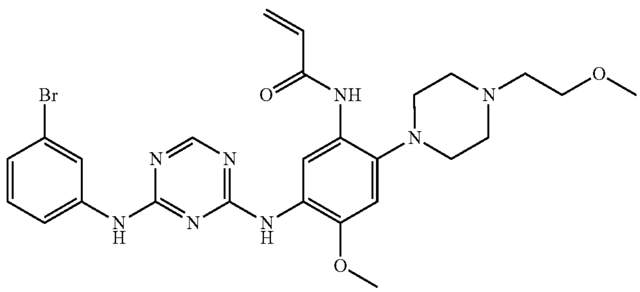 [SMILES: C=CC(=O)Nc1cc(Nc2ncnc(Nc3cccc(Br)c3)n2)c(OC)cc1N1CCN(CCOC)CC1] | N-{5-[4-(3-bromo-phenylamino]-[1,3,5]triazin-2-ylamino]-4-methoxyl-2-[4-(2-methoxyl-ethyl)-piperazin-1-yl])-phenyl}-acrylamide | $^{1}$H-NMR (DMSO-d$_6$) δ: 2.53 (t, 2H), 2.67 (m, 4H), 2.90 (m, 4H), 3.27 (s, 3H), 3.51 (t, 2H), 3.78 (s, 3H), 5.73 (d, 1H), 6.16 (d, 1H), 6.63 (m, 1H), 6.88 (s, 1H), 7.11 (m, 2H), 7.63 (s, 1H), 7.97 (m, 2H), 8.27 (s, 1H), 8.99 (m, 2H), 9.81 (s, 1H); ESI MH$^+$ 82.17 |
| 128 | 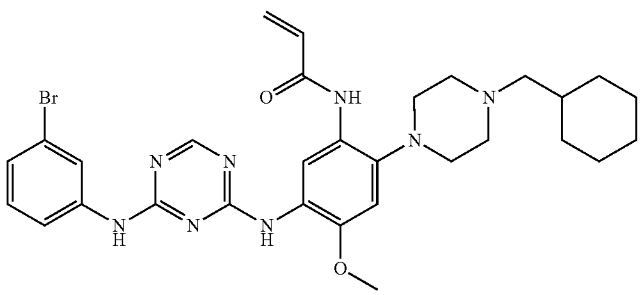 [SMILES: C=CC(=O)Nc1cc(Nc2ncnc(Nc3cccc(Br)c3)n2)c(OC)cc1N1CCN(CC2CCCCC2)CC1] | N-{5-(4-(3-bromo-phenylamino)-[1,3,5]triazin-2-ylamino)-2-(4-cyclohexyl-methyl-piperazin-1-yl)-4-methoxyl-phenyl)-acrylamide | $^{1}$H-NMR (DMSO-d$_6$): δ 0.89 (2H, s), 1.21 (m, 4H), 1.57 (s, 1H), 1.67 (m, 4H), 1.78 (d, 2H), 2.18 (m, 2H), 2.57 (m, 2H), 2.88 (4H), 3.79 (s, 3H), 5.70 (d, 1H), 6.20 (d, 1H), 6.61 (t, 1H), 6.89 (s, 1H), 7.11 (m, 2H), 7.63 (s, 1H), 7.98 (m, 2H), 8.27 (s, 1H), 8.97 (m, 2H), 9.81 (s, 1H); ESI MH$^+$ 620.22 |
| 129 | 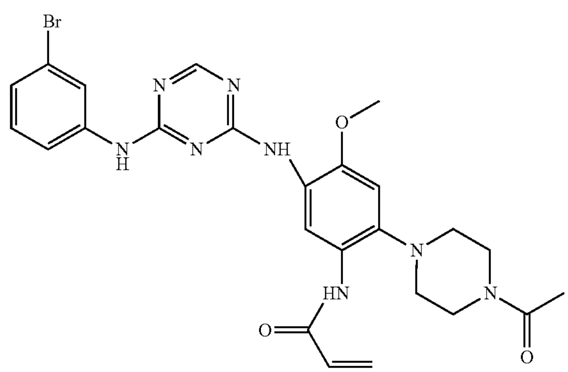 [SMILES: C=CC(=O)Nc1cc(Nc2ncnc(Nc3cccc(Br)c3)n2)c(OC)cc1N1CCN(C(C)=O)CC1] | N-{2-(4-acetyl-piperazin-1-yl)-5-[4-(3-bromo-phenylamino)-[1,3,5]triazin-2-amino]-4-methoxyl-phenyl}-acrylamide | $^{1}$H-NMR (CDCl3-d) δ: 2.19 (s, 2H), 2.88-2.91 (m, 4H), 3.66-3.67 (d, 2H), 3.82 (s, 2H), 3.89 (s, 3H), 5.80-5.83 (d, 1H), 6.26-6.33 (m, 1H), 6.41-6.45 (d, 1H), 6.73 (s, 1H), 7.21 (s, 2H), 7.53-7.59 (m, 2H), 7.93 (s, 1H), 8.44 (s, 2H),), 9.55 (s, 1H). m/z: ESI MH$^+$ 567.0 |
| 130 | 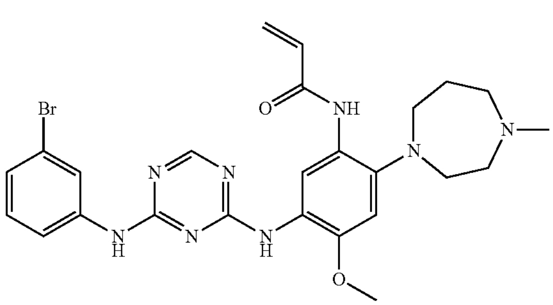 [SMILES: C=CC(=O)Nc1cc(Nc2ncnc(Nc3cccc(Br)c3)n2)c(OC)cc1N1CCCN(C)CC1] | N-[5-[4-(3-bromo-phenylamino)-[1,3,5]triazin-2-ylamino]-4-methoxyl-2-(4-methyl-[1,4]diazepane-1-yl)-phenyl]-acrylamide | $^{1}$HNMR (DMSO-d$_6$) δ: 1.87 (t, 2H), 2.33 (s, 3H), 2.68 (m, 4H), 3.16 (m, 4H), 3.77 (s, 3H), 5.71 (dd, 1H), 6.17 (d, 1H), 6.58 (m, 1H), 6.85 (s, 1H), 7.11 (m, 2H), 7.62 (s, 1H), 7.79 (s, 1H), 7.92 (s, 1H), 8.26 (s, 1H), 8.98 (s, 1H), 9.12 (s, 1H), 9.80 (s, 1H); m/z: ESI MH$^+$ 552.16 |

TABLE 4-continued

| Comp. | Structure | Name | Data |
|---|---|---|---|
| 131 | 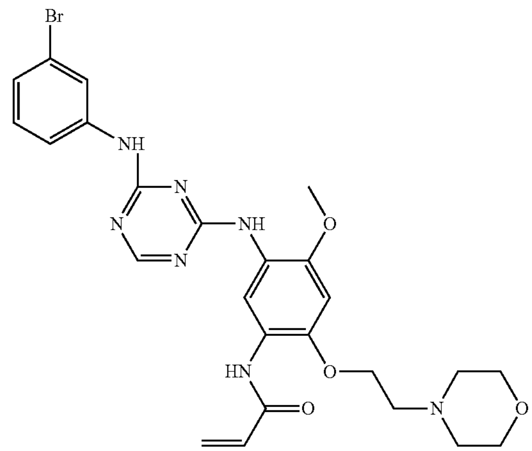 [SMILES: C=CC(=O)Nc1cc(Nc2ncnc(Nc3cccc(Br)c3)n2)c(OC)cc1OCCN1CCOCC1] | N-[5-[4-(3-bromo-phenylamino)-[1,3,5]triazin-2-amino]-4-methoxy1-2-(2-morpholin-4-yl-ethoxyl)-phenyl]-acrylamide | ¹H-NMR (CDCl3-d) δ: 2.58-2.60 (m, 4H), 2.75-2.77 (m, 2H), 3.78-3.80 (m, 4H), 3.88 (s, 3H), 4.20-4.22 (m, 2H), 5.77-5.80 (d, 1H), 6.35-6.39 (m, 1H), 6.41-6.43 (d, 1H), 6.60 (s, 1H), 7.18 (s, 2H), 7.49 (s, 2H), 7.91 (s, 1H), 8.40 (s, 2H), 9.33 (s, 1H). m/z: ESI MH⁺ 570.1 |
| 132 | 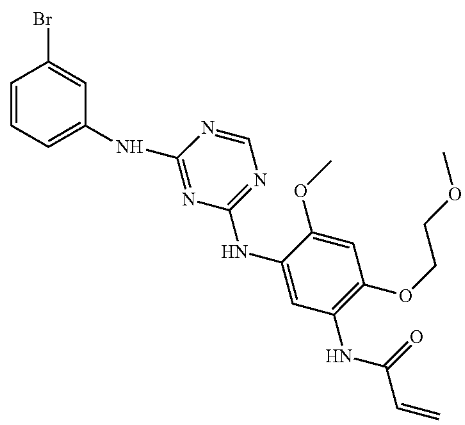 [SMILES: C=CC(=O)Nc1cc(Nc2ncnc(Nc3cccc(Br)c3)n2)c(OC)cc1OCCOC] | N-[5-[4-(3-bromo-phenylamino)-[1,3,5]triazin-2-ylamino]-4-methoxyl-2-(2-methoxyl-ethoxyl)-phenyl]-acrylamide | ¹H-NMR (CDCl$_3$-d) δ: 3.50-3.51 (d, 3H), 3.72-3.74 (m, 2H), 3.88 (s, 3H), 4.18-4.21 (m, 2H), 5.32-5.37 (d, 1H), 5.76-5.78 (d, 1H), 6.27-6.33 (dd, 1H), 6.42-646 (d, 1H), 6.65 (d, 1H), 7.19-7.26 (d, 2H), 7.51-7.54 (d, 2H), 7.93 (s, 1H), 8.32-8.41 (d, 2H), 9.45 (s, 1H). m/z: ESI MH⁺ 516.1. |

Example 10

Preparation of N-(5-(6-(3-bromophenylamino)-pyrimidin-4-ylamino)-2-((2-dimethylamino-ethyl)-methyl-amino)-4-methoxyl-phenyl)-acrylamide (Compound 133)

Compound 133

Step 1: Preparation of N-(6-chloropyrimidin-4-yl)-3-bromoaniline

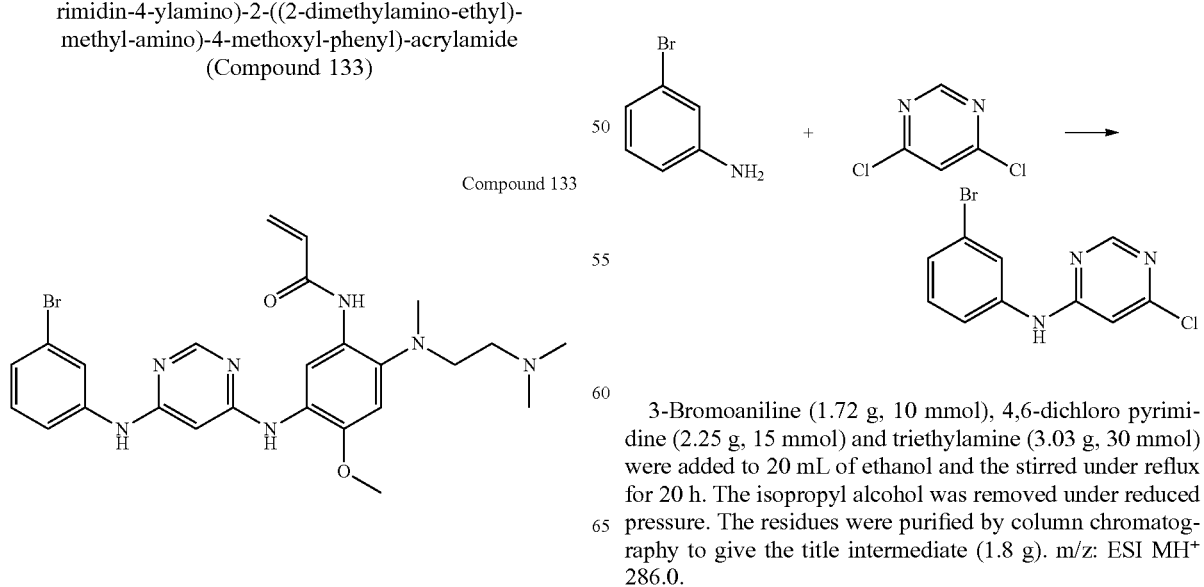

3-Bromoaniline (1.72 g, 10 mmol), 4,6-dichloro pyrimidine (2.25 g, 15 mmol) and triethylamine (3.03 g, 30 mmol) were added to 20 mL of ethanol and the stirred under reflux for 20 h. The isopropyl alcohol was removed under reduced pressure. The residues were purified by column chromatography to give the title intermediate (1.8 g). m/z: ESI MH⁺ 286.0.

Step 2: Preparation of N-(3-bromophenyl)-N'-(4-fluoro-2-methoxyl-5-nitrylphenyl)-pyrimidin-4,6-diamine toluenesulfonate

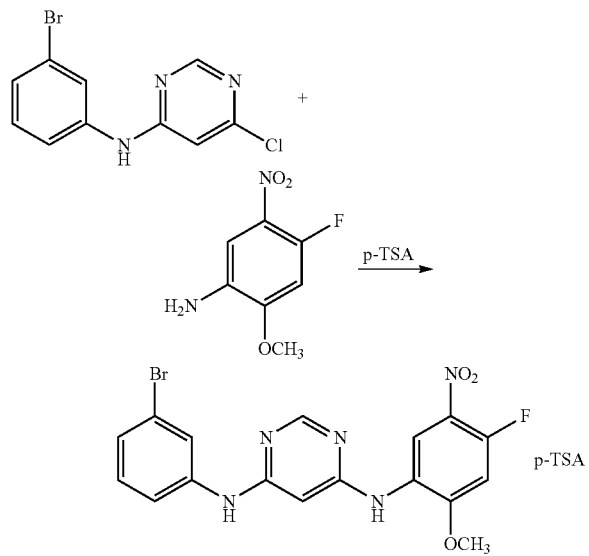

N-(6-chloropyrimidin-4-yl)-3-bromoaniline (1.43 g, 5 mmol), 4-fluoro-2-methoxyl-5-nitroaniline (0.93 g, 5 mmol) and p-toluenesulfonic acid (1.05 g, 6 mmol) were added to 20 mL of 2-amyl alcohol and then stirred for 15 h at 110° C. The reaction mixture was cooled down to room temperature and then filtered to give the title intermediate (0.8 g). m/z: ESI MH+ 434.1.

Step 3: Preparation of N-(3-bromophenyl)-N'-(4-((2-dimethylaminoethyl)-methylamino)-2-methoxyl-5-nitrophenyl)-pyrimidin-4,6-diamine

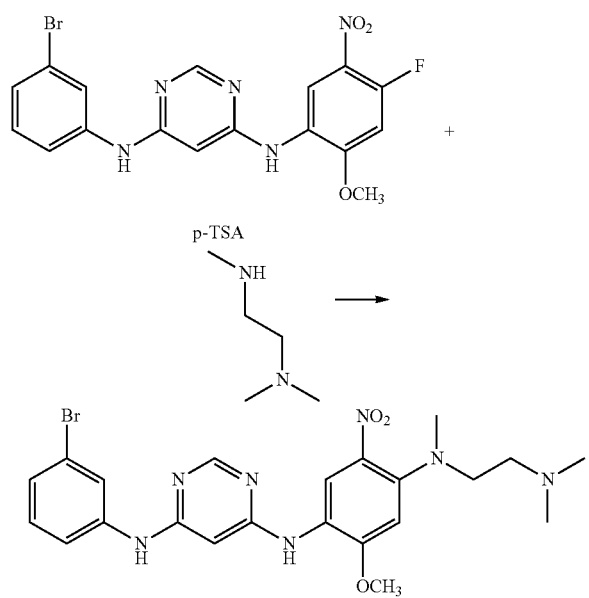

N-(3-Bromophenyl)-N'-(4-fluoro-2-methoxyl-5-nitrophenyl)-pyrimidin-4,6-diamine toluenesulfonate (0.61 g, 1 mmol), trimethyl ethylenediamine (0.15 g, 1.5 mmol) and potassium carbonate (0.56 g, 4 mmol) were added to 4 mL of DMF and then heated under oil bath at 70° C. for 2 h. The reaction mixture was added with water and ethyl acetate. The ethyl acetate layer was dried and then concentrated. The residues were purified by column chromatography to give the title intermediate (0.22 g). m/z: ESI MH+ 518.2.

Step 4: Preparation of N-(3-bromophenyl)-N'-(4-((2-dimethylaminoethyl)-methylamino)-2-methoxyl-5-amino phenyl)-pyrimidin-4,6-diamine

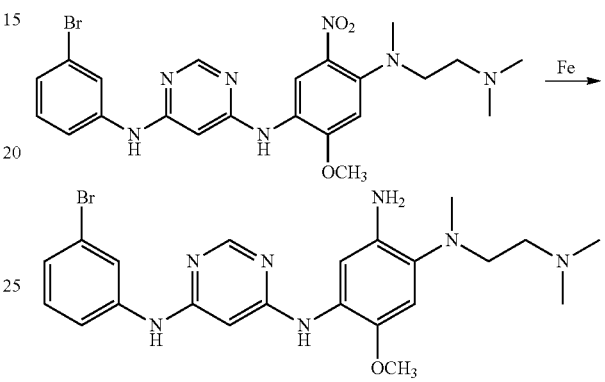

N-(3-bromophenyl)-N'-(4-((2-dimethylaminoethyl)-methylamino)-2-methoxyl-5-nitrophenyl)-pyrimidin-4,6-diamine (0.22 g, 0.42 mmol), iron powder (0.17 g, 3 mmol) and ammonium chloride (0.16 g, 3 mmol) were added to 10 mL of ethanol and 5 mL of water, and then heated under oil bath at 60° C. for 2 h. The iron sludge was filtered out and the filtrate was concentrated. The residues were purified by column chromatography to give the title intermediate (0.13 g). m/z: ESI MH+ 486.2.

Step 5: Preparation of N-(5-(6-(3-bromo-phenylamino)-pyrimidin-4-ylamino)-2-((2-dimethyl-amino-ethyl)-methyl-amino)-4-methoxyl-phenyl)-acrylamide

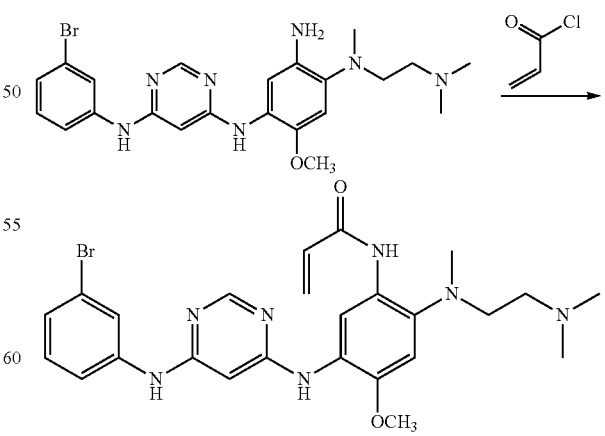

N-(3-Bromophenyl)-N'-(4-((2-dimethylaminoethyl)-methylamino)-2-methoxyl-5-amino phenyl)-pyrimidin-4,6-diamine (0.13 g, 0.29 mmol) and DIEA (0.13 g, 1 mmol)

were added to 5 mL of tetrahydrofuran, and then cooled under ice-salt bath. Acryloyl chloride (45 mg, 0.5 mmol) was added and then stirred for 1 h. The reaction mixture was added with water and ethyl acetate. The ethyl acetate layer was dried and then concentrated. The residues were purified by column chromatography to give the title intermediate (35 mg).

Example 11

Preparation of N-(5-(6-(3-chloro-4-fluoro-phenylamino)-pyrimidin-4-yl amino)-2-(2-dimethyl-amino-ethoxyl)-4-methoxyl-phenyl)-acrylamide Compound 148

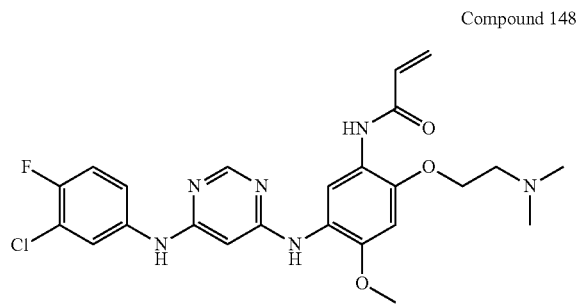 [SMILES: C=CC(=O)Nc1cc(Nc2cc(Nc3ccc(F)c(Cl)c3)ncn2)c(OC)cc1OCCN(C)C]

Steps 1 and 2: Preparation of N-(4-fluoro-3-chlorophenyl)-N'-(4-fluoro-2-methoxyl-5-nitrophenyl)-pyrimidin-4,6-diamine toluenesulfonate Steps 1 and 2 are the same as that in Examples 10 except for replacing 3-bromoaniline with 4-fluoro-3-chloroaniline.

Step 3: Preparation of N-(4-fluoro-3-chlorophenyl)-N'-(4-(2-dimethylamino-ethoxyl)-2-methoxyl-5-nitrophenyl)-pyrimidine-4,6-diamine

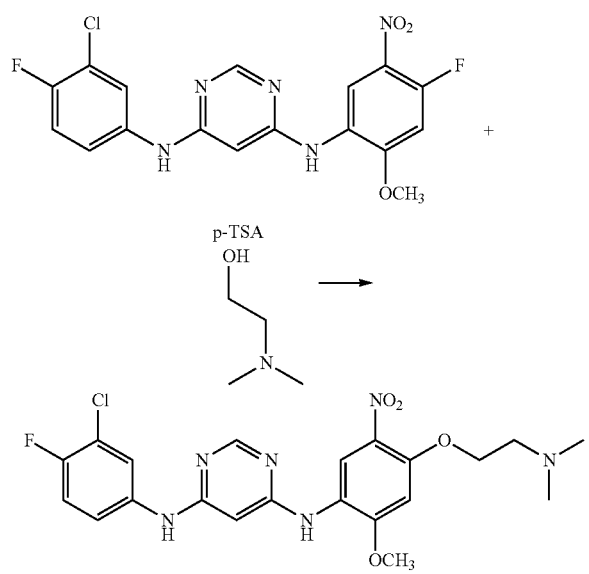

N-(4-Fluoro-3-chlorophenyl)-N'-(4-fluoro-2-methoxyl-5-nitrophenyl)-pyrimidin-4,6-diamine toluenesulfonate (0.58 g, 1 mmol), dimethylamino ethanol (0.18 g, 2 mmol) and sodium hydroxide (0.16 g, 4 mmol) were added to 4 mL of DMF and then heated under oil bath at 60° C. for 4 h. The reaction mixture was added with water and ethyl acetate. The ethyl acetate layer was dried and concentrated. The residues were purified by column chromatography to give the title intermediate (0.15 g). m/z: ESI MH+477.1.

Steps 4 and 5 of Example 10 were repeated to give the title compound.

Example 12

Preparation of N-(5-(6-(2, 4-dichloro-5-methoxyl-phenylamino)-pyrimidin-4-yl amino)-2-((2-dimethylamino-ethyl)-methyl-amino)-4-methoxyl-phenyl)-acrylamide (compound 136)

Compound 136

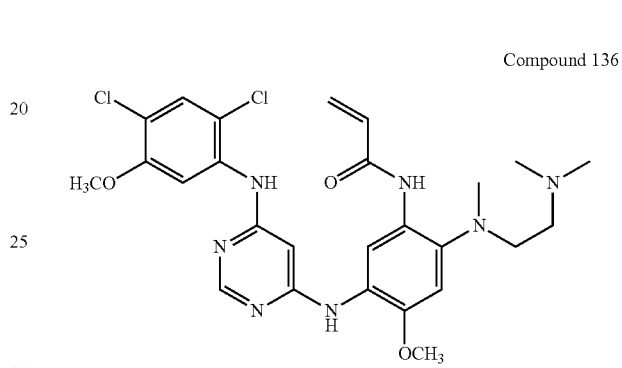

Step 1: Preparation of (6-chloro-pyrimidin-4-yl)-4-fluoro-2-methoxyl-5-nitroaniline

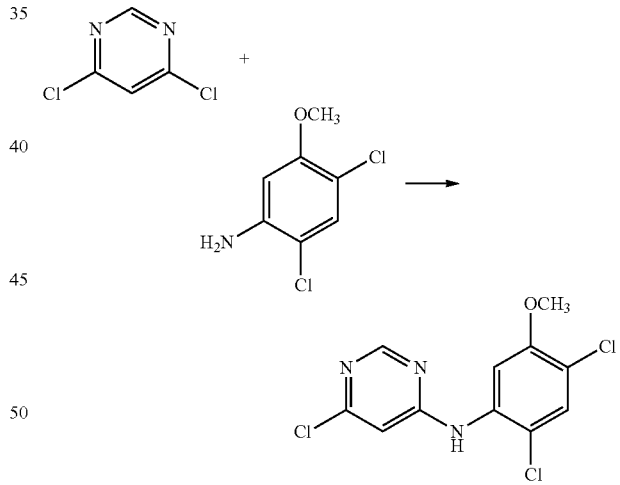

2,4-Dichloro-5-methoxyl aniline (11.5 g, 60 mmol), 4,6-dichloro pyrimidine (13.4 g, 90 mmol) and methanesulfonic acid (6.9 g, 72 mmol) were added to 100 mL of isopropyl alcohol and then stirred under reflux for 7 h. The reaction mixture was cooled to room temperature and the filtered to give the title intermediate (18 g). m/z: ESI MH+ 304.0.

Steps 2~5 of Example 10 were repeated to give the title compound.

Compounds 133-135, 138-147, 153-154 in Table 5 were prepared following the method in Example 10.

Compounds 148-152 in Table 5 were prepared following the method in Example 11.

Compounds 136-137 in Table 5 were prepared following the method in Example 12.

TABLE 5

| Comp. | Structure | Name | Data |
|---|---|---|---|
| 133 | 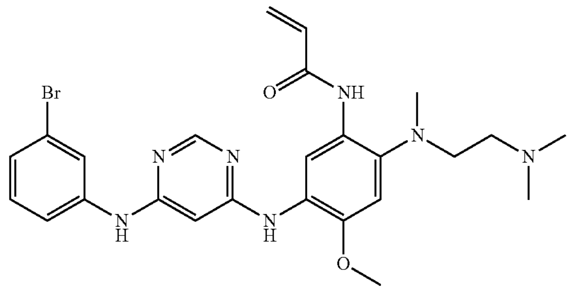 [SMILES: C=CC(=O)Nc1cc(Nc2cc(Nc3cccc(Br)c3)ncn2)c(OC)cc1N(C)CCN(C)C] | N-(5-(6-(3-bromo-phenylamino)-pyrimidin-4-ylamino)-2-((2-dimethylamino-ethyl)-methyl-amino)-4-methoxyl-phenyl)-acrylamide | $^1$H-NMR (CDCl$_3$-d) δ: 2.30 (s, 6H), 2.30 (m, 2H), 2.73 (s, 3H), 2.87-2.90 (t, 2H), 3.85 (s, 3H), 5.73-5.76 (m, 1H), 6.28-6.35 (m, 1H), 6.43-6.48 (m, 1H), 6.52 (s, 1H), 6.81 (s, 1H), 7.01 (s, 1H), 7.13-7.19 (m, 2H), 7.49-7.51 (m, 2H), 7.68 (s, 1H), 8.37 (s, 1H), 8.73 (s, 1H), 10.41 (s, 1H). m/z: ESI MH$^+$ 540.3 |
| 134 | 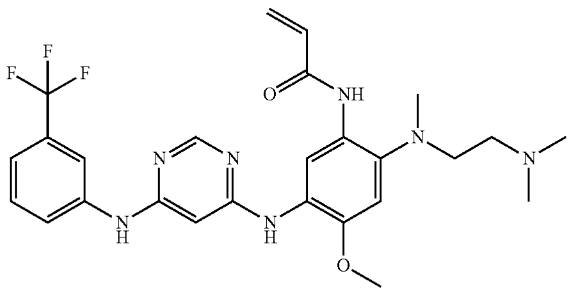 [SMILES: C=CC(=O)Nc1cc(Nc2cc(Nc3cccc(C(F)(F)F)c3)ncn2)c(OC)cc1N(C)CCN(C)C] | N-(2-((2-dimethylamino)-ethyl)-methyl-amino)-4-methoxyl-5-(6-(3-trifluoromethyl-phenylamino)-pyrimidin-4-ylamino)-phenyl)-acrylamide | $^1$H-NMR (CDCl$_3$-d) δ: 2.30 (s, 6H), 2.30 (m, 2H), 2.73 (s, 3H), 2.89 (m, 2H), 3.85 (s, 3H), 5.73-5.75 (m, 1H), 6.32-6.35 (m, 1H), 6.43-6.48 (m, 1H), 6.56 (s, 1H), 6.81 (s, 1H), 7.00 (s, 1H), 7.26 (m, 1H), 7.41-7.45 (t, 1H), 7.52 (s, 1H), 7.73 (s, 1H), 7.80-7.82 (d, 1H), 8.38 (s, 1H), 8.71 (s, 1H), 10.44 (s, 1H). m/z: ESI MH$^+$ 530.2 |
| 135 | 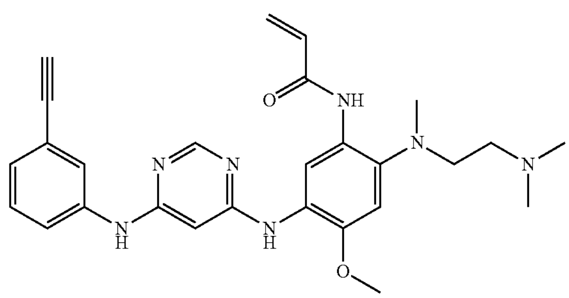 [SMILES: C#Cc1cccc(Nc2cc(Nc3cc(NC(=O)C=C)c(N(C)CCN(C)C)cc3OC)ncn2)c1] | N-(5-(6-(3-alkynyl-phenylamino)-pyrimidin-4-ylamino)-2-((2-dimethylamino-ethyl)-methyl-amino)-4-methoxyl-phenyl)-acrylamide | $^1$H-NMR (CDCl$_3$-d) δ: 2.30 (s, 6H), 2.33 (t, 2H), 2.72 (s, 3H), 2.87-2.90 (t, 2H), 3.07 (s, 1H), 3.85 (s, 3H), 5.72-5.75 (q, 1H), 6.30-6.37 (m, 1H), 6.47 (s, 1H), 6.80 (s, 1H), 7.02 (s, 1H), 7.15-7.197 (d, 1H), 7.25-7.29 (m, 2H), 7.43 (s, 1H), 7.52 (t, 1H), 7.60-7.61 (d, 1H), 8.36 (s, 1H), 8.78 (s, 1H), 10.03 (s, 1H). m/z: ESI MH$^+$ 486.2 |
| 136 | 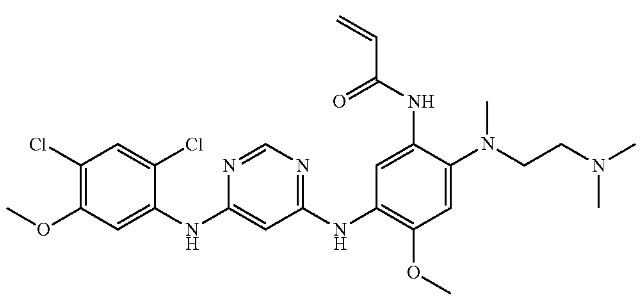 | N-(5-(6-(2,4-dichloro-5-methoxyl-phenylamino)-pyrimidin-4-ylamino)-2-((2-dimethylamino-ethyl)-methyl-amino)-4-methoxyl-phenyl)-acrylamide | $^1$H-NMR (CDCl$_3$-d) δ: 2.61 (s, 6H), 2.67 (t, 2H), 3.20 (s, 3H), 3.39 (t, 2H), 3.81 (s, 3H), 3.83 (s, 3H), 5.73-5.76 (dd, 1H), 6.02 (s, 1H), 6.23-6.27 (dd, 1H), 6.93 (s, 1H), 7.54 (s, 1H), 7.59 (s, 1H), 8.13 (s, 1H), 8.23 (s, 1H), 8.36 (s, 1H), 8.67 (s, 1H), 9.78-9.92 (m, 2H). m/z: ESI MH$^+$ 560.1 |
| 137 | 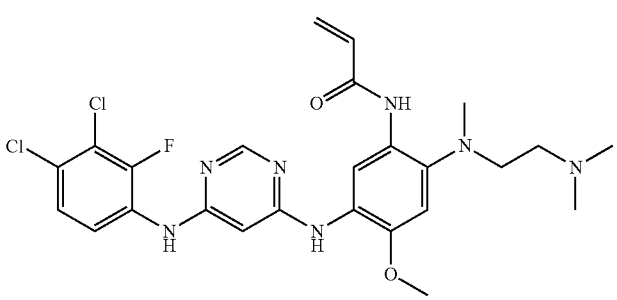 [SMILES: C=CC(=O)Nc1cc(Nc2cc(Nc3ccc(Cl)c(Cl)c3F)ncn2)c(OC)cc1N(C)CCN(C)C] | N-(5-(6-(2-fluoro-3,4-dichloro-phenylamino)-pyrimidin-4-ylamino)-2-((2-dimethylamino-ethyl)-methyl-amino)-4-methoxyl-phenyl)-acrylamide | $^1$H-NMR (CDCl$_3$-d) δ: 2.22 (s, 6H), 2.33 (t, 2H), 2.71 (s, 3H), 2.87 (t, 2H), 3.79 (s, 3H), 5.73-5.76 (dd, 1H), 6.01 (s, 1H), 6.20-6.25 (dd, 1H), 6.36-6.42 (m, 1H), 7.01 (s, 1H), 7.42-7.44 (dd, 1H), 7.98-8.02 (t, 1H), 8.16 (s, 1H), 8.36 (s, 1H), 8.43 (s, 1H), 9.08 (s, 1H), 10.08 (s, 1H). m/z: ESI MH$^+$ 548.3 |

TABLE 5-continued

| Comp. | Structure | Name | Data |
|---|---|---|---|
| 138 | 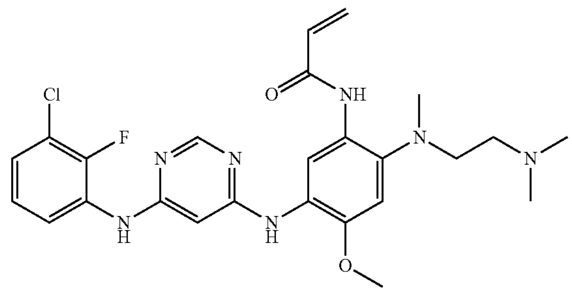 [SMILES: C=CC(=O)Nc1cc(Nc2cc(Nc3cccc(Cl)c3F)ncn2)c(OC)cc1N(C)CCN(C)C] | N-(5-(6-(2-fluoro-3-chloro-phenylamino)-pyrimidin-4-ylamino)-2-((2-dimethylamino-ethyl)-methyl-amino)-4-methoxyl-phenyl)-acrylamide | $^1$H-NMR (CDCl$_3$-d) δ: 2.29 (s, 6H), 2.32-2.33 (t, 2H), 2.73 (s, 3H), 2.87-2.89 (t, 2H), 3.85 (s, 3H), 5.73-5.76 (dd, 1H), 6.29-6.36 (m, 1H), 6.44-6.51 (dd, 1H), 6.58 (s, 1H), 6.81 (s, 1H), 7.01-7.08 (m, 3H), 7.24 (s, 1H), 8.02-8.06 (m, 1H), 8.38 (s, 1H), 8.78 (s, 1H), 10.33 (s, 1H). m/z: ESI MH$^+$ 514.2 |
| 139 | 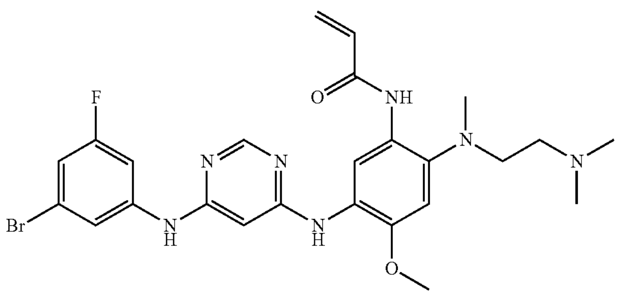 [SMILES: C=CC(=O)Nc1cc(Nc2cc(Nc3cc(F)cc(Br)c3)ncn2)c(OC)cc1N(C)CCN(C)C] | N-(5-(6-(3-bromo-5-fluoro-phenylamino)-pyrimidin-4-ylamino)-2-((2-dimethylamino-ethyl)-methyl-amino)-4-methoxyl-phenyl)-acrylamide | $^1$H-NMR (CDCl$_3$-d) δ: 2.61 (s, 6H), 2.65 (s, 2H), 3.22 (s, 2H), 3.40 (s, 3H), 3.82 (s, 3H), 5.70-5.73 (dd, 1H), 5.96 (s, 1H), 6.21-6.26 (dd, 1H), 6.95 (s, 1H), 7.00-7.02 (d, 1H), 7.60-7.63 (d, 1H), 7.69 (s, 1H), 8.17 (s, 1H), 8.25 (s, 1H), 8.52 (s, 1H), 9.53 (s, 1H), 9.84 (s, 1H), 10.34 (s, 1H). m/z: MH$^+$ 558.2 |
| 140 | 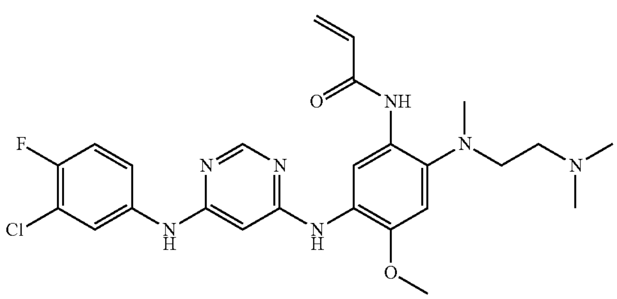 [SMILES: C=CC(=O)Nc1cc(Nc2cc(Nc3ccc(F)c(Cl)c3)ncn2)c(OC)cc1N(C)CCN(C)C] | N-(5-(6-(3-chloro-4-fluoro-phenylamino)-pyrimidin-4-ylamino)-2-((2-dimethylamino-ethyl)-methyl-amino)-4-methoxyl-phenyl)-acrylamide | $^1$H-NMR (CDCl$_3$-d) δ: 2.30 (s, 6H), 2.31-2.33 (m, 2H), 2.73 (s, 3H), 2.86-2.89 (t, 2H), 3.85 (s, 3H), 5.73-5.76 (m, 1H), 6.28-6.35 (m, 1H), 6.43-6.47 (m, 2H), 6.80 (s, 1H), 7.04 (s, 1H), 7.04-7.09 (t, 1H), 7.38-7.22 (m, 2H), 7.51-7.53 (dd, 1H), 8.33-8.34 (d, 1H), 8.74 (s, 1H), 10.36 (s, 1H). m/z: ESI MH$^+$ 514.1 |
| 141 | 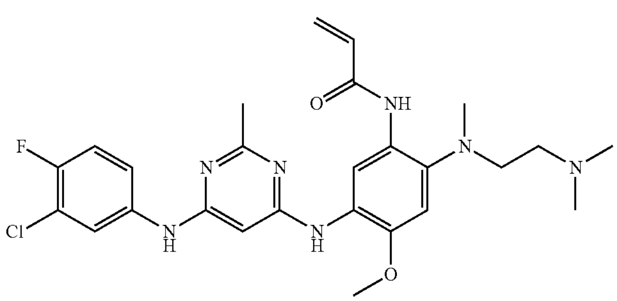 [SMILES: C=CC(=O)Nc1cc(Nc2cc(Nc3ccc(F)c(Cl)c3)nc(C)n2)c(OC)cc1N(C)CCN(C)C] | N-(5-(6-(3-chloro-4-fluoro-phenylamino)-2-methyl-pyrimidin-4-ylamino)-2-((2-dimethylamino-ethyl)-methyl-amino)-4-methoxyl-phenyl)-acrylamide | $^1$H-NMR (CDCl$_3$-d) δ: 2.31 (s, 6H), 2.31 (m, 2H), 2.49 (s, 3H), 2.72 (s, 3H), 2.89 (m, 2H), 3.84 (s, 3H), 5.74-5.77 (m, 1H), 6.36 (s, 1H), 6.43-6.44 (m, 1H), 6.79 (s, 1H), 6.94 (s, 1H), 7.05-7.10 (t, 1H), 7.14 (s, 1H), 7.43-7.47 (m, 1H), 7.51-7.54 (dd, 1H), 8.72 (s, 1H), 10.34 (s, 1H). m/z: ESI MH$^+$ 528.2 |
| 142 | 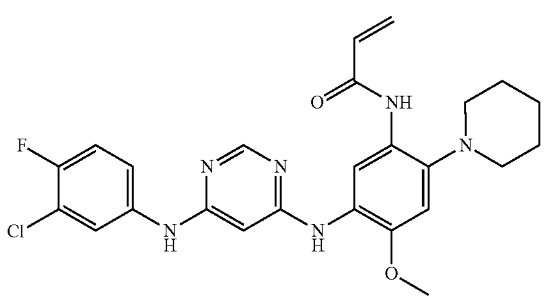 [SMILES: C=CC(=O)Nc1cc(Nc2cc(Nc3ccc(F)c(Cl)c3)ncn2)c(OC)cc1N1CCCCC1] | N-(5-(6-(3-chloro-4-fluoro-phenylamino)-pyrimidin-4-ylamino)-2-[piperidin-1-yl]-4-methoxyl-phenyl)-acrylamide | $^1$H-NMR (CDCl$_3$-d) δ: 1.54 (s, 2H), 1.72 (t, 4H), 2.80 (t, 4H), 3.79 (s, 3H), 5.72-5.74 (d, 1H), 5.83 (s, 1H), 6.19-6.23 (dd, 1H), 6.60-6.67 (d, 1H), 6.84 (s, 1H), 7.27-7.32 (t, 1H), 7.41-7.45 (m, 1H), 7.95-7.97 (dd, 1H), 8.04 (s, 1H), 8.19 (s, 1H), 8.37 (s, 1H), 8.95 (s, 1H), 9.23 (s, 1H). m/z: MH$^+$ 496.8 |

TABLE 5-continued

| Comp. | Structure | Name | Data |
|---|---|---|---|
| 143 | 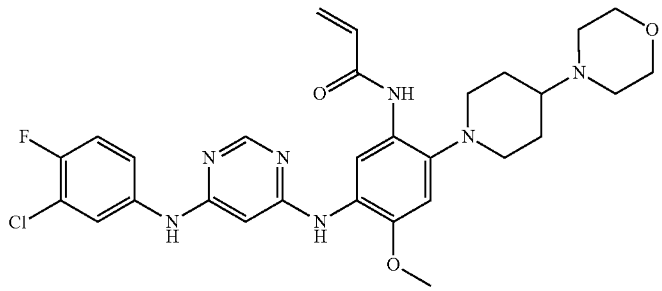 [SMILES: C=CC(=O)Nc1cc(Nc2cc(Nc3ccc(F)c(Cl)c3)ncn2)c(OC)cc1N1CCC(N2CCOCC2)CC1] | N-(5-(6-(3-chloro-4-fluoro-phenylamino)-pyrimidin-4-ylamino)-4-methoxyl-2-(4-morpholin-4-yl-piperidin-1-yl)-phenyl)-acrylamide | $^1$H-NMR (CDCl$_3$-d) δ: 1.62-1.68 (m, 2H), 2.08-2.11 (m, 2H), 2.29-2.33 (m, 1H), 2.6-2.65 (t, 4H), 2.72-2.77 (m, 2H), 3.05-3.07 (m, 2H), 3.78-3.81 (t, 4H), 3.84 (s, 3H), 5.80-5.83 (m, 1H), 6.25-6.31 (m, 1H), 641-6.45 (m, 2H), 6.76 (s, 1H), 6.99 (s, 1H), 7.07-7.12 (t, 1H), 7.23 (s, 1H), 7.38-7.42 (m, 1H), 7.50-7.53 (dd, 1H), 8.34 (s, 1H), 8.50 (s, 1H), 8.68 (s, 1H). m/z: ESI MH$^+$ 581.8 |
| 144 | 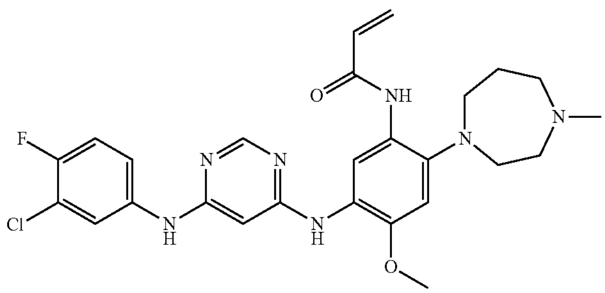 [SMILES: C=CC(=O)Nc1cc(Nc2cc(Nc3ccc(F)c(Cl)c3)ncn2)c(OC)cc1N1CCCN(C)CC1] | N-(5-(6-(3-chloro-4-fluoro-phenylamino)-pyrimidin-4-ylamino)-2-(4-methyl-[1,4]diazepin-1-yl)-4-methoxyl-phenyl)-acrylamide | $^1$H-NMR (CDCl$_3$-d) δ: 1.86-1.89 (t, 2H), 2.35 (s, 3H), 2.71 (s, 4H), 3.14 (s, 4H), 3.78 (s, 3H), 5.71-5.74 (dd, 1H), 5.82 (s, 1H), 6.18-6.23 (dd, 1H), 6.54-6.61 (m, 1H), 6.84 (s, 1H), 7.27-7.32 (t, 1H), 7.40-7.44 (m, 1H), 7.84 (s, 1H), 7.95-7.98 (dd, 1H), 8.19 (s, 1H), 8.36 (s, 1H), 9.13 (s, 1H), 9.23 (s, 1H). m/z: ESI MH$^+$ 525.8 |
| 145 | 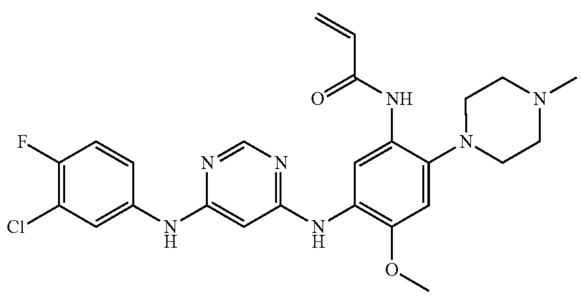 [SMILES: C=CC(=O)Nc1cc(Nc2cc(Nc3ccc(F)c(Cl)c3)ncn2)c(OC)cc1N1CCN(C)CC1] | N-(5-(6-(3-chloro-4-fluoro-phenylamino)-pyrimidin-4-ylamino)-4-methoxyl-2-(4-methyl-piperazin-1-yl)-phenyl)-acrylamide | $^1$H-NMR (CDCl$_3$-d) δ: 2.41 (s, 3H), 2.63 (m, 4H), 2.91-2.93 (t, 4H), 3.84 (s, 3H), 5.80-5.83 (m, 1H), 6.26-6.33 (m, 1H), 6.39 (s, 1H), 6.41-6.45 (dd, 1H), 6.80 (s, 1H), 7.01 (s, 1H), 7.07-7.11 (t, 1H), 7.22 (s, 1H), 7.36-7.40 (m, 1H), 7.46-7.48 (dd, 1H), 8.33-8.34 (d, 1H), 8.57 (s, 1H), 8.72 (s, 1H). m/z: ESI MH$^+$ 512.2 |
| 146 | 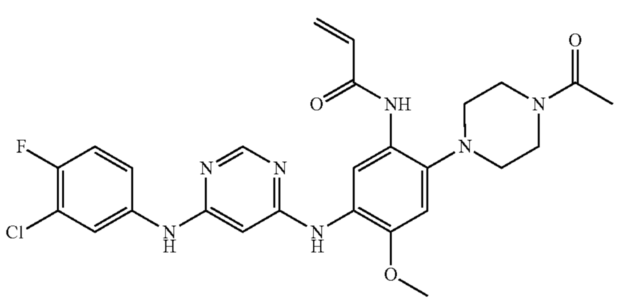 [SMILES: C=CC(=O)Nc1cc(Nc2cc(Nc3ccc(F)c(Cl)c3)ncn2)c(OC)cc1N1CCN(C(C)=O)CC1] | N-(2-(4-acetyl-piperazin-1-yl)-5-(6-(3-chloro-4-fluoro-phenylamino)-pyrimidin-4-ylamino)-4-methoxyl-phenyl)-acrylamide | $^1$H-NMR (CDCl$_3$-d) δ: 2.05 (s, 3H), 2.80-2.86 (m, 4H), 3.65 (m, 4H), 3.80 (s, 3H), 5.73-5.76 (m, 1H), 5.87 (s, 1H), 6.20-6.25 (dd, 1H), 6.64-6.71 (m, 1H), 6.89 (s, 1H), 7.28-7.32 (t, 1H), 7.42-7.45 (m, 1H), 7.95-7.98 (dd, 1H), 8.13 (s, 1H), 8.20 (s, 1H), 8.42 (s, 1H), 9.10 (s, 1H), 9.25 (s, 1H). m/z: MH$^+$ 539.8 |
| 147 | 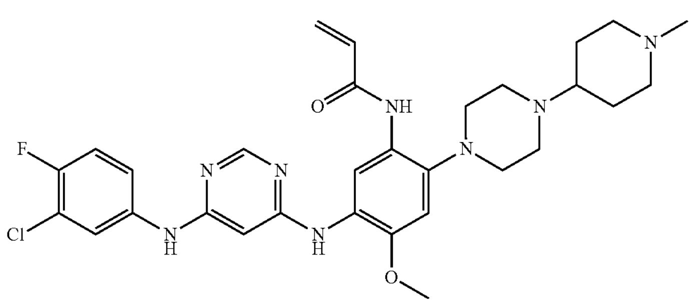 [SMILES: C=CC(=O)Nc1cc(Nc2cc(Nc3ccc(F)c(Cl)c3)ncn2)c(OC)cc1N1CCN(C2CCN(C)CC2)CC1] | N-(5-(6-(3-chloro-4-fluoro-phenylamino)-pyrimidin-4-ylamino)-4-methoxyl-2-(4-(1-methylpiperidin-4-yl)-piperazin-1-yl)-phenyl)-acrylamide | $^1$H-NMR (CDCl$_3$-d) δ: 1.65-1.69 (m, 2H), 1.87-1.90 (m, 2H), 1.98-2.04 (t, 2H), 2.31 (s, 3H), 2.33-2.35 (m, 1H), 2.77 (br, 4H), 2.91-2.93 (t, 4H), 2.94-2.99 (m, 2H), 3.83 (s, 3H), 5.81-5.83 (m, 1H), 6.26-6.36 (m, 1H), 6.41-6.45 (m, 2H), 6.82 (s, 1H), 6.99 (s, 1H), 7.07-7.11 (t, 1H), 7.20 (s, 1H), 7.38-7.42 (m, 1H), 7.50-7.52 (dd, 1H), 8.34-8.35 (d, 1H), 8.60 (s, 1H), 8.71 (s, 1H). m/z: ESI MH$^+$ 594. |

TABLE 5-continued

| Comp. | Structure | Name | Data |
|---|---|---|---|
| 148 | 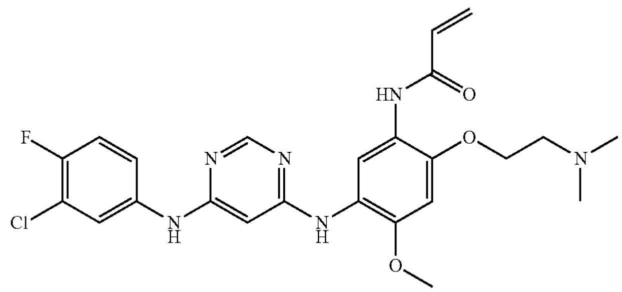 [SMILES: C=CC(=O)Nc1cc(Nc2cc(Nc3ccc(F)c(Cl)c3)ncn2)c(OC)cc1OCCN(C)C] | N-(5-(6-(3-chloro-4-fluoro-phenylamino)-pyrimidin-4-ylamino)-2-(2-dimethylamino-ethoxyl)-4-methoxyl-phenyl)-acrylamide | $^1$H-NMR (CDCl$_3$-d) δ: 2.37 (s, 6H), 2.59-2.61 (t, 2H), 3.84 (s, 3H), 4.13-4.16 (t, 2H), 5.74-5.77 (m, 1H), 6.26-6.33 (m, 1H), 6.40-6.47 (m, 2H), 6.64 (s, 1H), 6.89 (s, 1H), 7.04-7.09 (t, 1H), 7.38-7.42 (m, 1H), 7.51 (s, 1H), 7.56-7.58 (dd, 1H), 8.33 (d, 1H), 8.57 (s, 1H), 10.01 (s, 1H). m/z: ESI MH$^+$ 500.9 |
| 149 | 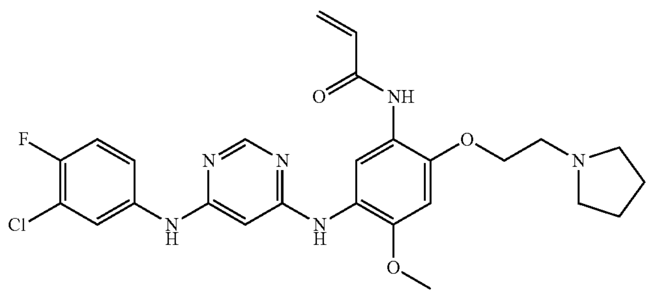 [SMILES: C=CC(=O)Nc1cc(Nc2cc(Nc3ccc(F)c(Cl)c3)ncn2)c(OC)cc1OCCN1CCCC1] | N-(5-(6-(3-chloro-4-fluoro-phenylamino)-pyrimidin-4-ylamino)-4-methoxyl-2-(2-pyrrolidin-1-yl-ethoxyl)-phenyl)-acrylamide | $^1$H-NMR (CDCl$_3$-d) δ: 1.89 (br, 4H), 2.67 (br, 4H), 2.79 (t, 2H), 3.85 (s, 3H), 4.18-4.20 (t, 2H), 5.74-5.77 (m, 1H), 6.34-6.46 (m, 3H), 6.62 (s, 1H), 6.87 (s, 1H), 7.04-7.09 (t, 1H), 7.38-7.43 (m, 2H), 7.54-7.56 (m, 1H), 8.33 (s, 1H), 8.56 (s, 1H), 9.60 (s, 1H). m/z: MH$^+$ 526.8 |
| 150 | 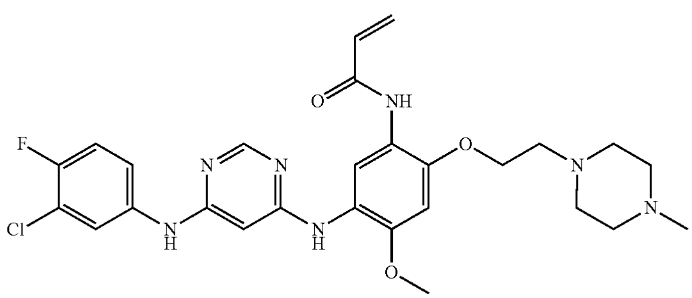 [SMILES: C=CC(=O)Nc1cc(Nc2cc(Nc3ccc(F)c(Cl)c3)ncn2)c(OC)cc1OCCN1CCN(C)CC1] | N-(5-(6-(3-chloro-4-fluoro-phenylamino)-pyrimidin-4-ylamino)-2-(2-(4-methyl-piperazin-1-yl)-ethoxyl)-4-methoxyl-phenyl)-acrylamide | $^1$H-NMR (CDCl$_3$-d) δ: 2.18 (s, 3H), 2.37 (s, 4H), 2.53 (s, 4H), 2.71-2.74 (t, 2H), 3.81 (s, 3H), 4.18-4.21 (t, 2H), 5.70-5.73 (dd, 1H), 5.76 (s, 1H), 6.17-6.22 (dd, 1H), 6.56-6.62 (m, 1H), 6.88 (s, 1H), 7.27-7.31 (t, 1H), 7.39-7.44 (m, 1H), 7.95-7.97 (dd, 1H), 7.99 (s, 1H), 8.18 (s, 1H), 8.33 (s, 1H), 9.20 (s, 1H), 9.25 (s, 1H). m/z: MH$^+$ 556.2 |
| 151 | 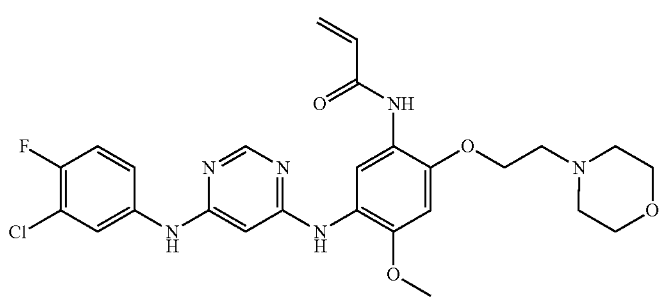 [SMILES: C=CC(=O)Nc1cc(Nc2cc(Nc3ccc(F)c(Cl)c3)ncn2)c(OC)cc1OCCN1CCOCC1] | N-(5-(6-(3-chloro-4-fluoro-phenylamino)-pyrimidin-4-ylamino)-4-methoxyl-2-(2-morpholin-4-yl-ethoxyl)-phenyl)-acrylamide | $^1$H-NMR (CDCl$_3$-d) δ: 2.57-2.60 (t, 4H), 2.7-2.77 (t, 2H), 3.77-3.80 (t, 4H), 3.85 (s, 3H), 4.19-4.22 (t, 2H), 5.80-5.83 (m, 1H), 6.36 (s, 1H), 6.42-6.45 (m, 2H), 6.60 (s, 1H), 6.83 (s, 1H), 7.05-7.10 (t, 1H), 7.37-7.41 (m, 2H), 7.55-7.57 (m, 1H), 8.33 (s, 1H), 8.56 (s, 1H), 8.71 (s, 1H). m/z: MH$^+$ 543.1 |
| 152 | 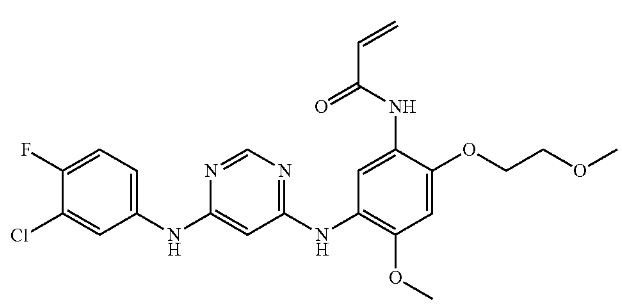 [SMILES: C=CC(=O)Nc1cc(Nc2cc(Nc3ccc(F)c(Cl)c3)ncn2)c(OC)cc1OCCOC] | N-(5-(6-(3-chloro-4-fluoro-phenylamino)-pyrimidin-4-ylamino)-2-(2-methoxylethoxyl)-4-methoxyl-phenyl)-acrylamide | $^1$H-NMR (CDCl$_3$-d) δ: 3.34 (s, 3H), 3.70-3.72 (t, 2H), 3.80 (s, 3H), 4.22-4.24 (t, 2H), 5.70-5.72 (dd, 1H), 5.76 (s, 1H), 6.18-6.22 (dd, 1H), 6.56-6.63 (m, 1H), 6.88 (s, 1H), 7.27-7.31 (t, 1H), 7.42 (m, 1H), 7.95-7.97 (dd, 1H), 8.01 (s, 1H), 8.18 (s, 1H), 8.33 (s, 1H), 9.17 (s, 1H), 9.21 (s, 1H). m/z: ESI MH$^+$ 488.7 |

TABLE 5-continued

| Comp. | Structure | Name | Data |
|---|---|---|---|
| 153 | 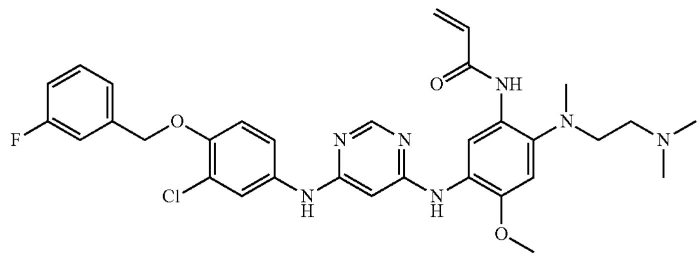 [SMILES: C=CC(=O)Nc1cc(Nc2cc(Nc3ccc(OCc4cccc(F)c4)c(Cl)c3)ncn2)c(OC)cc1N(C)CCN(C)C] | N-(5-(6-(3-chloro-4-(3-fluoro-benzyloxy)-phenylamino)-pyrimidin-4-ylamino)-2-((2-dimethylamino-ethyl)-methyl-amino)-4-methoxyl-phenyl)-acrylamide | $^1$H-NMR (CDCl$_3$-d) δ: 2.28 (s, 6H), 2.31 (m, 2H), 2.72 (s, 3H), 2.86-2.88 (t, 2H), 3.85 (s, 3H), 5.09 (s, 2H), 5.73-5.75 (m, 1H), 6.28-6.35 (m, 1H), 6.42 (s, 1H), 6.44-6.49 (dd, 1H), 6.80 (s, 1H), 6.92-6.95 (d, 1H), 6.96 (s, 1H), 7.01-7.03 (m, 1H), 7.10 (s, 1H), 7.19-7.23 (m, 2H), 7.34-7.41 (m, 2H), 7.47-7.48 (d, 1H), 8.33 (s, 1H), 8.77 (s, 1H), 10.34 (s, 1H). m/z: MH$^+$ 620.3 |
| 154 | 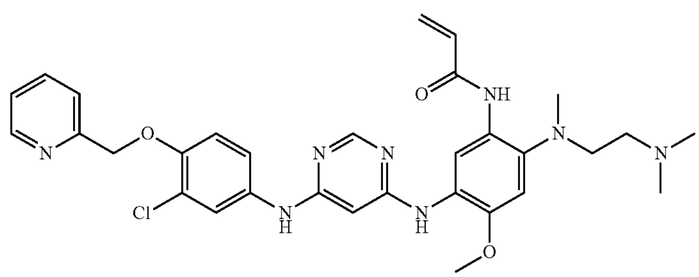 [SMILES: C=CC(=O)Nc1cc(Nc2cc(Nc3ccc(OCc4ccccn4)c(Cl)c3)ncn2)c(OC)cc1N(C)CCN(C)C] | N-(5-(6-(3-chloro-4-(pyridin-2-ylmethoxy)-phenylamino)-pyrimidin-4-ylamino)-2-((2-dimethylamino-ethyl)-methyl-amino)-4-methoxyl-phenyl)-acrylamide | $^1$H-NMR (CDCl$_3$-d) δ: 2.30 (s, 6H), 2.30 (m, 2H), 2.72 (s, 3H), 2.89 (m, 2H), 3.85 (s, 3H), 5.24 (s, 2H), 5.73-5.75 (m, 1H), 6.42-6.47 (m, 2H), 6.79 (s, 1H), 6.94 (s, 1H), 6.95-6.97 (d, 1H), 7.08 (s, 1H), 7.24-7.27 (m, 1H), 7.37-7.40 (dd, 1H), 7.51-7.52 (d, 1H), 7.64-7.66 (m, 1H), 7.74-7.78 (m, 1H), 8.33 (s, 1H), 8.60-8.61 (d, 1H), 8.76 (s, 1H), 10.32 (s, 1H). m/z: ESI MH$^+$ 603.3 |

Compounds 155-157 in Table 6 were prepared following the method in Example 8.

TABLE 6

| Comp. | Structure | Name | Data |
|---|---|---|---|
| 155 | 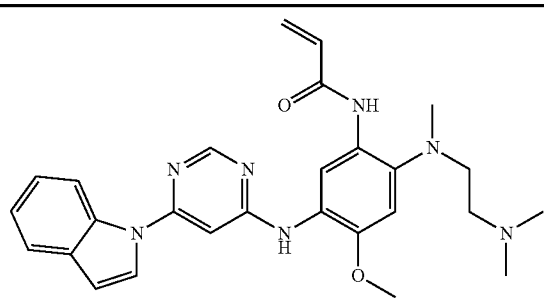 | N-(5-(6-(1H-indol-1-yl)-pyrimidin-4-ylamino)-2-(2-(dimethylamino-ethyl)-methyl-amino)-4-methoxyl-phenyl)-acrylamide | $^1$H-NMR (CDCl$_3$-d) δ: 2.49 (s, 6H), 2.56 (t, 2H), 2.63 (s, 3H), 3.15 (t, 2H), 3.87 (s, 3H), 5.72-5.75 (m, 1H), 6.23-6.28 (dd, 1H), 6.56 (s, 1H), 6.77-6.78 (d, 1H), 6.98 (s, 1H), 7.09 (s, 1H), 7.18-7.21 (t, 1H), 7.26-7.30 (t, 1H), 7.64-7.65 (d, 1H), 7.96-7.97 (d, 1H), 8.34-8.36 (d, 1H), 8.51 (s, 1H), 8.54 (s, 1H), 9.00 (s, 1H), 9.90 (s, 1H). m/z: ESI MH$^+$ 486.0 |
| 156 | 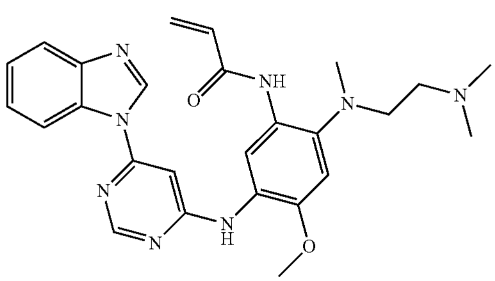 [SMILES: C=CC(=O)Nc1cc(Nc2cc(-n3cnc4ccccc43)ncn2)c(OC)cc1N(C)CCN(C)C] | N-(5-(6-benzimidazol-1-yl-pyrimidin-4-ylamino)-2-((2-dimethylamino-ethyl)-methyl-amino)-4-methoxyl-phenyl)-acrylamide | $^1$H-NMR (CDCl$_3$-d) δ: 2.32 (s, 6H), 2.35-2.38 (t, 2H), 2.76 (s, 3H), 2.89-2.92 (t, 2H), 3.89 (s, 3H), 5.76-5.79 (m, 1H), 6.30-6.37 (m, 1H), 6.54-6.59 (m, 1H), 6.86 (s, 1H), 7.34-7.41 (m, 4H), 7.84-7.86 (m, 1H), 8.37-8.40 (m, 1H), 8.70 (s, 1H), 8.95 (s, 1H), 8.99 (s, 1H), 10.40 (s, 1H). m/z: ESI MH$^+$ 487.3 |
| 157 | 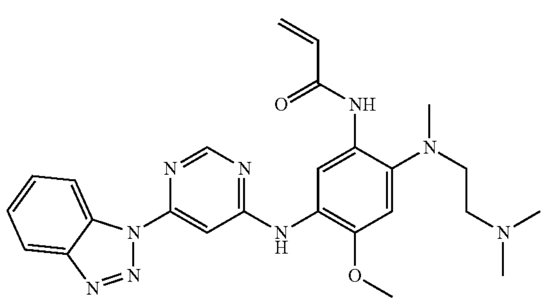 [SMILES: C=CC(=O)Nc1cc(Nc2cc(-n3nnc4ccccc43)ncn2)c(OC)cc1N(C)CCN(C)C] | N-(5-(6-benzotriazol-1-yl-pyrimidin-4-ylamino)-2-((2-dimethylamino-ethyl)-methyl-amino)-4-methoxyl-phenyl)-acrylamide | $^1$H-NMR (CDCl$_3$-d) δ: 2.22 (s, 6H), 2.36 (t, 2H), 2.75 (s, 3H), 2.89 (t, 2H), 3.83 (s, 3H), 5.74-5.77 (dd, 1H), 6.21 (dd, 1H), 6.37 (m, 1H), 7.06 (s, 1H), 7.39 (m, 1H), 7.55-7.58 (t, 1H), 7.72-7.76 (t, 1H), 8.20-8.22 (d, 1H), 8.52 (s, 1H), 8.61-8.63 (d, 1H), 8.67 (s, 1H), 9.41 (s, 1H), 10.12 (s, 1H). m/z: ESI MH$^+$ 488.3 |

Example 13

Preparation of N-(4-methoxyl-5-(6-(1-methyl-1H-indol-3-yl)-pyrimidin-4-ylamino)-2-(4-methylpiperazin-1-yl)-phenyl)-acrylamide (Compound 158)

Compound 158

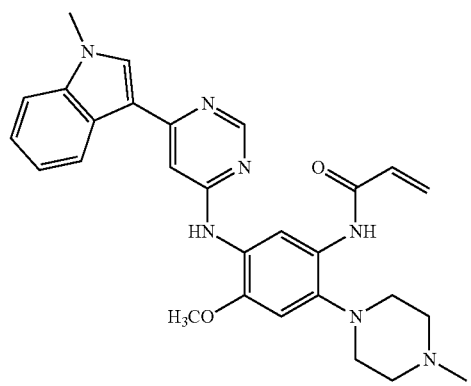

Step 1: Synthesis of 3-(6-chloropyrimidin-4-yl)-1-methyl-1H-indole

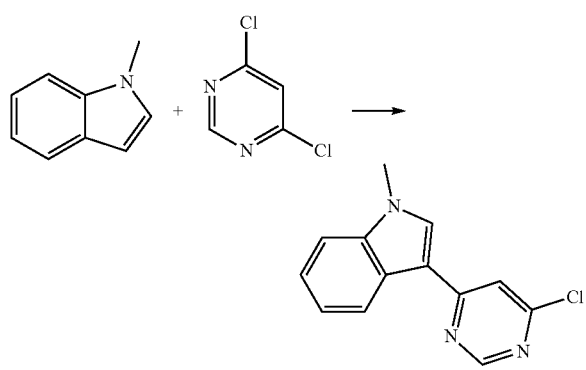

1-Methyl indole (2.5 mL, 23 mmol), 4,6-dichloro pyrimidine (3 g, 23 mmol) and anhydrous aluminium trichloride (3 g, 23 mmol) were added to 30 mL of 1,2-dichloroethane and then heated at 45° C. for 4 h. The reaction mixture was cooled down to room temperature, and the added with 1M of diluted hydrochloric acid and dichloromethane. The dichloromethane layer was dried and then concentrated. The residues were purified by column chromatography to give the title intermediate (3.5 g). m/z: ESI MH+ 244.1.

Step 2: Synthesis of (4-Fluoro-2-methoxyl-5-nitrophenyl)-(6-(1-methyl-1H-indol-3-yl)-pyrimidin-4-yl)-amine

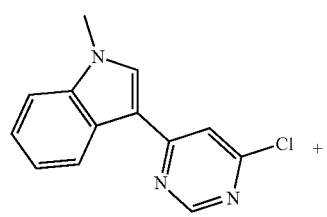

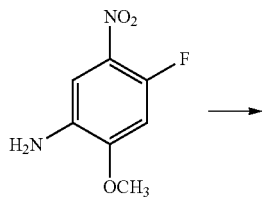

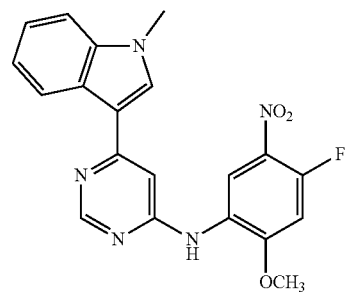

3-(6-chloroChloropyrimidin-4-yl)-1-methyl-1H-indole (1.2 g, 5 mmol), 2-methoxyl-4-fluoro-5-nitroaniline (0.9 g, 5 mmol) and p-toluenesulfonic acid (1.03 g, 6 mmol) were added to 15 mL of 2-amyl alcohol and then heated at 115° C. for 3 h. The reaction mixture was cooled to room temperature and then filtered. The filter cake was washed with methyl tertiary butyl ether twice and the dried to give the title intermediate (1.4 g). m/z: ESI MH+394.1.

Steps 3 to 5 are the same as that of Example 6 except for replacing trimethyl ethylenediamine with N-methylpiperazine.

Example 14

Preparation of N-(4-methoxyl-2-(2-methoxyl-ethoxyl)-5-(6-(1-methyl-1H-indol-3-yl)-pyrimidin-4-ylamino)-phenyl)-acrylamide (Compound 196)

Compound 196

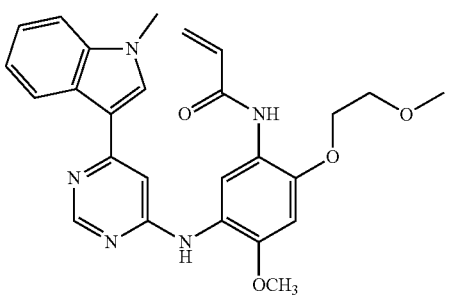

Steps 1 and 2: Synthesis of (4-fluoro-2-methoxyl-5-nitro-phenyl)-(6-(1-methyl-1H-indol-3-yl)-pyrimidin-4-yl)-amine Preparation method is the same as that in Example 13.

Step 3: Preparation of (2-methoxyl-4-(2-methoxyl-ethoxyl)-5-nitro-phenyl)-(6-(1-methyl-1H-indol-3-yl)-pyrimidin-4-yl)-amine

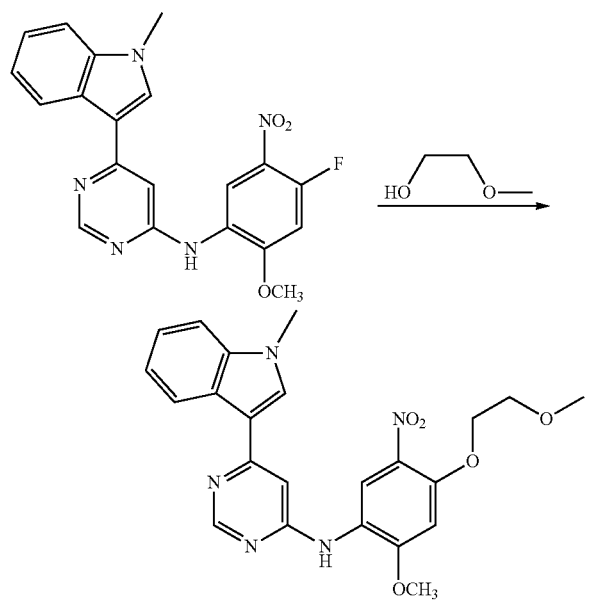

4-Fluoro-2-methoxyl-5-nitro-phenyl)-(6-(1-methyl-1H-indol-3-yl)-pyrimidin-4-yl)-amine (0.4 g, 1 mmol), ethylene glycol monomethyl ether (0.15 g, 2 mmol) and sodium hydroxide (0.16 g, 4 mmol) were added to 2 mL of DMF and then heated at 60° C. for 5 h. The reaction mixture was cooled to room temperature and then added with water and ethyl acetate. After concentration of ethyl acetate layer, iron powder (0.28 g, 5 mmol), ammonium chloride (0.27 g, 5 mmol), water (5 mL) and ethanol (15 mL) were added and then heated at 80° C. for 5 h. The iron sludge was filtered out when it is hot. The filtrate was concentrated and then added with water and dichloromethane. The dichloromethane layer was dried and then concentrated. The residues were purified by column chromatography to give the title intermediate (0.18 g). m/z: ESI MH+ 450.2.

Steps 4 and 5 of Example 13 were repeated to give the title compound.

Compounds 158-186 and 188-195 in Table 7 were prepared following the method in Example 13.

Compound 187 in Table 7 was prepared following the method in Example 6.

Compounds 196-199 in Table 7 were prepared following the method in Example 14.

TABLE 7

| Comp. | Structure | Name | Data |
|---|---|---|---|
| 158 | 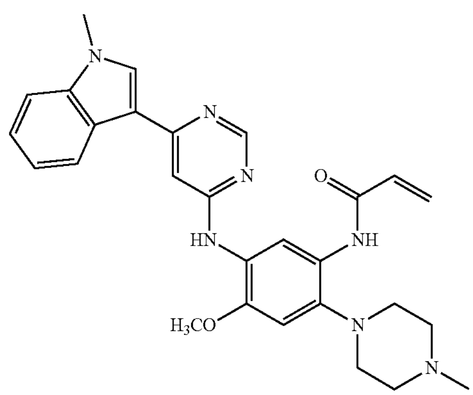 [SMILES: C=CC(=O)Nc1cc(Nc2cc(-c3cn(C)c4ccccc34)ncn2)c(OC)cc1N1CCN(C)CC1] | N-(4-methoxyl-5-(6-(1-methyl-1H-indol-3-yl)-pyrimidin-4-ylamino)-2-(4-methylpiperazin-1-yl)-phenyl)-acrylamide | $^1$H-NMR (DMSO-$d_6$) δ: 2.27 (s, 3H), 2.55 (br, 4H), 2.88 (br, 4H), 3.88 (s, 6H), 5.75 (m, 1H), 6.24 (dd, 1H), 6.63 (dd, 1H), 6.87 (s, 1H), 7.19-7.29 (m, 3H), 7.54 (d, 1H), 8.15 (s, 1H), 8.29 (d, 1H), 8.41 (s, 1H), 8.50 (s, 1H), 8.66 (s, 1H), 9.05 (s, 1H). m/z: ESI MH$^+$ 498.2 |
| 159 | 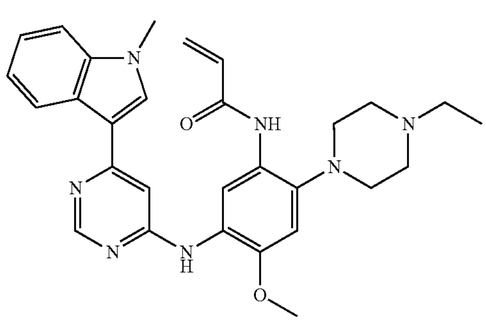 [SMILES: C=CC(=O)Nc1cc(Nc2cc(-c3cn(C)c4ccccc34)ncn2)c(OC)cc1N1CCN(CC)CC1] | N-(2-(4-ethyl-piperazin-1-yl)-4-methoxyl-5-(6-(1-methyl-1H-indol-3-yl)-pyrimidin-4-ylamino)-phenyl)-acrylamide | $^1$H-NMR (DMSO-$d_6$) δ: 1.05 (t, 3H), 2.41 (q, 2H), 2.59 (br, 4H), 2.89 (br, 4H), 3.88 (s, 6H), 5.75 (m, 1H), 6.23 (dd, 1H), 6.63 (dd, 1H), 6.88 (s, 1H), 7.19-7.30 (m, 3H), 7.53 (d, 1H), 8.15 (s, 1H), 8.29 (d, 1H), 8.42 (s, 1H), 8.51 (s, 1H), 8.66 (s, 1H), 9.06 (s, 1H). m/z: ESI MH$^+$ 512.2 |

TABLE 7-continued

| Comp. | Structure | Name | Data |
|---|---|---|---|
| 160 | 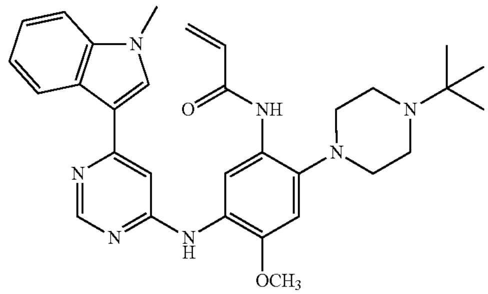 [SMILES: C=CC(=O)Nc1cc(Nc2cc(-c3cn(C)c4ccccc34)ncn2)c(OC)cc1N1CCN(C(C)(C)C)CC1] | N-(2-(4-tert-butyl-piperazin-1-yl)-4-methoxyl-5-(6-(1-methyl-1H-indol-3-yl)-pyrimidin-4-ylamino)-phenyl)-acrylamide | $^{1}$H-NMR (DMSO-d$_6$) δ: 1.07 (s, 9H), 2.72 (br, 4H), 2.88 (br, 4H), 3.86 (s, 3H), 3.87 (s, 3H), 5.75 (m, 1H), 6.23 (dd, 1H), 6.64 (dd, 1H), 6.89 (s, 1H), 7.18-7.28 (m, 3H), 7.53 (d, 1H), 8.14 (s, 1H), 8.28 (d, 1H), 8.42 (s, 1H), 8.49 (s, 1H), 8.64 (s, 1H), 9.06 (s, 1H). m/z: ESI MH$^+$ 540.2 |
| 161 | 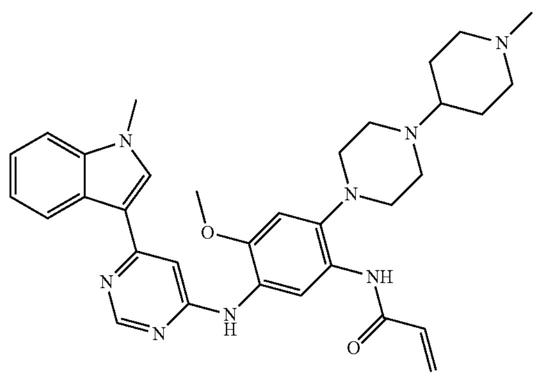 [SMILES: C=CC(=O)Nc1cc(Nc2cc(-c3cn(C)c4ccccc34)ncn2)c(OC)cc1N1CCN(C2CCN(C)CC2)CC1] | N-(4-methoxyl-5-(6-(1-methyl-1H-indol-3-yl)-pyrimidin-4-ylamino)-2-(4-(1-methylpiperidin-4-yl)-piperazin-1-yl)-phenyl)-acrylamide | $^{1}$H-NMR (DMSO-d$_6$) δ: 1.64 (m, 2H), 1.92 (m, 2H), 2.01 (m, 1H), 2.50 (s, 3H), , 2.52 (m, 4H), 2.72 (m, 4H), 2.90 (m, 4H), 3.87 (s, 3H), 3.88 (s, 3H), 5.75 (dd, 1H), 6.24 (dd, 1H), 6.65 (dd, 1H), 6.88 (s, 1H), 7.19-7.23 (m, 1H), 7.25-7.30 (m, 2H), 7.54 (d, 1H), 8.15 (s, 1H), 8.28 (d, 1H), 8.43 (s, 1H), 8.50 (s, 1H), 8.66 (s, 1H), 9.07 (s, 1H). m/z: ESI MH$^+$ 580.9 |
| 162 | 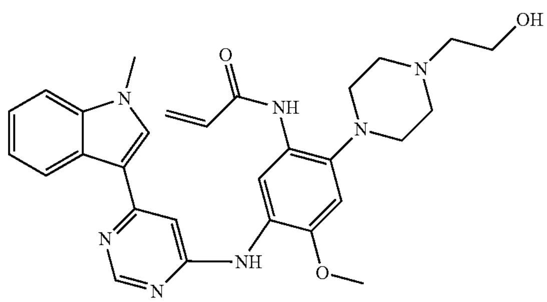 [SMILES: C=CC(=O)Nc1cc(Nc2cc(-c3cn(C)c4ccccc34)ncn2)c(OC)cc1N1CCN(CCO)CC1] | N-(2-(4-(2-hydroxyl-ethyl)-piperazin-1-yl)-4-methoxyl-5-(6-(1-methyl-1H-indol-3-yl)-pyrimidin-4-ylamino)-phenyl)-acrylamide | $^{1}$H-NMR (CDCl$_3$-d) δ: 2.72 (t, 2H), 2.79 (m, 4H), 2.99 (m, 4H), 3.74 (t, 2H), 3.89 (s, 3H), 3.91 (s, 3H), 5.82 (dd, 1H), 6.34 (dd, 1H), 6.48 (dd, 1H), 6.83 (s, 1H), 7.24-7.28 (m, 2H), 7.31 (dd, 1H), 7.38 (d, 1H), 7.45 (s, 1H), 8.12 (s, 1H), 8.40 (d, 1H), 8.51 (s, 1H), 8.74 (s, 1H), 9.00 (s, 1H). m/z: ESI MH$^+$ 527.9 |
| 163 | 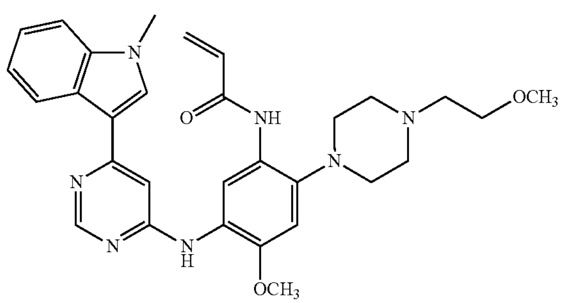 [SMILES: C=CC(=O)Nc1cc(Nc2cc(-c3cn(C)c4ccccc34)ncn2)c(OC)cc1N1CCN(CCOC)CC1] | N-(4-methoxyl-2-(4-(2-methoxyl-ethyl)-piperazin-1-yl)-5-(6-(1-methyl-1H-indol-3-yl)-pyrimidin-4-ylamino)-phenyl)-acrylamide | $^{1}$H-NMR (DMSO-d$_6$) δ: 2.56 (t, 2H), 2.64 (br, 4H), 2.87 (br, 4H), 3.26 (s, 3H), 3.48 (t, 2H), 3.87 (s, 3H), 3.88 (s, 3H), 5.74 (dd, 1H), 6.24 (dd, 1H), 6.63 (dd, 1H), 6.89 (s, 1H), 7.18-7.30 (m, 3H), 7.53 (d, 1H), 8.15 (s, 1H), 8.29 (d, 1H), 8.42 (s, 1H), 8.50 (s, 1H), 8.65 (s, 1H), 9.05 (s, 1H). m/z: ESI MH$^+$ 542.1 |
| 164 | 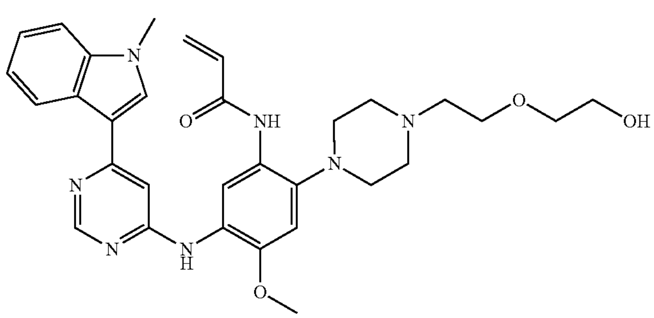 [SMILES: C=CC(=O)Nc1cc(Nc2cc(-c3cn(C)c4ccccc34)ncn2)c(OC)cc1N1CCN(CCOCCO)CC1] | N-(2-(4-(2-(2-hydroxyl-ethoxyl)-ethyl)-piperazin-1-yl)-4-methoxyl-5-(6-(1-methyl-1H-indol-3-yl)-pyrimidin-4-ylamino)-phenyl)-acrylamide | $^{1}$H-NMR (DMSO-d$_6$) δ: 2.57 (t, 2H), 2.66 (br, 4H), 2.87 (br, 4H), 3.44 (m, 2H), 3.52 (m, 2H), 3.56 (t, 2H), 3.88 (s, 6H), 4.68 (br, 1H), 5.74 (m, 1H), 6.24 (dd, 1H), 6.64 (dd, 1H), 6.89 (s, 1H), 7.19-7.30 (m, 3H), 7.53 (d, 1H), 8.15 (s, 1H), 8.29 (d, 1H), 8.43 (s, 1H), 8.51 (s, 1H), 8.66 (s, 1H), 9.06 (s, 1H). m/z: ESI MH$^+$ 572.1 |

TABLE 7-continued

| Comp. | Structure | Name | Data |
|---|---|---|---|
| 165 | 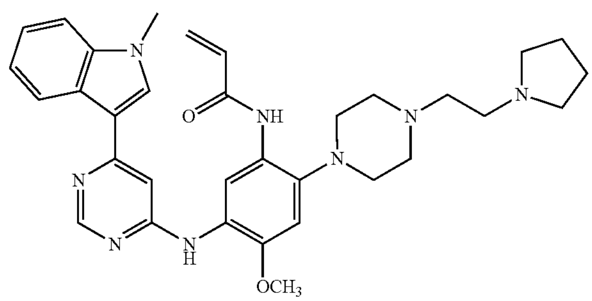 [SMILES: C=CC(=O)Nc1cc(Nc2cc(-c3cn(C)c4ccccc34)ncn2)c(OC)cc1N1CCN(CCN2CCCC2)CC1] | N-(4-methoxyl-5-(6-(1-methyl-1H-indol-3-yl)-pyrimidin-4-ylamino)-2-(4-(2-(pyrrolidin-1-yl)-ethyl)-piperazin-1-yl)-phenyl)-acrylamide | $^1$H-NMR (CD$_3$OD-d$_4$) δ: 1.92 (br, 4H), 2.67 (t, 2H), 2.76 (br, 4H), 2.85 (br, 4H), 2.91 (t, 2H), 2.99 (t, 4H), 3.36 (s, 2H), 3.90 (s, 3H), 3.92 (s, 3H), 5.83 (dd, 1H), 6.39 (dd, 1H), 6.57 (dd, 1H), 6.94 (s, 1H), 7.18-7.30 (m, 3H), 7.47 (d, 1H), 7.97 (s, 1H), 8.14 (d, 1H), 8.51-8.53 (m, 2H). m/z: ESI MH$^+$ 581.2 |
| 166 | 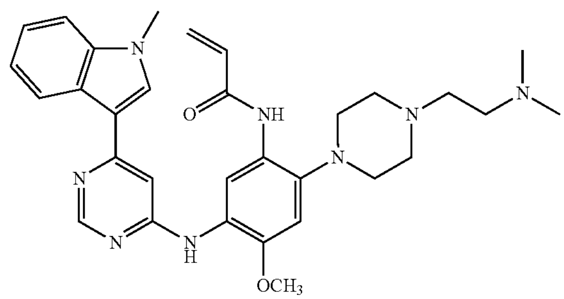 [SMILES: C=CC(=O)Nc1cc(Nc2cc(-c3cn(C)c4ccccc34)ncn2)c(OC)cc1N1CCN(CCN(C)C)CC1] | N-(2-(4-(2-(dimethylamino)-ethyl)-piperazin-1-yl)-4-methoxyl-5-(6-(1-methyl-1H-indol-3-yl)-pyrimidin-4-ylamino)-phenyl)-acrylamide | $^1$H-NMR (DMSO-d$_6$) δ: 2.33 (s, 6H), 2.52-2.71 (br, 8H), 2.87 (br, 4H), 3.87 (s, 3H), 3.88 (s, 3H), 5.74 (dd, 1H), 6.24 (dd, 1H), 6.63 (dd, 1H), 6.87 (s, 1H), 7.18-7.30 (m, 3H), 7.53 (d, 1H), 8.14 (s, 1H), 8.28 (d, 1H), 8.42 (s, 1H), 8.50 (s, 1H), 8.65 (s, 1H), 9.06 (s, 1H). m/z: ESI MH$^+$ 555.2 |
| 167 | 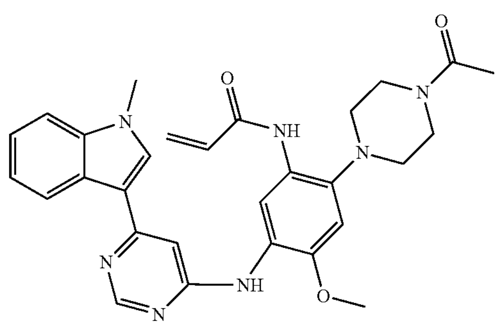 [SMILES: C=CC(=O)Nc1cc(Nc2cc(-c3cn(C)c4ccccc34)ncn2)c(OC)cc1N1CCN(C(C)=O)CC1] | N-(2-(4-acetylpiperazin-1-yl)-4-methoxyl-5-(6-(1-methyl-1H-indol-3-yl)-pyrimidin-4-ylamino)-phenyl)-acrylamide | $^1$H-NMR (CDCl$_3$-d) δ: 2.18 (s, 3H), 2.89 (m, 4H), 3.66 (m, 2H), 3.82 (m, 2H), 3.87 (s, 6H), 5.82 (dd, 1H), 6.33 (dd, 1H), 6.47 (dd, 1H), 6.73 (s, 1H), 7.27-7.30 (m, 2H), 7.31 (dd, 1H), 7.38 (d, 1H), 7.42 (s, 1H), 8.11 (s, 1H), 8.38 (d, 1H), 8.45 (s, 1H), 8.74 (s, 1H), 8.98 (s, 1H). m/z: ESI MH$^+$ 525.9 |
| 168 | 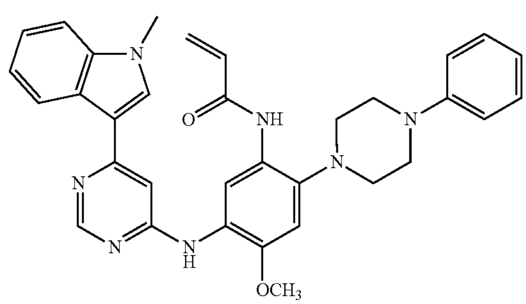 [SMILES: C=CC(=O)Nc1cc(Nc2cc(-c3cn(C)c4ccccc34)ncn2)c(OC)cc1N1CCN(c2ccccc2)CC1] | N-(4-methoxyl-5-(6-(1-methyl-1H-indol-3-yl)-pyrimidin-4-ylamino)-2-(4-phenylpiperazin-1-yl)-phenyl)-acrylamide | $^1$H-NMR (DMSO-d$_6$) δ: 2.50 (br, 4H), 3.04 (br, 4H), 3.88 (s, 3H), 3.90 (s, 3H), 5.72 (dd, 1H), 6.25 (dd, 1H), 6.67 (dd, 1H), 6.81 (t, 1H), 6.94 (s, 1H), 7.01 (d, 2H), 7.19-7.31 (m, 5H), 7.54 (d, 1H), 8.16 (s, 1H), 8.30 (d, 1H), 8.48 (s, 1H), 8.52 (s, 1H), 8.68 (s, 1H), 9.15 (s, 1H). m/z: ESI MH$^+$ 560.2 |
| 169 | 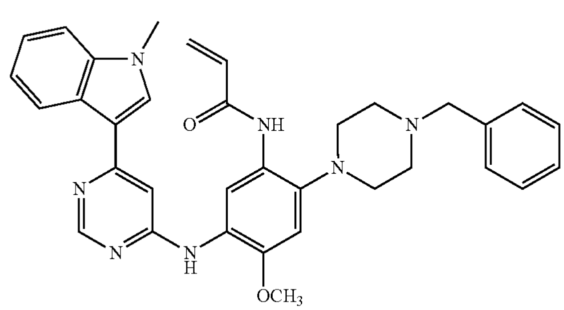 [SMILES: C=CC(=O)Nc1cc(Nc2cc(-c3cn(C)c4ccccc34)ncn2)c(OC)cc1N1CCN(Cc2ccccc2)CC1] | N-(2-(4-benzylpiperazin-1-yl)-4-methoxyl-5-(6-(1-methyl-1H-indol-3-yl)-pyrimidin-4-ylamino)-phenyl)-acrylamide | $^1$H-NMR (DMSO-d$_6$) δ: 2.60 (br, 4H), 2.90 (br, 4H), 3.57 (s, 2H), 3.87 (s, 3H), 3.88 (s, 3H), 5.74 (m, 1H), 6.23 (dd, 1H), 6.63 (dd, 1H), 6.91 (s, 1H), 7.19-7.30 (m, 4H), 7.33-7.36 (m, 4H), 7.54 (d, 1H), 8.15 (s, 1H), 8.29 (d, 1H), 8.43 (s, 1H), 8.50 (s, 1H), 8.65 (s, 1H), 9.07 (s, 1H). m/z: ESI MH$^+$ 574.2 |

TABLE 7-continued

| Comp. | Structure | Name | Data |
|---|---|---|---|
| 170 | 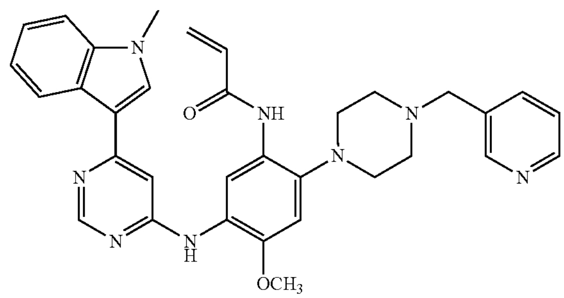 [SMILES: C=CC(=O)Nc1cc(Nc2cc(-c3cn(C)c4ccccc34)ncn2)c(OC)cc1N1CCN(Cc2cccnc2)CC1] | N-(4-methoxyl-5-(6-(1-methyl-1H-indol-3-yl)-pyrimidin-4-ylamino)-2-(4-(-(pyridin-3-ylmethyl)-piperazin-1-yl)-phenyl)-acrylamide | $^1$H-NMR (DMSO-d$_6$) δ: 2.61 (br, 4H), 2.90 (br, 4H), 3.61 (s, 2H), 3.87 (s, 3H), 3.88 (s, 3H), 5.74 (dd, 1H), 6.23 (dd, 1H), 6.63 (dd, 1H), 6.90 (s, 1H), 7.18-7.30 (m, 3H), 7.39 (m, 1H), 7.53 (d, 1H), 7.76 (m, 1H), 8.15 (s, 1H), 8.29 (d, 1H), 8.43 (s, 1H), 8.48-8.50 (m, 2H), 8.55 (d, 1H), 8.64 (s, 1H), 9.07 (s, 1H). m/z: ESI MH$^+$ 575.2 |
| 171 | 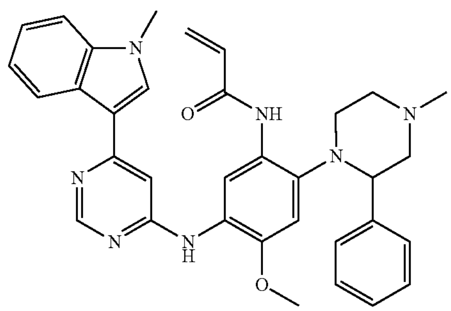 [SMILES: C=CC(=O)Nc1cc(Nc2cc(-c3cn(C)c4ccccc34)ncn2)c(OC)cc1N1CCN(C)CC1c1ccccc1] | N-(4-methoxyl-5-(6-(1-methyl-1H-indol-3-yl)-pyrimidin-4-ylamino)-2-(4-methyl-2-phenylpiperazin-1-yl)-phenyl)-acrylamide | $^1$H-NMR (DMSO-d$_6$) δ: 2.29 (s, 3H), 2.48 (m, 1H), 2.78-2.85 (br, 4H), 2.96 (br, 1H), 3.69 (s, 3H), 3.89 (s, 3H), 4.41 (dd, 1H), 5.81 (m, 1H), 6.28 (dd, 1H), 6.83 (dd, 1H), 6.87 (s, 1H), 7.09 (m, 1H), 7.16-7.33 (m, 5H), 7.45-7.47 (m, 2H), 7.53 (d, 1H), 8.11 (s, 1H), 8.24 (d, 1H), 8.46 (s, 1H), 8.51 (s, 1H), 8.53 (s, 1H), 9.09 (s, 1H). m/z: ESI MH$^+$ 574.2 |
| 172 | 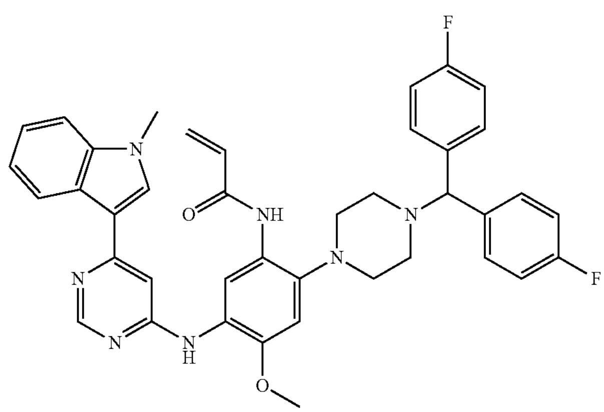 [SMILES: C=CC(=O)Nc1cc(Nc2cc(-c3cn(C)c4ccccc34)ncn2)c(OC)cc1N1CCN(C(c2ccc(F)cc2)c2ccc(F)cc2)CC1] | N-(2-(4-(bis-(4fluoro-phenyl)-methyl)-piperazin-1-yl)-4-methoxyl-5-(6-(1-methyl-1H-indol-3-yl)-pyrimidin-4-ylamino)-phenyl)-acrylamide | $^1$H-NMR (DMSO-d$_6$) δ: 2.50 (br, 4H), 2.92 (br, 4H), 3.87 (s, 3H), 3.88 (s, 3H), 4.46 (s, 1H), 5.71 (dd, 1H), 6.20 (dd, 1H), 6.58 (dd, 1H), 6.92 (s, 1H), 7.15-7.30 (m, 7H), 7.47-7.55 (m, 5H), 8.14 (s, 1H), 8.28 (d, 1H), 8.44 (s, 1H), 8.50 (s, 1H), 8.66 (s, 1H), 9.04 (s, 1H). m/z: ESI MH$^+$ 686.2. |
| 173 | 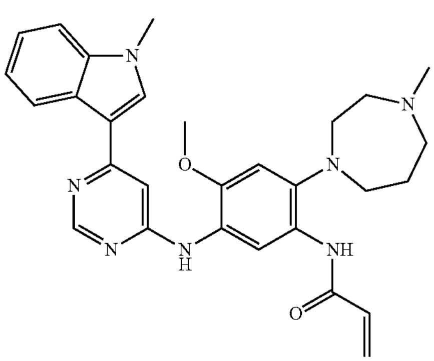 [SMILES: C=CC(=O)Nc1cc(Nc2cc(-c3cn(C)c4ccccc34)ncn2)c(OC)cc1N1CCCN(C)CC1] | N-(4-methoxyl-2-(4-methyl-[1,4]diazepin-1-yl)-5-(6-(1-methyl-1H-indol-3-yl)-pyrimidin-4-ylamino)-phenyl)-acrylamide | $^1$H-NMR (DMSO-d$_6$) δ: 2.08 (m, 2H), 2.50 (s, 3H), 2.76 (m, 4H), 3.09 (m, 4H), 3.88 (s, 3H), 3.87 (s, 3H), 5.77 (dd, 1H), 6.28 (dd, 1H), 6.81 (dd, 1H), 6.91 (s, 1H), 7.21 (m, 1H), 7.25-7.34 (m, 2H), 7.54 (d, 1H), 8.16 (s, 1H)? 8.30 (d, 1H), 8.35 (s, 1H) 8.51 (s, 1H), 8.65 (s, 1H), 9.39 (s, 1H). m/z: ESI MH$^+$ 511.9 |

TABLE 7-continued

| Comp. | Structure | Name | Data |
|---|---|---|---|
| 174 | 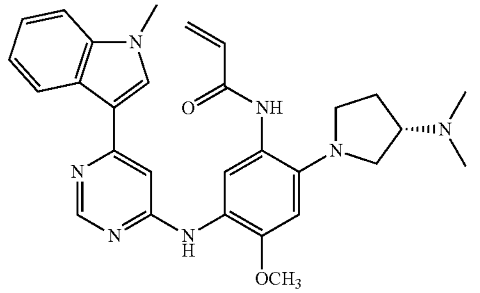 [SMILES: C=CC(=O)Nc1cc(Nc2cc(-c3cn(C)c4ccccc34)ncn2)c(OC)cc1N1CC[C@H](N(C)C)C1] | (S)-N-(2-(3-dimethylamino-pyrrolidin-1-yl)-4-methoxyl-5-(6-(1-methyl-1H-indol-3-yl)-pyrimidin-4-ylamino)-phenyl)-acrylamide | $^1$H-NMR (DMSO-d$_6$) δ: 1.71 (m, 1H), 2.05 (m, 1H), 2.17 (s, 6H), 2.68 (m, 1H), 3.19-3.29 (m, 3H), 3.36 (m, 1H), 3.86 (s, 3H), 3.87 (s, 3H), 5.71 (dd, 1H), 6.22 (dd, 1H), 6.50 (m, 2H), 7.15 (s, 1H), 7.18-7.28 (m, 2H), 7.52 (d, 1H), 7.69 (s, 1H), 8.12 (s, 1H), 8.27 (d, 1H), 8.47 (s, 1H), 8.52 (s, 1H), 9.44 (s, 1H). m/z: ESI MH$^+$ 512.2 |
| 175 | 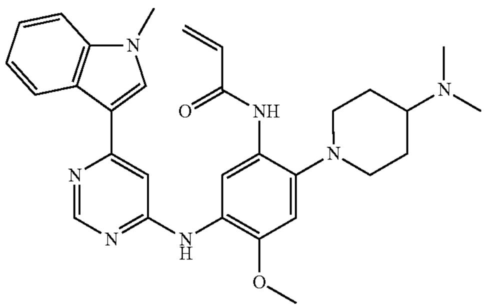 [SMILES: C=CC(=O)Nc1cc(Nc2cc(-c3cn(C)c4ccccc34)ncn2)c(OC)cc1N1CCC(N(C)C)CC1] | N-(2-(4-dimethylamino-piperidin-1-yl)-4-methoxyl-5-(6-(1-methyl-1H-indol-3-yl)-pyrimidin-4-ylamino)-phenyl)-acrylamide | $^1$H-NMR (DMSO-d$_6$) δ: 1.68 (q, 2H), 2.84 (d, 2H), 2.17-2.30 (m, 7H), 2.67 (t, 2H), 3.06 (d, 2H), 3.86 (s, 3H), 3.87 (s, 3H), 5.75 (m, 1H), 6.24 (dd, 1H), 6.68 (dd, 1H), 6.85 (s, 1H), 7.19-7.28 (m, 3H), 7.53 (d, 1H), 8.15 (s, 1H), 8.28 (d, 1H), 8.41 (s, 1H), 8.50 (s, 1H), 8.64 (s, 1H), 9.06 (s, 1H). m/z: ESI MH$^+$ 526.2 |
| 176 | 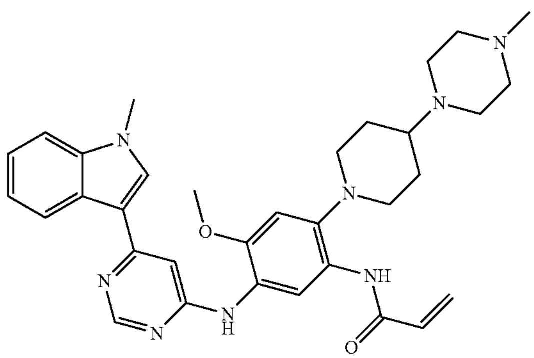 [SMILES: C=CC(=O)Nc1cc(Nc2cc(-c3cn(C)c4ccccc34)ncn2)c(OC)cc1N1CCC(N2CCN(C)CC2)CC1] | N-(4-methoxyl-5-(6-(1-methyl-1H-indol-3-yl)-pyrimidin-4-ylamino)-2-(4-(4-methylpiperazin-1-yl)-piperidin-1-yl)-phenyl)-acrylamide | $^1$H-NMR (DMSO-d$_6$) δ: , 1.73 (m, 2H), 1.86 (m, 2H), 2.34 (m, 1H), 2.42 (s, 3H), 2.51 (m, 4H), 2.70 (m, 6H), 3.08 (m, 2H), 3.86 (s, 3H), 3.88 (s, 3H), 5.75 (dd, 1H), 6.25 (dd, 1H), 6.68 (dd, 1H), 6.85 (s, 1H), 7.20 (m, 1H), 7.25-7.28 (m, 2H), 7.54 (d, 1H)? 8.15 (s, 1H), 8.28 (d, 1H)? 8.44 (s, 1H), 8.50 (s, 1H), 8.64 (s, 1H), 9.03 (s, 1H). m/z: ESI MH$^+$ 580.9 |
| 177 | 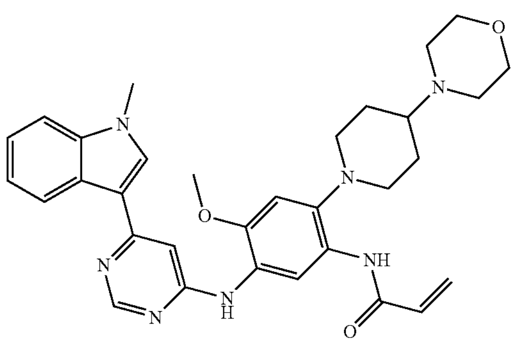 [SMILES: C=CC(=O)Nc1cc(Nc2cc(-c3cn(C)c4ccccc34)ncn2)c(OC)cc1N1CCC(N2CCOCC2)CC1] | N-(2-(4-(morpholin-4-yl)piperidin-1-yl)-4-methoxyl-5-(6-(1-methyl-1H-indol-3-yl)-pyrimidin-4-ylamino)-phenyl)-acrylamide | $^1$H-NMR (DMSO-d$_6$) δ: 1.72 (m, 2H), 1.88 (m, 2H), 2.26 (m, 1H), 2.51 (m, 4H), 2.68 (t, 2H), 3.07 (m, 2H), 3.61 (m, 4H), 3.86 (s, 3H), 3.87 (s, 3H), 5.74 (dd, 1H), 6.24 (dd, 1H), 6.68 (m, 1H), 6.85 (s, 1H), 7.21 (m, 1H)? 7.26 (m, 2H), 7.54 (d, 1H), 8.14 (s, 1H), 8.28 (d, 1H), 8.42 (s, 1H), 8.50 (s, 1H), 8.64 (s, 1H), 9.03 (s, 1H) m/z: ESI MH$^+$ 568.3 |
| 178 | 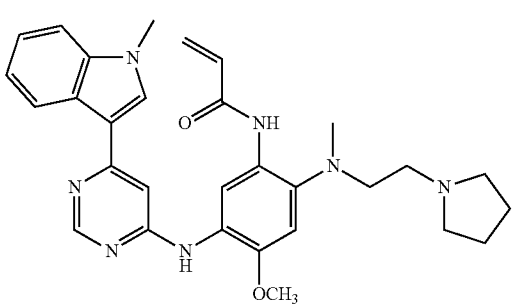 [SMILES: C=CC(=O)Nc1cc(Nc2cc(-c3cn(C)c4ccccc34)ncn2)c(OC)cc1N(C)CCN1CCCC1] | N-(4-methoxyl-5-(6-(1-methyl-1H-indol-3-yl)-pyrimidin-4-ylamino)-2-(methyl-(2-pyrrolidin-1-yl-ethyl)-amino)-phenyl)-acrylamide | $^1$H-NMR (DMSO-d$_6$) δ: 1.73 (br, 4H), 2.49 (br, 6H), 2.71 (s, 3H), 2.96 (t, 2H), 3.86 (s, 3H), 3.87 (s, 3H), 5.76 (dd, 1H), 6.24 (dd, 1H), 6.46 (dd, 1H), 7.01 (s, 1H), 7.18-7.29 (m, 3H), 7.53 (d, 1H), 8.14 (s, 1H), 8.26 (d, 1H), 8.51 (s, 1H), 8.64-8.66 (br, 1H), 9.83 (s, 1H). m/z: ESI MH$^+$ 526.4 |

TABLE 7-continued

| Comp. | Structure | Name | Data |
|---|---|---|---|
| 179 | 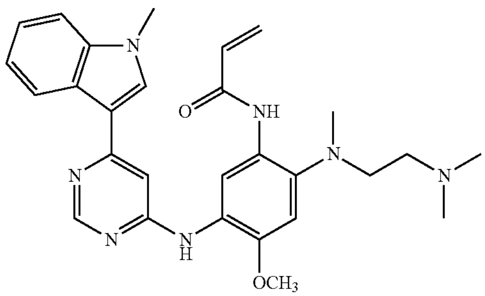 [SMILES: C=CC(=O)Nc1cc(Nc2cc(-c3cn(C)c4ccccc34)ncn2)c(OC)cc1N(C)CCN(C)C] | N-(5-(6-(1-methyl-1H-indol-3-yl)-pyrimidin-2-ylamino)-2-((2-(dimethylamino)-ethyl)-methyl-amino)-4-methoxyl-phenyl)-acrylamide | $^1$H-NMR (DMSO-d$_6$) δ: 2.27 (s, 6H), 2.31 (t, 2H), 2.71 (s, 3H), 2.93 (t, 2H), 3.87 (s, 3H), 3.88 (s, 3H), 5.76 (dd, 1H), 6.26 (dd, 1H), 6.43 (dd, 1H), 7.02 (s, 1H), 7.18-7.30 (m, 3H), 7.54 (d, 1H), 8.15 (s, 1H), 8.28 (d, 1H), 8.51 (s, 1H), 8.67 (s, 1H), 8.71 (s, 1H), 10.11 (s, 1H). m/z: ESI MH$^+$ 500.1 |
| 180 | 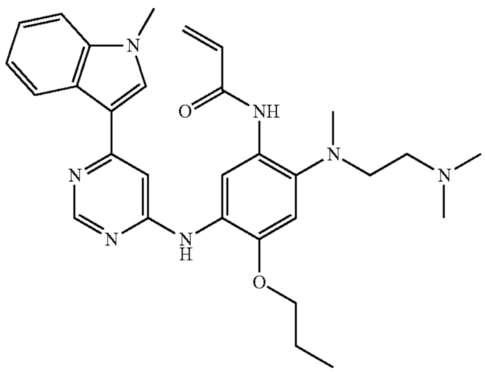 [SMILES: C=CC(=O)Nc1cc(Nc2cc(-c3cn(C)c4ccccc34)ncn2)c(OCCC)cc1N(C)CCN(C)C] | N-{2-[(2-dimethylamino-ethyl)-methyl-amino]-5-[6-(-methyl-1H-indol-3-yl)-pimidin-4-ylamino]-4-propoxyl-phenyl}-acrylamide | $^1$H-NMR (DMSO-d6) δ: 0.89 (t, 3H), 1.71 (m, 2H), 2.23 (s, 6H), 2.45 (br, 2H), 2.71 (s, 3H), 2.94 (br, 2H), 3.88 (s, 3H), 4.01 (t, 2H), 5.76 (dd, 1H), 6.26 (dd, 1H), 6.49 (br, 1H), 7.02 (s, 1H), 7.17-7.21 (m, 2H), 7.26 (t, 1H), 7.53 (d, 1H), 8.16 (s, 1H), 8.27 (d, 1H), 8.51 (s, 2H), 8.57 (s, 1H), 10.11 (s, 1H). m/z: ESI MH$^+$ 528.3 |
| 181 | 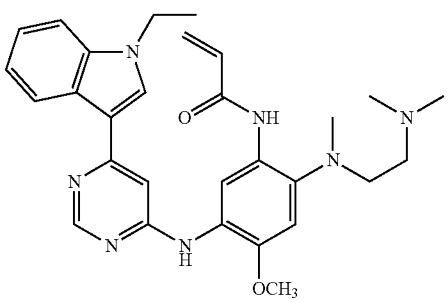 [SMILES: C=CC(=O)Nc1cc(Nc2cc(-c3cn(CC)c4ccccc34)ncn2)c(OC)cc1N(C)CCN(C)C] | N-{2-((2-dimethylamino-ethyl)-methylamino)-5-[6-(1-ethyl-1H-indol-3-yl)-pyrimidin-4-ylamino]-4-methoxyl-phenyl}-acrylamide | $^1$H-NMR (DMSO-d$_6$) δ: 1.41 (t, 3H), 2.20 (s, 6H), 2.31 (t, 2H), 2.71 (s, 3H), 2.87 (t, 2H), 3.85 (s, 3H), 4.29 (q, 2H), 5.75 (dd, 1H), 6.24 (dd, 1H), 6.40 (dd, 1H), 7.02 (s, 1H), 7.18 (t, 1H), 7.24 (t, 1H), 7.30 (s, 1H), 7.57 (d, 1H), 8.20 (s, 1H), 8.27 (d, 1H), 8.50 (s, 1H), 8.62 (s, 1H), 8.73 (s, 1H), 10.18 (s, 1H). m/z: ESI MH$^+$ 514.2 |
| 182 | 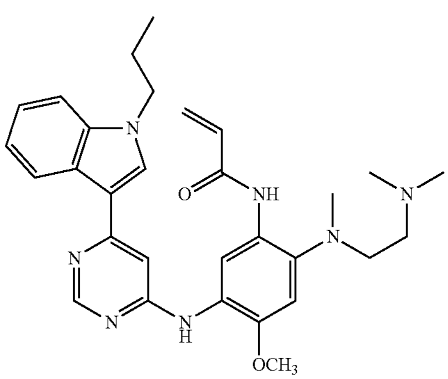 [SMILES: C=CC(=O)Nc1cc(Nc2cc(-c3cn(CCC)c4ccccc34)ncn2)c(OC)cc1N(C)CCN(C)C] | N-{2-[(2-dimethylamino-ethyl)-methylaminol-5-[6-(1-propyl-1H-indol-3-yl)-pyrimidin-4-ylaminol-4-methoxyl-phenyl}-acrylamide | $^1$H-NMR (DMSO-d$_6$) δ: 0.87 (t, 3H), 1.84 (m, 2H), 2.22 (s, 6H), 2.33 (t, 2H), 2.73 (s, 3H), 2.89 (t, 2H), 3.86 (s, 3H), 4.24 (t, 2H), 5.77 (dd, 1H), 6.26 (dd, 1H), 6.41 (dd, 1H), 7.03 (s, 1H), 7.18 (t, 1H), 7.24 (t, 1H), 7.33 (s, 1H), 7.59 (d, 1H), 8.20 (s, 1H), 8.28 (d, 1H), 8.52 (s, 1H), 8.62 (s, 1H), 8.75 (s, 1H), 10.18 (s, 1H). m/z: ESI MH$^+$ 528.2 |

| Comp. | Structure | Name | Data |
|---|---|---|---|
| 183 | 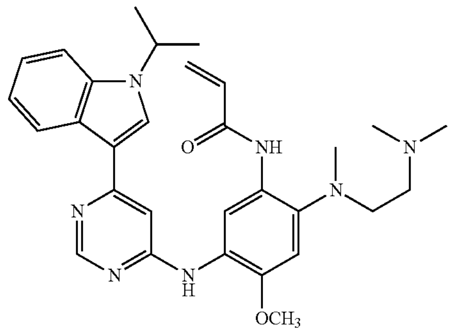 [SMILES: C=CC(=O)Nc1cc(Nc2cc(-c3cn(C(C)C)c4ccccc34)ncn2)c(OC)cc1N(C)CCN(C)C] | N-{2-[(2-dimethylamino-ethyl)-methylamino]-5-[(6-(1-isopropyl-1H-indol-3-yl)-pyrimidin-4-ylaminol-4-methoxyl-phenyl]-acrylamide | $^1$H-NMR (DMSO-d$_6$) δ: 1.52 (d, 6H), 2.22 (s, 6H), 2.32 (t, 2H), 2.72 (s, 3H), 2.88 (t, 2H), 3.86 (s, 3H), 4.84 (m, 1H), 5.77 (dd, 1H), 6.26 (dd, 1H), 6.41 (dd, 1H), 7.03 (s, 1H), 7.18 (t, 1H), 7.25 (t, 1H), 7.39 (s, 1H), 7.62 (d, 1H), 8.28 (s, 1H), 8.31 (d, 1H), 8.54 (s, 1H), 8.57 (s, 1H), 8.76 (s, 1H), 10.21 (s, 1H). m/z: ESI MH$^+$ 528.2 |
| 184 | 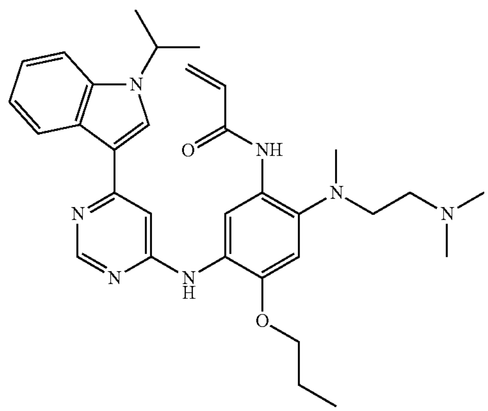 [SMILES: C=CC(=O)Nc1cc(Nc2cc(-c3cn(C(C)C)c4ccccc34)ncn2)c(OCCC)cc1N(C)CCN(C)C] | N-{2-[(2-dimethylamino-ethyl)-methyl-amino]-5-[6-(1-isopropyl-1H-indol-3-yl)-pyrimidin-4-ylaminol-4-propoxyl-phenyl}-acrylamide | $^1$H-NMR (DMSO-d6) δ: 0.94 (t, 3H), 1.53 (d, 6H), 1.73 (m, 2H), 2.32 (br, 6H), 2.48 (br, 2H), 2.70 (s, 3H), 2.96 (br, 2H), 4.02 (t, 2H), 4.84 (m, 1H), 5.77 (dd, 1H), 6.28 (dd, 1H), 6.54 (br, 1H), 6.99 (s, 1H), 7.17 (t, 1H), 7.22 (t, 1H), 7.31 (s, 1H), 7.62 (d, 1H), 8.29-8.33 (m, 2H), 8.42 (s, 1H), 8.54 (s, 1H), 8.56 (s, 1H), 10.14 (s, 1H). m/z: ESI MH$^+$ 556.3 |
| 185 | 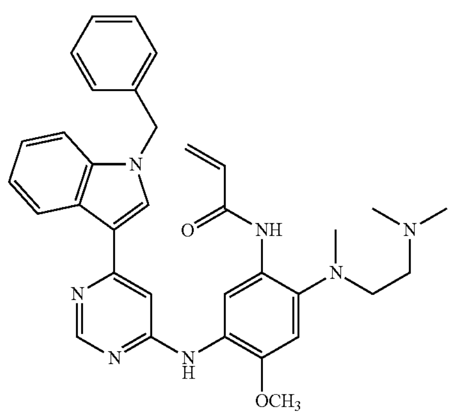 [SMILES: C=CC(=O)Nc1cc(Nc2cc(-c3cn(Cc4ccccc4)c4ccccc34)ncn2)c(OC)cc1N(C)CCN(C)C] | N-(5-(6-(1-benzyl-1H-indol-3-yl)-pyrimidin-4-ylamino)-2-((2-dimethylamino-ethyl)-methyl-amino)-4-methoxyl-phenyl)-acrylamide | $^1$H-NMR (DMSO-d$_6$) δ: 2.22 (s, 6H), 2.32 (t, 2H), 2.72 (s, 3H), 2.88 (t, 2H), 3.86 (s, 3H), 5.52 (s, 2H), 5.75 (dd, 1H), 6.24 (dd, 1H), 6.41 (dd, 1H), 7.02 (s, 1H), 7.16-7.36 (m, 8H), 7.57 (dd, 1H), 8.28 (dd, 1H), 8.32 (s, 1H), 8.52 (d, 1H), 8.67 (s, 1H), 8.78 (s, 1H), 10.16 (s, 1H). m/z: ESI MH$^+$ 576.2 |
| 186 | 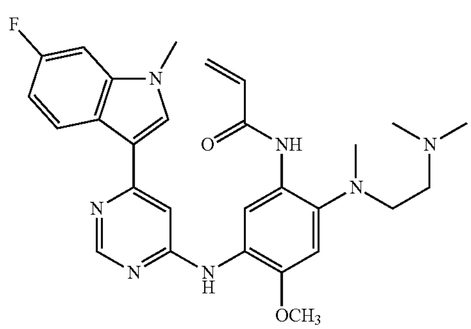 [SMILES: C=CC(=O)Nc1cc(Nc2cc(-c3cn(C)c4cc(F)ccc34)ncn2)c(OC)cc1N(C)CCN(C)C] | N-(4-methoxyl-5-(6-(6-fluoro-1-methyl-1H-indol-3-yl)-pyrimidin-4-ylamino)-2-(2-(dimethylamino-ethyl)-methyl-amino)-phenyl)-acrylamide | $^1$H-NMR (DMSO-d$_6$) δ: 2.22 (s, 6H), 2.32 (t, 2H), 2.72 (s, 3H), 2.88 (t, 2H), 3.85 (s, 3H), 3.86 (s, 3H), 5.76 (dd, 1H), 6.25 (dd, 1H), 6.41 (dd, 1H), 7.02 (s, 1H), 7.06 (m, 1H), 7.26 (s, 1H), 7.43 (m, 1H), 8.14 (dd, 1H), 8.30 (d, 1H), 8.52 (s, 1H), 8.64 (s, 1H), 8.73 (s, 1H), 10.17 (s, 1H). m/z: ESI MH$^+$ 518.1 |

| Comp. | Structure | Name | Data |
|---|---|---|---|
| 187 | 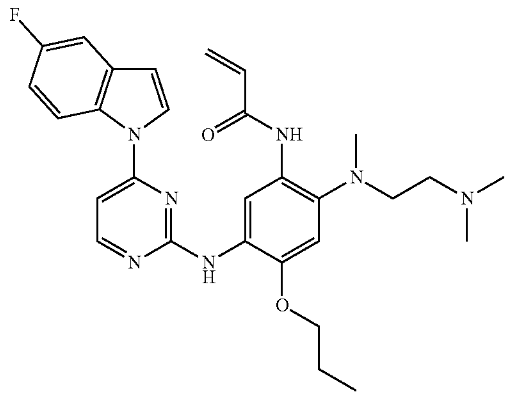 [SMILES: C=CC(=O)Nc1cc(Nc2nccc(-n3ccc4cc(F)ccc43)n2)c(OCCC)cc1N(C)CCN(C)C] | N-{2-[(2-dimethylamino)-ethyl)-methyl-amino]-5-[4-(5-fluoro-indol-1-yl)-pyrimidin-2-ylamino]-4-propoxyl-phenyl}-acrylamide | $^1$H-NMR (DMSO-d6) δ: 0.78 (t, 3H), 1.61 (m, 2H), 2.00 (m, 2H), 2.30-2.52 (br, 8H), 2.72 (s, 3H), 3.05 (br, 2H), 3.94 (t, 2H), 5.73 (dd, 1H), 6.22 (dd, 1H), 6.63 (br, 1H), 6.77 (d, 1H), 6.87 (t, 1H), 7.04 (s, 1H), 7.13 (d, 1H), 7.38 (dd, 1H), 8.22 (d, 1H), 8.36-8.42 (m, 3H), 8.67 (s, 1H), 10.00 (s, 1H). m/z: ESI MH$^+$ 532.3 |
| 188 | 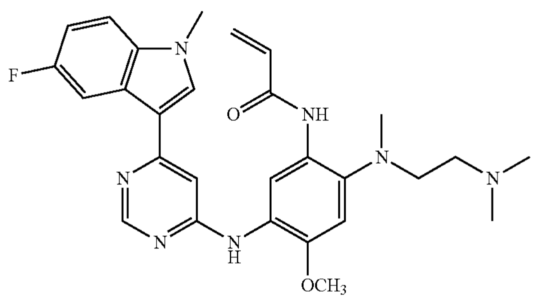 [SMILES: C=CC(=O)Nc1cc(Nc2cc(-c3cn(C)c4ccc(F)cc34)ncn2)c(OC)cc1N(C)CCN(C)C] | N-(2-((2-dimethylamino-ethyl)-methylamino)-5-(6-(5-fluoro-1-methyl-1H-indol-3-yl)-pyrimidin-4-ylamino)-4-methoxyl-phenyl)-acrylamide | $^1$H-NMR (DMSO-d$_6$) δ: 2.22 (s, 6H), 2.33 (t, 2H), 2.72 (s, 3H), 2.88 (t, 2H), 3.86 (s, 3H), 3.88 (s, 3H), 5.75 (dd, 1H), 6.25 (dd, 1H), 6.40 (dd, 1H), 7.02 (s, 1H), 7.12 (m, 1H), 7.24 (s, 1H), 7.56 (m, 1H), 8.05 (dd, 1H), 8.22 (s, 1H), 8.52 (s, 1H), 8.65 (br, 1H), 8.76 (s, 1H), 10.16 (s, 1H). m/z: ESI MH$^+$ 518.1 |
| 189 | 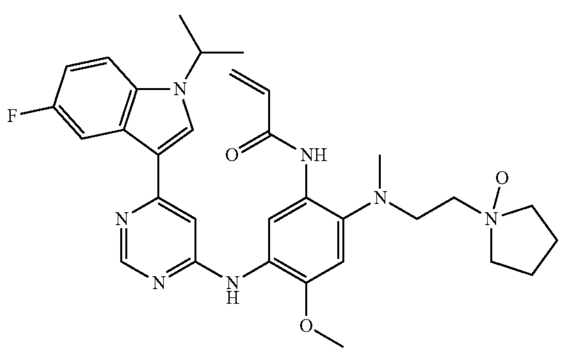 | N-(5-[6-(5-fluoro-1-isopropyl-1H-indol-3-yl)-pyrimidin-4-ylamino]-2-{[2-(1-oxy-pyrrolidin-1-yl)-ethyl]-methyl-amino}-4-methoxyl-phenyl)-acrylamide | $^1$H-NMR (DMSO-d$_6$) δ: 1.53 (d, 6H), 2.00 (m, 2H), 2.27 (m, 2H), 2.75 (s, 3H), 3.18 (br, 2H), 3.46 (m, 2H), 3.55 (br, 2H), 3.64 (br, 2H), 3.86 (s, 3H), 4.84 (m, 1H), 5.65 (dd, 1H), 6.22 (dd, 1H), 6.97 (s, 1H), 7.07 (m, 1H), 7.18 (dd, 1H), 7.38 (s, 1H), 7.65 (m, 1H), 8.14 (dd, 1H), 8.42 (s, 1H), 8.44 (s, 1H), 8.48 (s, 1H), 8.54 (s, 1H), 12.67 (br, 1H). m/z: ESI MH$^+$ 588.3 |
| 190 | 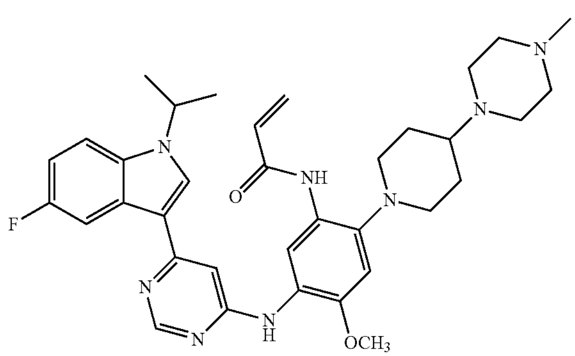 [SMILES: C=CC(=O)Nc1cc(Nc2cc(-c3cn(C(C)C)c4ccc(F)cc34)ncn2)c(OC)cc1N1CCC(N2CCN(C)CC2)CC1] | N-(5-(6-(5-fluoro-1-isopropyl-1H-indol-3-yl)-pyrimidin-4-ylamino)-4-methoxy-2-(4-(4-methyl-piperazin-1-yl)-piperidin-1-yl)-phenyl)-acrylamide | $^1$H-NMR (DMSO-d$_6$) δ: 1.52 (d, 6H), 1.69-1.72 (br, 2H), 1.84-1.87 (br, 2H), 3H), 2.24-2.46 (br, 6H), 2.50-2.56 (br, 3H), 2.68 (br, 2H), 3.06 (d, 2H), 3.87 (s, 3H), 4.84 (m, 1H), 5.74 (dd, 1H), 6.25 (dd, 1H), 6.68 (dd, 1H), 6.85 (s, 1H), 7.10 (m, 1H), 7.33 (s, 1H), 7.66 (m, 1H), 8.08 (dd, 1H), 8.35 (s, 1H), 8.44 (s, 1H), 8.53 (s, 1H), 8.54 (br, 1H), 9.04 (s, 1H). m/z: ESI MH$^+$ 627.4 |

TABLE 7-continued

| Comp. | Structure | Name | Data |
|---|---|---|---|
| 191 | 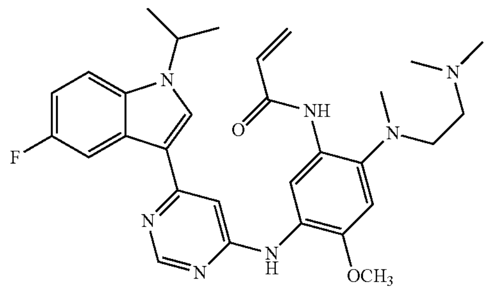 [SMILES: C=CC(=O)Nc1cc(Nc2cc(-c3cn(C(C)C)c4ccc(F)cc34)ncn2)c(OC)cc1N(C)CCN(C)C] | N-(5-(6-(5-fluoro-1-isopropyl-1H-indol-3-yl)-pyrimidin-4-ylamino)-4-methoxyl-2-((2-dimethylamino-ethyl)-methyl-amino)-phenyl)-acrylamide | ¹H-NMR (DMSO-d₆) δ: 1.52 (d, 6H), 2.73 (s, 3H), 3.24 (t, 2H), 3.29 (s, 6H), 3.49 (t, 2H), 3.86 (s, 3H), 4.84 (m, 1H), 5.65 (dd, 1H), 6.22 (dd, 1H), 6.96 (s, 1H), 7.07-7.17 (m, 2H), 7.37 (s, 1H), 7.65 (m, 1H), 8.13 (dd, 1H), 8.43-8.47 (m, 3H), 8.54 (s, 1H), 12.28 (s, 1H). m/z: ESI MH⁺ 546.4 |
| 192 | 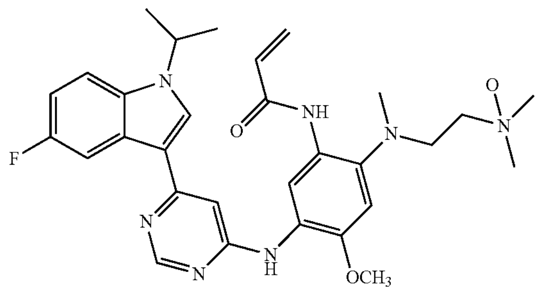 | 2-((2-acrylamido-5-methoxyl-4-((6-(1-isopropyl-5-fluoro-1H-indol-3-yl)-pyrimidin-4-yl)-amino)-phenyl)-methyl)-N,N-dimethyl-N-ethylamine oxide | ¹H-NMR (DMSO-d₆) δ: 1.52 (d, 6H), 2.22 (s, 6H), 2.33 (t, 2H), 2.71 (s, 3H), 2.89 (t, 2H), 3.87 (s, 3H), 4.84 (m, 1H), 5.77 (dd, 1H), 6.26 (dd, 1H), 6.41 (dd, 1H), 7.00 (s, 1H), 7.10 (m, 1H), 7.34 (s, 1H), 7.66 (m, 1H), 8.07 (dd, 1H), 8.34 (s, 1H), 8.53-8.55 (d, 2H), 8.75 (s, 1H), 10.20 (s, 1H). m/z: ESI MH⁺ 562.6 |
| 193 | 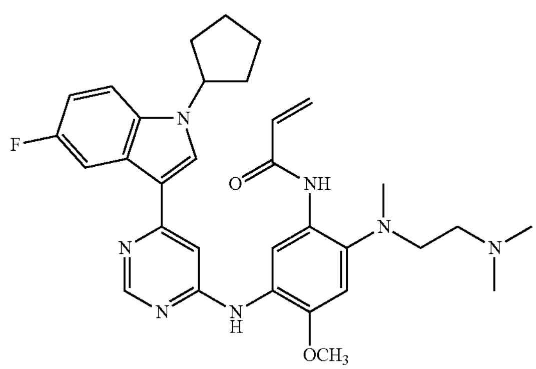 [SMILES: C=CC(=O)Nc1cc(Nc2cc(-c3cn(C4CCCC4)c4ccc(F)cc34)ncn2)c(OC)cc1N(C)CCN(C)C] | N-(5-(6-(5-fluoro-1-cyclopentyl-1H-indol-3-yl)-pyrimidin-4-ylamino)-4-methoxyl-2-((2-dimethylamino-ethyl)-methyl-amino)-phenyl)-acrylamide | ¹H-NMR (DMSO-d₆) δ: 1.71-1.77 (m, 2H), 1.82-1.95 (m, 4H), 2.16-2.26 (m, 8H), 2.33 (t, 2H), 2.72 (s, 3H), 2.88 (t, 2H), 3.86 (s, 3H), 4.96 (m, 1H), 5.77 (dd, 1H), 6.25 (dd, 1H), 6.41 (dd, 1H), 7.02 (s, 1H), 7.11 (m, 1H), 7.34 (s, 1H), 7.66 (m, 1H), 8.08 (dd, 1H), 8.27 (s, 1H), 8.53-8.55 (d, 2H), 8.75 (s, 1H), 10.21 (s, 1H). m/z: ESI MH⁺ 572.4 |
| 194 | 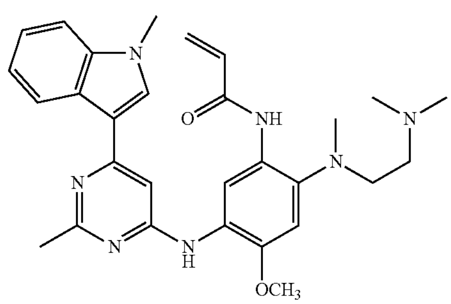 [SMILES: C=CC(=O)Nc1cc(Nc2cc(-c3cn(C)c4ccccc34)nc(C)n2)c(OC)cc1N(C)CCN(C)C] | N-(2-((2-(dimethylamino)-ethyl)-methyl-amino)-4-methoxyl-5-(2-methyl-6-(1-methyl-1H-indol-3-yl)-pyrimidin-4-yl-amino)-phenyl)-acrylamide | ¹H-NMR (DMSO-d₆) δ: 2.22 (s, 6H), 2.33 (t, 2H), 2.47 (s, 3H), 2.72 (s, 3H), 2.89 (t, 2H), 3.85 (s, 3H), 3.86 (s, 3H), 5.76 (m, 1H), 6.26 (dd, 1H), 6.42 (dd, 1H), 7.02 (s, 1H), 7.09 (s, 1H), 7.17 (t, 1H), 7.25 (t, 1H), 7.51 (d, 1H), 8.12 (s, 1H), 8.28 (d, 1H), 8.48 (s, 1H), 8.89 (s, 1H), 10.15 (s, 1H). m/z: ESI MH⁺ 514.2 |
| 195 | 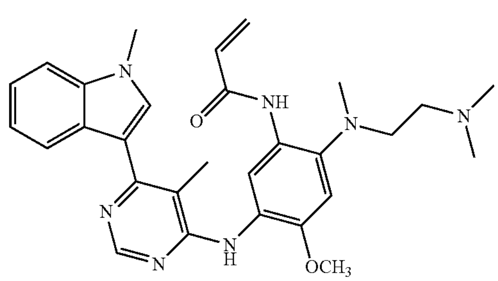 [SMILES: C=CC(=O)Nc1cc(Nc2ncnc(-c3cn(C)c4ccccc34)c2C)c(OC)cc1N(C)CCN(C)C] | N-(5-(5-methyl-6-(1-methyl-1H-indol-3-yl)-pyrimidin-4-ylamino)-4-methoxyl-2-((2-dimethylamino-ethyl)-methyl-amino)-phenyl)-acrylamide | ¹H-NMR (DMSO-d₆) δ: 2.25 (s, 6H), 2.35 (s, 3H), 2.38 (t, 2H), 2.72 (s, 3H), 2.91 (t, 2H), 3.82 (s, 3H), 3.90 (s, 3H), 5.76 (m, 1H), 6.24 (dd, 1H), 6.42 (dd, 1H), 7.02 (s, 1H), 7.13 (t, 1H), 7.24 (t, 1H), 7.51 (d, 1H), 7.80 (s, 1H), 7.85 (s, 1H), 8.02 (d, 1H), 8.41 (s, 1H), 8.56 (s, 1H), 10.08 (s, 1H). m/z: ESI MH⁺ 514.2 |

TABLE 7-continued

| Comp. | Structure | Name | Data |
|---|---|---|---|
| 196 | 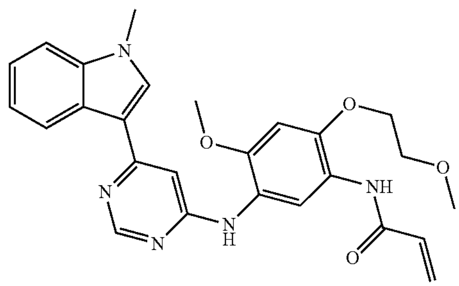 [SMILES: C=CC(=O)Nc1cc(Nc2cc(-c3cn(C)c4ccccc34)ncn2)c(OC)cc1OCCOC] | N-(4-methoxyl-2-(2-methoxyl-ethoxyl)-5-(6-(1-methyl-1H-indol-3-yl)-pyrimidin-4-ylamino)-phenyl)-acrylamide | $^1$H-NMR (DMSO-d$_6$) δ: 3.35 (s, 3H), 3.72 (t, 2H), 3.86 (s, 3H), 3.87 (s, 3H), 4.23 (t, 2H), 5.73 (dd, 1H), 6.23 (dd, 1H), 6.60 (dd, 1H), 6.90 (s, 1H), 7.17-7.22 (m, 2H), 7.24-7.28 (m, 1H), 7.53 (d, 1H), 8.13 (s, 1H), 8.27 (d, 1H), 8.33 (s, 1H), 8.49 (s, 1H), 8.62 (s, 1H), 9.23 (s, 1H). m/z: ESI MH$^+$ 474.2 |
| 197 | 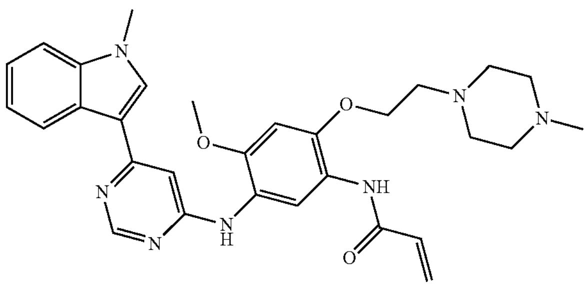 [SMILES: C=CC(=O)Nc1cc(Nc2cc(-c3cn(C)c4ccccc34)ncn2)c(OC)cc1OCCN1CCN(C)CC1] | N-(5-(6-(1-methyl-1H-indol-3-yl)-pyrimidin-4-ylamino)-4-methoxy-2-(2-(4-methylpiperazin-1-yl)-ethoxyl)-phenyl)-acrylamide | $^1$H-NMR (DMSO-d$_6$) δ: 2.21 (s, 3H), 2.22 (m, 4H), 2.41 (m, 4H), 2.74 (m, 2H), 3.87 (s, 6H), 4.21 (t, 2H), 5.75 (dd, 1H), 6.22 (dd, 1H), 6.60 (dd, 1H), 6.90 (s, 1H), 7.17-7.28 (m, 3H), 7.53 (d, 1H), 8.12 (s, 1H), 8.25-8.30 (m, 2H), 8.48 (s, 1H), 8.60 (s, 1H), 9.26 (s, 1H). m/z: ESI MH$^+$ 541.9 |
| 198 | 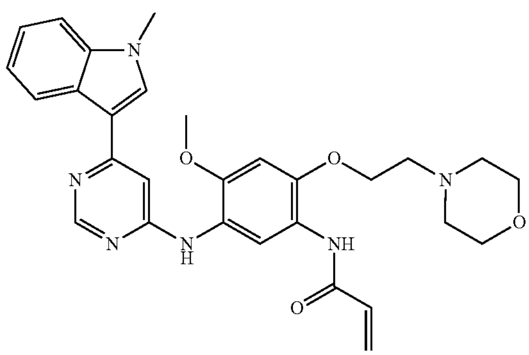 [SMILES: C=CC(=O)Nc1cc(Nc2cc(-c3cn(C)c4ccccc34)ncn2)c(OC)cc1OCCN1CCOCC1] | N-(5-(6-(1-methyl-1H-indol-3-yl)-pyrimidin-4-ylamino)-4-methoxy-2-(2-(morpholin-4-yl)-ethoxyl)-phenyl)-acrylamide | $^1$H-NMR (DMSO-d$_6$) δ: 2.51 (m, 4H), 2.73 (m, 2H), 3.59 (m, 4H), 3.87 (s, 3H), 3.88 (s, 3H), 4.23 (m, 2H), 5.74 (dd, 1H), 6.23 (dd, 1H), 6.59 (dd, 1H), 6.91 (s, 1H), 7.17-7.22 (m, 2H), 7.24-7.28 (m, 1H), 7.53 (d, 1H), 8.12 (s, 1H), 8.25-8.30 (m, 2H), 8.48 (d, 1H), 8.60 (s, 1H), 9.26 (s, 1H). m/z: ESI MH$^+$ 528.9 |
| 199 | 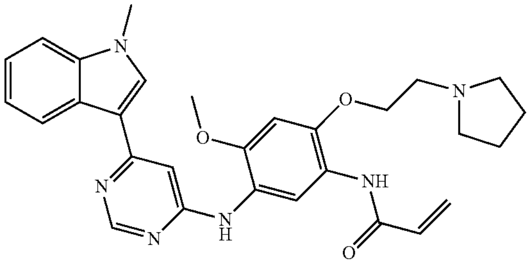 [SMILES: C=CC(=O)Nc1cc(Nc2cc(-c3cn(C)c4ccccc34)ncn2)c(OC)cc1OCCN1CCCC1] | N-(5-(6-(1-methyl-1H-indol-3-yl)-pyrimidin-4-ylamino)-4-methoxy-2-(2-(pyrrolidin-1-yl)-ethoxyl)-phenyl)-acrylamide | $^1$H-NMR (DMSO-d$_6$) δ: 1.84 (m, 4H), 2.51 (m, 4H), 2.86 (m, 2H), 3.87 (s, 3H), 3.88 (s, 3H), 4.29 (m, 2H), 5.73 (dd, 1H), 6.24 (dd, 1H), 6.67 (dd, 1H), 6.92 (s, 1H), 7.20-7.22 (m, 2H), 7.26 (m, 1H), 7.53 (d, 1H), 8.13 (s, 1H), 8.27 (d, 1H), 8.38 (s, 1H), 8.49 (s, 1H), 8.62 (s, 1H), 9.66 (s, 1H). m/z: ESI MH$^+$ 513.3 |

Example 15

Preparation of N-(5-(4-((3-chloro-4-(pyridin-2-yl-methoxyl)phenyl)-methyl-amino)-pyrimidin-2-ylamino)-2-((2-(dimethylamino)ethyl)(methyl)amino)-4-methoxyl-phenyl)-acrylamide (Compound 200)

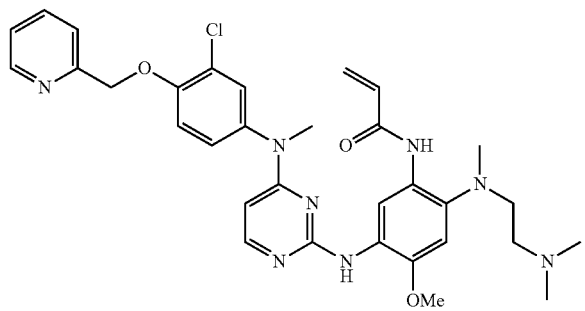 [SMILES: C=CC(=O)Nc1cc(Nc2nccc(N(C)c3ccc(OCc4ccccn4)c(Cl)c3)n2)c(OC)cc1N(C)CCN(C)C]

Compound 200

Step 1: Synthesis of 4-(3-chloro-4-(pyridin-2-yl-methoxyl) phenyl amino)-2-chloropyridine Step 1 is the same as that of Example 1.

Step 2: Synthesis of 4-((3-chloro-4-(pyridin-2-methoxyl) phenyl)-methyl-amino)-2-chloro-pyrimidine 4-(3-Chloro-4-(pyridin-2-ylmethoxyl) phenyl amino)-2-chloropyrimidine (0.7 g, 2 mmol), potassium carbonate (0.41 g, 3 mmol) and methyl iodide (0.34 g, 2.4 mmol) were added to 4 mL of DMF and then stirred for 36 h. The reaction mixture was added with water and ethyl acetate. The ethyl acetate layer was dried and then concentrated. The residues were purified by column chromatography to give 4-((3-chloro-4-(pyridin-2-methoxyl)phenyl)-methyl-amino)-2-chloropyrimidine (0.5 g). m/z: ESI MH+ 361.1.

Steps 3~5 of Example 3 were repeated to give the title compound.

Compound 200 in Table 8 was prepared following the method in Example 15.

Compound 201 in Table 8 was prepared following the method in Example 2.

TABLE 8

| | Structure | Name | $^1$H-NMR |
|---|---|---|---|
| 200 | 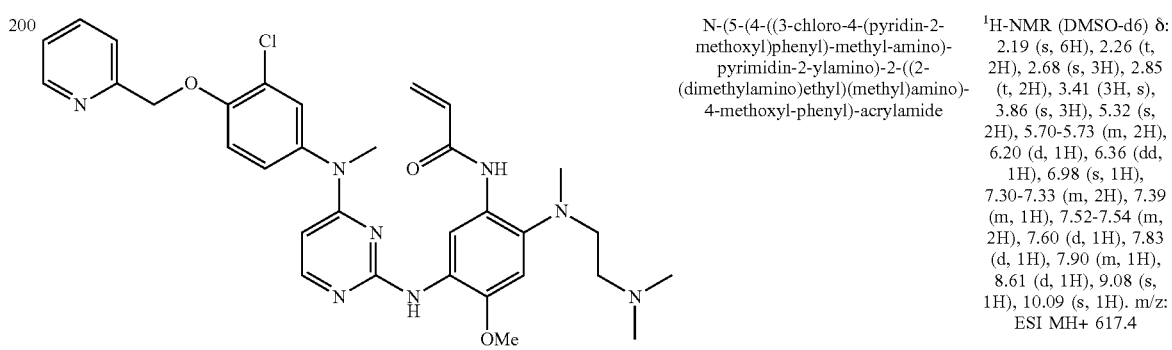 | N-(5-(4-((3-chloro-4-(pyridin-2-methoxyl)phenyl)-methyl-amino)-pyrimidin-2-ylamino)-2-((2-(dimethylamino)ethyl)(methyl)amino)-4-methoxyl-phenyl)-acrylamide | $^1$H-NMR (DMSO-d6) δ: 2.19 (s, 6H), 2.26 (t, 2H), 2.68 (s, 3H), 2.85 (t, 2H), 3.41 (3H, s), 3.86 (s, 3H), 5.32 (s, 2H), 5.70-5.73 (m, 2H), 6.20 (d, 1H), 6.36 (dd, 1H), 6.98 (s, 1H), 7.30-7.33 (m, 2H), 7.39 (m, 1H), 7.52-7.54 (m, 2H), 7.60 (d, 1H), 7.83 (d, 1H), 7.90 (m, 1H), 8.61 (d, 1H), 9.08 (s, 1H), 10.09 (s, 1H). m/z: ESI MH+ 617.4 |
| 201 | 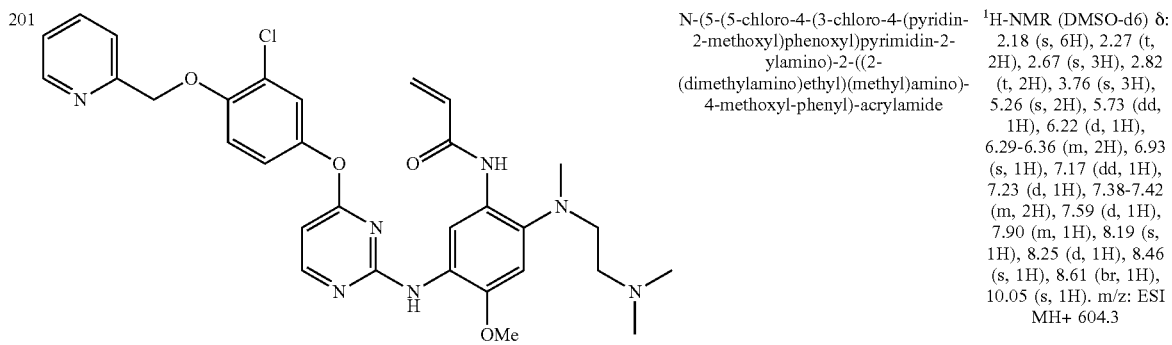 | N-(5-(5-chloro-4-(3-chloro-4-(pyridin-2-methoxyl)phenoxyl)pyrimidin-2-ylamino)-2-((2-(dimethylamino)ethyl)(methyl)amino)-4-methoxyl-phenyl)-acrylamide | $^1$H-NMR (DMSO-d6) δ: 2.18 (s, 6H), 2.27 (t, 2H), 2.67 (s, 3H), 2.82 (t, 2H), 3.76 (s, 3H), 5.26 (s, 2H), 5.73 (dd, 1H), 6.22 (d, 1H), 6.29-6.36 (m, 2H), 6.93 (s, 1H), 7.17 (dd, 1H), 7.23 (d, 1H), 7.38-7.42 (m, 2H), 7.59 (d, 1H), 7.90 (m, 1H), 8.19 (s, 1H), 8.25 (d, 1H), 8.46 (s, 1H), 8.61 (br, 1H), 10.05 (s, 1H). m/z: ESI MH+ 604.3 |

Example 16

Preparation of N-(5-(4-(4-methoxyl-1H-indol-1-yl)-5-trifluoromethyl pyrimidin-2-ylamino)-2-(2-(dimethylamino-ethyl)-methyl-amino)-4-methoxyl-phenyl)-acrylamide (Compound 202)

Compound 202

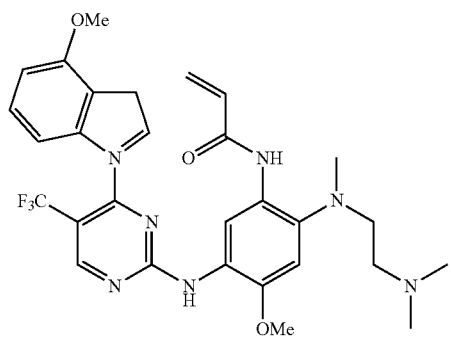 [SMILES: C=CC(=O)Nc1cc(Nc2ncc(C(F)(F)F)c(-n3ccc4c(OC)cccc43)n2)c(OC)cc1N(C)CCN(C)C]

Step 1: Synthesis of 4-chloro-2-(4-nitrophenoxyl)-5-trifluoromethyl pyrimidine

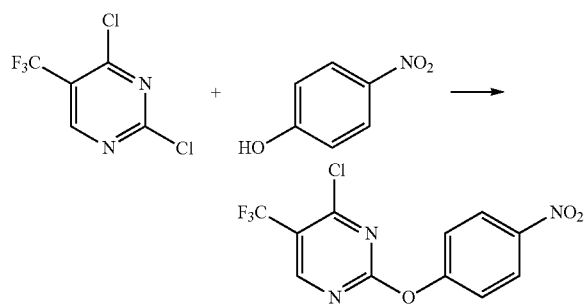

4-Nitrophenol (1.39 g, 10 mmol) and N-methyl morpholine (1.0 g, 10 mmol) were dissolved in 15 mL of isopropyl alcohol and then cooled under ice-salt bath and added with 2,4-dichloro-5-trifluoromethyl pyrimidine (2.17 g, 10 mmol). After stirring for 1 h, the reaction mixture was added with 35 mL of water and then filtered to give the crude product (3 g).

Step 2: Synthesis of 4-(4-methoxyl-1H-indol-1-yl)-2-(4-nitro phenoxyl)-5-trifluoromethyl pyrimidine

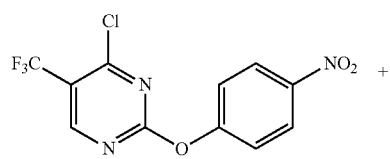

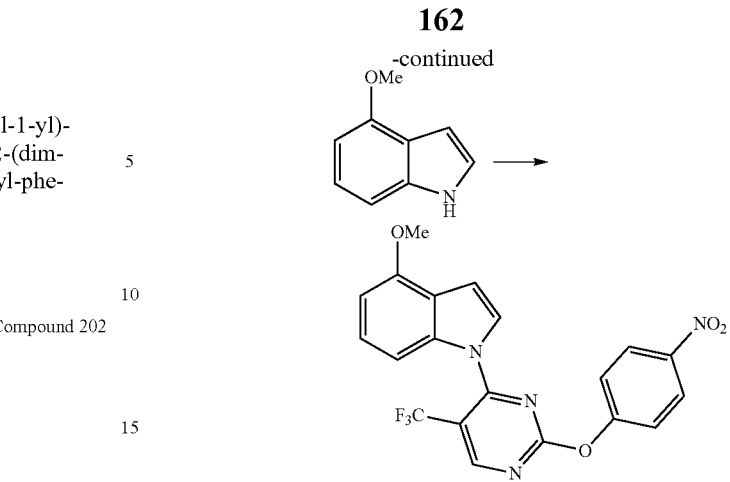

4-Chloro-2-(4-nitrophenoxyl)-5-trifluoromethyl pyrimidine (2.0 g, 6.25 mmol), 4-methoxyl-1H-indole (0.92 g, 6.25 mmol) and cesium carbonate (4.0 g, 12.5 mmol) were added to 8 mL of DMF and then stirred for 6 h. The reaction mixture was added with water and ethyl acetate. The ethyl acetate layer was dried and concentrated. The residues were purified by column chromatography to give the title intermediate (1.5 g). m/z: ESI MH+ 431.1.

Step 3: $N^4$-(2-dimethylaminoethyl)-2-methoxyl-N-(4-(4-methoxyl-indol-1-yl)-5-trifluoromethyl-pyrimidin-2-yl)-$N^4$-methyl-5-nitro-phenyl-1,4-diamine 4-(4-Methoxyl-1H-indol-1-yl)-2-(4-nitro phenoxyl-5-trifluoromethyl pyrimidine (0.86 g, 2 mmol) and $N^4$-(2-dimethylaminoethyl)-2-methoxyl-$N^4$-methyl-5-nitro-phenyl-1,4-diamine (0.54 g, 2 mmol) were added to 5 mL of DMF and then added with sodium hydride (240 mg, 6 mmol). The mixture was stirred for 3 h and then added with water and ethyl acetate. The organic layer was dried and then concentrated. The residues were purified by column chromatography to give the title intermediate in the (0.32 g). m/z: ESI MH+ 560.3.

Steps 4 and 5 are the same as that of Example 6 to give the title compound.

Example 17

Preparation of N-(5-(4-(4-methoxyl-1H-indol-1-yl)-5-chloro pyrimidin-2-ylamino)-2-(2-(dimethyl-amino-ethyl)-methyl-amino)-4-methoxyl-phenyl)-acrylamide (Compound 203)

Compound 203

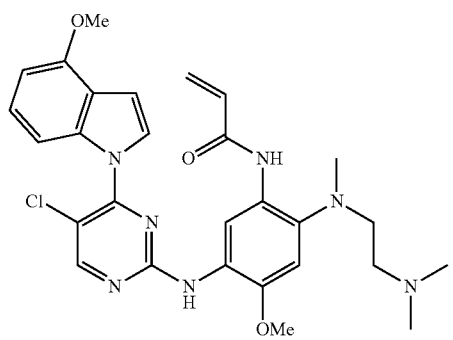

Step 1: Preparation of 1-(2,5-dichloropyrimidin-4-yl)-6-methoxyl-1H-indole

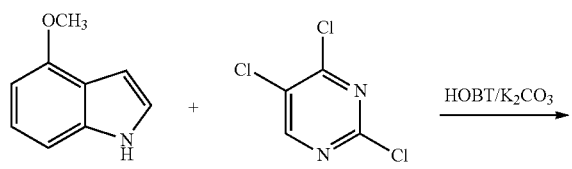

Step 1 is as same as that of Example 6 except for replacing 2,4-dichloro pyrimidine with 2,4,5-trichloropyrimidine.

Step 2: Preparation of (4-fluoro-2-methoxyl-5-nitro-phenyl)-(4-(4-methoxyl-indol-1-yl)-5-chloropyrimidin-2-yl)-amine benzenesulphonate

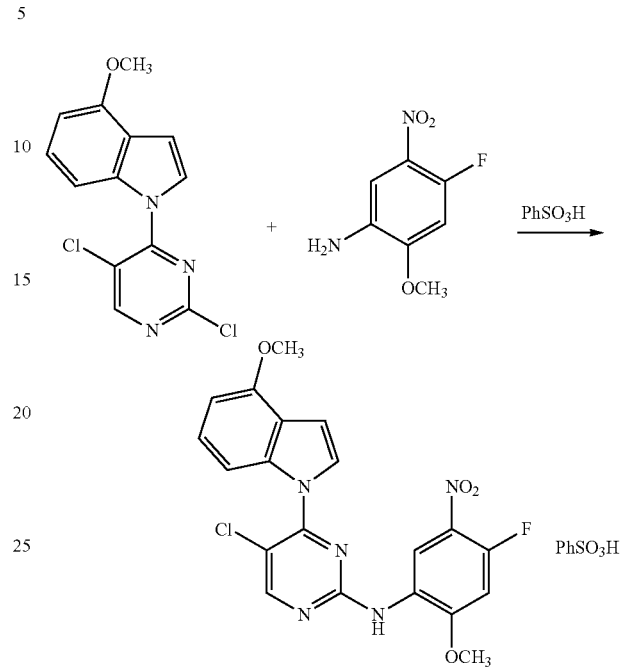

1-(2, 5-Dichloro pyrimidin-4-yl)-6-methoxyl-1H-indole (1 g, 3.4 mmol), 2-methoxyl-4-fluoro-5-nitroaniline (0.64 g, 3.4 mmol) and benzenesulfonic acid (0.65 g, 4.1 mmol) were added to 15 mL of chlorobenzene and then heated at 130° C. for 20 h. The reaction mixture was cooled to room temperature and then added with 15 mL of petroleum ether and filtered. The solid was dried to give get the crude intermediate (1.5 g). m/z: ESI MH+ 444.2.

Steps 3~5 of Example 6 were repeated to give the title compound.

Example 18

Preparation of N-(5-(4-(4-hydroxyl-1H-indol-1-yl)-pyrimidin-2-yl amino)-2-(2-(dimethylamino-ethyl)-methyl-amino)-4-methoxyl-phenyl)-acrylamide (Compound 204)

Compound 204

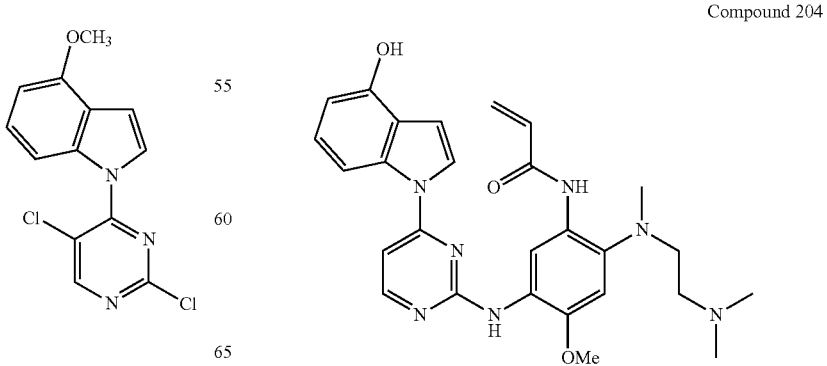

Steps 1~3: Preparation of N⁴-(2-dimethylamino-ethyl)-2-methoxyl-N-(4-(4-benzyloxy-indol-1-yl)-pyrimidin-2-yl)-N⁴-methyl-5-nitro-1,4-phenylenediamine

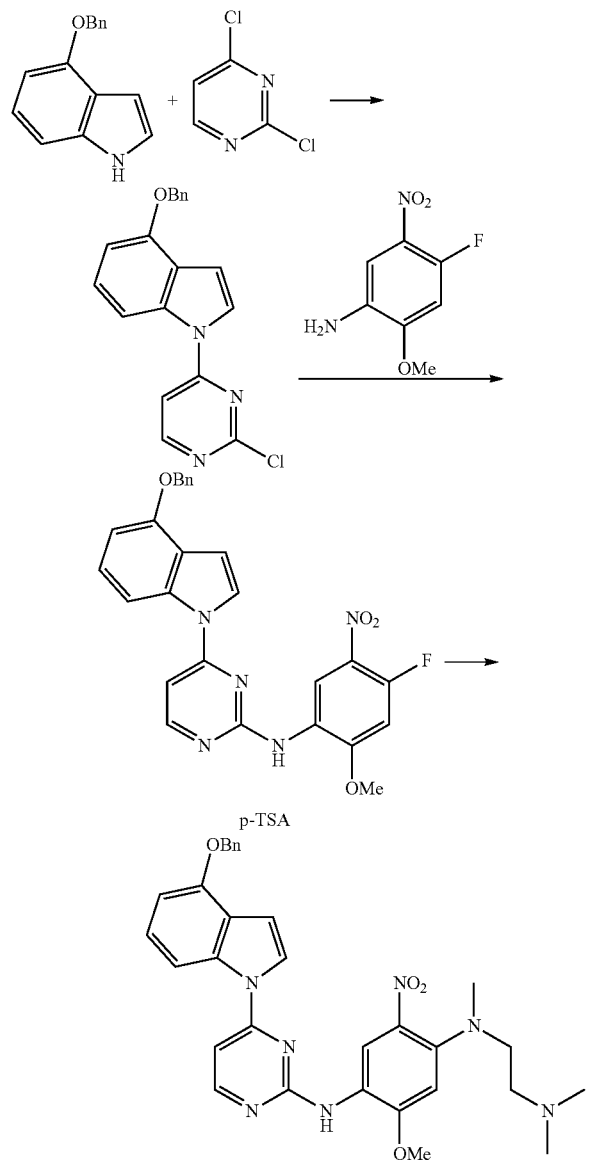

Steps 1~3 are the same as that of Example 6 except for replacing 4-methoxyl indole with 4-benzyloxy indole.

Step 4: Synthesis of 1-(2-(5-amino-4-((2-dimethyl-amino-ethyl)-methyl-amino)-2-methoxyl-phe-nylamino)-pyrimidin-4-yl)-1H-4-hydroxylindole

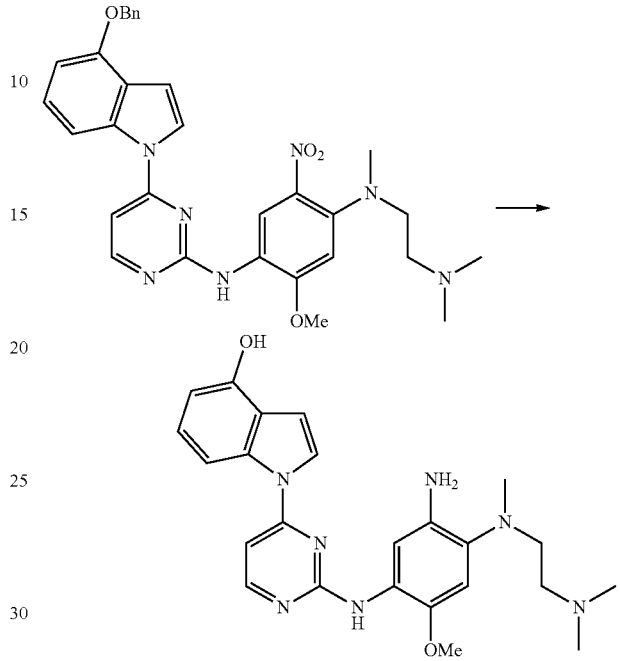

1-(2-(5-Amino-4-((2-dimethylamino-ethyl)-methyl-amino)-2-methoxyl-phenylamino)-pyrimidin-4-yl)-1H-4-benzyloxy indole (200 mg, 0.35 mmol) and palladium hydroxide (30 mg) were added to 5 mL of methanol and then stirred under hydrogen atmosphere over night. The palladium hydroxide was filtered out and the filtrate was concentrated to give the crude product which was directly used in the next step.

Step 5 of Example 6 was repeated to give the title compound.

Compound 202 in Table 9 was prepared following the method in Example 16.

Compound 203 in Table 9 was prepared following the method in Example 17.

Compound 204 in Table 9 was prepared following the method in Example 18.

Compounds 205-214 in Table 9 were be prepared following the method in Example 6.

TABLE 9

| 202 | 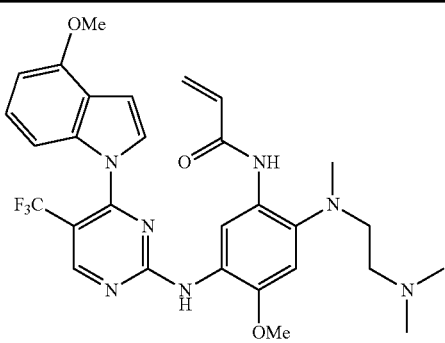 | N-(5-(4-(4-methoxyl-1H-indol-1-yl)-5-trifluoromethyl-pyrimidin-2-ylamino)-2-(2-(dimethylamino-ethyl)-methyl-amino)-4-methoxyl-phenyl)-acrylamide | 1H-NMR (DMSO-d6) δ: 2.20-2.80 (9H, br), 3.05-3.40 (4H, br), 3.74 (3H, s), 3.86 (3H, s), 5.72 (1H, dd), 6.22 (1H, dd), 6.67-6.69 (2H, m), 6.94 (1H, br), 7.10 (1H, s), 7.59 (1H, d), 8.09 (1H, d), 8.31 (1H, s), 8.65 (1H, s), 8.93 (1H, s), 10.05 (1H, s), 10.90 (1H, br). m/z: ESI MH+ 583.3 |

TABLE 9-continued

| 203 | 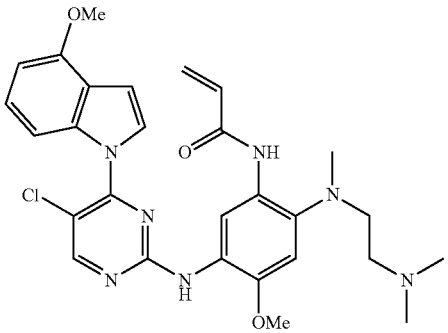 [SMILES: C=CC(=O)Nc1cc(Nc2ncc(Cl)c(-n3ccc4c(OC)cccc43)n2)c(OC)cc1N(C)CCN(C)C] | N-(5-(4-(4-methoxyl-1H-indol-1-yl)-5-chloro-pyrimidin-2-ylamino)-2-(2-(dimethylamino-ethyl)-methyl-amino)-4-methoxyl-phenyl)-acrylamide | $^1$H-NMR (DMSO-d$_6$) δ: 2.19 (6H, s), 2.30 (2H, t), 2.70 (3H, 3), 2.84 (2H, t), 3.79 (3H, s), 3.88 (3H, s), 5.76 (1H, dd), 6.24 (1H, dd), 6.40 (1H, dd), 6.66 (1H, d), 6.70 (1H, d), 7.00 (1H, s), 7.06 (1H, t), 7.32 (1H, d), 7.72 (1H, d), 8.42 (1H, s), 8.62 (1H, s), 9.01 (1H, s), 10.07 (1H, br). m/z: ESI MH+ 550.2 |
| --- | --- | --- | --- |
| 204 | 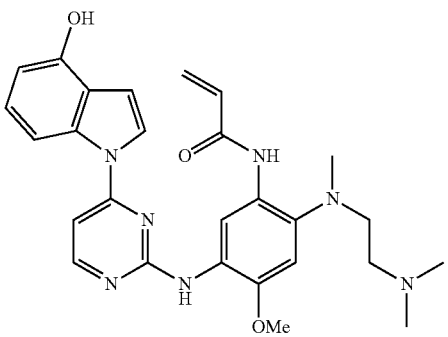 [SMILES: C=CC(=O)Nc1cc(Nc2nccc(-n3ccc4c(O)cccc43)n2)c(OC)cc1N(C)CCN(C)C] | N-(5-(4-(4-hydroxyl-1H-indol-1-yl)-5-chloro-pyrimidin-2-ylamino)-2-(2-(dimethylamino-ethyl)-methyl-amino)-4-methoxyl-phenyl)-acrylamide | $^1$H-NMR (DMSO-d6) δ: 2.23 (6H, s), 2.34 (2H, t), 2.75 (3H, s), 2.92 (2H, t), 3.78 (3H, s), 5.75 (1H, dd), 6.22 (1H, dd), 6.40 (1H, dd), 6.53 (1H, d), 6.80 (1H, d), 6.90 (1H, t), 7.05 (1H, s), 7.10 (1H, d), 7.83 (1H, d), 7.98 (1H, d), 8.38 (1H, d), 8.55 (1H, s), 8.58 (1H, s), 9.64 (1H, s), 10.11 (1H, s). m/z: ESI MH+ 502.3 |
| 205 | 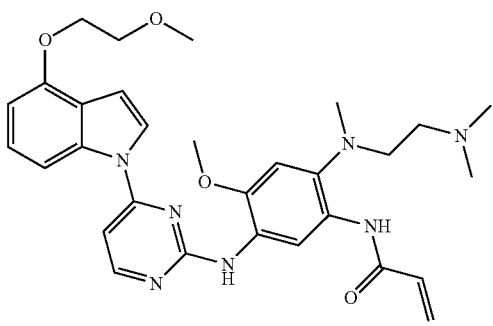 [SMILES: C=CC(=O)Nc1cc(Nc2nccc(-n3ccc4c(OCCOC)cccc43)n2)c(OC)cc1N(C)CCN(C)C] | N-(5-(4-(4-(2-methoxyl-ethoxyl)-1H-indol-1-yl)-pyrimidin-2-ylamino)-2-(2-(dimethylamino-ethyl)-methyl-amino)-4-methoxyl-phenyl)-acrylamide | $^1$H-NMR (DMSO-d6): 2.22 (6H, s), 2.34 (2H, t), 2.75 (3H, s), 2.91 (2H, t), 3.35 (3H, s), 3.74 (2H, t), 3.77 (3H, s), 4.22 (2H, t), 5.73 (1H, dd), 6.23 (1H, dd), 6.41 (1H, dd), 6.73 (2H, m), 7.03 (2H, m), 7.11 (1H, d), 7.98 (1H, d), 8.03 (1H, d), 8.39 (1H, d), 8.55 (1H, s), 8.63 (1H, s), 10.13 (1H, s); m/z: ES+ MH+ 560.2 |
| 206 | 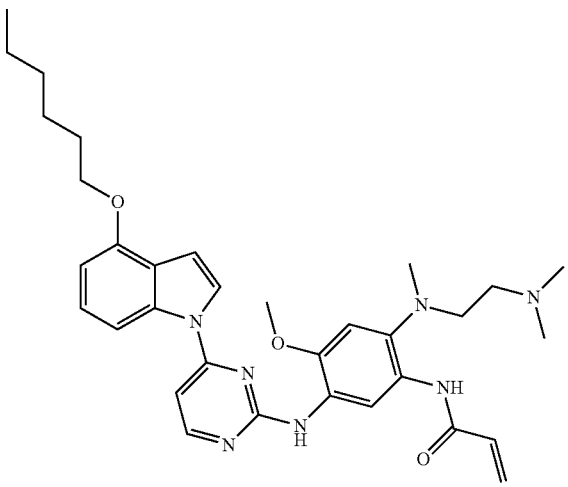 [SMILES: C=CC(=O)Nc1cc(Nc2nccc(-n3ccc4c(OCCCCCC)cccc43)n2)c(OC)cc1N(C)CCN(C)C] | N-(5-(4-(4-n-hexyloxy-1H-indol-1-yl)-pyrimidin-2-ylamino)-2-(2-(dimethylamino-ethyl)-methyl-amino)-4-methoxyl-phenyl)-acrylamide | $^1$H-NMR (DMSO-d6): 0.88 (3H, t), 1.33 (4H, m), 1.46 (2H, m), 1.78 (2H, m), 2.30 (6H, s), 2.97 (2H, br), 3.73 (3H, s), 3.78 (3H, s), 4.08 (2H, t), 5.73 (1H, dd), 6.24 (1H, dd), 6.46 (1H, br), 6.68 (1H, d), 6.73 (1H, d), 7.02 (2H, m), 7.11 (1H, d), 7.97 (1H, d), 8.02 (1H, d), 8.39 (1H, d), 8.50 (1H, s), 8.61 (1H, s), 10.06 (1H, s) ; m/z: ES+ MH+ 586.3 |

TABLE 9-continued

| 207 | 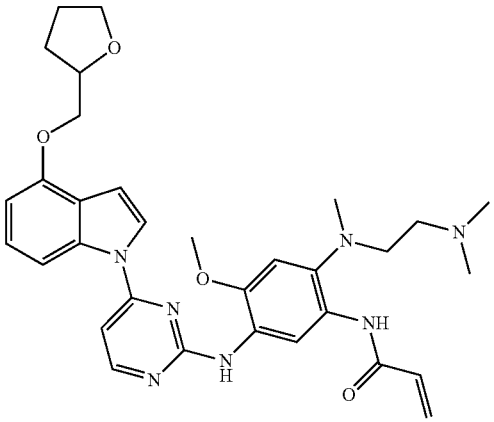 [SMILES: C=CC(=O)Nc1cc(Nc2nccc(-n3ccc4c(OCC5CCCO5)cccc43)n2)c(OC)cc1N(C)CCN(C)C] | N-(5-(4-(4-((tetrahydrofuran-2-yl)-methoxyl)-1H-indol-1-yl)-pyrimidin-2-ylamino)-2-(2-(dimethylamino-ethyl)-methyl-amino)-4-methoxyl-phenyl)-acrylamide | ¹H-NMR (DMSO-d6) hydrochloride: 2.09-1.73 (4H, br), 2.63 (3H, s), 2.76 (6H, d), 3.32 (4H, m), 3.71 (1H, m), 3.82 (4H, m), 4.07 (2H, m), 4.24 (1H, m), 5.71 (1H, dd), 6.23 (1H, dd), 6.72 (2H, m), 6.98 (1H, s), 7.08 (2H, m), 7.14 (1H, t), 8.03 (2H, d), 8.32 (1H, s), 8.40 (1H, d), 8.64 (1H, s), 9.79 (1H, s), 10.29 (1H, s); m/z: ES+ MH+ 586.3 |
| --- | --- | --- | --- |
| 208 | 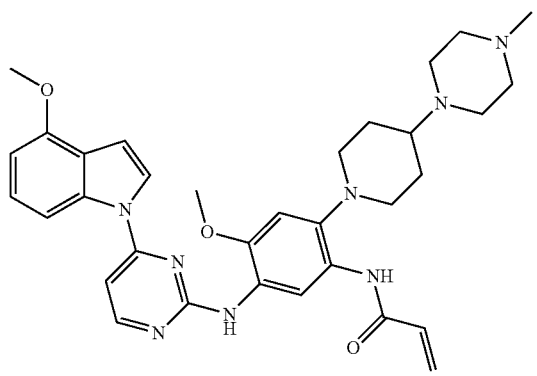 [SMILES: C=CC(=O)Nc1cc(Nc2nccc(-n3ccc4c(OC)cccc43)n2)c(OC)cc1N1CCC(N2CCN(C)CC2)CC1] | N-(5-(4-(4-methoxyl-1H-indol-1-yl)-pyrimidin-2-ylamino)-2-(4-(4-methyl-piperazin-1-yl)-piperidin-1-yl)-4-methoxyl-phenyl)-acrylamide | ¹H-NMR (DMSO-d6): 1.73 (2H, t), 1.88 (2H, t), 2.16 (3H, s), 2.34 (5H, m), 2.54 (4H, m), 2.71 (2H, t), 3.08 (2H, t), 3.77 (3H, s), 3.89 (3H, s), 5.72 (1H, d), 6.20 (1H, d), 6.69 (2H, m), 6.75 (1H, d), 6.88 (1H, s), 7.06 (1H, t), 7.11 (1H, d), 8.01 (2H, m), 8.25 (1H, s), 8.38 (1H, d), 8.61 (1H, s), 9.02 (1H, s); m/z: ESI+ MH+ 597.3 |
| 209 | 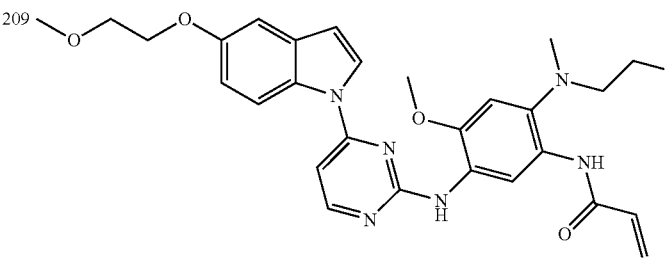 | N-(5-(4-(5-(2-methoxyl-ethoxyl)-1H-indol-1-yl)-pyrimidin-2-ylamino)-2-(2-(dimethylamino-ethyl)-methyl-amino)-4-methoxyl-phenyl)-acrylamide | ¹H-NMR (DMSO-d6): 2.22 (6H, s), 2.36 (2H, t), 2.76 (3H, s), 2.91 (2H, t), 3.32 (3H, s), 3.67 (2H, t), 3.77 (3H, s), 4.08 (2H, t), 5.72 (1H, d), 6.19 (1H, d), 6.41 (1H, m), 6.68 (2H, d), 7.08 (3H, m), 8.10 (1H, d), 8.33 (2H, m), 8.50 (1H, s), 8.66 (1H, s), 10.12 (1H, s). m/z: ES+ MH+ 560.3 |
| 210 | 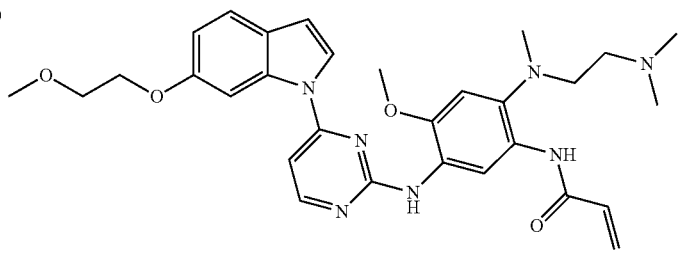 | N-(5-(4-(6-(2-methoxyl-ethoxyl)-1H-indol-1-yl)-pyrimidin-2-ylamino)-2-(2-(dimethylamino-ethyl)-methyl-amino)-4-methoxyl-phenyl)-acrylamide | ¹H-NMR (DMSO-d6): 2.21 (6H, s), 2.33 (2H, t), 2.73 (3H, s), 2.87 (2H, t), 3.33 (3H, s), 3.66 (2H, t), 3.80 (3H, s), 4.04 (2H, t), 5.73 (1H, dd), 6.22 (1H, d), 6.36 (1H, m), 6.70 (1H, d), 6.86 (1H, d), 7.02 (1H, s), 7.11 (1H, d), 7.48 (1H, d), 8.01 (1H, d), 8.07 (1H, s), 8.38 (1H, d), 8.59 (2H, d), 10.09 (1H, s). m/z: ES+ MH+ 560.3 |

TABLE 9-continued

| | | | |
|---|---|---|---|
| 211 | 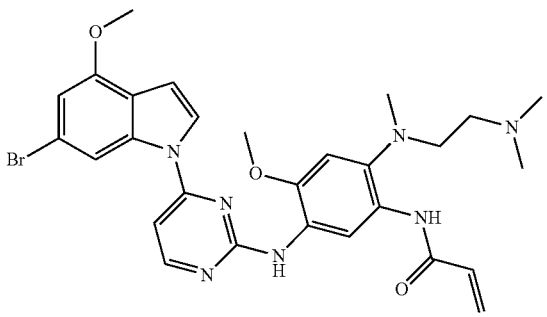 [SMILES: C=CC(=O)Nc1cc(Nc2nccc(-n3ccc4c(OC)cc(Br)cc43)n2)c(OC)cc1N(C)CCN(C)C] | N-(5-(4-(4-methoxyl-6-bromo-1H-indol-1-yl)-pyrimidin-2-ylamino)-2-(2-(dimethylamino-ethyl)-methyl-amino)-4-methoxyl-phenyl)-acrylamide | ¹HNMR (CDCl3): 2.62 (6H, s), 2.75 (3H, s), 2.85 (2H, br), 3.18 (2H, br), 3.93 (3H, s), 3.96 (3H, s), 5.74 (1H, d), 6.47 (1H, d), 6.78 (2H, d), 6.81 (1H, d), 6.90 (1H, d), 7.64 (1H, s), 7.98 (1H, s), 8.04 (1H, s), 8.51 (1H, d), 9.46 (1H, s), 9.60 (1H, s). m/z: ES+ MH+ 593.2 |
| 212 | 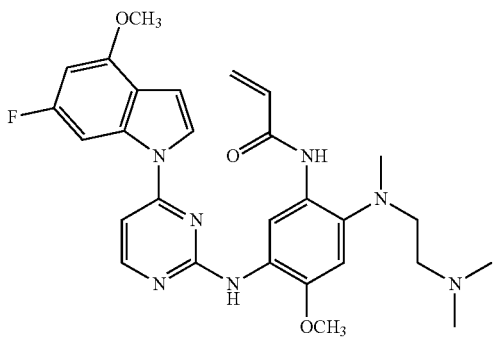 [SMILES: C=CC(=O)Nc1cc(Nc2nccc(-n3ccc4c(OC)cc(F)cc43)n2)c(OC)cc1N(C)CCN(C)C] | N-(5-(4-(4-methoxyl-6-fluoro-1H-indol-1-yl)-pyrimidin-2-ylamino)-2-(2-(dimethylamino-ethyl)-methyl-amino)-4-methoxyl-phenyl)-acrylamide | ¹H-NMR (CDCl3): 2.36-2.48 (8H, m), 2.74 (3H, s), 2.97 (2H, t), 3.91 (3H, s), 3.94 (3H, s), 5.68-5.71 (1H, m), 6.40-6.48 (3H, m), 6.79-6.85 (3H, m), 7.57 (1H, s), 7.70 (1H, d), 7.87 (1H, d), 8.49 (1H, d), 9.49 (1H, s), 10.04 (1H, br). m/z: ES+ MH+ 534.2 |
| 213 | 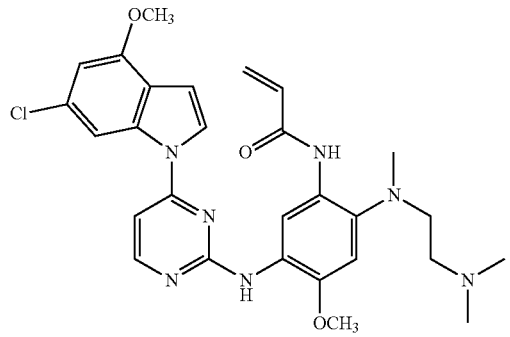 [SMILES: C=CC(=O)Nc1cc(Nc2nccc(-n3ccc4c(OC)cc(Cl)cc43)n2)c(OC)cc1N(C)CCN(C)C] | N-(5-(4-(4-methoxyl-6-chloro-1H-indol-1-yl)-pyrimidin-2-ylamino)-2-(2-(dimethylamino-ethyl-methyl-amino)-4-methoxyl-phenyl)-acrylamide | ¹H-NMR (CDCl3): 2.33-2.45 (8H, m), 2.74 (3H, s), 2.95 (2H, t), 3.92 (3H, s), 3.96 (3H, s), 5.68-5.72 (1H, m), 6.40-6.48 (2H, m), 6.66 (1H, d), 6.81-6.83 (2H, m), 6.89 (1H, d), 7.63 (1H, s), 7.92 (1H, s), 8.02 (1H, s), 8.52 (1H, d), 9.56 (1H, s), 10.03 (1H, br). m/z: ES+ MH+ 549.8 |
| 214 | 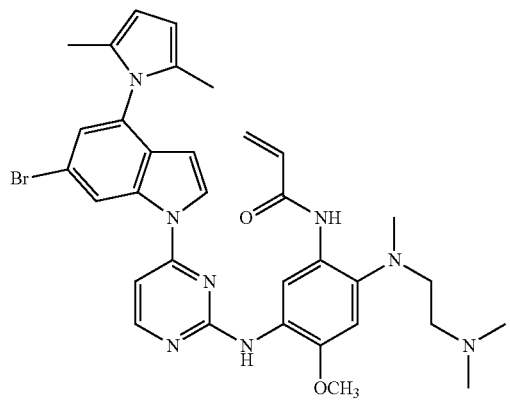 [SMILES: C=CC(=O)Nc1cc(Nc2nccc(-n3ccc4c(-n5c(C)ccc5C)cc(Br)cc43)n2)c(OC)cc1N(C)CCN(C)C] | N-(5-(4-(4-(2,5-dimethylpyrrol-1-yl)-6-bromo-1H-indol-1-yl)-pyrimidin-2-ylamino)-2-(2-(dimethylamino-ethyl-methyl-amino)-4-methoxyl-phenyl)-acrylamide | ¹H-NMR (DMSO-d₆): 9.52 (1H, s), 8.56 (1H, d), 8.51 (1H, br), 8.08 (1H, br), 7.66 (1H, s), 7.24 (1H, d), 6.90 (1H, d), 6.81 (1H, s), 6.38 (2H, m), 5.96 (2H, s), 5.68 (1H, dd), 3.94 (3H, s), 3.12 (2H, br), 2.76 (5H, br), 2.56 (6H, br), 2.00 (6H, s); m/z: ES⁺ MH⁺ 657.0 |

Compounds 215-238 in Table 10 were prepared following the method in Example 10.

Compounds 239-241 in Table 10 were prepared following the method in Example 12.

Compounds 242-248 in Table 10 were prepared by repeating the first two steps of Example 12 except for replacing dimethylamino ethanol with the corresponding alcohol.

Compound 249 in Table 10 was prepared by reference to the Examples 12 and 15.

TABLE 10

| | | | |
|---|---|---|---|
| 215 | 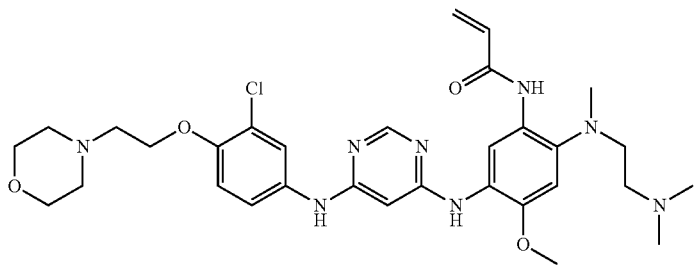 [SMILES: C=CC(=O)Nc1cc(Nc2cc(Nc3ccc(OCCN4CCOCC4)c(Cl)c3)ncn2)c(OC)cc1N(C)CCN(C)C] | N-(5-(6-(3-chloro-4-(2-morpholin-4-yl-ethoxyl)-phenylamino)-pyrimidin-4-ylamino)-2-((2-dimethylamino-ethyl)-methyl-amino)-4-methoxyphenyl)-acrylamide | ¹H-NMR (DMSO-d6) δ: 2.22 (6H, s), 2.34 (2H, br), 2.49 (4H, br), 2.69-2.74 (5H, m), 2.87 (2H, br), 3.58 (4H, t), 3.79 (3H, s), 4.11 (2H, t), 5.75 (1H, dd), 5.84 (1H, s), 6.23 (1H, dd), 6.37 (1H, dd), 7.00 (1H, s), 7.08 (1H, d), 7.35 (1H, dd), 7.72 (1H, d), 8.16 (1H, s), 8.29 (1H, s), 8.38 (1H, s), 9.01 (1H, s), 10.10 (1H, s). m/z: ESI MH+ 625.2 |
| 216 | 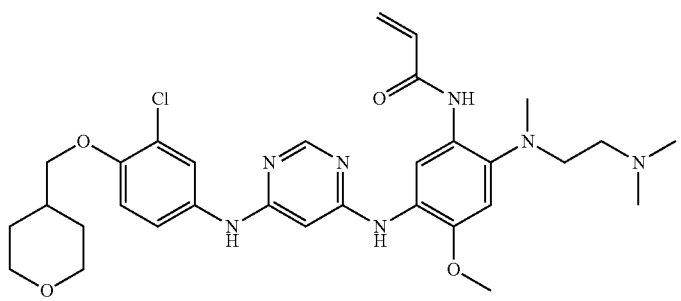 [SMILES: C=CC(=O)Nc1cc(Nc2cc(Nc3ccc(OCC4CCOCC4)c(Cl)c3)ncn2)c(OC)cc1N(C)CCN(C)C] | N-(5-(6-(3-chloro-4-(tetrahydropyran-4-yl-methoxyl)-phenylamino)-pyrimidin-4-ylamino)-2-((2-dimethylaminoethyl)-methyl-amino)-4-methoxyphenyl)-acrylamide | ¹H-NMR (DMSO-d6) δ: 1.34 (2H, m), 1.68 (2H, m), 2.00 (1H, m), 2.20 (6H, s), 2.31 (2H, t), 2.70 (3H, s), 2.85 (2H, t), 3.31 (2H, m), 3.78 (3H, s), 3.83-3.89 (4H, m), 5.73 (1H, dd), 5.82 (1H, s), 6.22 (1H, dd), 6.37 (1H, dd), 6.99 (1H, s), 7.04 (1H, d), 7.33 (1H, dd), 7.70 (1H, d), 8.14 (1H, s), 8.28 (1H, s), 8.38 (1H, s), 8.99 (1H, s), 10.09 (1H, s). m/z: ESI MH+ 610.2 |
| 217 | 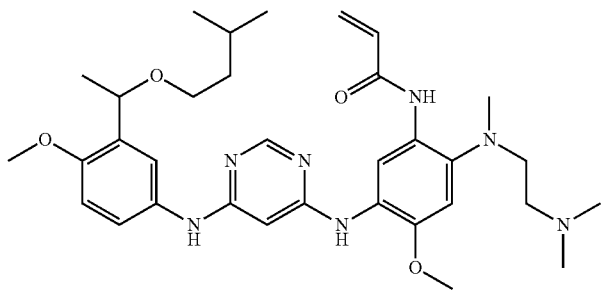 | N-(5-(6-(3-(1-(3-methylbutoxy)ethyl)-4-methoxylphenylamino)-pyrimidin-4-ylamino)-2-((2-methoxyphenyl)-methyl-amino)-4-methoxyl phenylamino)-acrylamide | ¹H-NMR (DMSO-d6) δ: 0.80-0.85 (6H, m), 1.24 (3H, d), 1.39 (2H, m), 1.67 (1H, m), 2.23 (6H, s), 2.33 (2H, br), 2.70 (3H, s), 2.87 (2H, br), 3.28 (2H, t), 3.75 (3H, s), 3.79 (3H, s), 4.68 (1H, q), 5.75 (1H, dd), 5.84 (1H, s), 6.23 (1H, dd), 6.41 (1H, dd), 6.89 (1H, d), 6.99 (1H, s), 7.33 (1H, m), 7.42 (1H, m), 8.09 (1H, s), 8.17 (1H, s), 8.39 (1H, s), 8.84 (1H, s), 10.07 (1H, s). m/z: ESI MH+ 606.3 |
| 218 | 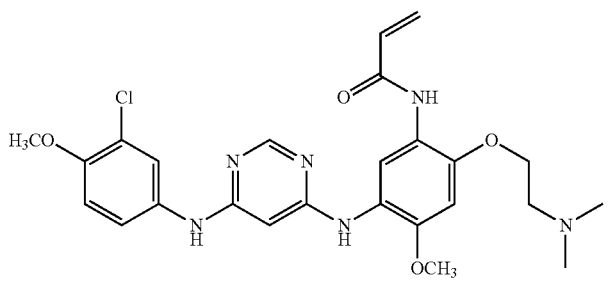 [SMILES: C=CC(=O)Nc1cc(Nc2cc(Nc3ccc(OC)c(Cl)c3)ncn2)c(OC)cc1OCCN(C)C] | N-(5-(6-(3-chloro-4-methoxyl-phenylamino)-pyrimidin-4-ylamino)-2-(2-dimethylamino-ethoxy)-4-methoxyl-phenyl)-acrylamide | ¹H-NMR (DMSO-d6) δ: 2.27 (6H, s), 2.61 (2H, br), 3.81 (3H, s), 4.19 (1H, br), 5.72-5.76 (2H, m), 6.22 (1H, dd), 6.48 (1H, dd), 6.92 (1H, s), 7.06 (1H, d), 7.35 (1H, dd), 7.74 (1H, d), 8.12 (1H, s), 8.15 (1H, s), 8.25 (1H, s), 8.97 (1H, s), 9.66 (1H, s). m/z: ESI MH+ 513.2 |
| 219 | 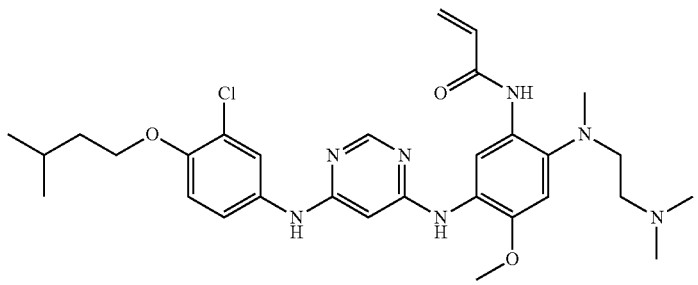 [SMILES: C=CC(=O)Nc1cc(Nc2cc(Nc3ccc(OCCC(C)C)c(Cl)c3)ncn2)c(OC)cc1N(C)CCN(C)C] | N-(5-(6-(3-chloro-4-(3-methylbutoxy)-phenylamino)-pyrimidin-4-ylamino)-2-((2-dimethylaminoethyl)-methyl-amino)-4-methoxyphenyl)-acrylamide | ¹H-NMR (DMSO-d6) δ: 0.94 (6H, d), 1.62 (2H, m), 1.80 (1H, m), 2.22 (6H, s), 2.34 (2H, br), 2.70 (3H, s), 2.87 (2H, br), 3.79 (3H, s), 4.01 (2H, t), 5.75 (1H, dd), 5.85 (1H, s), 6.23 (1H, dd), 6.40 (1H, dd), 7.00 (1H, s), 7.07 (1H, d), 7.33 (1H, dd), 7.70 (1H, d), 8.15 (1H, s), 8.28 (1H, br), 8.38 (1H, s), 8.99 (1H, s), 10.09 (1H, s). m/z: ESI MH+ 582.2 |

| | | | |
|---|---|---|---|
| 220 | 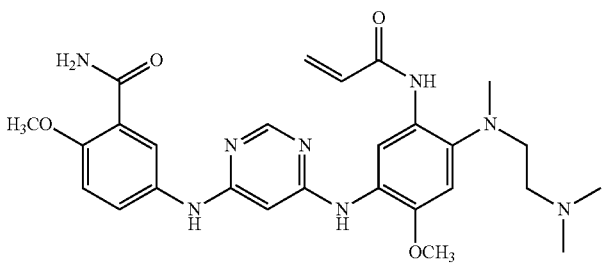 [SMILES: C=CC(=O)Nc1cc(Nc2cc(Nc3ccc(OC)c(C(N)=O)c3)ncn2)c(OC)cc1N(C)CCN(C)C] | 5-(6-(5-acrylamido-4-((2-methoxyphenyl)-methyl-amino)-2-methoxylphenylamino)-pyrimidin-4-yl)-2-methoxybenzamide | ¹H-NMR (DMSO-d6) δ: 2.22 (6H, s), 2.34 (2H, br), 2.70 (3H, s), 2.87 (2H, br), 3.80 (3H, s), 3.86 (3H, s), 5.75 (1H, dd), 5.86 (1H, s), 6.23 (1H, dd), 6.40 (1H, dd), 6.99 (1H, s), 7.06 (1H, d), 7.52 (1H, br), 7.66 (1H, br), 7.71 (1H, dd), 7.86 (1H, d), 8.13 (1H, s), 8.23 (1H, s), 8.40 (1H, s), 8.98 (1H, s), 10.09 (1H, s). m/z: ESI MH+ 535.2 |
| 221 | 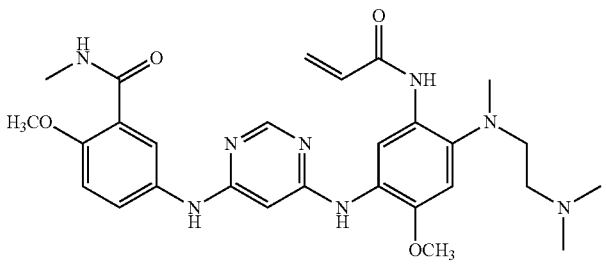 | 5-(6-(5-acrylamido-4-((2-methoxyphenyl)-methyl-amino)-2-methoxylphenylamino)-pyrimidin-4-yl)-2-methoxyl-N-methylbenzamide | ¹H-NMR (DMSO-d6) δ: 2.22 (6H, s), 2.34 (2H, br), 2.70 (3H, s), 2.80 (3H, d), 2.86 (2H, br), 3.80 (3H, s), 3.85 (3H, s), 5.75 (1H, dd), 5.86 (1H, s), 6.23 (1H, dd), 6.40 (1H, dd), 6.99 (1H, s), 7.05 (1H, d), 7.70 (1H, dd), 7.82 (1H, d), 8.13 (1H, s), 8.16 (1H, m), 8.23 (1H, s), 8.40 (1H, s), 8.99 (1H, s), 10.09 (1H, s). m/z: ESI MH+ 549.3 |
| 222 | 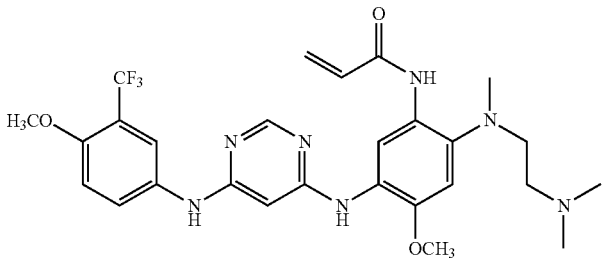 [SMILES: C=CC(=O)Nc1cc(Nc2cc(Nc3ccc(OC)c(C(F)(F)F)c3)ncn2)c(OC)cc1N(C)CCN(C)C] | N-(5-(6-(4-methoxyl-3-trifluoromethyl-phenylamino)-pyrimidin-4-yl-amino)-2-((2-dimethylamino-ethyl)-methyl-amino)-4-methoxyl-phenyl)-acrylamide | ¹H-NMR (DMSO-d6) δ: 2.21 (6H, s), 2.33 (2H, br), 2.70 (3H, s), 2.87 (2H, br), 3.79 (3H, s), 3.84 (3H, s), 5.75 (1H, dd), 5.84 (1H, s), 6.23 (1H, dd), 6.40 (1H, dd), 7.00 (1H, s), 7.19 (1H, d), 7.76 (1H, dd), 7.84 (1H, d), 8.16 (1H, s), 8.28 (1H, s), 8.38 (1H, s), 9.10 (1H, s), 10.10 (1H, s). m/z: ESI MH+ 560.2 |
| 223 | 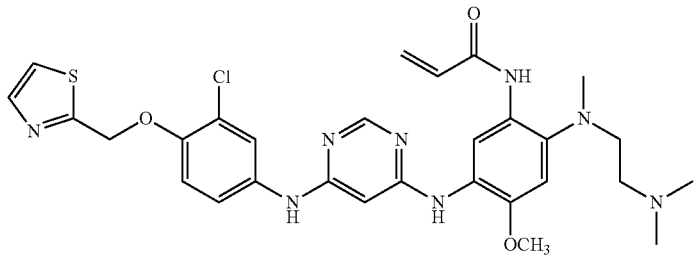 [SMILES: C=CC(=O)Nc1cc(Nc2cc(Nc3ccc(OCc4nccs4)c(Cl)c3)ncn2)c(OC)cc1N(C)CCN(C)C] | N-(5-(6-(3-chloro-4-(thiazol-2-ylmethoxy)-phenylamino)-pyrimidin-4-ylamino)-2-((2-dimethylamino-ethyl)-methyl-amino)-4-methoxyl-phenyl)-acrylamide | ¹H-NMR (DMSO-d6) δ: 2.22 (6H, s), 2.34 (2H, br), 2.72 (3H, s), 2.87 (2H, br), 3.80 (3H, s), 5.47 (2H, s), 5.75 (1H, dd), 5.85 (1H, s), 6.23 (1H, dd), 6.39 (1H, dd), 7.01 (1H, s), 7.21 (1H, d), 7.37 (1H, dd), 7.78-7.82 (2H, m), 7.86 (1H, d), 8.17 (1H, s), 8.32 (1H, s), 8.39 (1H, s), 9.07 (1H, s), 10.08 (1H, s). m/z: ESI MH+ 609.2 |
| 224 | 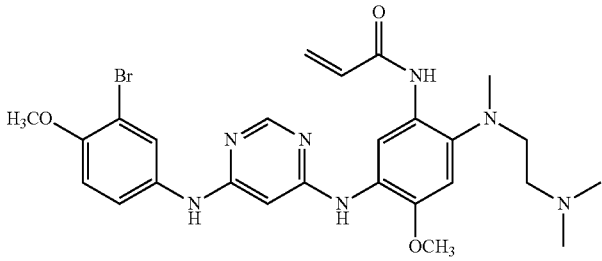 [SMILES: C=CC(=O)Nc1cc(Nc2cc(Nc3ccc(OC)c(Br)c3)ncn2)c(OC)cc1N(C)CCN(C)C] | N-(5-(6-(4-methoxyl-3-bromo-phenylamino)-pyrimidin-4-yl-amino)-2-((2-dimethylamino-ethyl)-methyl-amino)-4-methoxyl-phenyl)-acrylamide | ¹H-NMR (DMSO-d6) δ: 2.23 (6H, s), 2.35 (2H, br), 2.71 (3H, s), 2.88 (2H, br), 3.80 (6H, s), 5.75 (1H, dd), 5.85 (1H, s), 6.24 (1H, dd), 6.40 (1H, dd), 7.00 (1H, s), 7.04 (1H, d), 7.42 (1H, dd), 7.87 (1H, d), 8.16 (1H, s), 8.29 (1H, s), 8.39 (1H, s), 8.99 (1H, s), 10.07 (1H, s). m/z: ESI MH+ 570.2 |
| 225 | 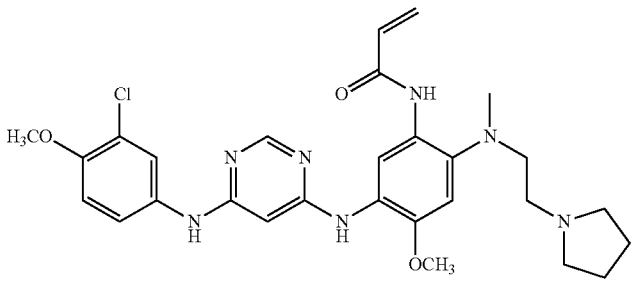 [SMILES: C=CC(=O)Nc1cc(Nc2cc(Nc3ccc(OC)c(Cl)c3)ncn2)c(OC)cc1N(C)CCN1CCCC1] | N-(5-(6-(4-methoxyl-3-chloro-phenylamino)-pyrimidin-4-yl-amino)-2(2-(pyrrolidin-1-yl)-ethoxyl)-4-methoxyl-phenyl)-acrylamide | ¹H-NMR (DMSO-d6) δ: 1.73 (4H, br), 2.42-2.55 (6H, br), 2.70 (3H, s), 2.95 (2H, br), 3.81 (6H, s), 5.74 (1H, dd), 5.86 (1H, s), 6.23 (1H, dd), 6.45 (1H, dd), 6.99 (1H, s), 7.07 (1H, d), 7.36 (1H, dd), 7.73 (1H, d), 8.16 (1H, s), 8.25-8.35 (2H, br), 9.00 (1H, s), 9.76 (1H, s). m/z: ESI MH+ 552.2 |

TABLE 10-continued

| | | | |
|---|---|---|---|
| 226 | 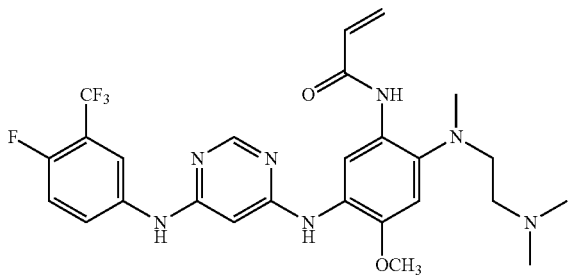 [SMILES: C=CC(=O)Nc1cc(Nc2cc(Nc3ccc(F)c(C(F)(F)F)c3)ncn2)c(OC)cc1N(C)CCN(C)C] | N-(5-(6-(4-fluoro-3-trifluoromethyl-phenylamino)-pyrimidin-4-yl-amino)-2-((2-dimethylamino-ethyl)-methyl-amino)-4-methoxyl-phenyl)-acrylamide | $^1$H-NMR (DMSO-d6) δ: 2.22 (6H, s), 2.34 (2H, br), 2.72 (3H, s), 2.87 (2H, br), 3.80 (3H, s), 5.75 (1H, dd), 5.87 (1H, s), 6.23 (1H, dd), 6.39 (1H, dd), 7.02 (1H, s), 7.40 (1H, t), 7.88 (1H, m), 8.09 (1H, dd), 8.22 (1H, s), 8.37 (1H, s), 8.42 (1H, s), 9.39 (1H, s), 10.09 (1H, s). m/z: ESI MH+ 548.2 |
| 227 | 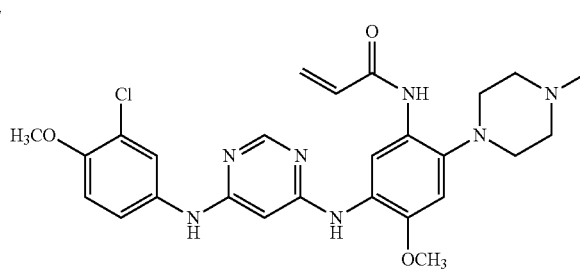 | N-(5-(6-(3-chloro-4-methoxyl-phenylamino)-pyrimidin-4-ylamino)-2-(4-(1-methylpiperidin-4-yl)-piperazin-1-yl)-4-methoxyl-phenyl)-acrylamide | $^1$H-NMR (DMSO-d6) δ: 1.46 (2H, m), 1.78 (2H, br), 1.90-1.95 (2H, m), 2.16-2.23 (4H, m), 2.69 (4H, br), 2.80-2.86 (6H, m), 3.80 (6H, s), 5.72 (1H, dd), 5.83 (1H, s), 6.22 (1H, dd), 6.61 (1H, dd), 6.87 (1H, s), 7.06 (1H, d), 7.36 (1H, m), 7.73 (1H, d), 8.06 (1H, s), 8.15 (1H, s), 8.28 (1H, s), 8.97 (1H, s), 8.99 (1H, s). m/z: ESI MH+ 607.2 |
| 228 | 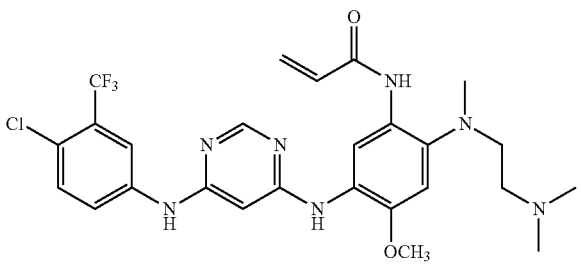 [SMILES: C=CC(=O)Nc1cc(Nc2cc(Nc3ccc(Cl)c(C(F)(F)F)c3)ncn2)c(OC)cc1N(C)CCN(C)C] | N-(5-(6-(4-chloro-3-trifluoromethyl-phenylamino)-pyrimidin-4-yl-amino)-2-((2-dimethylamino-ethyl)-methyl-amino)-4-methoxyl-phenyl)-acrylamide | $^1$H-NMR (DMSO-d6) δ: 2.2 (6H, s), 2.33 (2H, t), 2.72 (3H, s), 2.87 (2H, t), 3.80 (3H, s), 5.73 (1H, dd), 5.90 (1H, s), 6.23 (1H, dd), 6.38 (1H, dd), 7.02 (1H, s), 7.57 (1H, d), 7.93 (1H, dd), 8.20 (1H, d), 8.24 (1H, s), 8.37 (1H, s), 8.47 (1H, s), 9.53 (1H, s), 10.10 (1H, s). m/z: ESI MH+ 564.2 |
| 229 | 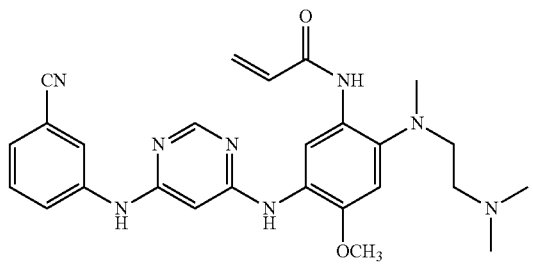 [SMILES: C=CC(=O)Nc1cc(Nc2cc(Nc3cccc(C#N)c3)ncn2)c(OC)cc1N(C)CCN(C)C] | N-(5-(6-(3-cyano-phenylamino)-pyrimidin-4-yl-amino)-2-((2-dimethylamino-ethyl)-methyl-amino)-4-methoxyl-phenyl)-acrylamide | $^1$H-NMR (DMSO-d6) δ: 2.26 (6H, s), 2.33 (2H, t), 2.71 (3H, s), 2.92 (2H, t), 3.81 (3H, s), 5.72 (1H, dd), 5.94 (1H, s), 6.23 (1H, dd), 6.43 (1H, dd), 7.01 (1H, s), 7.34 (1H, d), 7.46 (1H, t), 7.78 (1H, dd), 8.20 (1H, br), 8.25 (1H, s), 8.35 (1H, br), 8.46 (1H, s), 9.44 (1H, s), 10.05 (1H, s). m/z: ESI MH+ 487.3 |
| 230 | 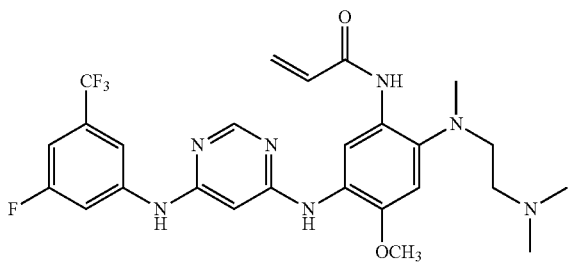 [SMILES: C=CC(=O)Nc1cc(Nc2cc(Nc3cc(F)cc(C(F)(F)F)c3)ncn2)c(OC)cc1N(C)CCN(C)C] | N-(5-(6-(5-fluoro-3-trifluoromethyl-phenylamino)-pyrimidin-4-yl-amino)-2-((2-dimethylamino-ethyl)-methyl-amino)-4-methoxyl-phenyl)-acrylamide | $^1$H-NMR (DMSO-d6) δ: 2.24 (6H, s), 2.36 (2H, t), 2.72 (3H, s), 2.89 (2H, t), 3.80 (3H, s), 5.73 (1H, dd), 5.92 (1H, s), 6.23 (1H, dd), 6.41 (1H, dd), 7.02 (1H, s), 7.11 (1H, m), 7.71 (1H, s), 7.96 (1H, m), 8.28 (1H, s), 8.36 (1H, br), 8.54 (1H, s), 9.65 (1H, s), 10.08 (1H, s). m/z: ESI MH+ 548.2 |

TABLE 10-continued

| | | | |
|---|---|---|---|
| 231 | 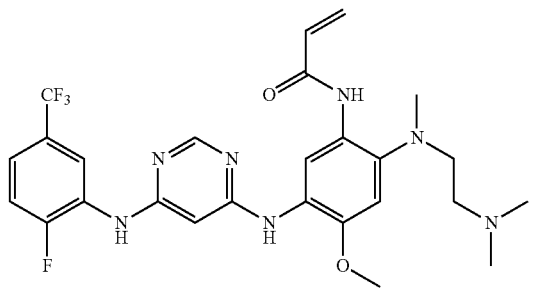 [SMILES: C=CC(=O)Nc1cc(Nc2cc(Nc3cc(C(F)(F)F)ccc3F)ncn2)c(OC)cc1N(C)CCN(C)C] | N-(5-(6-(2-fluoro-5-trifluoromethyl-phenylamino)-pyrimidin-4-yl-amino)-2-((2-dimethylamino-ethyl)-methyl-amino)-4-methoxyl-phenyl)-acrylamide | ¹H-NMR (DMSO-d6) δ: 2.21 (6H, s), 2.34 (2H, t), 2.72 (3H, s), 2.87 (2H, t), 3.79 (3H, s), 5.75 (1H, dd), 6.08 (1H, s), 6.23 (1H, dd), 6.39 (1H, dd), 7.02 (1H, s), 7.39 (1H, m), 7.43 (1H, m), 8.20 (1H, s), 8.34 (1H, s), 8.44 (1H, s), 8.57 (1H, dd), 9.11 (1H, s), 10.01 (1H, s). m/z: ESI MH+ 548.3 |
| 232 | 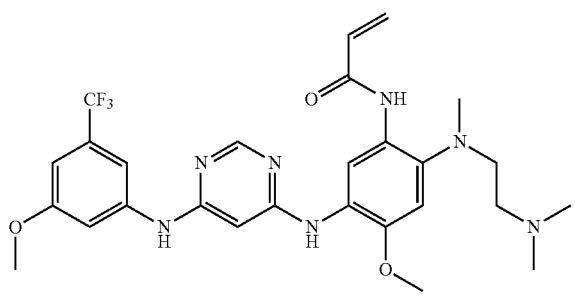 [SMILES: C=CC(=O)Nc1cc(Nc2cc(Nc3cc(OC)cc(C(F)(F)F)c3)ncn2)c(OC)cc1N(C)CCN(C)C] | N-(5-(6-(3-methoxyl-5-trifluoromethyl-phenylamino)-pyrimidin-4-yl-amino)-2-((2-dimethylamino-ethyl)-methyl-amino)-4-methoxyl-phenyl)-acrylamide | ¹H-NMR (DMSO-d6) δ: 2.23 (6H, s), 2.35 (2H, s), 2.72 (3H, s), 2.88 (2H, t), 3.80 (6H, d), 5.74 (1H, m), 5.91 (1H, s), 6.23 (1H, dd), 6.39 (1H, dd), 6.77 (1H, s), 7.02 (1H, s), 7.53 (1H, s), 7.63 (1H, s), 8.24 (1H, s), 8.36 (1H, s), 8.45 (1H, s), 9.39 (1H, s), 10.08 (1H, s). m/z: ESI MH+ 560.2 |
| 233 | 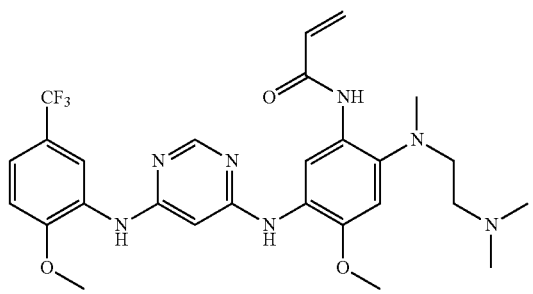 [SMILES: C=CC(=O)Nc1cc(Nc2cc(Nc3cc(C(F)(F)F)ccc3OC)ncn2)c(OC)cc1N(C)CCN(C)C] | N-(5-(6-(2-methoxyl-5-trifluoromethyl-phenylamino)-pyrimidin-4-yl-amino)-2-((2-dimethylamino-ethyl)-methyl-amino)-4-methoxyl-phenyl)-acrylamide | ¹H-NMR (DMSO-d6) δ: 2.22 (6H, s), 2.34 (2H, br), 2.72 (3H, s), 2.87 (2H, br), 3.78 (3H, s), 3.89 (3H, s), 5.75 (1H, m), 6.06 (1H, s), 6.23 (1H, dd), 6.39 (1H, dd), 7.00 (1H, s), 7.17 (1H, d), 7.33 (1H, d), 8.18 (1H, s), 8.31 (1H, s), 8.33 (1H, s), 8.44 (1H, d), 8.49 (1H, s), 10.09 (1H, s). m/z: ESI MH+ 560.2 |
| 234 | 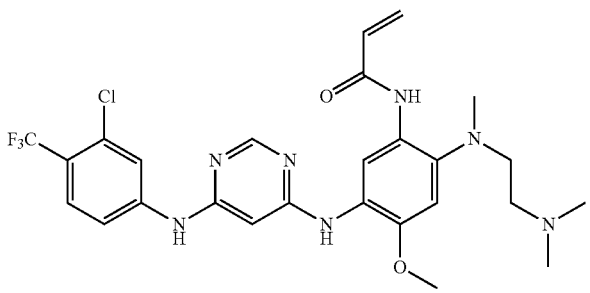 [SMILES: C=CC(=O)Nc1cc(Nc2cc(Nc3ccc(C(F)(F)F)c(Cl)c3)ncn2)c(OC)cc1N(C)CCN(C)C] | N-(5-(6-(3-chloro-4-trifluoromethyl-phenylamino)-pyrimidin-4-yl-amino)-2-((2-dimethylamino-ethyl)-methyl-amino)-4-methoxyl-phenyl)-acrylamide | ¹H-NMR (DMSO-d6) δ: 2.21 (6H, s), 2.34 (2H, br), 2.73 (3H, s), 2.87 (2H, br), 3.80 (3H, s), 5.75 (1H, dd), 5.95 (1H, s), 6.23 (1H, dd), 6.39 (1H, dd), 7.03 (1H, s), 7.64 (1H, dd), 7.70 (1H, d), 8.15 (1H, d), 8.29 (1H, s), 8.36 (1H, s), 8.57 (1H, s), 9.68 (1H, s), 10.10 (1H, s). m/z: ESI MH+ 564.1 |
| 235 | 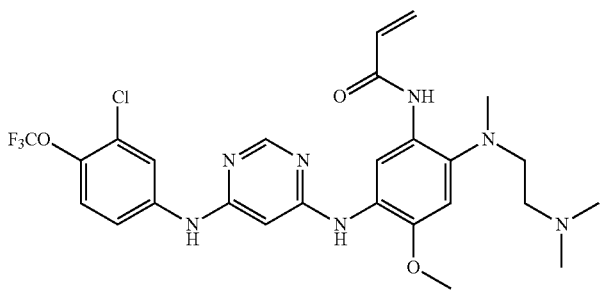 [SMILES: C=CC(=O)Nc1cc(Nc2cc(Nc3ccc(OC(F)(F)F)c(Cl)c3)ncn2)c(OC)cc1N(C)CCN(C)C] | N-(5-(6-(3-chloro-4-trifluoromethoxy-phenylamino)-pyrimidin-4-yl-amino)-2-((2-dimethylamino-ethyl)-methyl-amino)-4-methoxyl-phenyl)-acrylamide | ¹H-NMR (DMSO-d6) δ: 2.22 (6H, s), 2.34 (2H, br), 2.72 (3H, s), 2.87 (2H, br), 3.70 (3H, s), 5.75 (1H, dd), 5.90 (1H, s), 6.23 (1H, dd), 6.39 (1H, dd), 7.02 (1H, s), 7.44 (1H, d), 7.54 (1H, dd), 8.09 (1H, d), 8.24 (1H, s), 8.36 (1H, s), 8.48 (1H, s), 9.45 (1H, s), 10.10 (1H, s). m/z: ESI MH+ 580.2 |

TABLE 10-continued

| | | | |
|---|---|---|---|
| 236 | 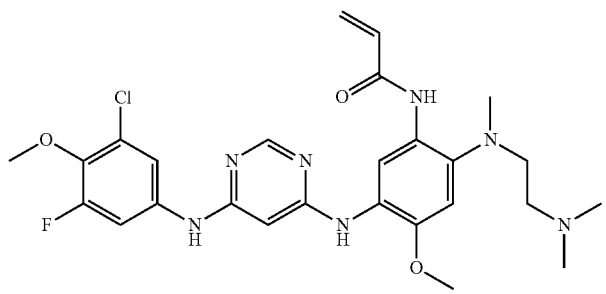 | N-(5-(6-(3-chloro-5-fluoro-4-methoxyphenylamino)-pyrimidin-4-yl-amino)-2-((2-dimethylamino-ethyl)-methyl-amino)-4-methoxyl-phenyl)-acrylamide | $^1$H-NMR (DMSO-d6) δ: 2.21 (6H, s), 2.33 (2H, t), 2.72 (3H, s), 2.85 (2H, t), 3.80 (3H, s), 3.81 (3H, s), 5.74 (1H, dd), 5.86 (1H, s), 6.23 (1H, dd), 6.39 (1H, dd), 7.02 (1H, dd), 7.54 (1H, m), 7.59 (1H, dd), 8.23 (1H, s), 8.37 (1H, s), 8.46 (1H, s), 9.31 (1H, s), 10.10 (1H, s). m/z: ESI MH+ 544.2 |
| 237 | 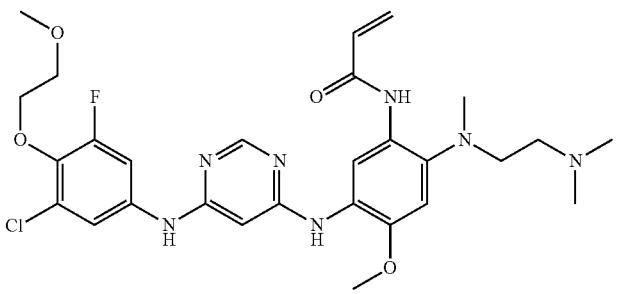 [SMILES: C=CC(=O)Nc1cc(Nc2cc(Nc3cc(F)c(OCCOC)c(Cl)c3)ncn2)c(OC)cc1N(C)CCN(C)C] | N-(5-(6-(3-chloro-5-fluoro-4-(2-methoxyl-ethoxyl)-phenylamino)-pyrimidin-4-yl-amino)-2-((2-dimethylamino-ethyl)-methyl-amino)-4-methoxyl-phenyl)-acrylamide | $^1$H-NMR (DMSO-d6) δ: 2.26 (6H, s), 2.36 (2H, br), 2.71 (3H, s), 2.90 (2H, br), 3.30 (3H, s), 3.62 (2H, t), 3.80 (3H, s), 4.09 (2H, t), 5.75 (1H, dd), 5.87 (1H, s), 6.23 (1H, dd), 6.43 (1H, dd), 7.01 (1H, s), 7.53 (1H, s), 7.60 (1H, dd), 8.23 (1H, s), 8.34 (1H, s), 8.45 (1H, s), 9.30 (1H, s), 10.05 (1H, s). m/z: ESI MH+ 588.2 |
| 238 | 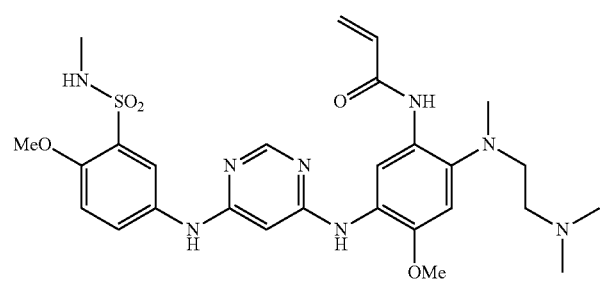 [SMILES: C=CC(=O)Nc1cc(Nc2cc(Nc3ccc(OC)c(S(=O)(=O)NC)c3)ncn2)c(OC)cc1N(C)CCN(C)C] | N-(5-(6-(3-methanesulfonamido-4-methyl-phenylamino)-pyrimidin-4-yl-amino)-2-((2-dimethylamino-ethyl)-methyl-amino)-4-methoxyl-phenyl)-acrylamide | $^1$H-NMR (DMSO-d6) δ: 2.41 (3H, d), 2.42-2.80 (11H, br), 2.71 (3H, s), 3.13 (2H, br), 3.81-3.85 (6H, m), 5.72 (1H, dd), 5.88 (1H, s), 6.23 (1H, dd), 6.69 (1H, dd), 6.95-7.01 (2H, m), 7.16 (1H, d), 7.85 (1H, dd), 7.90 (1H, d), 8.16 (1H, s), 8.20-8.34 (2H, m), 9.15 (1H, s), 9.90 (1H, br). m/z: ESI MH+ 585.1 |
| 239 | 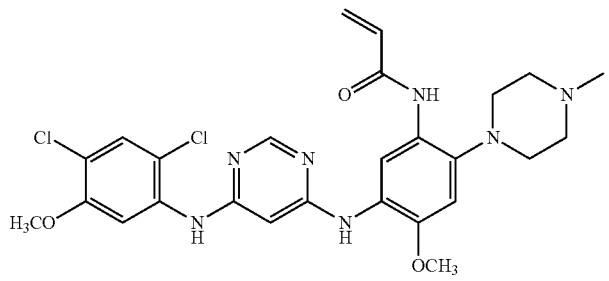 [SMILES: C=CC(=O)Nc1cc(Nc2cc(Nc3cc(OC)c(Cl)cc3Cl)ncn2)c(OC)cc1N1CCN(C)CC1] | N-(5-(6-(2,4-dichloro-5-methoxyl-phenylamino)-pyrimidin-4-yl-amino)-2-(4-methyl-piperazin-1-yl)-4-methoxyl-phenyl)-acrylamide | $^1$H-NMR (DMSO-d6) δ: 3.04 (4H, br), 3.81 (3H, t), 3.83 (3H, s), 5.74 (1H, dd), 6.00 (1H, s), 6.22 (1H, dd), 6.73 (1H, dd), 6.82 (1H, s), 7.56-7.59 (2H, m), 8.13-8.16 (2H, m), 8.37 (1H, s), 8.67 (1H, s), 9.07 (1H, s). Piperazine peak and solvent peak coincid, and some peaks are not shown. m/z: ESI MH+ 558.1 |
| 240 | 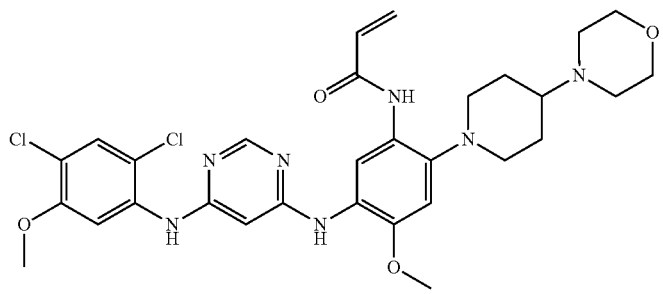 [SMILES: C=CC(=O)Nc1cc(Nc2cc(Nc3cc(OC)c(Cl)cc3Cl)ncn2)c(OC)cc1N1CCC(N2CCOCC2)CC1] | N-(5-(6-(2,4-dichloro-5-methoxyl-phenylamino)-pyrimidin-4-yl-amino)-2-(4-(morpholin-1-yl)-piperidin-1-yl)-4-methoxyl-phenyl)-acrylamide | $^1$H-NMR (DMSO-d6) δ: 2.66 (2H, t), 3.04 (2H, d), 3.18 (2H, d), 3.60 (4H, br), 3.78 (3H, s), 3.83 (3H, s), 5.73 (1H, d), 5.97 (1H, s), 6.22 (1H, dd), 6.67 (1H, q), 6.82 (1H, s), 7.58 (2H, d), 8.09 (1H, s), 8.12 (1H, s), 8.33 (1H, s), 8.64 (1H, s), 8.95 (1H, s). m/z: ESI MH+ 628.1 |

TABLE 10-continued

| | | | |
|---|---|---|---|
| 241 | 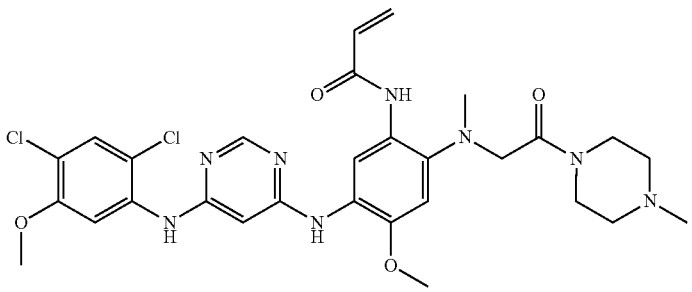 [SMILES: C=CC(=O)Nc1cc(Nc2cc(Nc3cc(OC)c(Cl)cc3Cl)ncn2)c(OC)cc1N(C)CC(=O)N1CCN(C)CC1] | N-(5-(6-(2,4-dichloro-5-methoxyl-phenylamino)-pyrimidin-4-yl-amino)-2-(methyl-(2-(4-methyl-piperazin-1-yl)-2-oxoethyl)-amino)-4-methoxyl-phenyl)-acrylamide | ¹H-NMR (DMSO-d6) δ: 2.17 (3H, s), 2.26 (4H, t), 2.74 (3H, s), 3.41 (2H, br), 3.51 (2H, br), 3.78 (5H, s), 3.83 (3H, s), 5.73 (1H, dd), 5.97 (1H, s), 6.22 (1H, dd), 6.47 (1H, dd), 6.93 (1H, s), 7.58 (2H, d), 8.12 (1H, s), 8.28 (1H, s), 8.33 (1H, s), 8.64 (1H, s), 9.80 (1H, s). m/z: ESI+ MH+ 629.2 |
| 242 | 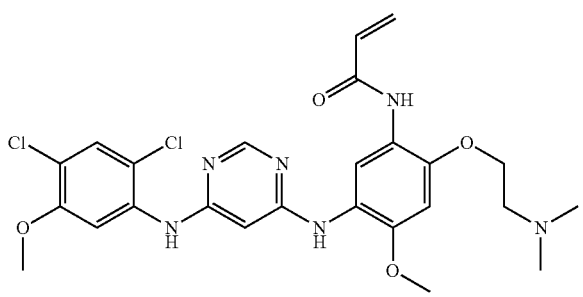 [SMILES: C=CC(=O)Nc1cc(Nc2cc(Nc3cc(OC)c(Cl)cc3Cl)ncn2)c(OC)cc1OCCN(C)C] | N-(5-(6-(2,4-dichloro-5-methoxyl-phenylamino)-pyrimidin-4-ylamino)-2-(2-dimethylamino-ethoxyl)-4-methoxyl-phenyl)-acrylamide | ¹H-NMR (DMSO-d6) δ: 2.26 (6H, s), 2.59 (2H, t), 3.79 (3H, s), 3.82 (3H, s), 4.17 (2H, t), 5.73 (1H, dd), 5.91 (1H, s), 6.21 (1H, dd), 6.47 (1H, dd), 6.90 (1H, s), 7.58 (2H, d), 8.12 (2H, d), 8.31 (1H, s), 8.62 (1H, s), 9.68 (1H, s). m/z: ESI MH+ 547.1 |
| 243 | 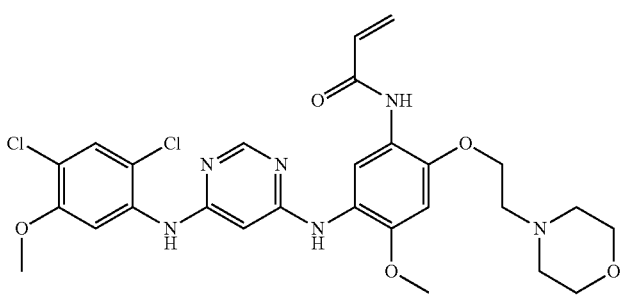 [SMILES: C=CC(=O)Nc1cc(Nc2cc(Nc3cc(OC)c(Cl)cc3Cl)ncn2)c(OC)cc1OCCN1CCOCC1] | N-(5-(6-(2,4-dichloro-5-methoxyl-phenylamino)-pyrimidin-4-yl-amino)-2-(2-(morpholin-4-yl)-ethoxyl-4-methoxyl-phenyl)-acrylamide | ¹H-NMR (DMSO-d6) δ: 2.50 (4H, br), 2.72 (2H, br), 3.57 (4H, t), 3.80 (6H, d), 4.20 (2H, t), 5.71 (1H, dd), 5.90 (1H, s), 6.20 (1H, dd), 6.58 (1H, dd), 6.86 (1H, s), 7.56 (1H, s), 7.59 (1H, s), 8.00 (1H, s), 8.11 (1H, s), 8.29 (1H, s), 8.60 (1H, s), 9.20 (1H, s). m/z: ESI MH+ 589.2 |
| 244 | 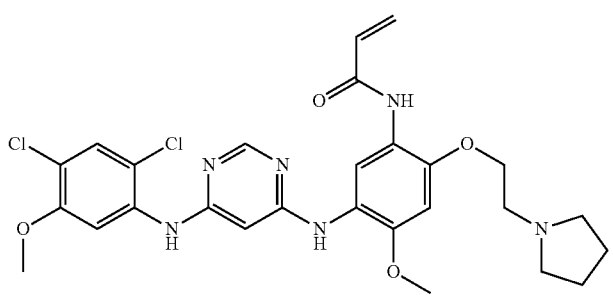 [SMILES: C=CC(=O)Nc1cc(Nc2cc(Nc3cc(OC)c(Cl)cc3Cl)ncn2)c(OC)cc1OCCN1CCCC1] | N-(5-(6-(2,4-dichloro-5-methoxyl-phenylamino)-pyrimidin-4-yl-amino)-2-(2-(pyrrolidin-1-yl)-ethoxyl)-4-methoxyl-phenyl)-acrylamide | ¹H-NMR (DMSO-d6) δ: 1.72 (4H, br), 2.72 (2H, t), 3.57 (4H, t), 3.80 (6H, d), 4.20 (2H, t), 5.71 (1H, dd), 5.90 (1H, s), 6.20 (1H, dd), 6.58 (1H, dd), 6.86 (1H, s), 7.56 (1H, s), 7.59 (1H, s), 8.00 (1H, s), 8.11 (1H, s), 8.29 (1H, s), 8.60 (1H, s), 9.20 (1H, s). m/z: ESI MH+ 573.2 |
| 245 | 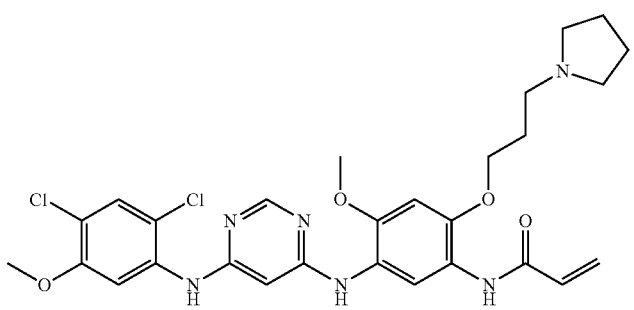 [SMILES: C=CC(=O)Nc1cc(Nc2cc(Nc3cc(OC)c(Cl)cc3Cl)ncn2)c(OC)cc1OCCCN1CCCC1] | N-(5-(6-(2,4-dichloro-5-methoxyl-phenylamino)-pyrimidin-4-yl-amino)-2-(3-(pyrrolidin-1-yl)-propyl)-4-methoxyl-phenyl)-acrylamide | ¹H-NMR (DMSO-d6) δ: 1.91-2.03 (4H, m), 2.16 (2H, t), 3.00 (2H, t), 3.28-3.30 (2H, m), 3.48-3.58 (2H, m), 3.82 (6H, d), 4.18 (2H, t), 5.72 (1H, dd), 5.92 (1H, s), 6.22 (1H, dd), 6.67 (1H, dd), 6.83 (1H, s), 7.57 (1H, d), 7.97 (1H, s), 8.11 (1H, s), 8.30 (1H, s), 8.61 (1H, s), 9.30 (1H, s). m/z: ESI+ MH+ 587.0 |

TABLE 10-continued

| 246 | 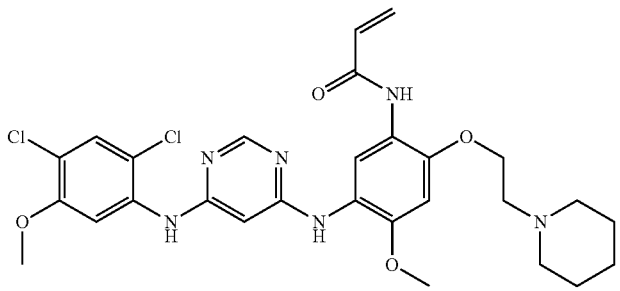 [SMILES: C=CC(=O)Nc1cc(Nc2cc(Nc3cc(OC)c(Cl)cc3Cl)ncn2)c(OC)cc1OCCN1CCCCC1] | N-(5-(6-(2,4-dichloro-5-methoxyl-phenylamino)-pyrimidin-4-yl-amino)-2-(2-(piperidin-1-yl)-ethoxyl-4-methoxyl-phenyl)-acrylamide | $^1$H-NMR (DMSO-d6) δ: 1.35-1.60 (6H, m), 2.35-2.82 (6H, m), 3.81 (6H, d), 4.23 (2H, t), 5.71 (1H, dd), 5.90 (1H, s), 6.19 (1H, dd), 6.64 (1H, dd), 6.87 (1H, s), 7.56 (1H, s), 7.59 (1H, s), 8.04 (1H, s), 8.11 (1H, s), 8.29 (1H, s), 8.60 (1H, s), 9.32 (1H, s). m/z: ESI+ MH+ 587.0 |
|---|---|---|---|
| 247 | 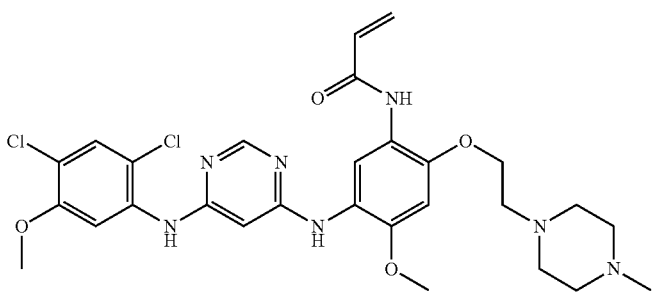 [SMILES: C=CC(=O)Nc1cc(Nc2cc(Nc3cc(OC)c(Cl)cc3Cl)ncn2)c(OC)cc1OCCN1CCN(C)CC1] | N-(5-(6-(2,4-dichloro-5-methoxyl-phenylamino)-pyrimidin-4-yl-amino)-2-(2-(4-methyl-piperazin-1-yl)-ethoxyl-4-methoxyl-phenyl)-acrylamide | $^1$H-NMR (DMSO-d6) δ: 2.20 (3H, s), 2.38-2.55 (8H, br), 2.72 (2H, t), 3.80 (6H, d), 4.19 (2H, t), 5.70 (H, dd), 5.90 (1H, s), 6.19 (1H, dd), 6.58 (1H, dd), 6.86 (1H, s), 7.58 (2H, d), 8.01 (1H, s), 8.10 (1H, s), 8.28 (1H, s), 8.60 (1H, s), 9.21 (1H, s). m/z: ESI+ MH+ 602.0 |
| 248 | 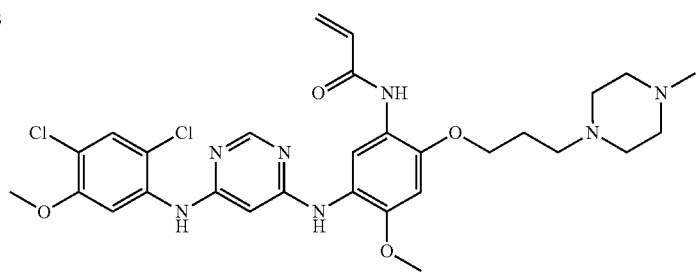 | N-(5-(6-(2,4-dichloro-5-methoxyl-phenylamino)-pyrimidin-4-yl-amino)-2-(3-(4-methyl-piperazin-1-yl)-propyl)-4-methoxyl-phenyl)-acrylamide | $^1$H-NMR (DMSO-d6) δ: 1.90 (2H, t), 2.14 (3H, s), 2.21-2.48 (10H, m), 3.79 (3H, s), 3.82 (3H, s), 4.10 (2H, t), 5.70 (H, dd), 5.89 (1H, s), 6.18 (1H, dd), 6.59 (1H, dd), 6.79 (1H, s), 7.56 (1H, s), 7.60 (1H, s), 7.96 (1H, s), 8.10 (1H, s), 8.28 (1H, s), 8.59 (1H, s), 9.16 (1H, s). m/z: ESI+ MH+ 616.2 |
| 249 | 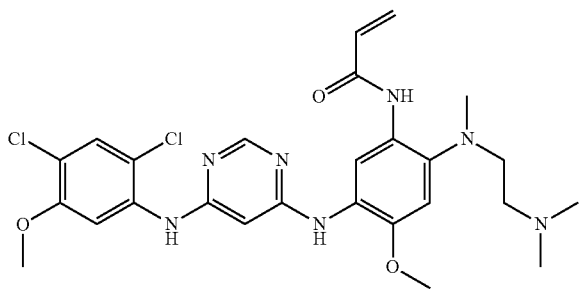 | N-(5-(6-((2,4-dichloro-5-methoxyl-phenyl)-methyl-amino)-pyrimidin-4-ylamino)-2-((2-dimethylamino-ethyl)-methyl-amino)-4-methoxyl-phenyl)-acrylamide | $^1$H-NMR (DMSO-d6) δ: 2.19 (6H, s), 2.26 (2H, t), 2.67 (3H, s), 2.82 (2H, t), 3.29 (3H, s), 3.75 (3H, s), 3.86 (3H, s), 5.58 (1H, d), 5.73 (1H, dd), 6.22 (1H, dd), 6.35 (1H, dd), 6.91 (1H, s), 7.29 (1H, s), 7.74 (1H, s), 8.15 (2H, d), 8.53 (1H, s), 10.08 (1H, s). m/z: ESI MH+ 574.2 |

Example 19

Preparation of N-(5-(6-(3-chloro-4-tert-butoxy-phenylamino)-pyrimidin-4-yl amino)-2-((2-dimethylaminoethyl)-methyl-amino)-4-methoxyl-phenyl)-acrylamide 5 (Compound 250)

Compound 250

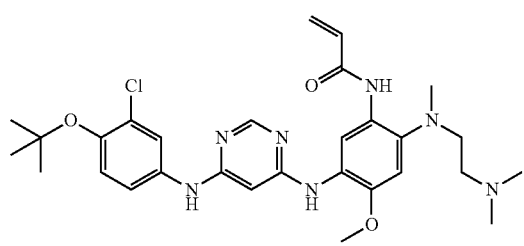

Step 1: Preparation of (6-chloro-pyrimidin-4-yl)-4-yl)-4-fluoro-2-methoxy-5-nitroaniline

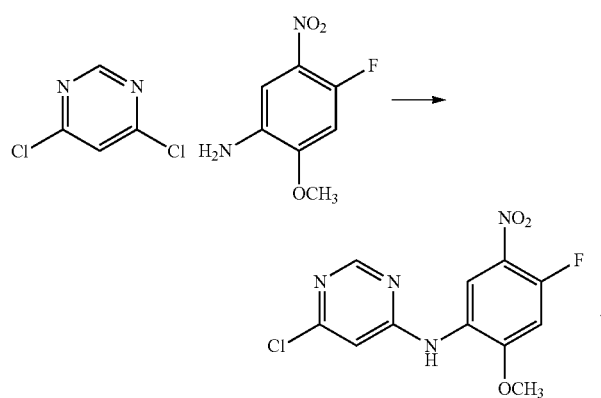

2-Methoxyl-4-fluoro-5-nitroaniline (9.3 g, 50 mmol), 4,6-dichloro pyrimidine (11.3 g, 75 mmol) and methanesulfonic acid (5.3 g, 55 mmol) were added to 150 mL of isopropyl alcohol and then stirred under reflux for 6 h. The reaction mixture was filtered to give the title intermediate (11.5 g). m/z: ESI MH⁺ 299.0.

Steps 2 and 3: Preparation of N-(4-tert-butoxy-3-chlorophenyl)-N'-(4-((2-dimethylaminoethyl)-methyl-amino)-2-methoxyl-5-nitrophenyl)-pyrimidine-4,6-diamine

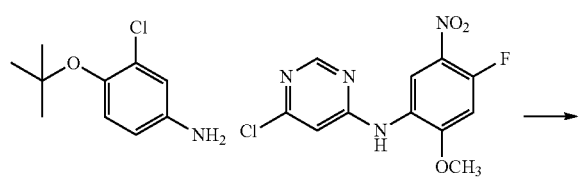

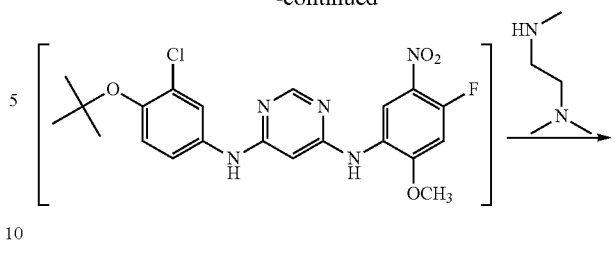

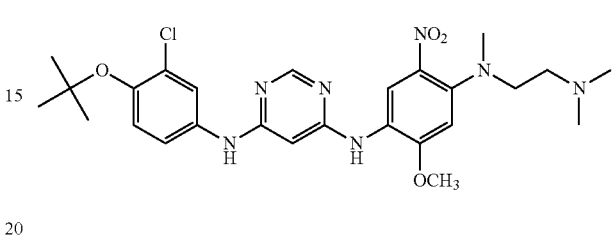

3-Chloro-4-tert-butoxy phenylamine (1.95 g, 10 mmol), (6-chloro-pyrimidin-4-yl)-4-fluoro-2-methoxyl-5-nitroaniline (0.75 g, 2.5 mmol) were mixed and then heated at 100° C. for 2 h under nitrogen atmosphere. The reaction mixture was cooled to room temperature and then added with trimethyl ethylenediamine (0.51 g, 5 mmol), potassium carbonate (1.38 g, 10 mmol) and 6 mL of DMA. The mixture was heated under oil bath at 85° C. for 1 h, and then added with water and ethyl acetate. The organic layer was dried and then concentrated. The residues were purified by column chromatography to give the title intermediate (0.45 g). m/z: ESI MH⁺ 544.2.

Steps 4 and 5 are the same as that of Example 1 to give the title compound.

Example 20

Preparation of N-(5-(6-(3-chloro-4-(3-methyl-oxetan-3-yl-methoxyl)-phenylamino)-pyrimidin-4-yl-amino)-2-((2-dimethylamino-ethyl)-methyl-amino)-4-methoxyl-phenyl)-acrylamide (compound 252)

Compound 252

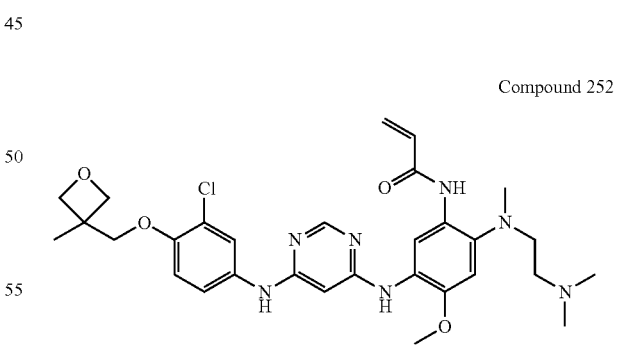

Steps 1~3: Preparation of 2-chloro-4-(6-(4-((2-dimethylamino-ethyl)-methyl-amino)-2-methoxyl-5-nitro-phenylamino)-pyrimidin-4-ylamino)-phenol Steps 1~3 of Example 19 were repeated except for replacing 3-chloro-4-tert-butoxy phenylamine with 2-chloro-4-amino phenol.

Step 4: Preparation of N-(4-(3-methyl-oxetan-3-yl-methoxyl)-3-chlorophenyl)-N'-(4-((2-dimethylam-inoethyl)-methyl-amino)-2-methoxyl-5-nitrophenyl)-pyrimidine-4,6-diamine

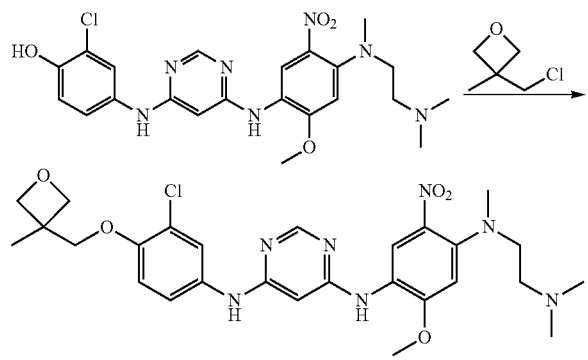

N-(4-hydroxyl-3-chlorophenyl)-N'-(4-((2-dimethylam-inoethyl)-methyl-amino)-2-methoxyl-5-nitrophenyl)-pyrimidin-4,6-diamine (0.49 g, 1 mmol, the preparation method is the same as specified in Example 19), 3-methyl-3-chloromethyl-oxetane (0.15 g, 1.2 mmol) and sodium hydroxide (0.08 g, 2 mmol) were added to 3 mL of DMA and then heated under oil bath at 55° C. for 20 h. The reaction mixture was added with water and ethyl acetate. The organic layer was dried and then concentrated. The residues were purified by column chromatography to give the product (0.23 g). m/z: ESI MH+ 572.2.

Steps 5 and 6 are the same as steps 4 and 5 in Example 19 to give the title compound.

Compounds 250-251 in Table 11 were prepared following the method in Example 19.

Compound 252 in Table 11 was prepared following the method in Example 20.

Compounds 253-256 in Table 11 were prepared following the method in Example 10.

TABLE 11

| | | | |
|---|---|---|---|
| 250 | 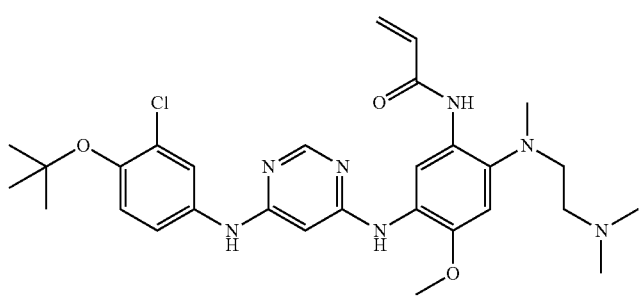 [SMILES: C=CC(=O)Nc1cc(Nc2cc(Nc3ccc(OC(C)(C)C)c(Cl)c3)ncn2)c(OC)cc1N(C)CCN(C)C] | N-(5-(6-(3-chloro-4-tert-butoxy-phenylamino)-pyrimidin-4-yl-amino)-2-((2-dimethylamino-ethyl)-methyl-amino)-4-methoxyl-phenyl)-acrylamide | ¹H-NMR (DMSO-d6) δ: 1.32 (9H, s), 2.22 (6H, s), 2.34 (2H, br), 2.71 (3H, s), 2.87 (2H, br), 3.80 (3H, s), 5.75 (1H, dd), 5.87 (1H, s), 6.23 (1H, dd), 6.40 (1H, dd), 7.01 (1H, s), 7.09 (1H, d), 7.34 (1H, dd), 7.79 (1H, d), 8.18 (1H, s), 8.35 (1H, s), 8.38 (1H, s), 9.12 (1H, s), 10.10 (1H, s). m/z: ESI MH+ 568.2 |
| 251 | 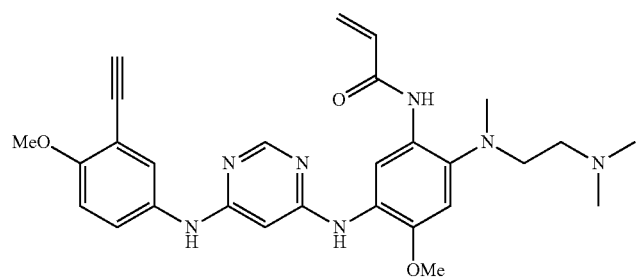 [SMILES: C#Cc1cc(Nc2cc(Nc3cc(NC(=O)C=C)c(N(C)CCN(C)C)cc3OC)ncn2)ccc1OC] | N-(5-(6-(3-acetenyl-4-methoxyl-phenylamino)-pyrimidin-4-yl-amino)-2-((2-dimethylamino-ethyl)-methyl-amino)-4-methoxyl-phenyl)-acrylamide | ¹H-NMR (DMSO-d6) δ: 2.31 (6H, s), 2.43 (2H, br), 2.74 (3H, s), 2.95 (2H, br), 3.82 (3H, s), 3.85 (3H, s), 4.26 (1H, s), 5.80 (1H, dd), 5.89 (1H, s), 6.28 (1H, dd), 6.42 (1H, dd), 7.01 (1H, d), 7.04 (1H, s), 7.49 (1H, dd), 7.65 (1H, d), 8.19 (1H, s), 8.32 (1H, s), 8.41 (1H, s), 8.97 (1H, s), 10.11 (1H, s). m/z: ESI MH+ 516.2 |
| 252 | 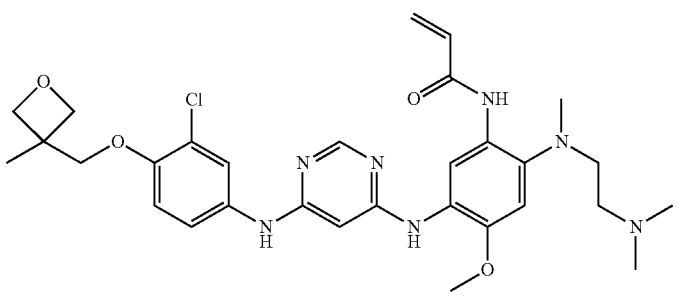 | N-(5-(6-(3-chloro-4-(3-methyl-oxetan-3-yl-methoxyl)-phenylamino)-pyrimidin-4-yl-amino)-2-((2-dimethylamino-ethyl)-methyl-amino)-4-methoxyl-phenyl)-acrylamide | ¹H-NMR (DMSO-d6) δ: 1.39 (3H, s), 2.22-2.60 (8H, br), 2.65 (3H, s), 3.05 (2H, br), 3.81 (3H, s), 4.07 (H, s), 4.32 (2H, d), 4.52 (2H, d), 5.75 (1H, dd), 5.90 (1H, s), 6.24 (1H, dd), 6.52 (1H, dd), 6.97 (1H, s), 7.13 (1H, d), 7.37 (1H, dd), 7.75 (1H, d), 8.17 (1H, s), 8.29 (1H, br), 8.33 (1H, s), 9.05 (1H, s), 9.93 (1H, s). m/z: ESI MH+ 596.2 |

TABLE 11-continued

| | | | |
|---|---|---|---|
| 253 | 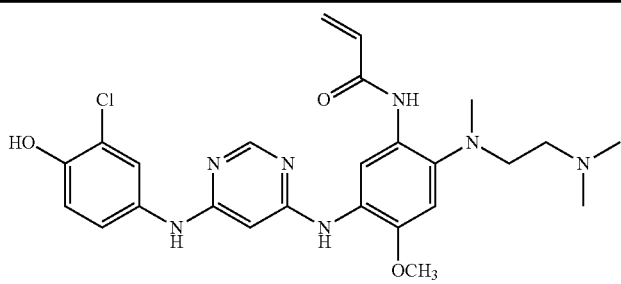 | N-(5-(6-(3-chloro-4-hydroxylphenylamino)-pyrimidin-4-ylamino)-2-((2-dimethylamino-ethyl)-methyl-amino)-4-methoxyl-phenyl)-acrylamide | $^1$H-NMR (DMSO-d6) δ: 2.21 (6H, s), 2.33 (2H, br), 2.70 (3H, s), 2.86 (2H, br), 3.79 (3H, s), 3.86 (3H, s), 5.75 (1H, dd), 5.82 (1H, s), 6.24 (1H, dd), 6.39 (1H, dd), 6.87 (1H, d), 6.99 (1H, s), 7.18 (1H, dd), 7.59 (1H, d), 8.13 (1H, s), 8.25 (1H, s), 8.40 (1H, s), 8.86 (1H, s), 9.75 (1H, br), 10.10 (1H, s). m/z: ESI MH+ 512.2 |
| 254 | 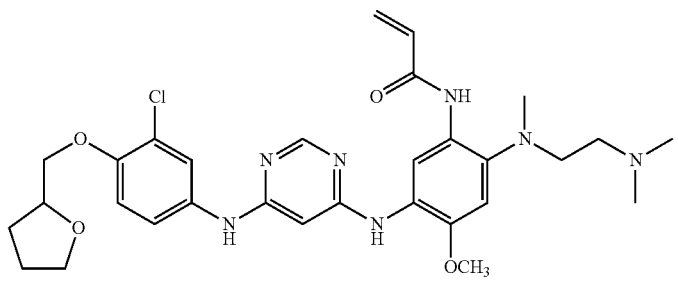 [SMILES: C=CC(=O)Nc1cc(Nc2cc(Nc3ccc(OCC4CCCO4)c(Cl)c3)ncn2)c(OC)cc1N(C)CCN(C)C] | N-(5-(6-(3-chloro-4-(tetrahydrofuran-2-ylmethoxy)-phenylamino)-pyrimidin-4-ylamino)-2-((2-dimethylamino-ethyl)-methyl-amino)-4-methoxyl-phenyl)-acrylamide | $^1$H-NMR (DMSO-d6) δ: 1.71-2.03 (4H, m), 2.20 (6H, s), 2.34 (2H, br), 2.71 (3H, s), 2.87 (2H, br), 3.66-3.71 (1H, m), 3.78-3.83 (4H, m), 3.94-4.00 (2H, m), 4.14-4.18 (1H, m), 5.75 (1H, dd), 5.84 (1H, s), 6.23 (1H, dd), 6.40 (1H, dd), 7.00 (1H, s), 7.06 (1H, d), 7.34 (1H, dd), 7.73 (1H, d), 8.16 (1H, s), 8.30 (1H, s), 8.38 (1H, s), 9.10 (1H, s), 10.09 (1H, s). m/z: ESI MH+ 596.3 |
| 255 | 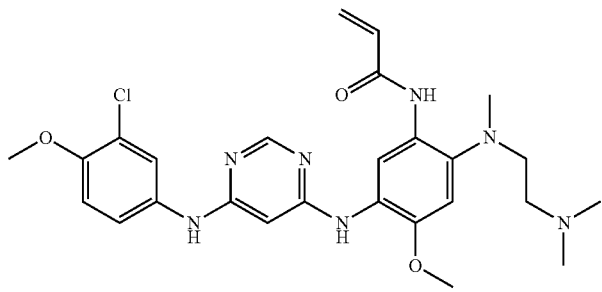 | N-(5-(6-(3-cyano-4-methoxyphenylamino)-pyrimidin-4-yl-amino)-2-((2-dimethylamino-ethyl)-methyl-amino)-4-methoxyl-phenyl)-acrylamide | $^1$H-NMR (DMSO-d6) δ: 2.20 (6H, s), 2.34 (2H, br), 2.71 (3H, s), 2.87 (2H, br), 3.80 (3H, s), 3.87 (3H, s), 5.75 (1H, dd), 5.85 (1H, s), 6.23 (1H, dd), 6.40 (1H, dd), 7.01 (1H, s), 7.18 (1H, d), 7.70 (1H, dd), 7.99 (1H, d), 8.18 (1H, s), 8.35 (1H, s), 8.38 (1H, s), 9.15 (1H, s), 10.10 (1H, s). m/z: ESI MH+ 517.2 |
| 256 | 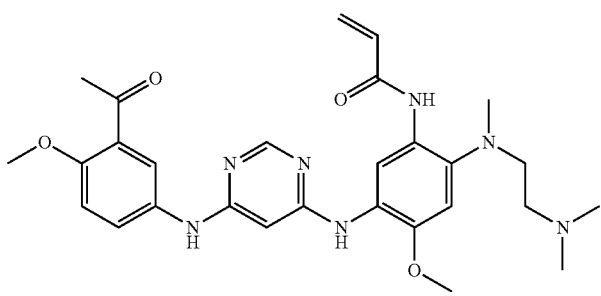 | N-(5-(6-(3-acetyl-4-methoxyphenylamino)-pyrimidin-4-yl-amino)-2-((2-dimethylamino-ethyl)-methyl-amino)-4-methoxyl-phenyl)-acrylamide | $^1$H-NMR (DMSO-d6) δ: 2.22 (6H, s), 2.34 (2H, br), 2.53 (3H, s), 2.71 (3H, s), 2.87 (2H, br), 3.80 (3H, s), 3.86 (3H, s), 5.75 (1H, dd), 5.84 (1H, s), 6.23 (1H, dd), 6.40 (1H, dd), 7.00 (1H, s), 7.11 (1H, d), 7.68 (1H, d), 7.75 (1H, dd), 8.13 (1H, s), 8.26 (1H, s), 8.39 (1H, s), 9.00 (1H, s), 10.09 (1H, s). m/z: ESI MH+ 534.3 |

Test Examples Determination of Activity of Compounds

Test Example 1

Determination of 50% Growth Inhibition (GI50) In Vitro of the Present Compounds in EGFR Wild Type and Mutant Cell Lines or HER2/ErbB2 Positive Tumor Cell Lines Experimental Materials and Methods 1. Tumor Cell Lines and Cell Culture Tumor cell lines are effective cell models to study the inhibition of tumor cell growth or prolifreation in vitro. Some typical tumor cell lines were selected to determine activity of the present compounds. All of the cell lines used in the experiment were purchased from ATCC and the Cell Bank of Chinese Academy of Sciences, respectively. Cell culture conditions and methods were carried out according to requirements of each cell line. Each cell line in vitro culture shall not exceed three passages. Monoclonal cell isolation and identification can be carried out for cell lines as required.

RPMI1640 (Gibco), MEM (Gibco), McCOY'SS5A (Gibco) and IMDM (Gibco) were selected as cell culture medium. The complete medium was prepared by supplement with 5~20% fetal calf serum (Gibco), 1% double-antibiotics (10000 units/mL penicillin and 10000 units/mL), 2 mM glutamine or 1 mM sodium pyruvate, respectively.

(1) EGFR Wild Type (WT) or Mutant Tumor Cell Lines

EGFR wild type cell lines: human epidermal cancer cell line A431 (EGFR WT, amplification and high expression, from Shanghai Cell Bank of Chinese Academy of Sciences and ATCC), NSCLC cell lines NCI-H460 (EGFR WT, Kras G61H and PI3KCA E545K mutants, ATCC) and NCI-H1299 (EGFR WT, ATCC), melanoma cell line A375 (EGFR WT and BRAF V600E mutant, from Shanghai Cell Bank of Chinese Academy of Sciences, ATCC), human lung cancer cell line NCI-H292 (EGFR WT, from human lung mucoepidermoid carcinoma/lymphatic metastasis, purchased from Shanghai Cell Bank of Chinese Academy of Sciences) were cultured with 1×RPMI1640 complete medium which was supplement with 10% FBS. NSCLC cell line A549 (EGFR WT and Kras G12S mutant, from Shanghai Cell Bank of Chinese Academy of Sciences) was cultured with 1×Ham'S F12K complete medium which was supplement with 10% FBS, 1% double-antibiotics and 2 mM glutamine.

EGFR mutant cell lines: Both NSCLC cell lines PC-9 (ATCC) and HCC827 (Shanghai Cell Bank of Chinese Academy of Sciences) have EGFR exon19 (E746-A750) deletion. Two cell lines are sensitive to the first-generation EGFR PTK inhibitor treatment. NSCLC cell line NCI-H1975 expresses EGFR L858R/T790M (ATCC) and is the first-generation EGFR inhibitor resistance. PC-9ER is an acquired Erlotinib resistance cell line of PC-9 cells developed by the investor. In this cell line, EGFR is the mutant type of delE746-A750/T790M, and the first-generation EGFR inhibitor resistance. The four cell lines above were cultured with 1×RPMI1640 complete medium (supplement with 10% FBS). Human colon cancer cell line SW48 (EGFR G719S positive, ATCC). was cultured with L15 complete medium (10% FB S).

(2) Cell Lines with HER2 Amplification and High Expression or Mutation

Human gastric cancer cell line NCI-N87 (ATCC), human breast cancer cell line ZR-75-30 (ATCC), human adenocarcinoma cell line AU565 (ATCC), human lung squamous cell carcinoma cell line NCI-H2170 (ATCC) and human breast cancer cell line HCC1954 (a both HER2/ERB2 selective reversible inhibitor Lapatinib and anti-HER2 McAb Herceptin resistant cell line) were cultured with 1×RPMI1640 complete medium (10% FBS), respectively. Human lung adenocarcinoma cell line Calu-3 (ATCC) was cultured with 1×MEM complete medium (10% FBS, 1% double-antibiotics, 1% NEAA (Gibco), 2 mM glutamine and 1 mM of sodium pyruvate). Human breast cancer cell line SK-BR-3 was cultured with McCOY'S5A complete medium (10% FBS). Human colon cancer cell line SNU1040 (HER2 V777M positive) (ATCC) and human bronchoalveolar adenocarcinoma cell line NCI-H1781 (expressing HER2 exon 20 G776VC mutation) (ATCC) were cultured with 1×RPMI1640 complete medium (10% FBS), respectively.

(3) Tumor Cell Lines with MET Gene Amplification

Human gastric cancer cell line MKN-45 (ATCC) and NSCLC cell line NCI-H1993 (ATCC) were cultured with 1×RPMI1640 complete medium which was supplement with 10% FBS, respectively.

(4) Tumor Cell Lines Expressing ALK Fusion and Mutant Genes

Human NSCLC cell line NCI-H2228 (ATCC) (EML4-ALK positive) and human ALCL cell line Karpas-299 (ATCC) (NPM-ALK positive) were cultured with 1×RPMI1640 complete medium (supplement with 10% FBS), respectively. Neuroblastoma cell line SH-SY5Y (ALK F1174L positive) (Shanghai Cell Bank of Chinese Academy of Sciences) was cultured with MEM complete medium (supplement with 10% FBS, 1% NEAA, 1% double-antibiotics and 1 mM of sodium pyruvate).

(5) BCR-ABL Positive Cell Line

Human leukemia cell line K562 (expressing BCR-ABL fusion protein) (ATCC) was cultured with 1×RPMI1640 complete medium (supplement with 10% FBS).

(6) FLT3-ITD Positive Cell Line

FLT3 is a kind of PTK and about 20-30% of patients with acute myelocytic leukemia (AML) in clinic express FLT3-ITD mutation protein. FLT3-ITD positive cell line MV4-11 was cultured with 1×RPMI1640 complete medium (supplement with 10% FBS).

(7) Jak2 V617F Positive Cell Line

Jak2 is a kind of non-receptor PTK (Janus Kinase 2) with great significance in cell growth, differentiation and transformation. Jak2 gene mutation often leads to bone marrow hyperplasia and transformation. Especially Jak2 V167F mutation is common for clinical patients. Human erythroleukemia cell line HEL expressing Jak2 V167F was cultured with 1×RPMI1640 complete medium (supplement with 10% FBS).

(8) Brutons Protein Tyrosine Kinase (BTK) Positive Cell Line

RAMOS is human B lymphocytic leukemia cell line positively expressing BTK. It was cultured with 1×RPMI1640 complete medium (supplement with 10% FBS).

(9) c-Kit Positive Cell Line

Kasumi-1 is a leukemia cell line positively expressing c-Kit N822K mutant Abnormal variation of c-Kit often appears in cancer patients. Kasumi-1 cell line was cultured with 1×RPMI1640 complete medium (supplement with 10% FBS).

(10) Cell Lines with FGFR1 or FGFR2 Amplification

Human NSCLC cell line NCI-H1581(ATCC) contains FGFR1 gene amplification and high expression. Human gastric cancer cell line SNU-16(ATCC) contains FGFR2 gene amplification and high expression. They were cultured with 1×RPMI1640 complete medium (10% FBS), respectively.

2. Drug Treatment

Adherent cells were digested with 0.25% pancreatin-EDTA (Gibco). The suspension cells were collected by centrifugation. The supernatant was discard and the cell pellet was resuspended and counted. Different cell concentrations ($5~10 \times 10^4$ cells/mL) were prepared according to the growth cycle of each cell line and then seeded on a 96-well plate (Corning), 100 µL/well. The cells were incubated over night at 37° C., 5% $CO_2$. The compounds were added to the cells on the second day with 2 wells in parallel. The final concentration of organic solvent shall not exceed 1%. The cells were continually incubated for 72 h, and then subjected to MTT assay.

The present compounds and the reference compounds were dissolved with DMSO (Sigma), respectively. The purity of compound was more than 98%. The storage concentration of compounds was 10 mM and kept at −20° C. They were diluted by 2 times or 10 times with serial dilution before using.

3. MTT assay and GI50 Calculation

Dojindo CCK8 reagent kit was used as MTT assay. THERMO MULTISKAN FC meter was used as microplate reader.

Adherent cell culture medium was discard and immediately replaced with fresh prepared medium which contains 10% CCK8 reagent (100 µL/well). For the suspension cells, CCK8 was directly added to 10% of the final concentration. The cells were continually incubated for 1~4 h. When the color of control wells turned to dark yellow, the absorption value was measured at OD450 nm. The cell growth rate was calculated according to the following formula: cell growth rate (%)=$100*(T-T_0)/(C-T_0)$, T=optical density of drug treatment cell well—optical density of blank control well; T0=optical density of cell well before drug treatment— optical density of blank control well; C=optical density of cell well of solvent control group—optical density of blank control well. The concentration value of 50% inhibition of cell growth (GI50) was calculated. The experiment was independently repeated 1~3 times, and subject to biological statistical analysis.

Experiment Results

The results of this study are summarized in Table 12 and Table 13 that 50% growth inhibition (or cell apoptosis) of the present compounds was tested in the selected wild type or mutant EGFR cell lines as well as HER2/ErbB2 positive cell lines. The growth inhibitory activity of the present compounds will be stronger when GI50 value shows smaller. If the present compound has a small GI50 value in the mutant EGFR cells (e.g. H1975, PC9, PC9ER and HCC827) and a big GI50 value in the WT EGFR cells such as A431, A549, H460 and H1299, or a big ratio of WT EGFR GI50 to mutant EGFR GI50, this indicates that the compound has more selective for mutant EGFR than WT EGFR.

TABLE 12

Range of GI50
++++: <10 nM; +++: 10~100 nM; ++: 100~1000 nM; +: >1000 nM; nd: not determined

| Comp. | EGFR mutant cell line | | | | HER2 positive cell line | | | EGFR wild type cell line | | | |
|---|---|---|---|---|---|---|---|---|---|---|---|
| | H1975 | PC9ER | PC-9 | HCC827 | N87 | AU-565 | SK-BR-3 | A431 | A549 | H460 | H1299 |
| 1 | +++ | +++ | +++ | ++++ | +++ | +++ | +++ | ++ | + | + | + |
| 2 | +++ | ++++ | ++++ | ++++ | ++++ | +++ | +++ | ++ | + | + | + |
| 3 | +++ | ++++ | ++++ | ++++ | +++ | +++ | +++ | ++ | + | + | + |
| 8 | +++ | ++++ | +++ | +++ | +++ | ++ | +++ | ++ | + | + | + |
| 13 | +++ | +++ | +++ | +++ | +++ | +++ | +++ | ++ | + | + | + |
| 14 | ++ | ++ | +++ | +++ | ++ | ++ | ++ | + | + | + | + |
| 16 | +++ | +++ | +++ | +++ | ++ | ++ | ++ | + | + | + | + |
| 18 | +++ | ++++ | +++ | +++ | +++ | +++ | +++ | ++ | + | + | + |
| 19 | ++++ | ++++ | ++++ | ++++ | +++ | +++ | +++ | ++ | + | + | + |
| 28 | +++ | +++ | +++ | +++ | +++ | +++ | +++ | ++ | + | + | + |
| 31 | +++ | ++++ | +++ | +++ | ++ | ++ | ++ | ++ | + | + | + |
| 32 | +++ | ++++ | +++ | +++ | +++ | +++ | ++ | ++ | + | + | + |
| 57 | +++ | +++ | ++ | +++ | ++ | ++ | ++ | ++ | + | + | + |
| 58 | +++ | +++ | +++ | +++ | ++ | ++ | ++ | ++ | + | + | + |
| 59 | +++ | +++ | +++ | +++ | ++ | ++ | ++ | ++ | + | + | + |
| 60 | ++ | ++ | ++ | ++ | ++ | ++ | ++ | + | + | + | + |
| 61 | ++++ | ++++ | +++ | +++ | ++ | ++ | ++ | ++ | + | + | + |
| 62 | +++ | +++ | +++ | ++++ | +++ | +++ | +++ | ++ | + | + | + |
| 63 | +++ | +++ | ++++ | ++++ | +++ | ++ | ++ | ++ | + | + | + |
| 77 | +++ | +++ | ++ | ++ | ++ | ++ | ++ | ++ | + | + | + |
| 78 | ++++ | +++ | +++ | +++ | ++++ | +++ | +++ | ++ | + | + | + |
| 83 | ++++ | +++ | +++ | ++++ | +++ | ++ | ++ | ++ | + | + | + |
| 98 | +++ | +++ | +++ | +++ | +++ | ++ | +++ | ++ | + | + | + |
| 99 | ++++ | ++++ | +++ | +++ | ++++ | +++ | +++ | ++ | + | + | + |
| 103 | +++ | +++ | +++ | +++ | +++ | ++ | ++ | ++ | + | + | + |
| 106 | +++ | +++ | +++ | +++ | +++ | +++ | +++ | ++ | + | + | + |
| 107 | +++ | +++ | +++ | +++ | +++ | ++ | +++ | + | + | + | + |
| 108 | +++ | ++++ | ++++ | ++++ | ++++ | +++ | +++ | ++ | + | + | + |
| 109 | +++ | +++ | +++ | +++ | +++ | +++ | +++ | ++ | + | + | + |
| 110 | +++ | ++++ | ++++ | ++++ | ++++ | +++ | +++ | ++ | + | + | + |
| 113 | +++ | ++++ | ++++ | ++++ | +++ | +++ | ++ | ++ | + | + | + |
| 114 | +++ | +++ | ++++ | ++++ | ++++ | ++++ | ++++ | ++ | + | + | + |
| 115 | +++ | ++++ | ++++ | ++++ | ++++ | +++ | ++++ | ++ | + | + | + |
| 118 | ++++ | ++++ | ++++ | ++++ | ++++ | ++++ | +++ | ++ | nd | nd | nd |
| 119 | ++++ | nd | ++++ | ++++ | ++++ | ++++ | +++ | ++ | nd | nd | nd |
| 126 | ++++ | nd | ++++ | ++++ | ++++ | ++++ | +++ | ++ | nd | nd | nd |
| 130 | +++ | nd | +++ | ++++ | ++++ | ++++ | +++ | ++ | nd | nd | nd |
| 133 | ++++ | ++++ | ++++ | ++++ | ++++ | ++++ | ++++ | +++ | + | + | + |
| 134 | +++ | +++ | ++++ | ++++ | +++ | +++ | +++ | ++ | + | + | + |
| 135 | ++++ | ++++ | ++++ | ++++ | +++ | ++++ | ++++ | +++ | + | + | + |
| 136 | +++ | ++++ | +++ | +++ | +++ | +++ | +++ | ++ | + | + | + |
| 139 | +++ | ++++ | ++++ | ++++ | ++++ | ++++ | ++++ | ++ | + | + | + |
| 140 | ++++ | ++++ | ++++ | ++++ | ++++ | ++++ | ++++ | +++ | + | + | + |
| 143 | ++++ | ++++ | ++++ | ++++ | ++++ | ++++ | ++++ | +++ | + | + | + |
| 144 | ++++ | ++++ | ++++ | ++++ | ++++ | ++++ | ++++ | +++ | + | + | + |
| 145 | +++ | ++++ | ++++ | ++++ | ++++ | +++ | +++ | +++ | + | + | + |
| 147 | ++++ | ++++ | ++++ | ++++ | ++++ | ++++ | ++++ | +++ | + | + | + |
| 148 | ++++ | ++++ | ++++ | ++++ | +++ | ++++ | ++++ | +++ | + | + | + |
| 150 | ++++ | ++++ | ++++ | ++++ | +++ | ++++ | ++++ | +++ | + | + | + |
| 165 | ++ | +++ | ++++ | +++ | ++ | ++ | ++ | +++ | + | + | + |
| 176 | +++ | +++ | ++++ | ++++ | +++ | ++ | +++ | ++ | + | + | + |
| 178 | +++ | +++ | ++++ | ++++ | +++ | ++ | ++ | ++ | + | + | + |
| 179 | +++ | +++ | ++++ | ++++ | +++ | +++ | +++ | ++ | + | + | + |
| 181 | +++ | ++++ | ++++ | ++++ | +++ | +++ | +++ | ++ | + | + | + |
| 182 | +++ | +++ | +++ | +++ | ++ | +++ | +++ | ++ | + | + | + |
| 183 | +++ | +++ | ++++ | ++++ | +++ | +++ | +++ | ++ | + | + | + |
| 186 | +++ | +++ | +++ | +++ | +++ | +++ | +++ | ++ | + | + | + |
| 188 | +++ | ++++ | ++++ | ++++ | +++ | +++ | ++++ | ++ | + | + | + |

TABLE 12-continued

Range of GI50
++++: <10 nM; +++: 10~100 nM; ++: 100~1000 nM; +: >1000 nM; nd: not determined

| Comp. | EGFR mutant cell line | | | | HER2 positive cell line | | | EGFR wild type cell line | | | |
|---|---|---|---|---|---|---|---|---|---|---|---|
|  | H1975 | PC9ER | PC-9 | HCC827 | N87 | AU-565 | SK-BR-3 | A431 | A549 | H460 | H1299 |
| 191 | ++++ | ++++ | ++++ | ++++ | ++++ | +++ | ++++ | ++ | + | + | + |
| 193 | +++ | +++ | ++++ | ++++ | ++ | ++ | + | + | + | + | + |

TABLE 13

| Comp. | Range of GI50 | | | |
|---|---|---|---|---|
|  | H1975 (EGFR L858R/T790M) | PC-9 (EGFR dE746-A750) | N87 (HER2 Amp) | A549 (EGFR WT) |
| 203 | ++++ | ++++ | ++++ | + |
| 204 | +++ | +++ | ++++ | + |
| 205 | ++++ | ++++ | ++++ | + |
| 206 | ++ | ++ | ++ | + |
| 207 | +++ | +++ | +++ | + |
| 208 | ++ | ++ | +++ | + |
| 211 | +++ | ++++ | ++++ | + |
| 212 | ++++ | ++++ | ++++ | + |
| 213 | ++++ | ++++ | ++++ | + |
| 214 | +++ | +++ | +++ | + |
| 215 | +++ | ++++ | +++ | + |
| 216 | ++++ | ++++ | ++++ | + |
| 218 | +++ | ++++ | +++ | + |
| 219 | +++ | ++++ | +++ | + |
| 222 | +++ | ++++ | +++ | + |
| 223 | +++ | +++ | +++ | + |
| 224 | +++ | ++++ | +++ | + |
| 225 | +++ | +++ | +++ | nd |
| 226 | +++ | ++++ | +++ | + |
| 227 | ++ | ++++ | +++ | + |
| 228 | +++ | ++++ | +++ | + |
| 229 | +++ | ++++ | ++++ | + |
| 230 | +++ | ++++ | ++++ | + |
| 231 | +++ | ++++ | ++++ | + |
| 232 | +++ | ++++ | ++++ | + |
| 233 | +++ | ++++ | ++++ | + |
| 234 | +++ | +++ | +++ | + |
| 235 | +++ | +++ | +++ | + |
| 236 | ++++ | ++++ | ++++ | + |
| 237 | +++ | +++ | +++ | + |
| 238 | ++ | ++ | ++ | + |
| 239 | +++ | ++++ | +++ | + |
| 240 | +++ | ++++ | ++++ | + |
| 241 | ++ | ++ | ++ | + |
| 242 | ++++ | ++++ | ++++ | + |
| 243 | +++ | +++ | +++ | + |
| 244 | +++ | +++ | +++ | + |
| 245 | +++ | +++ | +++ | + |
| 246 | +++ | +++ | +++ | + |
| 247 | +++ | ++++ | ++++ | + |
| 248 | +++ | ++++ | ++++ | + |
| 249 | +++ | ++++ | ++++ | + |
| 250 | +++ | ++++ | ++++ | + |
| 251 | ++++ | ++++ | ++++ | + |
| 252 | +++ | +++ | +++ | + |
| 253 | +++ | +++ | +++ | + |
| 254 | +++ | +++ | +++ | + |
| 255 | +++ | +++ | +++ | + |
| 256 | +++ | +++ | +++ | + |

++++: <10 nM;
+++: 10~100 nM;
++: 100~1000 nM;
+: >1000 nM;
nd: not determined

The results of Table 12 and Table 13 show that the present compounds have significant growth inhibition activity in EGFR mutation cell lines H1975, PC9ER, PC-9 and HCC827, and HER2/ErbB2 amplification cell lines N87, AU565 and SK-BR-3. The GI50 value can be less than 10 nM. However, for most of wild type EGFR cell lines A539, H460 and H1299, the GI50 value is over 1000 nM. Even in human epidermoid carcinoma A431 cells, a wild type EGFR amplification/high expression cell line, the present compounds have relatively weak growth inhibition activity compared to activing or T790M EGFR mutation cells.

Test Example 2

Determination of the GI50 Values of the Present Compounds in Different Oncogene Expression Tumor Cell Lines Firstly, nine compounds of the present invention (2, 18, 19, 106, 114, 118, 140, 147 and 183) were selected and AZD9291, a third-generation EGFR inhibitor, was adopted for reference. Growth inhibition assay was conducted in the cell lines shown Table 14 with the different oncogene mutations. Each compound started at 1000 nM as an initial concentration and was diluted by 2 times with serial dilution to 0.03 nM. The GI50 value of each compound was calculated according to Test Example 1.3. The results are shown in Table 14.

Reference compound AZD9291 was synthesized in accordance with the method in WO2013/014448 A1.

TABLE 14

| Cell line | Gene type | | Compound (GI50 nM) | | | | | | | | |
|---|---|---|---|---|---|---|---|---|---|---|---|
|  | EGFR | Others | AZD9291 | 18 | 19 | 2 | 106 | 114 | 118 | 140 | 147 | 183 |
| H1975 | L858R/T790M |  | 15.6 | 14.6 | 4.9 | 14.6 | 15.2 | 10 | 9.4 | 3.8 | 4.6 | 12.5 |
| PC-9 | dE746-A750 |  | 13.9 | 14.5 | 7.3 | 5.4 | 15.6 | 2 | 2.38 | 0.38 | 0.58 | 3.38 |
| HCC827 | dE746-A750 |  | 15.6 | 9.4 | 6.4 | 2.3 | 12.6 | 1.1 | 2.3 | 1.1 | 4.7 | 9 |
| N87 | wt | Her2 amp | 234 | 19.5 | 19.5 | 10 | 23.6 | 4.8 | 4.8 | 4.8 | 4.8 | 19.5 |
| AU565 | wt | Her2 amp | 312 | 15.6 | 17.5 | 15.4 | 19.5 | 10 | 4.8 | 2.6 | 2.6 | 19.5 |
| SK-BR-3 | wt | Her2 amp | 643. | 39.1 | 39.1 | 19.5 | 101 | 4.8 | 29.2 | 5.6 | 5.6 | 78.1 |

TABLE 14-continued

| Cell line | Gene type | | Compound (GI50 nM) | | | | | | | | |
|---|---|---|---|---|---|---|---|---|---|---|---|
| | EGFR | Others | AZD9291 | 18 | 19 | 2 | 106 | 114 | 118 | 140 | 147 | 183 |
| H2170 | wt | Her2 amp | 117 | 19.5 | 14.6 | 12.6 | 9.4 | 4.8 | 6.8 | 4.8 | 4.8 | 12.5 |
| ZR-75-30 | wt | Her2 amp | 31 | 2.1 | 2.1 | 6 | 12 | 1.1 | 2.6 | 1.5 | 1.5 | 6 |
| Calu-3 | wt | Her2 amp | 686 | 23.4 | 19.5 | 31.2 | nd | 7.2 | 14.6 | 12.5 | 12.5 | 23.4 |
| HCC1954 | wt | Her2 amp | >1000 | 312 | 312 | 375 | 375 | 37.5 | 37.5 | 26.5 | 26.5 | 156 |
| A431 | wt | | 468 | 438 | 625 | 156 | 498 | 117 | 156 | 37.5 | 37.5 | 315 |
| H292 | wt | | >1000 | >1000 | >1000 | >1000 | >1000 | >1000 | >1000 | >1000 | >1000 | >1000 |
| A549 | wt | Kras G12S | >1000 | >1000 | 978 | >1000 | >1000 | >1000 | nd | >1000 | 896 | >1000 |
| H460 | wt | Kras G61H | >1000 | >1000 | >1000 | >1000 | >1000 | >1000 | nd | >1000 | >1000 | >1000 |
| H1299 | wt | Nras Q61K | >1000 | >1000 | >1000 | >1000 | >1000 | >1000 | nd | >1000 | >1000 | >1000 |
| HCT116 | wt | Kras G13D | >1000 | >1000 | >1000 | >1000 | >1000 | >1000 | >1000 | >1000 | >1000 | >1000 |
| A375 | wt | BRAF V600E | >1000 | >1000 | >1000 | >1000 | >1000 | 465 | 465 | >1000 | >1000 | >1000 |
| MKN-45 | wt | Met amp | >1000 | >1000 | 500 | >1000 | >1000 | 465 | 465 | >1000 | >1000 | 500 |
| H1993 | wt | Met amp | >1000 | >1000 | >1000 | >1000 | >1000 | >1000 | nd | >1000 | >1000 | >1000 |
| H2228 | wt | EML4-ALK | >500 | >500 | >500 | >500 | >500 | >500 | >500 | >500 | >500 | >500 |
| Karpas-299 | wt | NPM-ALK | >1000 | >1000 | 500 | 500 | >1000 | >1000 | 500 | >1000 | >1000 | >1000 |
| SH-SY5Y | wt | ALK F1174L | >1000 | >1000 | >1000 | >1000 | >1000 | >1000 | nd | >1000 | >1000 | >1000 |
| Kasumi-1 | | Kit N822K | >1000 | >1000 | >1000 | >1000 | >1000 | <100 | <100 | >1000 | >1000 | >1000 |
| Ramos | | BTK | 937 | 937 | nd | 234 | 234 | 96.6 | 148 | 58.6 | 46.8 | 78.1 |
| MV4-11 | | FLT3-ITD | >1000 | >1000 | >1000 | >1000 | >1000 | 124 | 156 | >1000 | >1000 | >1000 |
| K562 | | BCR-ABL | >1000 | >1000 | >1000 | >1000 | >1000 | >1000 | >1000 | >1000 | >1000 | >1000 |
| HEL | | Jak2 V167F | >1000 | >1000 | >1000 | >1000 | >1000 | >1000 | >1000 | >1000 | >1000 | >1000 |
| H1581 | wt | FGFR1 amp | >1000 | >1000 | >1000 | >1000 | >1000 | >1000 | >1000 | >1000 | >1000 | >1000 |
| SNU-16 | wt | FGFR2 amp | >1000 | >1000 | >1000 | >1000 | >1000 | >1000 | >1000 | >1000 | >1000 | >1000 |

The results show that the present compounds have selectively high growth inhibition activity in EGFR mutation cell lines H1975, PC-9 and HCC827 as well as HER2/ErbB2 amplification cell lines (N87, AU565, SK-BR-3, H2178, ZR-75-30, Calu-3 and HCC1954). GI50 is less than 20 nM. A relatively high GI50 is required to show obvious inhibition effect on EGFR WT overexpressed cell line A431. However, in most EGFR normal expressed cell lines, they show little, if any, inhibition effect. The activity of the present compounds against ErbB2 positive cells is much higher than that of reference compound AZD9291. Except that compounds 114, 118, 140, 147 and 183 have moderate inhibition effects on the FLT3-ITD$^+$ MV4-11 and BTK$^+$ Ramos cells, the present compounds show little, if any, inhibition effects on other oncogene positive cell lines.

Test Example 3

Comparison of the Inhibition Activity (GI50) of the Present Compounds in EGFR Wild Type and Mutant Tumor Cell Lines Furthermore, the present compounds (99, 136, 205, 211, 212, 213, 216, 229, 230, 231, 232, 233 and 236) were selected to carry out growth inhibition test for some tumor cell lines which express wild type and mutation EGFR. AZD9291, an EGFR third-generation inhibitor, was used for reference (AZD9291 was synthesized in accordance with method A1 in WO2013/014448).

Each compound started at 1000 nM as an initial concentration and was diluted by 1 times with serial dilution to 0.03 nM. The GI50 value of each compound was calculated according to Test Example 1.3. The results are shown in Table 15.

TABLE 15

| | GI50 (nM) | | | | |
|---|---|---|---|---|---|
| Compound | A549 (EGFR WT) | H292 (EGFR WT) | H1975 (EGFR L858R/T790M) | PC-9 (EGFR dE746-A750) | SW48 (EGFR G719S) |
| AZD9291 | >1000 | >1000 | 15.6 | 13.9 | 156.25 |
| 99 | >1000 | >1000 | 9.25 | 14.1 | nd |
| 136 | >1000 | >1000 | 10.14 | 10.46 | nd |
| 205 | >1000 | >1000 | 4.9 | 7.81 | nd |
| 211 | >1000 | >1000 | 19.6 | 7.89 | nd |
| 212 | >1000 | >1000 | 8.56 | 6.82 | nd |
| 213 | >1000 | >1000 | 9.8 | 7.83 | nd |
| 216 | >1000 | >1000 | 8.96 | 9.87 | nd |
| 229 | >1000 | >1000 | 19.15 | 0.98 | 4.92 |
| 230 | >1000 | >1000 | 18.97 | 0.37 | 5.87 |
| 231 | >1000 | >1000 | 19.5 | 0.19 | 3.13 |
| 232 | >1000 | >1000 | 16.95 | 2.43 | 4.87 |
| 233 | >1000 | >1000 | 19.2 | 0.49 | 4.19 |
| 236 | >1000 | >1000 | 3.88 | 1.49 | 4.23 |

The results show that the present compounds have high inhibition activities against H1975, PC-9 and SW48 cell lines (GI50<20 nM), while little, if any, inhibition on cell lines A548 and H292 which express wild type EGFR, even at 1000 nM.

Test Example 4

Comparison of the Inhibition Activity (GI50) of the Present Compounds on the Growth of Tumor Cells with HER2 Amplification/High Expression or Mutation Furthermore, the present compounds (99, 136, 205, 211, 212, 213, 216, 229, 230, 231, 232, 233 and 236) were selected to carry out growth inhibition test for HER2/ERBB2 gene amplified or high expressed or mutant tumor cells. Afatinib and AZD9291 were used for references as second- and third-generation inhibitors of EGFR.

Afatinib was synthesized according to the method in U.S. Pat. No. 6,251,912.

Each compound started at 1000 nM as an initial concentration and was diluted by 2 times with serial dilution to 0.03 nM. The GI50 value of each compound was calculated according to Test Example 1.3. The results are shown in Table 16.

TABLE 16

| Compound | GI50 (nM) | | | |
|---|---|---|---|---|
| | N87 (HER2 amp) | Calu3 (HER2 amp) | H1781 (HER2 G776VC) | SNU-1040 (HER2 V777M) |
| AZD9291 | 219.2 | 657 | 195 | 156.2 |
| Afatinib | 1.25 | 2.62 | 1.17 | 79.1 |
| 99 | 1.35 | 3.26 | 1.92 | 19.53 |
| 136 | 11.25 | 14.68 | 7.32 | 16.2 |
| 205 | 5.61 | 7.88 | 1.52 | 14.28 |
| 211 | 6.76 | nd | 31.5 | nd |
| 212 | 2.67 | nd | 15.6 | nd |
| 213 | 1.95 | nd | 15.6 | nd |
| 216 | 19.53 | nd | 19.53 | nd |
| 229 | 1.95 | 1.26 | 0.95 | 10.3 |
| 230 | 3.9 | 2.67 | 1.91 | 13.2 |
| 231 | 4.21 | 5.6 | 1.79 | 6.75 |
| 232 | 1.92 | 2.49 | 1.02 | 6.82 |
| 233 | 0.95 | 0.98 | 0.87 | 7.21 |
| 236 | 0.82 | 1.46 | 0.96 | 5.42 |

The results show that the present compounds used in the experiment have significant inhibition activity in HER2 amplified/overexpressed or mutant tumor cells. Their inhibitory activities are in the same range with that of Afatinib, but are much stronger than that of AZD9291.

Test Example 5

In Vivo Tumor Growth Inhibition Experiment

Tumor xenograft models of immunodeficient mice are an effective tool to test the antitumor activity of the compound in vivo. Generally, the effectiveness of human tumor cell xenograft is positively correlated with the clinical treatment of human tumor. Bab/c immunodeficient mouse is one of the most commonly used xenograft animals with human tumor cells. In order to test whether the present compounds can inhibit the in vivo growth of the tumor cells expressing EGFR mutantion or HER2/ErbB2 overexpression, H1975, PC-9 and NCI-N87 cell lines were used in the experiments. When H1975, PC-9 and NCI-N87 cells were in growth logarithmic phase, they were digested with pancreatin. An appropriate amount of 1×RPMI1640 culture medium (serum-free) was added to stop digestion. The cells were collected to a 50 ml centrifuge tube (Corning), and centrifuged at 1700 rm for 3 min. The supernatant was discard, then the cells were suspended with 1×RPMI1640 culture medium and count the number. 5' $10 \times 10^7$ cells/mL was prepared and then placed on ice. 5~$10 \times 10^6$ (0.2 ml) cells were inoculated subcutaneously on the right side of the back of 6~8 week old female Bab/c nude mice (about 20 g in weight). When the tumor average volume growed to 100~200 mm$^3$, the mice were randomly divide into groups (3-6 mice per group), and marked by ear pierced tags and weighted. The test compounds and the reference compound (with a purity over 99% and individual impurity not higher than 0.2%) were formulated to emulsion suspension with CM (30% polyethylene glycol 400, 0.5% Tween-80 and 2.5% propylene glycol) respectively. Intragastric administration was continued once daily at a dosage of 25 mg/kg (0.1 ml/10 g mouse). The tumor was measured 3 times per week. When the average volume of the tumor in CM control group was up to 1500 mm$^3$ or after administration for 30 days, the experiment was ended.

The volume of tumor (V) was calculated as $V=\frac{1}{2}*a*b^2$ (a represents length of tumors, b represents width of tumors). Tumor growth inhibition (TGI) was calculated as: TGI (%)=100−(VT−VT0)/(VC−VC0)*100%; where VT0 and VT are the tumor volumes of the beginning and finish days of dosed groups; and VC0 and VC are the tumor volumes of the beginning and finish days for the control group, respectively.

The results of in vivo tumor growth inhibition (TGI) of the present compounds on PC-9 and H1975 tumor cells (day 19) are shown in Table 17.

TABLE 17

| Compound | TGI (%) | |
|---|---|---|
| | H1975 | PC-9 |
| 18 | 96.72 | 98.28 |
| 63 | 98.27 | 98.3 |
| 99 | 94.60 | 95.8 |
| 115 | 59.13 | 97.1 |
| 140 | 98.37 | 97.88 |
| 176 | 98.19 | 98.6 |
| 179 | 93.57 | 98.08 |
| 183 | 97.38 | 98.8 |
| 191 | 99.33 | 98.83 |
| 205 | 99.48 | 96.54 |
| AZD9291 | 98.41 | 97.24 |

The results of in vivo tumor growth inhibition (TGI) of the present compounds in HER2/ErbB2 amplified cell line N87 (day 19) are shown in Table 18.

TABLE 18

| Compound | TGI (%) |
|---|---|
| 63 | 94.71 |
| 99 | 95.40 |
| 115 | 97.84 |
| 136 | 96.69 |
| 183 | 97.70 |
| 191 | 96.58 |
| 216 | 97.6 |
| 236 | 97.5 |
| Afatinib | 98.3 |

The results indicate that the compounds at the tested dose can effectively inhibit the growth of EGFR mutant cell lines PC-9 and H1975 as well as HER2/ErbB2 positive cell line N87 in xenograft nude mice without reducing body weight of the animals.

Test Example 6

Study of Pharmacokinetics of the Present Compounds in Rat

Sprague-Dawley (SD) rats (male) were purchased from Shanghai SIPPR BK Laboratory Animals Co. and kept under specific pathogen-free conditions adaptively for 7 days in the Shanghai University of Traditional Chinese Medicine animal care facility (All animal studies were conducted with the approval of the University Ethics Committee). The rats were randomly divided to 2 groups (3 rats/group) for each compound. One group was administrated by tail vein injection (iv) and the other group was intragastrically administrated. The compound was formulated into a clear aqueous solution with methanesulfonic acid, PH>3.5. The rats were starved for 12 hours before drug administration and the blood samples were collected from the orbital plexus at 0 min (before drug administration), 2 min, 5 min, 15 min, 30 min, 1 h, 2 h, 4 h, 6 h, 8 h and 24 h, respectively. Each blood sample was added to a 1.5 mL centrifuge tube with heparin sodium and then centrifuged at 8000 rpm at 4° C. for 3 min. Upper blood serum was collected. The compound concentration in plasma was determined by LC-MS/MS. The pharmacokinetics parameters were calculated with the professional pharmacokinetics software WinNonlin. The experiment was repeated once. The results are shown in Table 19.

TABLE 19

| Compound | 18 | 63 | 99 |
|---|---|---|---|
| Solvent | water | water | water |
| iv | 5 mg/kg | 5 mg/kg | 5 mg/kg |
| po | 25 mg/kg | 25 mg/kg | 50 mg/kg |
| SD rat | 12 | 12 | 12 |
| Bioavailability (%) | 50.3 | 55.8 | 40.9 |

The results indicate that the present compounds show good oral bioavailability in rat.

The invention claimed is:

1. A compound of formula (I), or the pharmaceutically acceptable salts thereof:

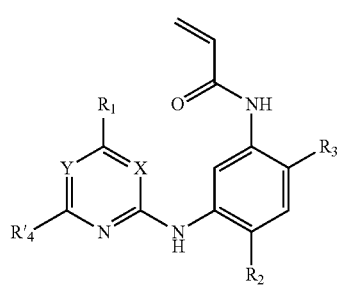

wherein:
$R_1$ is $-NR_5R_6$, X is $CR_4$, and Y is N;
$R_2$ is selected from the group consisting of alkoxy, alkylsulphanyl or $NR_6R_6$;
$R_3$ is selected from the group consisting of hydrogen, $N(R^y)(R^z)$, $-N(R^v)R^uN(R^y)(R^z)$, $-OR^uOR_6$, $-OR^uN(R^y)(R^z)$, $-SR_6$ and $-SR^uN(R^y)(R^z)$;
$R_4$ and $R'_4$ are each selected from the group consisting of hydrogen, halogen, alkyl, alkoxy, haloalkyl and cyano;
$R_5$ is optionally substituted phenyl or optionally substituted 6-membered heteroaryl; and when $R_5$ is substituted, the substituent is selected from 1-5 $R_7$ groups; wherein, each $R_7$ group is independently selected from the group consisting of hydrogen, halogen, cyano, alkyl, alkenyl, alkynyl, alkoxy, hydroxyl, haloalkoxy, haloalkyl, wherein the alkyl, alkenyl, alkynyl, or alkoxy, is optionally substituted with 1-5 groups selected from halogen, alkyl, 5- or 6-membered aryl, hydroxyl, alkoxy, haloalkoxy, cycloalkyl, ester group and cyano;
$R_6$ is selected from hydrogen and alkyl;
$R^u$ is each independently selected from the group consisting of alkylene, alkenylene and alkynylene;
$R^v$ is selected from hydrogen and alkyl;
$R^y$ and $R^z$ are each independently selected from the following a) or b):

a) $R^y$ and $R^z$ are each independently selected from the group consisting of hydrogen, alkyl, cycloalkyl, alkoxyalkyl, hydroxylalkyl, pyrrolidinyl, alkylamino or haloalkyl;

b) $R^y$ and $R^z$ form heterocyclyl or heteroaryl together with the nitrogen atoms attached to them, and the ring contains 0-4 heteroatoms independently selected from O, S and N; the ring is optionally substituted with 1-4 groups selected from hydrogen, halogen, alkyl, alkoxy, haloalkoxy, and haloalkyl.

2. The compound or the pharmaceutically acceptable salts thereof according to claim 1, wherein the compound of formula (I) is the compound of formula (IIc),

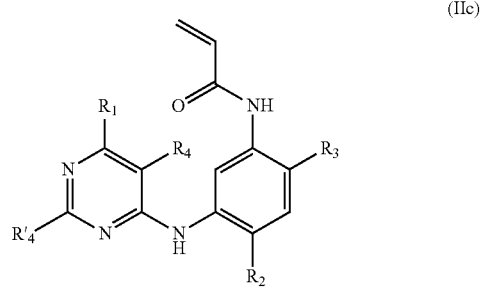

wherein,
$R_1$ is $-NR_5R_6$;
$R_2$ is alkoxy;
$R_3$ is selected from the group consisting of hydrogen, $N(R^y)(R^z)$, $-N(R^v)R^uN(R^y)(R^z)$, $-OR^uOR_6$, and $-OR^uN(R^y)(R^z)$;
$R_4$ and $R'_4$ are each selected from the group consisting of hydrogen, halogen, alkyl and haloalkyl;
$R_5$ is optionally substituted phenyl; and when $R_5$ is substituted, the substituent is selected from 1-5 $R_7$ groups; wherein each $R_7$ group is independently selected from the group consisting of hydrogen, halogen, cyano, alkyl, alkenyl, alkynyl, alkoxy, hydroxyl, haloalkoxy, haloalkyl; wherein, the alkyl, alkenyl, alkynyl, alkoxy, is optionally substituted with 1-5 groups selected from halogen, alkyl, aryl, hydroxyl, alkoxy, haloalkoxy, cycloalkyl, ester group and cyano;
$R_6$ is selected from hydrogen and alkyl;
$R^u$ is each independently selected from alkylene;
$R^v$ is selected from hydrogen and alkyl;
Ry and Rz are each independently selected from the following a) or b):

a) $R^y$ and $R^z$ are each selected from hydrogen, alkyl and haloalkyl;

b) $R^y$ and $R^z$ form heterocyclyl together with the nitrogen atoms attached to them, and the ring contains 0-4 heteroatoms independently selected from O, S and N; and the ring is optionally substituted with 1-4 groups selected from hydrogen, halogen, haloalkyl, alkyl, alkoxy, and haloalkoxy.

3. The compound or the pharmaceutically acceptable salts thereof according to claim 2, wherein the compound of formula (IIc) is the compound of formula (VII):

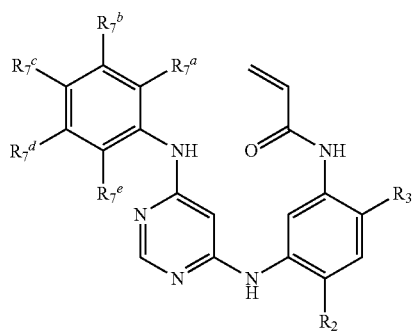

(VII)

wherein, $R_7^a$, $R_7^b$, $R_7^c$, $R_7^d$ and $R_7^e$ are identical or different from each other, and are each independently selected from the group consisting of hydrogen, halogen, cyano, alkyl, alkenyl, alkynyl, alkoxy, hydroxyl, haloalkoxy, haloalkyl, wherein, the alkyl, alkenyl, alkynyl, or alkoxy, is optionally substituted with 1-5 groups selected from the group consisting of halogen, alkyl, alkenyl, alkynyl, aryl, hydroxyl, alkoxy, haloalkoxy, cycloalkyl, ester group and cyano;

$R_2$ is selected from C1-C6 alkoxy;

$R_3$ is as defined in claim 2.

4. The compound or the pharmaceutically acceptable salts thereof according to claim 2, wherein in the compound of formula (VII):

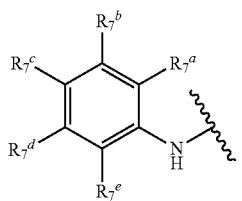

is selected from:

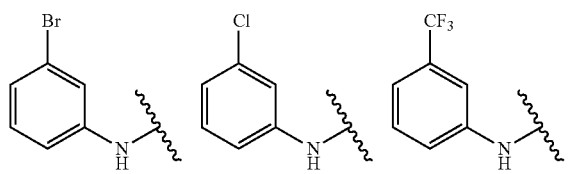

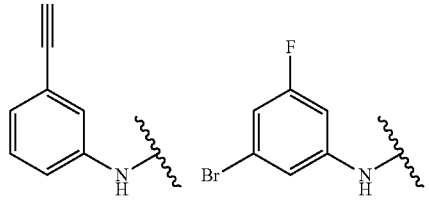

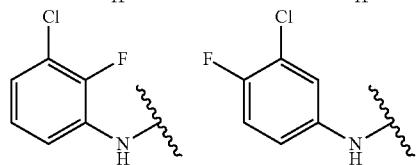

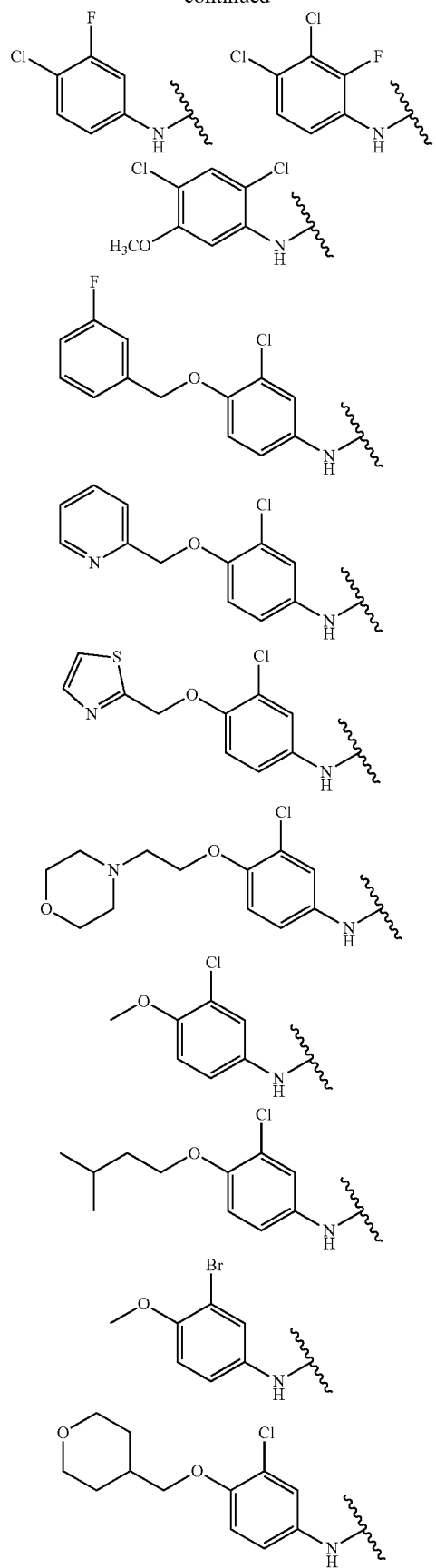

-continued
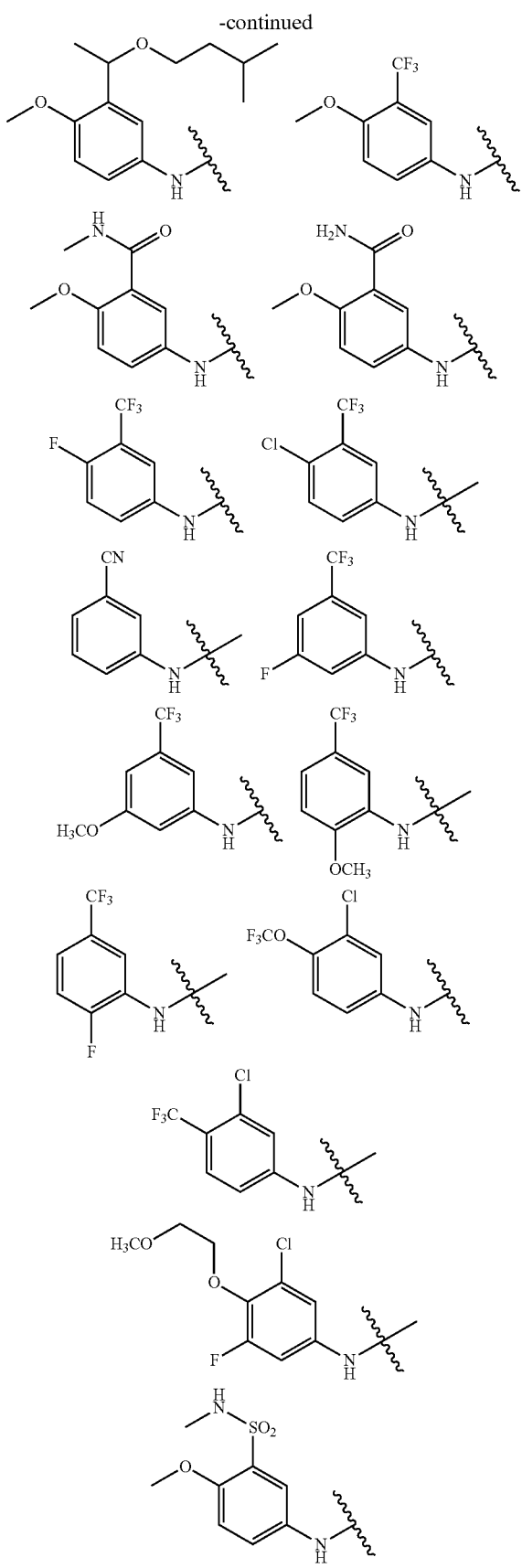
R<sub>2</sub> is C1-C6 alkoxy;
R$_3$ is selected from:
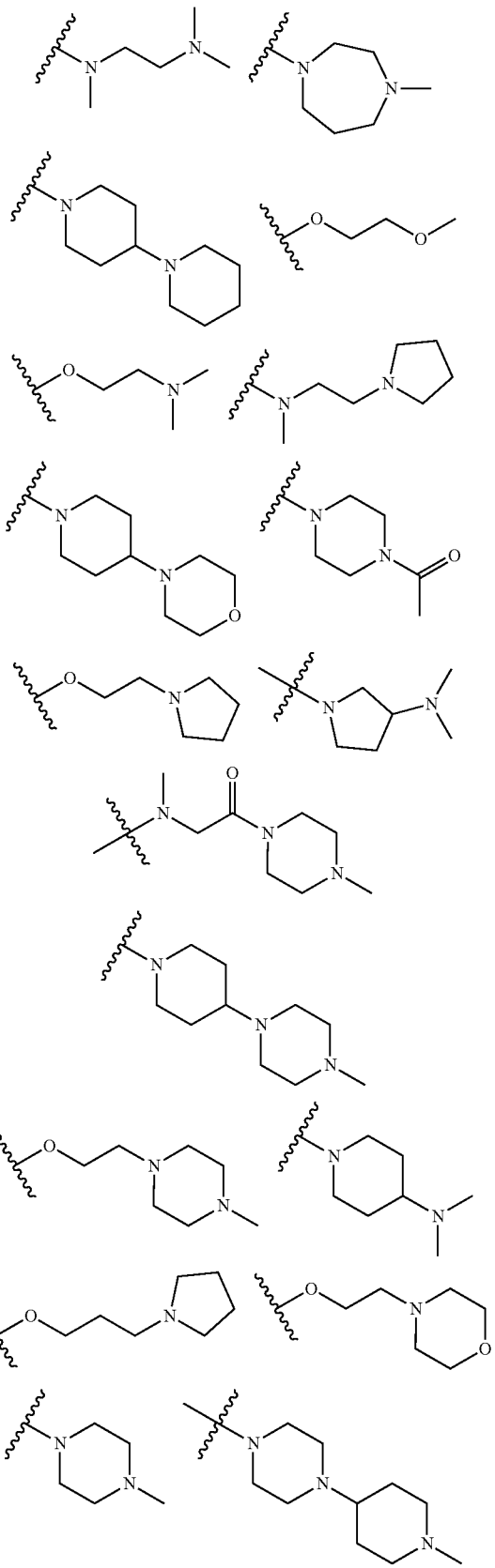

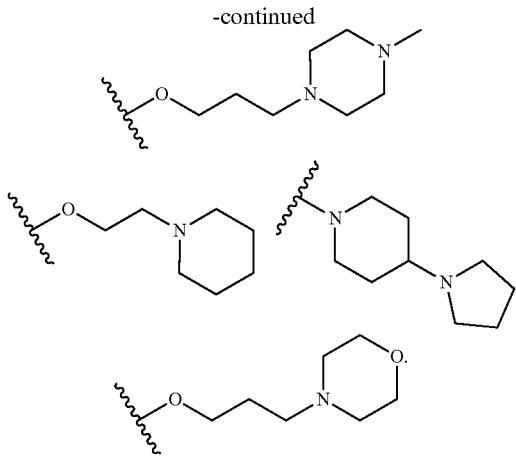

5. The compound or the pharmaceutically acceptable salts thereof according to claim 1, wherein the compound is selected from the group consisting of:
- N-(5-(6-(3-bromo-phenylamino)-pyrimidin-4-ylamino)-2-((2-dimethylamino-ethyl)-methyl-amino)-4-methoxyl-phenyl)-acrylamide;
- N-(2-((2-dimethylamino)-ethyl)-methyl-amino)-4-methoxyl-5-(6-(3-trifluoromethyl-phenylamino)-pyrimidin-4-ylamino)-phenyl)-acrylamide;
- N-(5-(6-(3-alkynyl-phenylamino)-pyrimidin-4-ylamino)-2-((2-dimethylamino-ethyl)-methyl-amino)-4-methoxyl-phenyl)-acrylamide;
- N-(5-(6-(2,4-dichloro-5-methoxyl-phenylamino)-pyrimidin-4-ylamino)-2-((2-dimethylamino-ethyl)-methyl-amino)-4-methoxyl-phenyl)-acrylamide;
- N-(5-(6-(2-fluoro-3,4-dichloro-phenylamino)-pyrimidin-4-ylamino)-2-((2-dimethylamino-ethyl)-methyl-amino)-4-methoxyl-phenyl)-acrylamide;
- N-(5-(6-(2-fluoro-3-chloro-phenylamino)-pyrimidin-4-ylamino)-2-((2-dimethylamino-ethyl)-methyl-amino)-4-methoxyl-phenyl)-acrylamide;
- N-(5-(6-(3-bromo-5-fluoro-phenylamino)-pyrimidin-4-ylamino)-2-((2-dimethylamino-ethyl)-methyl-amino)-4-methoxyl-phenyl)-acrylamide;
- N-(5-(6-(3-chloro-4-fluoro-phenylamino)-pyrimidin-4-ylamino)-2-((2-dimethylamino-ethyl)-methyl-amino)-4-methoxyl-phenyl)-acrylamide;
- N-(5-(6-(3-chloro-4-fluoro-phenylamino)-2-methyl-pyrimidin-4-ylamino)-2-((2-dimethylamino-ethyl)-methyl-amino)-4-methoxyl-phenyl)-acrylamide;
- N-(5-(6-(3-chloro-4-fluoro-phenylamino)-pyrimidin-4-ylamino)-2-[piperidin-1-yl]-4-methoxyl-phenyl)-acrylamide;
- N-(5-(6-(3-chloro-4-fluoro-phenylamino)-pyrimidin-4-ylamino)-4-methoxyl-2-(4-morpholin-4-yl-piperidin-1-yl)-phenyl)-acrylamide;
- N-(5-(6-(3-chloro-4-fluoro-phenylamino)-pyrimidin-4-ylamino)-2-(4-methyl-[1,4]diazepin-1-yl)-4-methoxyl-phenyl)-acrylamide;
- N-(5-(6-(3-chloro-4-fluoro-phenylamino)-pyrimidin-4-ylamino)-4-methoxyl-2-(4-methyl-piperazin-1-yl)-phenyl)-acrylamide;
- N-(2-(4-acetyl-piperazin-1-yl)-5-(6-(3-chloro-4-fluoro-phenylamino)-pyrimidin-4-ylamino)-4-methoxyl-phenyl)-acrylamide;
- N-(5-(6-(3-chloro-4-fluoro-phenylamino)-pyrimidin-4-ylamino)-4-methoxyl-2-(4-(1-methylpiperidin-4-yl)-piperazin-1-yl)-phenyl)-acrylamide;
- N-(5-(6-(3-chloro-4-fluoro-phenylamino)-pyrimidin-4-ylamino)-2-(2-dimethylamino-ethoxyl)-4-methoxyl-phenyl)-acrylamide;
- N-(5-(6-(3-chloro-4-fluoro-phenylamino)-pyrimidin-4-ylamino)-4-methoxyl-2-(2-pyrrolidin-1-yl-ethoxyl)-phenyl)-acrylamide;
- N-(5-(6-(3-chloro-4-fluoro-phenylamino)-pyrimidin-4-ylamino)-2-(2-(4-methyl-piperazin-1 yl)-ethoxyl)-4-methoxyl-phenyl)-acrylamide;
- N-(5-(6-(3-chloro-4-fluoro-phenylamino)-pyrimidin-4-ylamino)-4-methoxyl-2-(2-morpholin-4-yl-ethoxyl)-phenyl)-acrylamide;
- N-(5-(6-(3-chloro-4-fluoro-phenylamino)-pyrimidin-4-ylamino)-2-(2-methoxylethoxyl)-4-methoxyl-phenyl)-acrylamide;
- N-(5-(6-(3-chloro-4-(3-fluoro-benzyloxy)-phenylamino)-pyrimidin-4-ylamino)-2-((2-dimethylamino-ethyl)-methyl-amino)-4-methoxyl-phenyl)-acrylamide;
- N-(5-(6-(3-chloro-4-(pyridin-2-ylmethoxy)-phenylamino)-pyrimidin-4-ylamino)-2-((2-dimethylamino-ethyl)-methyl-amino)-4-methoxyl-phenyl)-acrylamide;
- N-(5-(6-(3-chloro-4-(2-morpholin-4-yl-ethoxy)-phenylamino)-pyrimidin-4-ylamino)-2-((2-dimethylaminoethyl)-methyl-amino)-4-methoxyphenyl)-acrylamide;
- N-(5-(6-(3-chloro-4-(tetrahydropyran-4-yl-methoxyl)-phenylamino)-pyrimidin-4-ylamino)-2-((2-dimethylaminoethyl)-methyl-amino)-4-methoxyphenyl)-acrylamide;
- N-(5-(6-(3-(1-(3-methylbutoxy)ethyl)-4-methoxylphenylamino)-pyrimidin-4-ylamino)-2-((2-dimethylaminoethyl)-methyl-amino)-4-methoxylphenylamino)-acrylamide;
- N-(5-(6-(3-chloro-4-methoxyl-phenylamino)-pyrimidin-4-ylamino)-2-(2-dimethylamino-ethoxyl)-4-methoxyl-phenyl)-acrylamide;
- N-(5-(6-(3-chloro-4-(3-methylbutoxy)-phenylamino)-pyrimidin-4-ylamino)-2-((2-dimethylaminoethyl)-methyl-amino)-4-methoxyphenyl)-acrylamide;
- 5-(6-(5-acrylamido-4-((2-methoxyphenyl)-methyl-amino)-2-methoxylphenylamino)-pyrimidin-4-yl)-2-methoxybenzamide;
- 5-(6-(5-acrylamido-4-((2-methoxyphenyl)-methyl-amino)-2-methoxylphenylamino)-pyrimidin-4-yl)-2-methoxyl-N-methylbenzamide;
- N-(5-(6-(4-methoxyl-3-trifluoromethyl-phenylamino)-pyrimidin-4-yl-amino)-2-((2-dimethylamino-ethyl)-methyl-amino)-4-methoxyl-phenyl)-acrylamide;
- N-(5-(6-(3-chloro-4-(thiazol-2-ylmethoxy)-phenylamino)-pyrimidin-4-ylamino)-2-((2-dimethyl-amino-ethyl)-methyl-amino)-4-methoxyl-phenyl)-acrylamide;
- N-(5-(6-(4-methoxyl-3-bromo-phenylamino)-pyrimidin-4-yl-amino)-2-((2-dimethylamino-ethyl)-methyl-amino)-4-methoxyl-phenyl)-acrylamide;
- N-(5-(6-(4-methoxyl-3-chloro-phenylamino)-pyrimidin-4-yl-amino)-2-(2-(pyrrolidin-1-yl)-ethoxyl)-4-methoxyl-phenyl)-acrylamide;
- N-(5-(6-(4-fluoro-3-trifluoromethyl-phenylamino)-pyrimidin-4-yl-amino)-2-((2-dimethylamino-ethyl)-methyl-amino)-4-methoxyl-phenyl)-acrylamide;
- N-(5-(6-(3-chloro-4-methoxyl-phenylamino)-pyrimidin-4-ylamino)-2-(4-(1-methylpiperidin-4-yl)-piperazin-1-yl)-4-methoxyl-phenyl)-acrylamide;

N-(5-(6-(4-chloro-3-trifluoromethyl-phenylamino)-pyrimidin-4-yl-amino)-2-((2-dimethylamino-ethyl)-methyl-amino)-4-methoxyl-phenyl)-acrylamide;

N-(5-(6-(3-cyano-phenylamino)-pyrimidin-4-yl-amino)-2-((2-dimethylamino-ethyl)-methyl-amino)-4-methoxyl-phenyl)-acrylamide;

N-(5-(6-(5-fluoro-3-trifluoromethyl-phenylamino)-pyrimidin-4-yl-amino)-2-((2-dimethylamino-ethyl)-methyl-amino)-4-methoxyl-phenyl)-acrylamide;

N-(5-(6-(2-fluoro-5-trifluoromethyl-phenylamino)-pyrimidin-4-yl-amino)-2-((2-dimethylamino-ethyl)-methyl-amino)-4-methoxyl-phenyl)-acrylamide;

N-(5-(6-(3-methoxyl-5-trifluoromethyl-phenylamino)-pyrimidin-4-yl-amino)-2-((2-dimethylamino-ethyl)-methyl-amino)-4-methoxyl-phenyl)-acrylamide;

N-(5-(6-(2-methoxyl-5-trifluoromethyl-phenylamino)-pyrimidin-4-yl-amino)-2-((2-dimethylamino-ethyl)-methyl-amino)-4-methoxyl-phenyl)-acrylamide;

N-(5-(6-(3-chloro-4-trifluoromethyl-phenylamino)-pyrimidin-4-yl-amino)-2-((2-dimethylamino-ethyl)-methyl-amino)-4-methoxyl-phenyl)-acrylamide;

N-(5-(6-(3-chloro-4-trifluoromethoxy-phenylamino)-pyrimidin-4-yl-amino)-2-((2-dimethylamino-ethyl)-methyl-amino)-4-methoxyl-phenyl)-acrylamide;

N-(5-(6-(3-chloro-5-fluoro-4-(2-methoxyl-ethoxyl)-phenylamino)-pyrimidin-4-yl-amino)-2-((2-dimethyl-amino-ethyl)-methyl-amino)-4-methoxyl-phenyl)-acrylamide;

N-(5-(6-(3-methanesulfonamido-4-methoxyl-phenylamino)-pyrimidin-4-yl-amino)-2-((2-dimethyl-amino-ethyl)-methyl-amino)-4-methoxyl-phenyl)-acrylamide;

N-(5-(6-(2,4-dichloro-5-methoxyl-phenylamino)-pyrimidin-4-yl-amino)-2-(4-methyl-piperazin-1-yl)-4-methoxyl-phenyl)-acrylamide;

N-(5-(6-(2,4-dichloro-5-methoxyl-phenylamino)-pyrimidin-4-yl-amino)-2-(4-(morpholin-1-yl)-piperidin-1-yl)-4-methoxyl-phenyl)-acrylamide;

N-(5-(6-(2,4-dichloro-5-methoxyl-phenylamino)-pyrimidin-4-yl-amino)-2-(methyl-(2-(4-methyl-piperazin-1-yl)-2-oxoethyl)-amino)-4-methoxyl-phenyl)-acrylamide;

N-(5-(6-(2,4-dichloro-5-methoxyl-phenylamino)-pyrimidin-4-ylamino)-2-(2-dimethylamino-ethoxyl)-4-methoxyl-phenyl)-acrylamide;

N-(5-(6-(2,4-dichloro-5-methoxyl-phenylamino)-pyrimidin-4-yl-amino)-2-(2-(morpholin-4-yl)-ethoxyl-4-methoxyl-phenyl)-acrylamide;

N-(5-(6-(2,4-dichloro-5-methoxyl-phenylamino)-pyrimidin-4-yl-amino)-2-(2-(pyrrolidin-1-yl)-ethoxyl)-4-methoxyl-phenyl)-acrylamide;

N-(5-(6-(2,4-dichloro-5-methoxyl-phenylamino)-pyrimidin-4-yl-amino)-2-(2-(4-methyl-piperazin-1-yl)-ethoxyl)-4-methoxyl-phenyl)-acrylamide;

N-(5-(6-(2,4-dichloro-5-methoxyl-phenylamino)-pyrimidin-4-yl-amino)-2-(3-(pyrrolidin-1-yl)-propyl)-4-methoxyl-phenyl)-acrylamide;

N-(5-(6-(2,4-dichloro-5-methoxyl-phenylamino)-pyrimidin-4-yl-amino)-2-(2-(piperidin-1-yl)-ethoxyl-4-methoxyl-phenyl)-acrylamide;

N-(5-(6-(2,4-dichloro-5-methoxyl-phenylamino)-pyrimidin-4-yl-amino)-2-(3-(4-methyl-piperazin-1-yl)-propyl)-4-methoxyl-phenyl)-acrylamide;

N-(5-(6-((2,4-dichloro-5-methoxyl-phenyl)-methyl-amino)-pyrimidin-4-ylamino)-2-((2-dimethylamino-ethyl)-methyl-amino)-4-methoxyl-phenyl)-acrylamide;

N-(5-(6-(2,4-dichloro-5-methoxyl-phenylamino)-pyrimidin-4-yl-amino)-2-(3-(morpholin-4-yl)-propoxyl-4-methoxyl-phenyl)-acrylamide;

N-(5-(6-(3-chloro-4-tert-butoxy-phenylamino)-pyrimidin-4-yl-amino)-2-((2-dimethylamino-ethyl)-methyl-amino)-4-methoxyl-phenyl)-acrylamide;

N-(5-(6-(3-acetenyl-4-methoxyl-phenylamino)-pyrimidin-4-yl-amino)-2-((2-dimethylamino-ethyl)-methyl-amino)-4-methoxyl-phenyl)-acrylamide;

N-(5-(6-(3-chloro-4-(3-methyl-oxetan-3-yl-methoxyl)-phenylamino)-pyrimidin-4-yl-amino)-2-((2-dimethyl-amino-ethyl)-methyl-amino)-4-methoxy-phenyl)-acrylamide;

N-(5-(6-(3-chloro-4-hydroxylphenylamino)-pyrimidin-4-ylamino)-2-((2-dimethylamino-ethyl)-methyl-amino)-4-methoxyl-phenyl)-acrylamide;

N-(5-(6-(3-chloro-4-(tetrahydrofuran-2-ylmethoxy)-phenylamino)-pyrimidin-4-ylamino)-2-((2-dimethyl-amino-ethyl)-methyl-amino)-4-methoxyl-phenyl)-acrylamide;

N-(5-(6-(3-cyano-4-methoxyphenylamino)-pyrimidin-4-yl-amino)-2-((2-dimethylamino-ethyl)-methyl-amino)-4-methoxyl-phenyl)-acrylamide;

N-(5-(6-(3-acetyl-4-methoxyphenylamino)-pyrimidin-4-yl-amino)-2-((2-dimethylamino-ethyl)-methyl-amino)-4-methoxyl-phenyl)-acrylamide.

6. A pharmaceutical composition comprising the compound or the pharmaceutically acceptable salts thereof according to claim 1 as active ingredient and one or more of pharmaceutically acceptable excipients.

7. A method for the treatment of cancer in a subject suffering therefrom, comprising administering to the subject a compound or the pharmaceutically acceptable salts thereof according to claim 1 or a pharmaceutical composition according to claim 6, wherein the cancer is selected from the group consisting of lung cancer, breast cancer, gastric cancer, and colon cancer.

\* \* \* \* \*